US011011252B1

(12) United States Patent
Shak et al.

(10) Patent No.: US 11,011,252 B1
(45) Date of Patent: *May 18, 2021

(54) GENE EXPRESSION PROFILE ALGORITHM AND TEST FOR DETERMINING PROGNOSIS OF PROSTATE CANCER

(71) Applicant: Genomic Health, Inc., Redwood City, CA (US)

(72) Inventors: Steven Shak, Hillsborough, CA (US); Mark Lee, Los Altos Hills, CA (US); William F. Novotny, Menlo Park, CA (US); Tara Maddala, Sunnyvale, CA (US); Michael R. Crager, Menlo Park, CA (US); Diana Cherbavaz, San Francisco, CA (US); Robert J. Pelham, Belmont, CA (US); Carl L. Millward, Carmel, IN (US); Dejan Knezevic, Palo Alto, CA (US)

(73) Assignee: Genomic Health, Inc., Redwood City, CA (US)

(*) Notice: Subject to any disclaimer, the term of this patent is extended or adjusted under 35 U.S.C. 154(b) by 1052 days.

This patent is subject to a terminal disclaimer.

(21) Appl. No.: 15/584,963

(22) Filed: May 2, 2017

Related U.S. Application Data

(60) Division of application No. 14/221,556, filed on Mar. 21, 2014, now abandoned, which is a continuation of application No. 13/752,199, filed on Jan. 28, 2013, now Pat. No. 8,725,426.

(60) Provisional application No. 61/713,734, filed on Oct. 15, 2012, provisional application No. 61/672,679, filed on Jul. 17, 2012, provisional application No. 61/593,106, filed on Jan. 31, 2012.

(51) Int. Cl.
*G16B 25/00* (2019.01)
*C12Q 1/6886* (2018.01)
*G16H 50/30* (2018.01)

(52) U.S. Cl.
CPC ........... *G16B 25/00* (2019.02); *C12Q 1/6886* (2013.01); *G16H 50/30* (2018.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,692,916 B2 | 2/2004 | Bevilacqua et al. |
| 6,960,439 B2 | 11/2005 | Bevilacqua et al. |
| 6,964,850 B2 | 11/2005 | Bevilacqua et al. |
| 7,695,913 B2 | 4/2010 | Cowens et al. |
| 7,957,909 B2 | 6/2011 | Bevilacqua et al. |
| 8,067,178 B2 | 11/2011 | Baker et al. |
| 8,114,597 B2 | 2/2012 | Liew |
| 8,725,426 B2 * | 5/2014 | Shak ............... C12Q 1/6886 702/20 |
| 2002/0173461 A1 | 11/2002 | Pennica et al. |
| 2003/0087818 A1 | 5/2003 | Jiang et al. |
| 2003/0148410 A1 | 8/2003 | Berger et al. |
| 2003/0198970 A1 | 10/2003 | Roberts |
| 2003/0219771 A1 | 11/2003 | Bevilacqua et al. |
| 2003/0229455 A1 | 12/2003 | Bevilacqua et al. |
| 2004/0053317 A1 | 3/2004 | Glinskii |
| 2004/0133352 A1 | 7/2004 | Bevilacqua et al. |
| 2005/0048542 A1 | 3/2005 | Baker et al. |
| 2005/0112705 A1 | 5/2005 | Bracco et al. |
| 2005/0191673 A1 | 9/2005 | Schlegel et al. |
| 2005/0260646 A1 | 11/2005 | Baker et al. |
| 2006/0088823 A1 | 4/2006 | Haab et al. |
| 2006/0281122 A1 | 12/2006 | Bryant et al. |
| 2007/0048738 A1 | 3/2007 | Donkena et al. |
| 2007/0099209 A1 | 5/2007 | Clarke et al. |
| 2007/0105133 A1 | 5/2007 | Clarke et al. |
| 2007/0212702 A1 | 9/2007 | Tomlins et al. |
| 2007/0224596 A1 | 9/2007 | Nacht et al. |
| 2007/0275398 A1 | 11/2007 | Kiefer et al. |
| 2008/0015448 A1 | 1/2008 | Keely et al. |
| 2008/0085519 A1 | 4/2008 | Gabrin et al. |
| 2008/0254481 A1 | 10/2008 | Love et al. |
| 2009/0023149 A1 | 1/2009 | Knudsen |
| 2009/0042965 A1 | 2/2009 | Dervan et al. |
| 2009/0123439 A1 | 5/2009 | Yun et al. |
| 2009/0170075 A1 | 7/2009 | Petrovics et al. |
| 2009/0233279 A1 | 9/2009 | Glinskii |
| 2009/0258795 A1 | 10/2009 | Cowens et al. |

(Continued)

FOREIGN PATENT DOCUMENTS

| | | |
|---|---|---|
| JP | 2005211023 A | 8/2005 |
| WO | 9964626 A2 | 12/1999 |

(Continued)

OTHER PUBLICATIONS

Marguerat et al. RNA-seq: from technology to biology Cellular and Molecular Life Sciences vol. 67, pp. 569-579 (Year: 2010).*
Godfrey et al. Quantitative mRNA Expression Analysis from Formalin-Fixed, Paraffin-Embedded Tissues Using 5' Nuclease Qantitative Reverse Transcription-Polymerase Chain Reaction Journal of Molecular Diagnostics vol. 2, pp. 84-91 (Year: 2000).*
Specht et al. Quantitative Gene Expression Analysis in Microdissected Archival Formalin-Fixed and Paraffin-Embedded Tumor Tissue American Journal of Pathology vol. 158, pp. 419-429 (Year: 2001).*
VanGuilder et al. Twenty-five years of Quantitative PCR for gene expression analysis BioTechniques vol. pages . (Year: 2008).*
Cooperberg et al. Active Surveillance for Prostate Cancer: Progress and Promise Journal of Clinical Oncology vol. 29, pp. 3669-3676 (Year: 2011).*

(Continued)

*Primary Examiner* — John S Brusca
(74) *Attorney, Agent, or Firm* — McNeill Baur PLLC

(57) ABSTRACT

The present invention provides algorithm-based molecular assays that involve measurement of expression levels of genes, or their co-expressed genes, from a biological sample obtained from a prostate cancer patient. The genes may be grouped into functional gene subsets for calculating a quantitative score useful to predict a likelihood of a clinical outcome for a prostate cancer patient.

13 Claims, 14 Drawing Sheets

Specification includes a Sequence Listing.

(56) References Cited

U.S. PATENT DOCUMENTS

| | | |
|---|---|---|
| 2009/0298082 A1 | 12/2009 | Klee et al. |
| 2009/0305277 A1 | 12/2009 | Baker et al. |
| 2010/0124745 A1 | 5/2010 | Liew |
| 2010/0227317 A1 | 9/2010 | Thomson Okatsu et al. |
| 2010/0291573 A1 | 11/2010 | Cowens et al. |
| 2010/0297657 A1 | 11/2010 | Chinnaiyan |
| 2010/0303795 A1 | 12/2010 | Sorensen et al. |
| 2011/0039269 A1 | 2/2011 | Cowens et al. |
| 2011/0039271 A1 | 2/2011 | Cowens et al. |
| 2011/0059447 A1 | 3/2011 | Liew |
| 2011/0097759 A1 | 4/2011 | Cowens et al. |
| 2011/0111421 A1 | 5/2011 | Cowens et al. |
| 2011/0123990 A1 | 5/2011 | Baker et al. |
| 2011/0153534 A1 | 6/2011 | Chudin et al. |
| 2011/0171633 A1 | 7/2011 | Cowens et al. |
| 2011/0236903 A1 | 9/2011 | Depinho et al. |
| 2012/0028264 A1 | 2/2012 | Shak et al. |
| 2012/0040842 A1 | 2/2012 | Baker et al. |
| 2012/0136583 A1 | 5/2012 | Lazar et al. |
| 2012/0171688 A1 | 7/2012 | Cowens et al. |

FOREIGN PATENT DOCUMENTS

| | | |
|---|---|---|
| WO | 9964627 A2 | 12/1999 |
| WO | 00/50899 A1 | 8/2000 |
| WO | 0231209 A2 | 4/2002 |
| WO | 03050243 A2 | 6/2003 |
| WO | 2003053223 A2 | 7/2003 |
| WO | 03/089932 A1 | 10/2003 |
| WO | 2004108896 A2 | 12/2004 |
| WO | 2005008213 A2 | 1/2005 |
| WO | 2005012875 A2 | 2/2005 |
| WO | 2005076005 A2 | 8/2005 |
| WO | 2005117943 A2 | 12/2005 |
| WO | 2006028655 A2 | 3/2006 |
| WO | 2006091776 A2 | 8/2006 |
| WO | 2006124836 A1 | 11/2006 |
| WO | 2007070621 A2 | 6/2007 |
| WO | 2007072225 A2 | 6/2007 |
| WO | 2007082099 A2 | 7/2007 |
| WO | 2008067065 A2 | 6/2008 |
| WO | 2009143603 A1 | 12/2009 |
| WO | 2010009337 A2 | 1/2010 |
| WO | 2010056993 A2 | 5/2010 |
| WO | 2010080933 A1 | 7/2010 |

OTHER PUBLICATIONS

Tang S.C., et al. "Expression of Glutathione S-Transferase M2 in Stage I/II Non-Small Cell Lung Cancer and Alleviation of DNA Damage Exposure to Benzo[a]pyrene", Toxicology Letters, vol. 192, 2010, pp. 316-323.

Perner et al. "TMPRSS2-ETS Gene Fusion in Prostate Cancer", vol. 46, No. 7, 2007, pp. 754-760.

Cuzick et al. Prognostic value of an RNA expression signature derived from cell cycle proliferation genes in patients with prostate cancer: a retrospective study Lancet Oncology vol. 12, pp. 245-255 (2011).

Kidokoro et al. CDC20, a potential cancer therapeutic target, is negatively regulated by p53, Oncogene vol. 27, pp. 1562-1571 (2008).

Extended European Search Report for European Patent Application No. 13743785.1, dated Jan. 8, 2016.

Supplementary Partial European Search Report dated Sep. 10, 2015, for European Patent Application No. 13743785.1.

Johnson et aL. 99th Annual Meeting of the United States and Canadian Academy of Pathology, Abstract 881, "Validation of Molecular Markers of Aggressiveness in Prostate Cancer", 2010, pp. 174A-232A.

Kai et al., International Journal of Cancer, "Loss of Heterozygosity and Tumor Suppressor Activity of B!N 1 in Prostate Carcinoma". vol. 86, No. 2, 2000. pp. 155-161.

McDonnell et al., BMC Medical Genomics. "Biomarker Expression Patterns that Correlate with High Grade Features in Treatment Naive, Organ-Confined Prostate Cancer", vol. 1. No. 1, 2008, pp. 1-9.

Murphy et al., Nature Reviews Urology, "Patented Prostate Cancer Biomarkers", vol. 9, No. 8. 2012, pp. 464-472.

Rowlands et al., "Cancer Causes and Control, Serum Insulin-Like Growth Factors and Mortality in Localised and Advanced Clinically Detected Prostate Cancer," vol. 23, No. 2, 2011, pp. 347-354.

Anders M., et al., "Microarray Meta-analysis Defines Global Angiogenesis-related Gene Expression Signatures in Human Carcinomas," Molecular Carcinogenesis, 2011, 1 O pages.

Clarke R.A., et al., "Markers for Detection of Prostate Cancer," Cancers, 2010, vol. 2, pp. 1125-1154.

International Search Report and Written Opinion for Application No. PCT/US11/45253, dated Feb. 27, 2012, 13 pages.

International Search Report and Written Opinion for Application No. PCT/US2013/023409, dated Jun. 7, 2013, 12 pages.

Nishidate T., et al., "Genome-wide Gene-expression Profiles of Breast-cancer Cells Purified with Laser Microbeam Microdissection: Identification of Genes Associated with Progression and Metastasis," International Journal of Oncology, 2004, vol. 25 (4), pp. 797-819.

Peters D., et al., "Genome-wide Transcriptional Analysis of Carboplatin Response in Chemosensitive and Chemoresistant Ovarian Cancer Cells," Molecular Cancer Therapeutics, 2005, vol. 4 (10), pp. 1605-1616.

Shen R., et al., "Prognostic Meta-signature of Breast Cancer Developed by Two-stage Mixture Modeling of Microarray Data," BMC Genomics, 2004, vol. 5 (1 ), 16 pages.

Taioli E., et al., "Multi-institutional Prostate Cancer Study of Genetic Susceptibility in Populations of African Descent," Carcinogenesis, 2011, vol. 32 (9), pp. 1361-1365.

True L., et al., "A Molecular Correlate to the Gleason Grading System for Prostate Adenocarcinoma," Proceedings of the National Academy of Sciences, 2006, vol. 103 (29), pp. 10991-10996.

Turashvili G., et al., "Novel Markers for Differentiation of Lobular and Ductal Invasive Breast Carcinomas by Laser Microdissection and Microarray Analysis," BMC Cancer, 2007, vol. 7, 20 pages.

Vaarala M., "Differential Gene Expression in Prostate Cancer," Biocenter Oulu, 2000, 71 pages.

Descazeaud et al., "Characterization of ZAG Protein Expression in Prostate Cancer using a Semi-Automated Microscope System," Prostate 66(10):1037-1043, 2006.

Extended Search Report issued in European Application No. 19173920.0, dated Jul. 19, 2019, 7 pages.

Extended Search Report issued in European Application No. 16191856.0, dated Aug. 16, 2017, 16 pages.

Ohl et al., Gene expression studies in prostate cancer tissue: which reference gene should be selected for normalization?, J. Mol. Med. (Berl) 83(12):1014-24, Abstract, 2005.

Edwards et al., "Expression Analysis Onto Microarrays of Randomly Selected cDNA Clones Highlights HOXBI3 as a Marker of Human Prostate Cancer", British Journal of Cancer, vol. 92, 2005, pp. 376-381.

Lapointe et al., "Gene Expression Profiling Identifies Clinically Relevant Subtypes of Prostate Cancer", PNAS, vol. 101, 2004, pp. 811-816.

Nakagawa et al., "A Tissue Biomarker Panel Predicting Systemic Progression After PSA Recurrence Post-Definitive Prostate Cancer Therapy", Plos One, vol. 3, 2008, 14 pgs.

Whitehead et al., "Variation in Tissue-Specific Gene Expression Among Natural Populations", Genome Biology, 6: R13, 2005, 14 pgs.

Haller et al., "Equivalence Test in Quantitative Reverse Transcription Polymerase Chain Reaction: Confirmation of Reference Genes Suitable for Normalization", Analytical Biochemistry, vol. 335, No. 1, 2004, pp. 1-9.

Yang et al., "A Molecular Classification of Papillary Renal Cell Carcinoma", Cancer Research, vol. 65, 2005, pp. 5628-5637.

Yao et al., "A Three-Gene Expression Signature Model to Predict Clinical Outcome of Clear Cell Renal Carcinoma", Int. J. Cancer, vol. 123, No. 5, 2008, pp. 1126-1132.

(56) References Cited

OTHER PUBLICATIONS

Partial European Search Report dated May 8, 2017, for European Patent Application No. 17153152.8.
Li et al., "Prostatic intraepithelial neoplasia and adenocarcinoma in mice expressing a probasin-Neu oncogenic transgene," Carcinogenesis, vol. 27, No. 5, May 1, 2006, pp. 1054-1067.
Partial Search Report issued in European Application No. 16191856. 0, dated May 11, 2017, 19 pages.
Barwick et al., "Prostate Cancer Genes Associated with TMPRSS2-ERG Gene Fusion and Prognostic of Biochemical Recurrence in Multiple Cohorts," British Journal of Cancer, 2010, vol. 102 (3), pp. 570-576.
Cheville et al., "Gene Panel Model Predictive of Outcome in Men at High-Risk of Systemic Progression and Death From Prostate Cancer After Radical Retropubic Prostatectomy," Journal of Clinical Oncology, 2008, vol. 26 (24), pp. 3930-3936.
Erickson et al., "Quantitative RT-PCR Gene Expression Analysis of Laser Microdissected Tissue Samples," Nature Protocols, 2009, vol. 4(6), pp. 902-922.
Ornish et al., "Changes in Prostate Gene Expression in Men Undergoing an Intensive Nutrition and Lifestyle Intervention," PNAS, 2008, vol. 105 (24), pp. 8369-8374.
Singh et al., "Annotation of Androgen Dependence to Human Prostate Cancer-Associated Genes by Microarray Analysis of Mouse Prostate," Cancer Letters vol. 237, 2006, pp. 298-304.
Tomlins et al., "Integrative Molecular Concept Modeling of Prostate Cancer Progression," Nature Genetics, vol. 39, 2007, pp. 41-51.
Partial European Search Report issued in European Application No. 20180564.5, dated Sep. 24, 2020, 14 pages.

\* cited by examiner

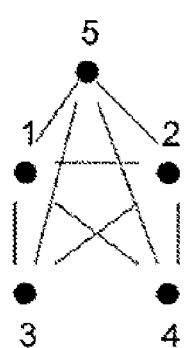
Fig. 5A
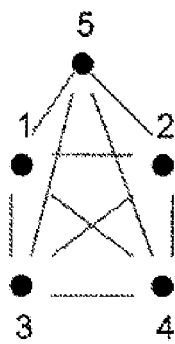
Fig. 5B
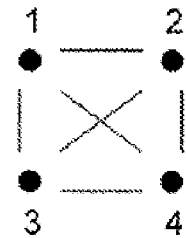
Fig. 5C
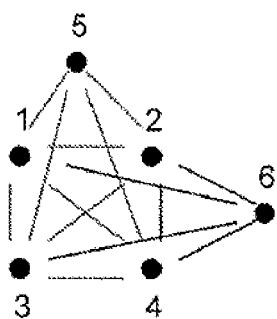
Fig. 6
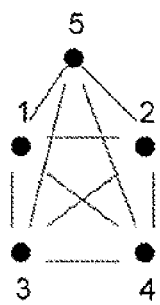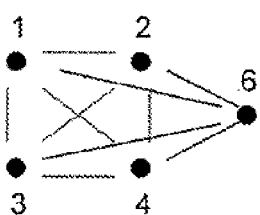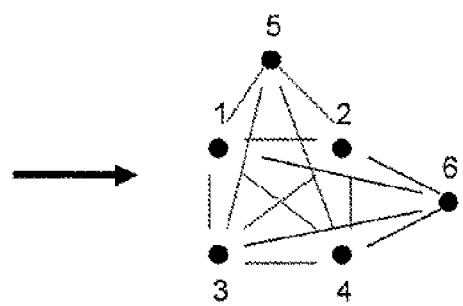
Fig. 7A    Fig. 7B    Fig. 7C

SEQUENCE LISTING

<160> NUMBER OF SEQ ID NOS: 344

<210> SEQ ID NO 1
<211> LENGTH: 20
<212> TYPE: DNA
<213> ORGANISM: Artificial Sequence
<220> FEATURE:
<223> OTHER INFORMATION: Synthesized DNA

<400> SEQUENCE: 1
cacgtctgtc cctctctgct                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthesized DNA

<400> SEQUENCE: 2
gaccgtggct caactttgta t                                                 21

<210> SEQ ID NO 3
<211> LENGTH: 24
<212> TYPE: DNA
<213> ORGANISM: Artificial Sequence
<220> FEATURE:
<223> OTHER INFORMATION: Synthesized DNA

<400> SEQUENCE: 3
tctctgtagg gcccagctct cagg                                              24

<210> SEQ ID NO 4
<211> LENGTH: 67
<212> TYPE: DNA
<213> ORGANISM: Artificial Sequence
<220> FEATURE:
<223> OTHER INFORMATION: Synthesized DNA

<400> SEQUENCE: 4
cacgtctgtc cctctctgct ttctctgtag ggcccagctc tcaggaatac aaagttgagc       60
cacggtc                                                                 67

<210> SEQ ID NO 5
<211> LENGTH: 22
<212> TYPE: DNA
<213> ORGANISM: Artificial Sequence
<220> FEATURE:
<223> OTHER INFORMATION: Synthesized DNA

<400> SEQUENCE: 5
ccaccttgga ccaaagtaaa gc                                                22

<210> SEQ ID NO 6
<211> LENGTH: 21
<212> TYPE: DNA
<213> ORGANISM: Artificial Sequence
<220> FEATURE:
<223> OTHER INFORMATION: Synthesized DNA

<400> SEQUENCE: 6
tctcagcgtc acctggtagg a                                                 21

<210> SEQ ID NO 7
<211> LENGTH: 22

```
<212> TYPE: DNA
<213> ORGANISM: Artificial Sequence
<220> FEATURE:
<223> OTHER INFORMATION: Synthesized DNA

<400> SEQUENCE: 7
ctccccaaca cgctgaaacc cg                                             22

<210> SEQ ID NO 8
<211> LENGTH: 83
<212> TYPE: DNA
<213> ORGANISM: Artificial Sequence
<220> FEATURE:
<223> OTHER INFORMATION: Synthesized DNA

<400> SEQUENCE: 8
ccaccttgga ccaaagtaaa gcgtggaatc gttaccgcct ccccaacacg ctgaaacccg    60
attcctaccg ggtgacgctg aga                                            83

<210> SEQ ID NO 9
<211> LENGTH: 19
<212> TYPE: DNA
<213> ORGANISM: Artificial Sequence
<220> FEATURE:
<223> OTHER INFORMATION: Synthesized DNA

<400> SEQUENCE: 9
cgacttcacc gcacctgat                                                 19

<210> SEQ ID NO 10
<211> LENGTH: 22
<212> TYPE: DNA
<213> ORGANISM: Artificial Sequence
<220> FEATURE:
<223> OTHER INFORMATION: Synthesized DNA

<400> SEQUENCE: 10
tgacacaagt gggactggga ta                                             22

<210> SEQ ID NO 11
<211> LENGTH: 22
<212> TYPE: DNA
<213> ORGANISM: Artificial Sequence
<220> FEATURE:
<223> OTHER INFORMATION: Synthesized DNA

<400> SEQUENCE: 11
accatgccgc cagggtacca ca                                             22

<210> SEQ ID NO 12
<211> LENGTH: 77
<212> TYPE: DNA
<213> ORGANISM: Artificial Sequence
<220> FEATURE:
<223> OTHER INFORMATION: Synthesized DNA

<400> SEQUENCE: 12
cgacttcacc gcacctgatg tgtggtaccc tggcggcatg gtgagcagag tgccctatcc    60
cagtcccact tgtgtca                                                   77

<210> SEQ ID NO 13
<211> LENGTH: 20
<212> TYPE: DNA
<213> ORGANISM: Artificial Sequence
<220> FEATURE:
```

<223> OTHER INFORMATION: Synthesized DNA

<400> SEQUENCE: 13
cagtagagat ccccgcaact                                       20

<210> SEQ ID NO 14
<211> LENGTH: 20
<212> TYPE: DNA
<213> ORGANISM: Artificial Sequence
<220> FEATURE:
<223> OTHER INFORMATION: Synthesized DNA

<400> SEQUENCE: 14
acaagcacat ggctatggaa                                       20

<210> SEQ ID NO 15
<211> LENGTH: 22
<212> TYPE: DNA
<213> ORGANISM: Artificial Sequence
<220> FEATURE:
<223> OTHER INFORMATION: Synthesized DNA

<400> SEQUENCE: 15
cttgtccttg ggtcaccctg ca                                    22

<210> SEQ ID NO 16
<211> LENGTH: 64
<212> TYPE: DNA
<213> ORGANISM: Artificial Sequence
<220> FEATURE:
<223> OTHER INFORMATION: Synthesized DNA

<400> SEQUENCE: 16
cagtagagat ccccgcaact cgcttgtcct tgggtcaccc tgcattccat agccatgtgc    60
ttgt                                                        64

<210> SEQ ID NO 17
<211> LENGTH: 20
<212> TYPE: DNA
<213> ORGANISM: Artificial Sequence
<220> FEATURE:
<223> OTHER INFORMATION: Synthesized DNA

<400> SEQUENCE: 17
cattgccact tcaactctaa                                       20

<210> SEQ ID NO 18
<211> LENGTH: 20
<212> TYPE: DNA
<213> ORGANISM: Artificial Sequence
<220> FEATURE:
<223> OTHER INFORMATION: Synthesized DNA

<400> SEQUENCE: 18
attgttagtg tccaggctct                                       20

<210> SEQ ID NO 19
<211> LENGTH: 24
<212> TYPE: DNA
<213> ORGANISM: Artificial Sequence
<220> FEATURE:
<223> OTHER INFORMATION: Synthesized DNA

<400> SEQUENCE: 19
tatccctttg gaagaccttg cttg                                  24

<210> SEQ ID NO 20
<211> LENGTH: 81
<212> TYPE: DNA
<213> ORGANISM: Artificial Sequence
<220> FEATURE:
<223> OTHER INFORMATION: Synthesized DNA

<400> SEQUENCE: 20
cattgccact tcaactctaa ggaatatttt tgagatatcc ctttggaaga ccttgcttgg    60
aagagcctgg acactaacaa t                                              81

<210> SEQ ID NO 21
<211> LENGTH: 18
<212> TYPE: DNA
<213> ORGANISM: Artificial Sequence
<220> FEATURE:
<223> OTHER INFORMATION: Synthesized DNA

<400> SEQUENCE: 21
ccgctttcgc tacagcat                                                  18

<210> SEQ ID NO 22
<211> LENGTH: 21
<212> TYPE: DNA
<213> ORGANISM: Artificial Sequence
<220> FEATURE:
<223> OTHER INFORMATION: Synthesized DNA

<400> SEQUENCE: 22
tgggagtatc ggatgtagct g                                              21

<210> SEQ ID NO 23
<211> LENGTH: 24
<212> TYPE: DNA
<213> ORGANISM: Artificial Sequence
<220> FEATURE:
<223> OTHER INFORMATION: Synthesized DNA

<400> SEQUENCE: 23
tccagcctgt ctccagtagg ccac                                           24

<210> SEQ ID NO 24
<211> LENGTH: 66
<212> TYPE: DNA
<213> ORGANISM: Artificial Sequence
<220> FEATURE:
<223> OTHER INFORMATION: Synthesized DNA

<400> SEQUENCE: 24
ccgctttcgc tacagcatgg tggcctactg gagacaggct ggactcagct acatccgata    60
ctccca                                                               66

<210> SEQ ID NO 25
<211> LENGTH: 19
<212> TYPE: DNA
<213> ORGANISM: Artificial Sequence
<220> FEATURE:
<223> OTHER INFORMATION: Synthesized DNA

<400> SEQUENCE: 25
gaggccagct aggaagcaa                                                 19

<210> SEQ ID NO 26

```
<211> LENGTH: 19
<212> TYPE: DNA
<213> ORGANISM: Artificial Sequence
<220> FEATURE:
<223> OTHER INFORMATION: Synthesized DNA

<400> SEQUENCE: 26
caggaagggc agctactgg                                                    19

<210> SEQ ID NO 27
<211> LENGTH: 24
<212> TYPE: DNA
<213> ORGANISM: Artificial Sequence
<220> FEATURE:
<223> OTHER INFORMATION: Synthesized DNA

<400> SEQUENCE: 27
tctgagatcc cacattgcct ccaa                                              24

<210> SEQ ID NO 28
<211> LENGTH: 66
<212> TYPE: DNA
<213> ORGANISM: Artificial Sequence
<220> FEATURE:
<223> OTHER INFORMATION: Synthesized DNA

<400> SEQUENCE: 28
gaggccagct aggaagcaag ggttggaggc aatgtgggat ctcagaccca gtagctgccc       60
ttcctg                                                                  66

<210> SEQ ID NO 29
<211> LENGTH: 18
<212> TYPE: DNA
<213> ORGANISM: Artificial Sequence
<220> FEATURE:
<223> OTHER INFORMATION: Synthesized DNA

<400> SEQUENCE: 29
gagctccgca aggatgac                                                     18

<210> SEQ ID NO 30
<211> LENGTH: 20
<212> TYPE: DNA
<213> ORGANISM: Artificial Sequence
<220> FEATURE:
<223> OTHER INFORMATION: Synthesized DNA

<400> SEQUENCE: 30
cttgttgttc accaggacga                                                   20

<210> SEQ ID NO 31
<211> LENGTH: 24
<212> TYPE: DNA
<213> ORGANISM: Artificial Sequence
<220> FEATURE:
<223> OTHER INFORMATION: Synthesized DNA

<400> SEQUENCE: 31
caagggtctc cagcacctct acgc                                              24

<210> SEQ ID NO 32
<211> LENGTH: 66
<212> TYPE: DNA
<213> ORGANISM: Artificial Sequence
<220> FEATURE:
<223> OTHER INFORMATION: Synthesized DNA
```

```
<400> SEQUENCE: 32
gagctccgca aggatgactt caagggtctc cagcacctct acgccctcgt cctggtgaac    60
aacaag                                                               66

<210> SEQ ID NO 33
<211> LENGTH: 20
<212> TYPE: DNA
<213> ORGANISM: Artificial Sequence
<220> FEATURE:
<223> OTHER INFORMATION: Synthesized DNA

<400> SEQUENCE: 33
cctgcaaaag ggaacaagag                                                20

<210> SEQ ID NO 34
<211> LENGTH: 20
<212> TYPE: DNA
<213> ORGANISM: Artificial Sequence
<220> FEATURE:
<223> OTHER INFORMATION: Synthesized DNA

<400> SEQUENCE: 34
cgtggttgac tctgatctcg                                                20

<210> SEQ ID NO 35
<211> LENGTH: 21
<212> TYPE: DNA
<213> ORGANISM: Artificial Sequence
<220> FEATURE:
<223> OTHER INFORMATION: Synthesized DNA

<400> SEQUENCE: 35
cttcgcctcc agatggctcc c                                              21

<210> SEQ ID NO 36
<211> LENGTH: 76
<212> TYPE: DNA
<213> ORGANISM: Artificial Sequence
<220> FEATURE:
<223> OTHER INFORMATION: Synthesized DNA

<400> SEQUENCE: 36
cctgcaaaag ggaacaagag cccttcgcct ccagatggct cccctgccgc cacccccgag    60
atcagagtca accacg                                                    76

<210> SEQ ID NO 37
<211> LENGTH: 20
<212> TYPE: DNA
<213> ORGANISM: Artificial Sequence
<220> FEATURE:
<223> OTHER INFORMATION: Synthesized DNA

<400> SEQUENCE: 37
gtgcagacct tggttcacct                                                20

<210> SEQ ID NO 38
<211> LENGTH: 19
<212> TYPE: DNA
<213> ORGANISM: Artificial Sequence
<220> FEATURE:
<223> OTHER INFORMATION: Synthesized DNA

<400> SEQUENCE: 38
```
cttagttggc gcacagcac                                                 19

<210> SEQ ID NO 39
<211> LENGTH: 24
<212> TYPE: DNA
<213> ORGANISM: Artificial Sequence
<220> FEATURE:
<223> OTHER INFORMATION: Synthesized DNA

<400> SEQUENCE: 39
tgaaccccga gtatgtcccc aaac                                           24

<210> SEQ ID NO 40
<211> LENGTH: 66
<212> TYPE: DNA
<213> ORGANISM: Artificial Sequence
<220> FEATURE:
<223> OTHER INFORMATION: Synthesized DNA

<400> SEQUENCE: 40
gtgcagacct tggttcacct tatgaacccc gagtatgtcc ccaaaccgtg ctgtgcgcca    60
actaag                                                               66

<210> SEQ ID NO 41
<211> LENGTH: 19
<212> TYPE: DNA
<213> ORGANISM: Artificial Sequence
<220> FEATURE:
<223> OTHER INFORMATION: Synthesized DNA

<400> SEQUENCE: 41
atgtctgagt gtgaggcgg                                                 19

<210> SEQ ID NO 42
<211> LENGTH: 20
<212> TYPE: DNA
<213> ORGANISM: Artificial Sequence
<220> FEATURE:
<223> OTHER INFORMATION: Synthesized DNA

<400> SEQUENCE: 42
aggccttatg ctggtgacag                                                20

<210> SEQ ID NO 43
<211> LENGTH: 24
<212> TYPE: DNA
<213> ORGANISM: Artificial Sequence
<220> FEATURE:
<223> OTHER INFORMATION: Synthesized DNA

<400> SEQUENCE: 43
atgctctgcc ctctgcatct caga                                           24

<210> SEQ ID NO 44
<211> LENGTH: 69
<212> TYPE: DNA
<213> ORGANISM: Artificial Sequence
<220> FEATURE:
<223> OTHER INFORMATION: Synthesized DNA

<400> SEQUENCE: 44
atgtctgagt gtgaggcggg cgctctgaga tgcagagggc agagcatctc tgtcaccagc    60
ataaggcct                                                            69

```
<210> SEQ ID NO 45
<211> LENGTH: 20
<212> TYPE: DNA
<213> ORGANISM: Artificial Sequence
<220> FEATURE:
<223> OTHER INFORMATION: Synthesized DNA

<400> SEQUENCE: 45
ccaccaccat ccttaccatc                                              20

<210> SEQ ID NO 46
<211> LENGTH: 18
<212> TYPE: DNA
<213> ORGANISM: Artificial Sequence
<220> FEATURE:
<223> OTHER INFORMATION: Synthesized DNA

<400> SEQUENCE: 46
gatccactgc cctgatcg                                                18

<210> SEQ ID NO 47
<211> LENGTH: 24
<212> TYPE: DNA
<213> ORGANISM: Artificial Sequence
<220> FEATURE:
<223> OTHER INFORMATION: Synthesized DNA

<400> SEQUENCE: 47
tcttcacctg ctcgggaatc tgtg                                         24

<210> SEQ ID NO 48
<211> LENGTH: 69
<212> TYPE: DNA
<213> ORGANISM: Artificial Sequence
<220> FEATURE:
<223> OTHER INFORMATION: Synthesized DNA

<400> SEQUENCE: 48
ccaccaccat ccttaccatc atcacagatt cccgagcagg tgaagaaggc tcgatcaggg   60
cagtggatc                                                          69

<210> SEQ ID NO 49
<211> LENGTH: 20
<212> TYPE: DNA
<213> ORGANISM: Artificial Sequence
<220> FEATURE:
<223> OTHER INFORMATION: Synthesized DNA

<400> SEQUENCE: 49
ccaaaggatg cgatacacag                                              20

<210> SEQ ID NO 50
<211> LENGTH: 21
<212> TYPE: DNA
<213> ORGANISM: Artificial Sequence
<220> FEATURE:
<223> OTHER INFORMATION: Synthesized DNA

<400> SEQUENCE: 50
ggatgacttg ggaatcatgt c                                            21

<210> SEQ ID NO 51
<211> LENGTH: 27
<212> TYPE: DNA
<213> ORGANISM: Artificial Sequence
<220> FEATURE:
```

<223> OTHER INFORMATION: Synthesized DNA

<400> SEQUENCE: 51
ccactgtgca gccttatttc tccaatg                                27

<210> SEQ ID NO 52
<211> LENGTH: 69
<212> TYPE: DNA
<213> ORGANISM: Artificial Sequence
<220> FEATURE:
<223> OTHER INFORMATION: Synthesized DNA

<400> SEQUENCE: 52
ccaaaggatg cgatacacag accactgtgc agccttattt ctccaatgga catgattccc    60
aagtcatcc                                                           69

<210> SEQ ID NO 53
<211> LENGTH: 20
<212> TYPE: DNA
<213> ORGANISM: Artificial Sequence
<220> FEATURE:
<223> OTHER INFORMATION: Synthesized DNA

<400> SEQUENCE: 53
ggcaccactg cttatgaagg                                        20

<210> SEQ ID NO 54
<211> LENGTH: 20
<212> TYPE: DNA
<213> ORGANISM: Artificial Sequence
<220> FEATURE:
<223> OTHER INFORMATION: Synthesized DNA

<400> SEQUENCE: 54
gatgctcatg gtgaatgagg                                        20

<210> SEQ ID NO 55
<211> LENGTH: 24
<212> TYPE: DNA
<213> ORGANISM: Artificial Sequence
<220> FEATURE:
<223> OTHER INFORMATION: Synthesized DNA

<400> SEQUENCE: 55
actggaaccc agaagcacac cctc                                   24

<210> SEQ ID NO 56
<211> LENGTH: 67
<212> TYPE: DNA
<213> ORGANISM: Artificial Sequence
<220> FEATURE:
<223> OTHER INFORMATION: Synthesized DNA

<400> SEQUENCE: 56
ggcaccactg cttatgaagg aaactggaac ccagaagcac ccctcccct cattcaccat    60 gagcatc                                                             67

<210> SEQ ID NO 57
<211> LENGTH: 20
<212> TYPE: DNA
<213> ORGANISM: Artificial Sequence
<220> FEATURE:
<223> OTHER INFORMATION: Synthesized DNA

<400> SEQUENCE: 57

```
agtgacctgc actcgctgct                                              20

<210> SEQ ID NO 58
<211> LENGTH: 20
<212> TYPE: DNA
<213> ORGANISM: Artificial Sequence
<220> FEATURE:
<223> OTHER INFORMATION: Synthesized DNA

<400> SEQUENCE: 58
ggcttccttg gctttgcgct                                              20

<210> SEQ ID NO 59
<211> LENGTH: 24
<212> TYPE: DNA
<213> ORGANISM: Artificial Sequence
<220> FEATURE:
<223> OTHER INFORMATION: Synthesized DNA

<400> SEQUENCE: 59
ccaatgcacc ccctgcgcgc tggc                                         24

<210> SEQ ID NO 60
<211> LENGTH: 84
<212> TYPE: DNA
<213> ORGANISM: Artificial Sequence
<220> FEATURE:
<223> OTHER INFORMATION: Synthesized DNA

<400> SEQUENCE: 60
agtgacctgc actcgctgct tcagctggat gcacccatcc ccaatgcacc ccctgcgcgc  60
tggcagcgca aagccaagga agcc                                         84

<210> SEQ ID NO 61
<211> LENGTH: 21
<212> TYPE: DNA
<213> ORGANISM: Artificial Sequence
<220> FEATURE:
<223> OTHER INFORMATION: Synthesized DNA

<400> SEQUENCE: 61
tgaagggaac ctgcccttgc a                                            21

<210> SEQ ID NO 62
<211> LENGTH: 23
<212> TYPE: DNA
<213> ORGANISM: Artificial Sequence
<220> FEATURE:
<223> OTHER INFORMATION: Synthesized DNA

<400> SEQUENCE: 62
tgtgcttcac caggaactcc acc                                          23

<210> SEQ ID NO 63
<211> LENGTH: 28
<212> TYPE: DNA
<213> ORGANISM: Artificial Sequence
<220> FEATURE:
<223> OTHER INFORMATION: Synthesized DNA

<400> SEQUENCE: 63
tggctgccaa agaaggccac ctccgggt                                     28

<210> SEQ ID NO 64
```

<211> LENGTH: 74
<212> TYPE: DNA
<213> ORGANISM: Artificial Sequence
<220> FEATURE:
<223> OTHER INFORMATION: Synthesized DNA

<400> SEQUENCE: 64
tgaagggaac ctgcccttgc acttggctgc caaagaaggc cacctccggg tggtggagtt    60
cctggtgaag caca    74

<210> SEQ ID NO 65
<211> LENGTH: 19
<212> TYPE: DNA
<213> ORGANISM: Artificial Sequence
<220> FEATURE:
<223> OTHER INFORMATION: Synthesized DNA

<400> SEQUENCE: 65
accgtatgga cagccacag    19

<210> SEQ ID NO 66
<211> LENGTH: 21
<212> TYPE: DNA
<213> ORGANISM: Artificial Sequence
<220> FEATURE:
<223> OTHER INFORMATION: Synthesized DNA

<400> SEQUENCE: 66
tgactacagg atcagcgctt c    21

<210> SEQ ID NO 67
<211> LENGTH: 24
<212> TYPE: DNA
<213> ORGANISM: Artificial Sequence
<220> FEATURE:
<223> OTHER INFORMATION: Synthesized DNA

<400> SEQUENCE: 67
tctcacatgc tgtacccaaa gcca    24

<210> SEQ ID NO 68
<211> LENGTH: 67
<212> TYPE: DNA
<213> ORGANISM: Artificial Sequence
<220> FEATURE:
<223> OTHER INFORMATION: Synthesized DNA

<400> SEQUENCE: 68
accgtatgga cagccacagc ctggctttgg gtacagcatg tgagatgaag cgctgatcct    60
gtagtca    67

<210> SEQ ID NO 69
<211> LENGTH: 18
<212> TYPE: DNA
<213> ORGANISM: Artificial Sequence
<220> FEATURE:
<223> OTHER INFORMATION: Synthesized DNA

<400> SEQUENCE: 69
gtggccatcc agctgacc    18

<210> SEQ ID NO 70
<211> LENGTH: 23
<212> TYPE: DNA
<213> ORGANISM: Artificial Sequence

```
<220> FEATURE:
<223> OTHER INFORMATION: Synthesized DNA

<400> SEQUENCE: 70
cagtggtagg tgatgttctg gga                                             23

<210> SEQ ID NO 71
<211> LENGTH: 21
<212> TYPE: DNA
<213> ORGANISM: Artificial Sequence
<220> FEATURE:
<223> OTHER INFORMATION: Synthesized DNA

<400> SEQUENCE: 71
tcctgcgcct gatgtccacc g                                               21

<210> SEQ ID NO 72
<211> LENGTH: 68
<212> TYPE: DNA
<213> ORGANISM: Artificial Sequence
<220> FEATURE:
<223> OTHER INFORMATION: Synthesized DNA

<400> SEQUENCE: 72
gtggccatcc agctgacctt cctgcgcctg atgtccaccg aggcctccca gaacatcacc     60
taccactg                                                              68

<210> SEQ ID NO 73
<211> LENGTH: 24
<212> TYPE: DNA
<213> ORGANISM: Artificial Sequence
<220> FEATURE:
<223> OTHER INFORMATION: Synthesized DNA

<400> SEQUENCE: 73
cagccaagaa ctggtatagg agct                                            24

<210> SEQ ID NO 74
<211> LENGTH: 19
<212> TYPE: DNA
<213> ORGANISM: Artificial Sequence
<220> FEATURE:
<223> OTHER INFORMATION: Synthesized DNA

<400> SEQUENCE: 74
aaactggctg ccagcattg                                                  19

<210> SEQ ID NO 75
<211> LENGTH: 30
<212> TYPE: DNA
<213> ORGANISM: Artificial Sequence
<220> FEATURE:
<223> OTHER INFORMATION: Synthesized DNA

<400> SEQUENCE: 75
tctcctagcc agacgtgttt cttgtccttg                                      30

<210> SEQ ID NO 76
<211> LENGTH: 80
<212> TYPE: DNA
<213> ORGANISM: Artificial Sequence
<220> FEATURE:
<223> OTHER INFORMATION: Synthesized DNA

<400> SEQUENCE: 76
```
cagccaagaa ctggtatagg agctccaagg acaagaaaca cgtctggcta ggagaaacta    60
tcaatgctgg cagccagttt    80

<210> SEQ ID NO 77
<211> LENGTH: 19
<212> TYPE: DNA
<213> ORGANISM: Artificial Sequence
<220> FEATURE:
<223> OTHER INFORMATION: Synthesized DNA

<400> SEQUENCE: 77
ggaggttctg gacctgctg    19

<210> SEQ ID NO 78
<211> LENGTH: 18
<212> TYPE: DNA
<213> ORGANISM: Artificial Sequence
<220> FEATURE:
<223> OTHER INFORMATION: Synthesized DNA

<400> SEQUENCE: 78
accaggactg ccacgttc    18

<210> SEQ ID NO 79
<211> LENGTH: 24
<212> TYPE: DNA
<213> ORGANISM: Artificial Sequence
<220> FEATURE:
<223> OTHER INFORMATION: Synthesized DNA

<400> SEQUENCE: 79
ctcctggtcc ccaaggtgtc aaag    24

<210> SEQ ID NO 80
<211> LENGTH: 66
<212> TYPE: DNA
<213> ORGANISM: Artificial Sequence
<220> FEATURE:
<223> OTHER INFORMATION: Synthesized DNA

<400> SEQUENCE: 80
ggaggttctg gacctgctgg tcctcctggt ccccaaggtg tcaaaggtga acgtggcagt    60
cctggt    66

<210> SEQ ID NO 81
<211> LENGTH: 18
<212> TYPE: DNA
<213> ORGANISM: Artificial Sequence
<220> FEATURE:
<223> OTHER INFORMATION: Synthesized DNA

<400> SEQUENCE: 81
acaaaggcct cccaggat    18

<210> SEQ ID NO 82
<211> LENGTH: 20
<212> TYPE: DNA
<213> ORGANISM: Artificial Sequence
<220> FEATURE:
<223> OTHER INFORMATION: Synthesized DNA

<400> SEQUENCE: 82
gagtcccagg aagacctgct    20

<210> SEQ ID NO 83
<211> LENGTH: 24
<212> TYPE: DNA
<213> ORGANISM: Artificial Sequence
<220> FEATURE:
<223> OTHER INFORMATION: Synthesized DNA

<400> SEQUENCE: 83
ctcctttgac accagggatg ccat                                          24

<210> SEQ ID NO 84
<211> LENGTH: 66
<212> TYPE: DNA
<213> ORGANISM: Artificial Sequence
<220> FEATURE:
<223> OTHER INFORMATION: Synthesized DNA

<400> SEQUENCE: 84
acaaaggcct cccaggattg gatggcatcc ctggtgtcaa aggagaagca ggtcttcctg    60
ggactc                                                              66

<210> SEQ ID NO 85
<211> LENGTH: 18
<212> TYPE: DNA
<213> ORGANISM: Artificial Sequence
<220> FEATURE:
<223> OTHER INFORMATION: Synthesized DNA

<400> SEQUENCE: 85
ggtcgaggaa cccaaggt                                                 18

<210> SEQ ID NO 86
<211> LENGTH: 19
<212> TYPE: DNA
<213> ORGANISM: Artificial Sequence
<220> FEATURE:
<223> OTHER INFORMATION: Synthesized DNA

<400> SEQUENCE: 86
gcctggaggt ccaactctg                                                19

<210> SEQ ID NO 87
<211> LENGTH: 24
<212> TYPE: DNA
<213> ORGANISM: Artificial Sequence
<220> FEATURE:
<223> OTHER INFORMATION: Synthesized DNA

<400> SEQUENCE: 87
ccaggaaatc ctgtagcacc aggc                                          24

<210> SEQ ID NO 88
<211> LENGTH: 72
<212> TYPE: DNA
<213> ORGANISM: Artificial Sequence
<220> FEATURE:
<223> OTHER INFORMATION: Synthesized DNA

<400> SEQUENCE: 88
ggtcgaggaa cccaaggtcc gcctggtgct acaggatttc ctggttctgc gggcagagtt    60
ggacctccag gc                                                       72

<210> SEQ ID NO 89
<211> LENGTH: 19
<212> TYPE: DNA

```
<213> ORGANISM: Artificial Sequence
<220> FEATURE:
<223> OTHER INFORMATION: Synthesized DNA

<400> SEQUENCE: 89
ggagaccctg gtgaagctg                                                    19

<210> SEQ ID NO 90
<211> LENGTH: 18
<212> TYPE: DNA
<213> ORGANISM: Artificial Sequence
<220> FEATURE:
<223> OTHER INFORMATION: Synthesized DNA

<400> SEQUENCE: 90
tctccaggga caccaacg                                                     18

<210> SEQ ID NO 91
<211> LENGTH: 24
<212> TYPE: DNA
<213> ORGANISM: Artificial Sequence
<220> FEATURE:
<223> OTHER INFORMATION: Synthesized DNA

<400> SEQUENCE: 91
cttctcttcc ctgatcaccc tgcg                                              24

<210> SEQ ID NO 92
<211> LENGTH: 68
<212> TYPE: DNA
<213> ORGANISM: Artificial Sequence
<220> FEATURE:
<223> OTHER INFORMATION: Synthesized DNA

<400> SEQUENCE: 92
ggagaccctg gtgaagctgg cccgcagggt gatcagggaa gagaaggccc cgttggtgtc       60
cctggaga                                                                68

<210> SEQ ID NO 93
<211> LENGTH: 18
<212> TYPE: DNA
<213> ORGANISM: Artificial Sequence
<220> FEATURE:
<223> OTHER INFORMATION: Synthesized DNA

<400> SEQUENCE: 93
tggtgttcca gggcttct                                                     18

<210> SEQ ID NO 94
<211> LENGTH: 19
<212> TYPE: DNA
<213> ORGANISM: Artificial Sequence
<220> FEATURE:
<223> OTHER INFORMATION: Synthesized DNA

<400> SEQUENCE: 94
ccctgtaaac cctgatccc                                                    19

<210> SEQ ID NO 95
<211> LENGTH: 24
<212> TYPE: DNA
<213> ORGANISM: Artificial Sequence
<220> FEATURE:
<223> OTHER INFORMATION: Synthesized DNA

<400> SEQUENCE: 95
```

```
cctaagggag agccaggaat ccca                                           24

<210> SEQ ID NO 96
<211> LENGTH: 66
<212> TYPE: DNA
<213> ORGANISM: Artificial Sequence
<220> FEATURE:
<223> OTHER INFORMATION: Synthesized DNA

<400> SEQUENCE: 96
tggtgttcca gggcttctcg gacctaaggg agagccagga atcccagggg atcagggttt   60
acaggg                                                               66

<210> SEQ ID NO 97
<211> LENGTH: 18
<212> TYPE: DNA
<213> ORGANISM: Artificial Sequence
<220> FEATURE:
<223> OTHER INFORMATION: Synthesized DNA

<400> SEQUENCE: 97
tgcagcggct gattgaca                                                  18

<210> SEQ ID NO 98
<211> LENGTH: 25
<212> TYPE: DNA
<213> ORGANISM: Artificial Sequence
<220> FEATURE:
<223> OTHER INFORMATION: Synthesized DNA

<400> SEQUENCE: 98
caactgttcc tggtctacaa actca                                          25

<210> SEQ ID NO 99
<211> LENGTH: 28
<212> TYPE: DNA
<213> ORGANISM: Artificial Sequence
<220> FEATURE:
<223> OTHER INFORMATION: Synthesized DNA

<400> SEQUENCE: 99
tcagatggag acctcgtgcc aaattaca                                       28

<210> SEQ ID NO 100
<211> LENGTH: 74
<212> TYPE: DNA
<213> ORGANISM: Artificial Sequence
<220> FEATURE:
<223> OTHER INFORMATION: Synthesized DNA

<400> SEQUENCE: 100
tgcagcggct gattgacagt cagatggaga cctcgtgcca aattcattt gagtttgtag    60 accaggaaca gttg                                                      74

<210> SEQ ID NO 101
<211> LENGTH: 18
<212> TYPE: DNA
<213> ORGANISM: Artificial Sequence
<220> FEATURE:
<223> OTHER INFORMATION: Synthesized DNA

<400> SEQUENCE: 101
acccaagacc ctgcctct                                                  18
```

<210> SEQ ID NO 102
<211> LENGTH: 18
<212> TYPE: DNA
<213> ORGANISM: Artificial Sequence
<220> FEATURE:
<223> OTHER INFORMATION: Synthesized DNA

<400> SEQUENCE: 102 gcagggtgg agtgatgt                                                    18

<210> SEQ ID NO 103
<211> LENGTH: 24
<212> TYPE: DNA
<213> ORGANISM: Artificial Sequence
<220> FEATURE:
<223> OTHER INFORMATION: Synthesized DNA

<400> SEQUENCE: 103
ccacccttct ccagggaccc ttag                                            24

<210> SEQ ID NO 104
<211> LENGTH: 69
<212> TYPE: DNA
<213> ORGANISM: Artificial Sequence
<220> FEATURE:
<223> OTHER INFORMATION: Synthesized DNA

<400> SEQUENCE: 104
acccaagacc ctgcctcttc cactccaccc ttctccaggg acccttagat cacatcactc     60
cacccctgc                                                             69

<210> SEQ ID NO 105
<211> LENGTH: 21
<212> TYPE: DNA
<213> ORGANISM: Artificial Sequence
<220> FEATURE:
<223> OTHER INFORMATION: Synthesized DNA

<400> SEQUENCE: 105
tcattgccca gtatggagat g                                               21

<210> SEQ ID NO 106
<211> LENGTH: 20
<212> TYPE: DNA
<213> ORGANISM: Artificial Sequence
<220> FEATURE:
<223> OTHER INFORMATION: Synthesized DNA

<400> SEQUENCE: 106
gacaggcttg cctttctctg                                                 20

<210> SEQ ID NO 107
<211> LENGTH: 24
<212> TYPE: DNA
<213> ORGANISM: Artificial Sequence
<220> FEATURE:
<223> OTHER INFORMATION: Synthesized DNA

<400> SEQUENCE: 107
tcccgcctca agtttctcac caat                                            24

<210> SEQ ID NO 108
<211> LENGTH: 68
<212> TYPE: DNA
<213> ORGANISM: Artificial Sequence

```
<220> FEATURE:
<223> OTHER INFORMATION: Synthesized DNA

<400> SEQUENCE: 108
tcattgccca gtatggagat gtattggtga gaaacttgag gcgggaagca gagaaaggca    60
agcctgtc                                                             68

<210> SEQ ID NO 109
<211> LENGTH: 18
<212> TYPE: DNA
<213> ORGANISM: Artificial Sequence
<220> FEATURE:
<223> OTHER INFORMATION: Synthesized DNA

<400> SEQUENCE: 109
acttctcact ggccgacg                                                  18

<210> SEQ ID NO 110
<211> LENGTH: 19
<212> TYPE: DNA
<213> ORGANISM: Artificial Sequence
<220> FEATURE:
<223> OTHER INFORMATION: Synthesized DNA

<400> SEQUENCE: 110
gctccacctt ctcgttggt                                                 19

<210> SEQ ID NO 111
<211> LENGTH: 24
<212> TYPE: DNA
<213> ORGANISM: Artificial Sequence
<220> FEATURE:
<223> OTHER INFORMATION: Synthesized DNA

<400> SEQUENCE: 111
tgaaccagga gtttctgacc acgc                                           24

<210> SEQ ID NO 112
<211> LENGTH: 66
<212> TYPE: DNA
<213> ORGANISM: Artificial Sequence
<220> FEATURE:
<223> OTHER INFORMATION: Synthesized DNA

<400> SEQUENCE: 112
acttctcact ggccgacgcg gtgaaccagg agtttctgac cacgcgcacc aacgagaagg    60
tggagc                                                               66

<210> SEQ ID NO 113
<211> LENGTH: 18
<212> TYPE: DNA
<213> ORGANISM: Artificial Sequence
<220> FEATURE:
<223> OTHER INFORMATION: Synthesized DNA

<400> SEQUENCE: 113
gtcctgggat cgggaagt                                                  18

<210> SEQ ID NO 114
<211> LENGTH: 20
<212> TYPE: DNA
<213> ORGANISM: Artificial Sequence
<220> FEATURE:
<223> OTHER INFORMATION: Synthesized DNA
```

```
<400> SEQUENCE: 114
gtactcccac cgggatacag                                              20

<210> SEQ ID NO 115
<211> LENGTH: 24
<212> TYPE: DNA
<213> ORGANISM: Artificial Sequence
<220> FEATURE:
<223> OTHER INFORMATION: Synthesized DNA

<400> SEQUENCE: 115
cggctattcc acacttgaac acgc                                         24

<210> SEQ ID NO 116
<211> LENGTH: 69
<212> TYPE: DNA
<213> ORGANISM: Artificial Sequence
<220> FEATURE:
<223> OTHER INFORMATION: Synthesized DNA

<400> SEQUENCE: 116
gtcctgggat cgggaagtgg cgtgttcaag tgtggaatag ccgtggcgcc tgtatcccgg  60
tgggagtac                                                          69

<210> SEQ ID NO 117
<211> LENGTH: 20
<212> TYPE: DNA
<213> ORGANISM: Artificial Sequence
<220> FEATURE:
<223> OTHER INFORMATION: Synthesized DNA

<400> SEQUENCE: 117
agacatcagc tcctggttca                                              20

<210> SEQ ID NO 118
<211> LENGTH: 20
<212> TYPE: DNA
<213> ORGANISM: Artificial Sequence
<220> FEATURE:
<223> OTHER INFORMATION: Synthesized DNA

<400> SEQUENCE: 118
gacaaacacc cttcctccag                                              20

<210> SEQ ID NO 119
<211> LENGTH: 26
<212> TYPE: DNA
<213> ORGANISM: Artificial Sequence
<220> FEATURE:
<223> OTHER INFORMATION: Synthesized DNA

<400> SEQUENCE: 119
cgaggccatt gacttcatag actcca                                       26

<210> SEQ ID NO 120
<211> LENGTH: 76
<212> TYPE: DNA
<213> ORGANISM: Artificial Sequence
<220> FEATURE:
<223> OTHER INFORMATION: Synthesized DNA

<400> SEQUENCE: 120
agacatcagc tcctggttca acgaggccat tgacttcata gactccatca agaatgctgg  60
aggaagggtg tttgtc                                                  76
```

<210> SEQ ID NO 121
<211> LENGTH: 19
<212> TYPE: DNA
<213> ORGANISM: Artificial Sequence
<220> FEATURE:
<223> OTHER INFORMATION: Synthesized DNA

<400> SEQUENCE: 121
gtccccgctg cagatctct                                                    19

<210> SEQ ID NO 122
<211> LENGTH: 24
<212> TYPE: DNA
<213> ORGANISM: Artificial Sequence
<220> FEATURE:
<223> OTHER INFORMATION: Synthesized DNA

<400> SEQUENCE: 122
ctccagctta gggtagttgt ccat                                              24

<210> SEQ ID NO 123
<211> LENGTH: 23
<212> TYPE: DNA
<213> ORGANISM: Artificial Sequence
<220> FEATURE:
<223> OTHER INFORMATION: Synthesized DNA

<400> SEQUENCE: 123
cggatccttt cctcactcgc cca                                               23

<210> SEQ ID NO 124
<211> LENGTH: 76
<212> TYPE: DNA
<213> ORGANISM: Artificial Sequence
<220> FEATURE:
<223> OTHER INFORMATION: Synthesized DNA

<400> SEQUENCE: 124
gtccccgctg cagatctctg acccgttcgg atcctttcct cactcgccca ccatggacaa      60
ctaccctaag ctggag                                                      76

<210> SEQ ID NO 125
<211> LENGTH: 20
<212> TYPE: DNA
<213> ORGANISM: Artificial Sequence
<220> FEATURE:
<223> OTHER INFORMATION: Synthesized DNA

<400> SEQUENCE: 125
ccatgtggat gaatgaggtg                                                  20

<210> SEQ ID NO 126
<211> LENGTH: 20
<212> TYPE: DNA
<213> ORGANISM: Artificial Sequence
<220> FEATURE:
<223> OTHER INFORMATION: Synthesized DNA

<400> SEQUENCE: 126
tgcctgagaa gaggtgaggt                                                  20

<210> SEQ ID NO 127
<211> LENGTH: 24
<212> TYPE: DNA

```
<213> ORGANISM: Artificial Sequence
<220> FEATURE:
<223> OTHER INFORMATION: Synthesized DNA

<400> SEQUENCE: 127
acccagtctc accttctccc cacc                                              24

<210> SEQ ID NO 128
<211> LENGTH: 78
<212> TYPE: DNA
<213> ORGANISM: Artificial Sequence
<220> FEATURE:
<223> OTHER INFORMATION: Synthesized DNA

<400> SEQUENCE: 128
ccatgtggat gaatgaggtg tctcctttcc atacccagtc tcaccttctc cccaccctac       60
ctcacctctt ctcaggca                                                    78

<210> SEQ ID NO 129
<211> LENGTH: 18
<212> TYPE: DNA
<213> ORGANISM: Artificial Sequence
<220> FEATURE:
<223> OTHER INFORMATION: Synthesized DNA

<400> SEQUENCE: 129
ccaacactag gctcccca                                                    18

<210> SEQ ID NO 130
<211> LENGTH: 19
<212> TYPE: DNA
<213> ORGANISM: Artificial Sequence
<220> FEATURE:
<223> OTHER INFORMATION: Synthesized DNA

<400> SEQUENCE: 130
cctccgccag gtctttagt                                                   19

<210> SEQ ID NO 131
<211> LENGTH: 24
<212> TYPE: DNA
<213> ORGANISM: Artificial Sequence
<220> FEATURE:
<223> OTHER INFORMATION: Synthesized DNA

<400> SEQUENCE: 131
agccatatgc cttctcatct gggc                                             24

<210> SEQ ID NO 132
<211> LENGTH: 70
<212> TYPE: DNA
<213> ORGANISM: Artificial Sequence
<220> FEATURE:
<223> OTHER INFORMATION: Synthesized DNA

<400> SEQUENCE: 132
ccaacactag gctccccacc agccatatgc cttctcatct gggcacttac tactaaagac       60
ctggcggagg                                                             70

<210> SEQ ID NO 133
<211> LENGTH: 19
<212> TYPE: DNA
<213> ORGANISM: Artificial Sequence
<220> FEATURE:
<223> OTHER INFORMATION: Synthesized DNA
```

<400> SEQUENCE: 133
aaggagcaaa ccatccagg                                                    19

<210> SEQ ID NO 134
<211> LENGTH: 19
<212> TYPE: DNA
<213> ORGANISM: Artificial Sequence
<220> FEATURE:
<223> OTHER INFORMATION: Synthesized DNA

<400> SEQUENCE: 134
gcagggtttc attgagcac                                                    19

<210> SEQ ID NO 135
<211> LENGTH: 24
<212> TYPE: DNA
<213> ORGANISM: Artificial Sequence
<220> FEATURE:
<223> OTHER INFORMATION: Synthesized DNA

<400> SEQUENCE: 135
cccgggctca acatcactac ctgt                                              24

<210> SEQ ID NO 136
<211> LENGTH: 70
<212> TYPE: DNA
<213> ORGANISM: Artificial Sequence
<220> FEATURE:
<223> OTHER INFORMATION: Synthesized DNA

<400> SEQUENCE: 136
aaggagcaaa ccatccaggt gcccgggctc aacatcacta cctgtcatga tgtgctcaat       60
gaaaccctgc                                                              70

<210> SEQ ID NO 137
<211> LENGTH: 20
<212> TYPE: DNA
<213> ORGANISM: Artificial Sequence
<220> FEATURE:
<223> OTHER INFORMATION: Synthesized DNA

<400> SEQUENCE: 137
ttctgcccag gccttcccac                                                   20

<210> SEQ ID NO 138
<211> LENGTH: 21
<212> TYPE: DNA
<213> ORGANISM: Artificial Sequence
<220> FEATURE:
<223> OTHER INFORMATION: Synthesized DNA

<400> SEQUENCE: 138
aggagctggg gtgtacggag a                                                 21

<210> SEQ ID NO 139
<211> LENGTH: 24
<212> TYPE: DNA
<213> ORGANISM: Artificial Sequence
<220> FEATURE:
<223> OTHER INFORMATION: Synthesized DNA

<400> SEQUENCE: 139
tctccgaggc tccccagggc cccg                                              24

<210> SEQ ID NO 140
<211> LENGTH: 73
<212> TYPE: DNA
<213> ORGANISM: Artificial Sequence
<220> FEATURE:
<223> OTHER INFORMATION: Synthesized DNA

<400> SEQUENCE: 140
ttctgcccag gccttcccac caggaatctc cgaggctccc cagggccccg cttctccgta      60 cacccagct cct                                                         73

<210> SEQ ID NO 141
<211> LENGTH: 19
<212> TYPE: DNA
<213> ORGANISM: Artificial Sequence
<220> FEATURE:
<223> OTHER INFORMATION: Synthesized DNA

<400> SEQUENCE: 141
atcttcaaag cggagagcg                                                  19

<210> SEQ ID NO 142
<211> LENGTH: 20
<212> TYPE: DNA
<213> ORGANISM: Artificial Sequence
<220> FEATURE:
<223> OTHER INFORMATION: Synthesized DNA

<400> SEQUENCE: 142
gctggatacc acatgctctg                                                 20

<210> SEQ ID NO 143
<211> LENGTH: 24
<212> TYPE: DNA
<213> ORGANISM: Artificial Sequence
<220> FEATURE:
<223> OTHER INFORMATION: Synthesized DNA

<400> SEQUENCE: 143
tcctgacttt ctccgtggct cctc                                            24

<210> SEQ ID NO 144
<211> LENGTH: 66
<212> TYPE: DNA
<213> ORGANISM: Artificial Sequence
<220> FEATURE:
<223> OTHER INFORMATION: Synthesized DNA

<400> SEQUENCE: 144
atcttcaaag cggagagcgg gaggagccac ggagaaagtc aggagacaga gcatgtggta      60
tccagc                                                                66

<210> SEQ ID NO 145
<211> LENGTH: 19
<212> TYPE: DNA
<213> ORGANISM: Artificial Sequence
<220> FEATURE:
<223> OTHER INFORMATION: Synthesized DNA

<400> SEQUENCE: 145
gttggctcac gtgggttac                                                  19

<210> SEQ ID NO 146
<211> LENGTH: 20

```
<212> TYPE: DNA
<213> ORGANISM: Artificial Sequence
<220> FEATURE:
<223> OTHER INFORMATION: Synthesized DNA

<400> SEQUENCE: 146
gacaggaccg aaacattctg                                                   20

<210> SEQ ID NO 147
<211> LENGTH: 27
<212> TYPE: DNA
<213> ORGANISM: Artificial Sequence
<220> FEATURE:
<223> OTHER INFORMATION: Synthesized DNA

<400> SEQUENCE: 147
agccactgca aacatactcg ttcatca                                           27

<210> SEQ ID NO 148
<211> LENGTH: 76
<212> TYPE: DNA
<213> ORGANISM: Artificial Sequence
<220> FEATURE:
<223> OTHER INFORMATION: Synthesized DNA

<400> SEQUENCE: 148
gttggctcac gtgggttact gatgaacgag tatgtttgca gtggctaaaa agagtccaga       60
atgtttcggt cctgtc                                                       76

<210> SEQ ID NO 149
<211> LENGTH: 19
<212> TYPE: DNA
<213> ORGANISM: Artificial Sequence
<220> FEATURE:
<223> OTHER INFORMATION: Synthesized DNA

<400> SEQUENCE: 149
caggacaatg gtgatggct                                                    19

<210> SEQ ID NO 150
<211> LENGTH: 19
<212> TYPE: DNA
<213> ORGANISM: Artificial Sequence
<220> FEATURE:
<223> OTHER INFORMATION: Synthesized DNA

<400> SEQUENCE: 150
tgatggtgta ctcgccagg                                                    19

<210> SEQ ID NO 151
<211> LENGTH: 24
<212> TYPE: DNA
<213> ORGANISM: Artificial Sequence
<220> FEATURE:
<223> OTHER INFORMATION: Synthesized DNA

<400> SEQUENCE: 151
atgtgctgtc agctacctgc ccac                                              24

<210> SEQ ID NO 152
<211> LENGTH: 67
<212> TYPE: DNA
<213> ORGANISM: Artificial Sequence
<220> FEATURE:
<223> OTHER INFORMATION: Synthesized DNA
```

```
<400> SEQUENCE: 152
caggacaatg gtgatggctc atgtgctgtc agctacctgc ccacggagcc tggcgagtac      60
accatca                                                               67

<210> SEQ ID NO 153
<211> LENGTH: 21
<212> TYPE: DNA
<213> ORGANISM: Artificial Sequence
<220> FEATURE:
<223> OTHER INFORMATION: Synthesized DNA

<400> SEQUENCE: 153
ggaagtgaca gacgtgaagg t                                               21

<210> SEQ ID NO 154
<211> LENGTH: 18
<212> TYPE: DNA
<213> ORGANISM: Artificial Sequence
<220> FEATURE:
<223> OTHER INFORMATION: Synthesized DNA

<400> SEQUENCE: 154
acacggtagc cggtcact                                                   18

<210> SEQ ID NO 155
<211> LENGTH: 24
<212> TYPE: DNA
<213> ORGANISM: Artificial Sequence
<220> FEATURE:
<223> OTHER INFORMATION: Synthesized DNA

<400> SEQUENCE: 155
actctcaggc ggtgtccaca tgat                                            24

<210> SEQ ID NO 156
<211> LENGTH: 69
<212> TYPE: DNA
<213> ORGANISM: Artificial Sequence
<220> FEATURE:
<223> OTHER INFORMATION: Synthesized DNA

<400> SEQUENCE: 156
ggaagtgaca gacgtgaagg tcaccatcat gtggacaccg cctgagagtg cagtgaccgg     60
ctaccgtgt                                                             69

<210> SEQ ID NO 157
<211> LENGTH: 21
<212> TYPE: DNA
<213> ORGANISM: Artificial Sequence
<220> FEATURE:
<223> OTHER INFORMATION: Synthesized DNA

<400> SEQUENCE: 157
cgagcccttt gatgacttcc t                                               21

<210> SEQ ID NO 158
<211> LENGTH: 18
<212> TYPE: DNA
<213> ORGANISM: Artificial Sequence
<220> FEATURE:
<223> OTHER INFORMATION: Synthesized DNA

<400> SEQUENCE: 158
ggagcgggct gtctcaga                                                   18
```

<210> SEQ ID NO 159
<211> LENGTH: 22
<212> TYPE: DNA
<213> ORGANISM: Artificial Sequence
<220> FEATURE:
<223> OTHER INFORMATION: Synthesized DNA

<400> SEQUENCE: 159
tcccagcatc atccaggccc ag                                              22

<210> SEQ ID NO 160
<211> LENGTH: 67
<212> TYPE: DNA
<213> ORGANISM: Artificial Sequence
<220> FEATURE:
<223> OTHER INFORMATION: Synthesized DNA

<400> SEQUENCE: 160
cgagcccttt gatgacttcc tgttcccagc atcatccagg cccagtggct ctgagacagc     60
ccgctcc                                                               67

<210> SEQ ID NO 161
<211> LENGTH: 20
<212> TYPE: DNA
<213> ORGANISM: Artificial Sequence
<220> FEATURE:
<223> OTHER INFORMATION: Synthesized DNA

<400> SEQUENCE: 161
accctcgaca agaccacact                                                 20

<210> SEQ ID NO 162
<211> LENGTH: 20
<212> TYPE: DNA
<213> ORGANISM: Artificial Sequence
<220> FEATURE:
<223> OTHER INFORMATION: Synthesized DNA

<400> SEQUENCE: 162
tgggagttca tgggtacaga                                                 20

<210> SEQ ID NO 163
<211> LENGTH: 20
<212> TYPE: DNA
<213> ORGANISM: Artificial Sequence
<220> FEATURE:
<223> OTHER INFORMATION: Synthesized DNA

<400> SEQUENCE: 163
tgggagttca tgggtacaga                                                 20

<210> SEQ ID NO 164
<211> LENGTH: 70
<212> TYPE: DNA
<213> ORGANISM: Artificial Sequence
<220> FEATURE:
<223> OTHER INFORMATION: Synthesized DNA

<400> SEQUENCE: 164
accctcgaca agaccacact ttgggacttg ggagctgggg ctgaagttgc tctgtaccca     60
tgaactccca                                                            70

<210> SEQ ID NO 165

<211> LENGTH: 18
<212> TYPE: DNA
<213> ORGANISM: Artificial Sequence
<220> FEATURE:
<223> OTHER INFORMATION: Synthesized DNA

<400> SEQUENCE: 165
atgtgcttgg agtggcct                                                   18

<210> SEQ ID NO 166
<211> LENGTH: 21
<212> TYPE: DNA
<213> ORGANISM: Artificial Sequence
<220> FEATURE:
<223> OTHER INFORMATION: Synthesized DNA

<400> SEQUENCE: 166
tgtagaacat aaacacgggc a                                               21

<210> SEQ ID NO 167
<211> LENGTH: 24
<212> TYPE: DNA
<213> ORGANISM: Artificial Sequence
<220> FEATURE:
<223> OTHER INFORMATION: Synthesized DNA

<400> SEQUENCE: 167
cgctgagaaa ccaaacacac ccag                                            24

<210> SEQ ID NO 168
<211> LENGTH: 66
<212> TYPE: DNA
<213> ORGANISM: Artificial Sequence
<220> FEATURE:
<223> OTHER INFORMATION: Synthesized DNA

<400> SEQUENCE: 168
atgtgcttgg agtggcctgg ctgggtgtgt ttggtttctc agcggtgccc gtgtttatgt     60
tctaca                                                                66

<210> SEQ ID NO 169
<211> LENGTH: 20
<212> TYPE: DNA
<213> ORGANISM: Artificial Sequence
<220> FEATURE:
<223> OTHER INFORMATION: Synthesized DNA

<400> SEQUENCE: 169
agtacaagca ggctgccaag                                                 20

<210> SEQ ID NO 170
<211> LENGTH: 19
<212> TYPE: DNA
<213> ORGANISM: Artificial Sequence
<220> FEATURE:
<223> OTHER INFORMATION: Synthesized DNA

<400> SEQUENCE: 170
gcagctcagg gaagtcaca                                                  19

<210> SEQ ID NO 171
<211> LENGTH: 24
<212> TYPE: DNA
<213> ORGANISM: Artificial Sequence
<220> FEATURE:
<223> OTHER INFORMATION: Synthesized DNA

```
<400> SEQUENCE: 171
cctcctgctg gcttcctttg atca                                           24

<210> SEQ ID NO 172
<211> LENGTH: 66
<212> TYPE: DNA
<213> ORGANISM: Artificial Sequence
<220> FEATURE:
<223> OTHER INFORMATION: Synthesized DNA

<400> SEQUENCE: 172
agtacaagca ggctgccaag tgcctcctgc tggcttcctt tgatcactgt gacttccctg    60
agctgc                                                               66

<210> SEQ ID NO 173
<211> LENGTH: 22
<212> TYPE: DNA
<213> ORGANISM: Artificial Sequence
<220> FEATURE:
<223> OTHER INFORMATION: Synthesized DNA

<400> SEQUENCE: 173
cttctgctaa gcggtacatc ga                                             22

<210> SEQ ID NO 174
<211> LENGTH: 20
<212> TYPE: DNA
<213> ORGANISM: Artificial Sequence
<220> FEATURE:
<223> OTHER INFORMATION: Synthesized DNA

<400> SEQUENCE: 174
ggctcaaagc cttgcttcac                                                20

<210> SEQ ID NO 175
<211> LENGTH: 21
<212> TYPE: DNA
<213> ORGANISM: Artificial Sequence
<220> FEATURE:
<223> OTHER INFORMATION: Synthesized DNA

<400> SEQUENCE: 175
acccagccaa tcgggatcgg c                                              21

<210> SEQ ID NO 176
<211> LENGTH: 85
<212> TYPE: DNA
<213> ORGANISM: Artificial Sequence
<220> FEATURE:
<223> OTHER INFORMATION: Synthesized DNA

<400> SEQUENCE: 176
cttctgctaa gcggtacatc gagacggacc cagccaatcg ggatcggcgg acgcccatca    60
ccgtggtgaa gcaaggcttt gagcc                                          85

<210> SEQ ID NO 177
<211> LENGTH: 27
<212> TYPE: DNA
<213> ORGANISM: Artificial Sequence
<220> FEATURE:
<223> OTHER INFORMATION: Synthesized DNA

<400> SEQUENCE: 177
```
aagctatgag gaaaagaagt acacgat                                        27

<210> SEQ ID NO 178
<211> LENGTH: 20
<212> TYPE: DNA
<213> ORGANISM: Artificial Sequence
<220> FEATURE:
<223> OTHER INFORMATION: Synthesized DNA

<400> SEQUENCE: 178
ggcccagctt gaattttca                                                 20

<210> SEQ ID NO 179
<211> LENGTH: 30
<212> TYPE: DNA
<213> ORGANISM: Artificial Sequence
<220> FEATURE:
<223> OTHER INFORMATION: Synthesized DNA

<400> SEQUENCE: 179
tcagccactg gcttctgtca taatcaggag                                     30

<210> SEQ ID NO 180
<211> LENGTH: 86
<212> TYPE: DNA
<213> ORGANISM: Artificial Sequence
<220> FEATURE:
<223> OTHER INFORMATION: Synthesized DNA

<400> SEQUENCE: 180
aagctatgag gaaaagaagt acacgatggg ggacgctcct gattatgaca gaagccagtg    60
gctgaatgaa aaattcaagc tgggcc                                         86

<210> SEQ ID NO 181
<211> LENGTH: 20
<212> TYPE: DNA
<213> ORGANISM: Artificial Sequence
<220> FEATURE:
<223> OTHER INFORMATION: Synthesized DNA

<400> SEQUENCE: 181
ctgcaggcac tccctgaaat                                                20

<210> SEQ ID NO 182
<211> LENGTH: 20
<212> TYPE: DNA
<213> ORGANISM: Artificial Sequence
<220> FEATURE:
<223> OTHER INFORMATION: Synthesized DNA

<400> SEQUENCE: 182
ccaagaaacc atggctgctt                                                20

<210> SEQ ID NO 183
<211> LENGTH: 26
<212> TYPE: DNA
<213> ORGANISM: Artificial Sequence
<220> FEATURE:
<223> OTHER INFORMATION: Synthesized DNA

<400> SEQUENCE: 183
ctgaagctct actcacagtt tctggg                                         26

<210> SEQ ID NO 184
<211> LENGTH: 68

```
<212> TYPE: DNA
<213> ORGANISM: Artificial Sequence
<220> FEATURE:
<223> OTHER INFORMATION: Synthesized DNA

<400> SEQUENCE: 184
ctgcaggcac tccctgaaat gctgaagctc tactcacagt ttctggggaa gcagccatgg    60
tttcttgg                                                             68

<210> SEQ ID NO 185
<211> LENGTH: 19
<212> TYPE: DNA
<213> ORGANISM: Artificial Sequence
<220> FEATURE:
<223> OTHER INFORMATION: Synthesized DNA

<400> SEQUENCE: 185
caccctgcag gtgtctgag                                                 19

<210> SEQ ID NO 186
<211> LENGTH: 22
<212> TYPE: DNA
<213> ORGANISM: Artificial Sequence
<220> FEATURE:
<223> OTHER INFORMATION: Synthesized DNA

<400> SEQUENCE: 186
ggtacctagg agcagaaggt ga                                             22

<210> SEQ ID NO 187
<211> LENGTH: 24
<212> TYPE: DNA
<213> ORGANISM: Artificial Sequence
<220> FEATURE:
<223> OTHER INFORMATION: Synthesized DNA

<400> SEQUENCE: 187
taagtgatct gccctccagg tggc                                           24

<210> SEQ ID NO 188
<211> LENGTH: 69
<212> TYPE: DNA
<213> ORGANISM: Artificial Sequence
<220> FEATURE:
<223> OTHER INFORMATION: Synthesized DNA

<400> SEQUENCE: 188
caccctgcag gtgtctgaga ctaagtgatc tgccctccag gtggcgatca ccttctgctc    60
ctaggtacc                                                            69

<210> SEQ ID NO 189
<211> LENGTH: 21
<212> TYPE: DNA
<213> ORGANISM: Artificial Sequence
<220> FEATURE:
<223> OTHER INFORMATION: Synthesized DNA

<400> SEQUENCE: 189
tccggagctg tgatctaagg a                                              21

<210> SEQ ID NO 190
<211> LENGTH: 20
<212> TYPE: DNA
<213> ORGANISM: Artificial Sequence
<220> FEATURE:
```

<223> OTHER INFORMATION: Synthesized DNA

<400> SEQUENCE: 190
cggacagagc gagctgactt                                        20

<210> SEQ ID NO 191
<211> LENGTH: 24
<212> TYPE: DNA
<213> ORGANISM: Artificial Sequence
<220> FEATURE:
<223> OTHER INFORMATION: Synthesized DNA

<400> SEQUENCE: 191
tgtattgcgc acccctcaag cctg                                   24

<210> SEQ ID NO 192
<211> LENGTH: 76
<212> TYPE: DNA
<213> ORGANISM: Artificial Sequence
<220> FEATURE:
<223> OTHER INFORMATION: Synthesized DNA

<400> SEQUENCE: 192
tccggagctg tgatctaagg aggctggaga tgtattgcgc acccctcaag cctgccaagt    60
cagctcgctc tgtccg                                            76

<210> SEQ ID NO 193
<211> LENGTH: 19
<212> TYPE: DNA
<213> ORGANISM: Artificial Sequence
<220> FEATURE:
<223> OTHER INFORMATION: Synthesized DNA

<400> SEQUENCE: 193
gtggacagca ccatgaaca                                         19

<210> SEQ ID NO 194
<211> LENGTH: 20
<212> TYPE: DNA
<213> ORGANISM: Artificial Sequence
<220> FEATURE:
<223> OTHER INFORMATION: Synthesized DNA

<400> SEQUENCE: 194
ccttcatacc cgacttgagg                                        20

<210> SEQ ID NO 195
<211> LENGTH: 20
<212> TYPE: DNA
<213> ORGANISM: Artificial Sequence
<220> FEATURE:
<223> OTHER INFORMATION: Synthesized DNA

<400> SEQUENCE: 195
cttccggcca gcactgcctc                                        20

<210> SEQ ID NO 196
<211> LENGTH: 73
<212> TYPE: DNA
<213> ORGANISM: Artificial Sequence
<220> FEATURE:
<223> OTHER INFORMATION: Synthesized DNA

<400> SEQUENCE: 196
gtggacagca ccatgaacat gttgggcggg ggaggcagtg ctggccggaa gcccctcaag    60
tcgggtatga agg                                                      73

<210> SEQ ID NO 197
<211> LENGTH: 20
<212> TYPE: DNA
<213> ORGANISM: Artificial Sequence
<220> FEATURE:
<223> OTHER INFORMATION: Synthesized DNA

<400> SEQUENCE: 197
tgaaccgcag agaccaacag                                               20

<210> SEQ ID NO 198
<211> LENGTH: 20
<212> TYPE: DNA
<213> ORGANISM: Artificial Sequence
<220> FEATURE:
<223> OTHER INFORMATION: Synthesized DNA

<400> SEQUENCE: 198
gtcttggaca cccgcagaat                                               20

<210> SEQ ID NO 199
<211> LENGTH: 25
<212> TYPE: DNA
<213> ORGANISM: Artificial Sequence
<220> FEATURE:
<223> OTHER INFORMATION: Synthesized DNA

<400> SEQUENCE: 199
atccaggcac ctctaccacg ccctc                                         25

<210> SEQ ID NO 200
<211> LENGTH: 77
<212> TYPE: DNA
<213> ORGANISM: Artificial Sequence
<220> FEATURE:
<223> OTHER INFORMATION: Synthesized DNA

<400> SEQUENCE: 200
tgaaccgcag agaccaacag aggaatccag gcacctctac cacgccctcc cagcccaatt   60
ctgcgggtgt ccaagac                                                  77

<210> SEQ ID NO 201
<211> LENGTH: 20
<212> TYPE: DNA
<213> ORGANISM: Artificial Sequence
<220> FEATURE:
<223> OTHER INFORMATION: Synthesized DNA

<400> SEQUENCE: 201
ggcctaatgt tccagatcct                                               20

<210> SEQ ID NO 202
<211> LENGTH: 20
<212> TYPE: DNA
<213> ORGANISM: Artificial Sequence
<220> FEATURE:
<223> OTHER INFORMATION: Synthesized DNA

<400> SEQUENCE: 202
aaaattgtgc cttggaggag                                               20

<210> SEQ ID NO 203

```
<211> LENGTH: 25
<212> TYPE: DNA
<213> ORGANISM: Artificial Sequence
<220> FEATURE:
<223> OTHER INFORMATION: Synthesized DNA

<400> SEQUENCE: 203
catattgccc agtggtcacc tcaca                                          25

<210> SEQ ID NO 204
<211> LENGTH: 74
<212> TYPE: DNA
<213> ORGANISM: Artificial Sequence
<220> FEATURE:
<223> OTHER INFORMATION: Synthesized DNA

<400> SEQUENCE: 204
ggcctaatgt tccagatcct tcaaagagtc atattgccca gtggtcacct cacactcctc    60
caaggcacaa tttt                                                      74

<210> SEQ ID NO 205
<211> LENGTH: 19
<212> TYPE: DNA
<213> ORGANISM: Artificial Sequence
<220> FEATURE:
<223> OTHER INFORMATION: Synthesized DNA

<400> SEQUENCE: 205
gtgcccgagc catatagca                                                 19

<210> SEQ ID NO 206
<211> LENGTH: 23
<212> TYPE: DNA
<213> ORGANISM: Artificial Sequence
<220> FEATURE:
<223> OTHER INFORMATION: Synthesized DNA

<400> SEQUENCE: 206
cggtagtggt tgatgactgt tga                                            23

<210> SEQ ID NO 207
<211> LENGTH: 25
<212> TYPE: DNA
<213> ORGANISM: Artificial Sequence
<220> FEATURE:
<223> OTHER INFORMATION: Synthesized DNA

<400> SEQUENCE: 207
acgtccgggt cctcactgtc cttcc                                          25

<210> SEQ ID NO 208
<211> LENGTH: 72
<212> TYPE: DNA
<213> ORGANISM: Artificial Sequence
<220> FEATURE:
<223> OTHER INFORMATION: Synthesized DNA

<400> SEQUENCE: 208
gtgcccgagc catatagcag gcacgtccgg gtcctcactg tccttccact caacagtcat    60
caaccactac cg                                                        72

<210> SEQ ID NO 209
<211> LENGTH: 22
<212> TYPE: DNA
<213> ORGANISM: Artificial Sequence
```

<220> FEATURE:
<223> OTHER INFORMATION: Synthesized DNA

<400> SEQUENCE: 209
gatatgattg gtcgctgctt tg                                    22

<210> SEQ ID NO 210
<211> LENGTH: 21
<212> TYPE: DNA
<213> ORGANISM: Artificial Sequence
<220> FEATURE:
<223> OTHER INFORMATION: Synthesized DNA

<400> SEQUENCE: 210
agaacttcca ttccccacca t                                     21

<210> SEQ ID NO 211
<211> LENGTH: 21
<212> TYPE: DNA
<213> ORGANISM: Artificial Sequence
<220> FEATURE:
<223> OTHER INFORMATION: Synthesized DNA

<400> SEQUENCE: 211
cagccaggac ctggccatcc g                                     21

<210> SEQ ID NO 212
<211> LENGTH: 79
<212> TYPE: DNA
<213> ORGANISM: Artificial Sequence
<220> FEATURE:
<223> OTHER INFORMATION: Synthesized DNA

<400> SEQUENCE: 212
gatatgattg gtcgctgctt tgtgctcagc caggacctgg ccatccggga tgagttggat    60
ggtggggaat ggaagttct                                                 79

<210> SEQ ID NO 213
<211> LENGTH: 20
<212> TYPE: DNA
<213> ORGANISM: Artificial Sequence
<220> FEATURE:
<223> OTHER INFORMATION: Synthesized DNA

<400> SEQUENCE: 213
gactgcaaag atggaaacga                                       20

<210> SEQ ID NO 214
<211> LENGTH: 20
<212> TYPE: DNA
<213> ORGANISM: Artificial Sequence
<220> FEATURE:
<223> OTHER INFORMATION: Synthesized DNA

<400> SEQUENCE: 214
tagccataag gtccgctctc                                       20

<210> SEQ ID NO 215
<211> LENGTH: 24
<212> TYPE: DNA
<213> ORGANISM: Artificial Sequence
<220> FEATURE:
<223> OTHER INFORMATION: Synthesized DNA

<400> SEQUENCE: 215
ctatgacgat gccctcaacg cctc                                                 24

<210> SEQ ID NO 216
<211> LENGTH: 81
<212> TYPE: DNA
<213> ORGANISM: Artificial Sequence
<220> FEATURE:
<223> OTHER INFORMATION: Synthesized DNA

<400> SEQUENCE: 216
gactgcaaag atggaaacga ccttctatga cgatgccctc aacgcctcgt tcctcccgtc         60
cgagagcgga ccttatggct a                                                   81

<210> SEQ ID NO 217
<211> LENGTH: 19
<212> TYPE: DNA
<213> ORGANISM: Artificial Sequence
<220> FEATURE:
<223> OTHER INFORMATION: Synthesized DNA

<400> SEQUENCE: 217
agtctcggat tgtgggagg                                                      19

<210> SEQ ID NO 218
<211> LENGTH: 18
<212> TYPE: DNA
<213> ORGANISM: Artificial Sequence
<220> FEATURE:
<223> OTHER INFORMATION: Synthesized DNA

<400> SEQUENCE: 218
tgtacacagc cacctgcc                                                       18

<210> SEQ ID NO 219
<211> LENGTH: 24
<212> TYPE: DNA
<213> ORGANISM: Artificial Sequence
<220> FEATURE:
<223> OTHER INFORMATION: Synthesized DNA

<400> SEQUENCE: 219
ttgggaatgc ttctcacact ccca                                                24

<210> SEQ ID NO 220
<211> LENGTH: 66
<212> TYPE: DNA
<213> ORGANISM: Artificial Sequence
<220> FEATURE:
<223> OTHER INFORMATION: Synthesized DNA

<400> SEQUENCE: 220
agtctcggat tgtgggaggc tgggagtgtg agaagcattc ccaaccctgg caggtggctg         60
tgtaca                                                                    66

<210> SEQ ID NO 221
<211> LENGTH: 20
<212> TYPE: DNA
<213> ORGANISM: Artificial Sequence
<220> FEATURE:
<223> OTHER INFORMATION: Synthesized DNA

<400> SEQUENCE: 221
gcctggttct tcagcaagac                                                     20

```
<210> SEQ ID NO 222
<211> LENGTH: 21
<212> TYPE: DNA
<213> ORGANISM: Artificial Sequence
<220> FEATURE:
<223> OTHER INFORMATION: Synthesized DNA

<400> SEQUENCE: 222
cttgctggtc tggatcattt c                                              21

<210> SEQ ID NO 223
<211> LENGTH: 24
<212> TYPE: DNA
<213> ORGANISM: Artificial Sequence
<220> FEATURE:
<223> OTHER INFORMATION: Synthesized DNA

<400> SEQUENCE: 223
tgaacaaaga ggtggcctcc aaca                                           24

<210> SEQ ID NO 224
<211> LENGTH: 75
<212> TYPE: DNA
<213> ORGANISM: Artificial Sequence
<220> FEATURE:
<223> OTHER INFORMATION: Synthesized DNA

<400> SEQUENCE: 224
gcctggttct tcagcaagac tgaggagctg aacaaagagg tggcctccaa cacagaaatg    60
atccagacca gcaag                                                     75

<210> SEQ ID NO 225
<211> LENGTH: 20
<212> TYPE: DNA
<213> ORGANISM: Artificial Sequence
<220> FEATURE:
<223> OTHER INFORMATION: Synthesized DNA

<400> SEQUENCE: 225
tcagtggaga aggagttgga                                                20

<210> SEQ ID NO 226
<211> LENGTH: 20
<212> TYPE: DNA
<213> ORGANISM: Artificial Sequence
<220> FEATURE:
<223> OTHER INFORMATION: Synthesized DNA

<400> SEQUENCE: 226
tgccatatcc agaggaaaca                                                20

<210> SEQ ID NO 227
<211> LENGTH: 28
<212> TYPE: DNA
<213> ORGANISM: Artificial Sequence
<220> FEATURE:
<223> OTHER INFORMATION: Synthesized DNA

<400> SEQUENCE: 227
ccagtcaaca tctctgttgt cacaagca                                       28

<210> SEQ ID NO 228
<211> LENGTH: 69
<212> TYPE: DNA
<213> ORGANISM: Artificial Sequence
<220> FEATURE:
```

<223> OTHER INFORMATION: Synthesized DNA

<400> SEQUENCE: 228
tcagtggaga aggagttgga ccagtcaaca tctctgttgt cacaagcagt gtttcctctg    60
gatatggca                                                            69

<210> SEQ ID NO 229
<211> LENGTH: 20
<212> TYPE: DNA
<213> ORGANISM: Artificial Sequence
<220> FEATURE:
<223> OTHER INFORMATION: Synthesized DNA

<400> SEQUENCE: 229
actgaccaag cctgagacct                                                20

<210> SEQ ID NO 230
<211> LENGTH: 20
<212> TYPE: DNA
<213> ORGANISM: Artificial Sequence
<220> FEATURE:
<223> OTHER INFORMATION: Synthesized DNA

<400> SEQUENCE: 230
gtcacacttg cagcatttca                                                20

<210> SEQ ID NO 231
<211> LENGTH: 23
<212> TYPE: DNA
<213> ORGANISM: Artificial Sequence
<220> FEATURE:
<223> OTHER INFORMATION: Synthesized DNA

<400> SEQUENCE: 231
ccactcgcca tactgggtgc agt                                            23

<210> SEQ ID NO 232
<211> LENGTH: 67
<212> TYPE: DNA
<213> ORGANISM: Artificial Sequence
<220> FEATURE:
<223> OTHER INFORMATION: Synthesized DNA

<400> SEQUENCE: 232
actgaccaag cctgagacct actgcaccca gtatggcgag tggcagatga aatgctgcaa    60
gtgtgac                                                              67

<210> SEQ ID NO 233
<211> LENGTH: 20
<212> TYPE: DNA
<213> ORGANISM: Artificial Sequence
<220> FEATURE:
<223> OTHER INFORMATION: Synthesized DNA

<400> SEQUENCE: 233
agcggaaaat ggcagacaat                                                20

<210> SEQ ID NO 234
<211> LENGTH: 20
<212> TYPE: DNA
<213> ORGANISM: Artificial Sequence
<220> FEATURE:
<223> OTHER INFORMATION: Synthesized DNA

<400> SEQUENCE: 234
cttgagggtt tgggtttcca                                              20

<210> SEQ ID NO 235
<211> LENGTH: 25
<212> TYPE: DNA
<213> ORGANISM: Artificial Sequence
<220> FEATURE:
<223> OTHER INFORMATION: Synthesized DNA

<400> SEQUENCE: 235
acccagataa cgcatcatgg agcga                                        25

<210> SEQ ID NO 236
<211> LENGTH: 69
<212> TYPE: DNA
<213> ORGANISM: Artificial Sequence
<220> FEATURE:
<223> OTHER INFORMATION: Synthesized DNA

<400> SEQUENCE: 236
agcggaaaat ggcagacaat ttttcgctcc atgatgcgtt atctgggtct ggaaacccaa   60
accctcaag                                                          69

<210> SEQ ID NO 237
<211> LENGTH: 20
<212> TYPE: DNA
<213> ORGANISM: Artificial Sequence
<220> FEATURE:
<223> OTHER INFORMATION: Synthesized DNA

<400> SEQUENCE: 237
cctggaggct gcaacatacc                                              20

<210> SEQ ID NO 238
<211> LENGTH: 23
<212> TYPE: DNA
<213> ORGANISM: Artificial Sequence
<220> FEATURE:
<223> OTHER INFORMATION: Synthesized DNA

<400> SEQUENCE: 238
tacaatggct ttggaggata gca                                          23

<210> SEQ ID NO 239
<211> LENGTH: 25
<212> TYPE: DNA
<213> ORGANISM: Artificial Sequence
<220> FEATURE:
<223> OTHER INFORMATION: Synthesized DNA

<400> SEQUENCE: 239
atcctcctga agccctttc gcagc                                         25

<210> SEQ ID NO 240
<211> LENGTH: 90
<212> TYPE: DNA
<213> ORGANISM: Artificial Sequence
<220> FEATURE:
<223> OTHER INFORMATION: Synthesized DNA

<400> SEQUENCE: 240
cctggaggct gcaacatacc tcaatcctgt cccaggccgg atcctcctga agcccttttc   60
gcagcactgc tatcctccaa agccattgta                                   90

```
<210> SEQ ID NO 241
<211> LENGTH: 18
<212> TYPE: DNA
<213> ORGANISM: Artificial Sequence
<220> FEATURE:
<223> OTHER INFORMATION: Synthesized DNA

<400> SEQUENCE: 241
gccgagatcg ccaagatg                                                   18

<210> SEQ ID NO 242
<211> LENGTH: 27
<212> TYPE: DNA
<213> ORGANISM: Artificial Sequence
<220> FEATURE:
<223> OTHER INFORMATION: Synthesized DNA

<400> SEQUENCE: 242
cttttgatgg tagagttcca gtgattc                                         27

<210> SEQ ID NO 243
<211> LENGTH: 24
<212> TYPE: DNA
<213> ORGANISM: Artificial Sequence
<220> FEATURE:
<223> OTHER INFORMATION: Synthesized DNA

<400> SEQUENCE: 243
cagcattgtc tgtcctccct ggca                                            24

<210> SEQ ID NO 244
<211> LENGTH: 74
<212> TYPE: DNA
<213> ORGANISM: Artificial Sequence
<220> FEATURE:
<223> OTHER INFORMATION: Synthesized DNA

<400> SEQUENCE: 244
gccgagatcg ccaagatgtt gccagggagg acagacaatg ctgtgaagaa tcactggaac     60
tctaccatca aaag                                                       74

<210> SEQ ID NO 245
<211> LENGTH: 19
<212> TYPE: DNA
<213> ORGANISM: Artificial Sequence
<220> FEATURE:
<223> OTHER INFORMATION: Synthesized DNA

<400> SEQUENCE: 245
ctgaacccct ctcctggtc                                                  19

<210> SEQ ID NO 246
<211> LENGTH: 18
<212> TYPE: DNA
<213> ORGANISM: Artificial Sequence
<220> FEATURE:
<223> OTHER INFORMATION: Synthesized DNA

<400> SEQUENCE: 246
aggaaacgat ggcgaggt                                                   18

<210> SEQ ID NO 247
<211> LENGTH: 24
<212> TYPE: DNA
<213> ORGANISM: Artificial Sequence
```

<220> FEATURE:
<223> OTHER INFORMATION: Synthesized DNA

<400> SEQUENCE: 247
cgagaatcag tccccgtgga gttc                                            24

<210> SEQ ID NO 248
<211> LENGTH: 70
<212> TYPE: DNA
<213> ORGANISM: Artificial Sequence
<220> FEATURE:
<223> OTHER INFORMATION: Synthesized DNA

<400> SEQUENCE: 248
ctgaacccct ctcctggtca ccgagaatca gtccccgtgg agttcccct ccacctcgcc      60 atcgtttcct                                                            70

<210> SEQ ID NO 249
<211> LENGTH: 19
<212> TYPE: DNA
<213> ORGANISM: Artificial Sequence
<220> FEATURE:
<223> OTHER INFORMATION: Synthesized DNA

<400> SEQUENCE: 249
tcagaactga ggccgacac                                                  19

<210> SEQ ID NO 250
<211> LENGTH: 21
<212> TYPE: DNA
<213> ORGANISM: Artificial Sequence
<220> FEATURE:
<223> OTHER INFORMATION: Synthesized DNA

<400> SEQUENCE: 250
ccagatagtc tacctcccgc t                                               21

<210> SEQ ID NO 251
<211> LENGTH: 24
<212> TYPE: DNA
<213> ORGANISM: Artificial Sequence
<220> FEATURE:
<223> OTHER INFORMATION: Synthesized DNA

<400> SEQUENCE: 251
cagacgatcc actctcccgg agat                                            24

<210> SEQ ID NO 252
<211> LENGTH: 66
<212> TYPE: DNA
<213> ORGANISM: Artificial Sequence
<220> FEATURE:
<223> OTHER INFORMATION: Synthesized DNA

<400> SEQUENCE: 252
tcagaactga ggccgacacc atctccggga gagtggatcg tctggagcgg gaggtagact     60
atctgg                                                                66

<210> SEQ ID NO 253
<211> LENGTH: 21
<212> TYPE: DNA
<213> ORGANISM: Artificial Sequence
<220> FEATURE:
<223> OTHER INFORMATION: Synthesized DNA

```
<400> SEQUENCE: 253
gaatctcagc aagaggaacc a                                              21

<210> SEQ ID NO 254
<211> LENGTH: 20
<212> TYPE: DNA
<213> ORGANISM: Artificial Sequence
<220> FEATURE:
<223> OTHER INFORMATION: Synthesized DNA

<400> SEQUENCE: 254
gttcttcgat cggaggtgtt                                                20

<210> SEQ ID NO 255
<211> LENGTH: 29
<212> TYPE: DNA
<213> ORGANISM: Artificial Sequence
<220> FEATURE:
<223> OTHER INFORMATION: Synthesized DNA

<400> SEQUENCE: 255
ccaactgaca atcaggatat tgaacctgg                                      29

<210> SEQ ID NO 256
<211> LENGTH: 85
<212> TYPE: DNA
<213> ORGANISM: Artificial Sequence
<220> FEATURE:
<223> OTHER INFORMATION: Synthesized DNA

<400> SEQUENCE: 256
gaatctcagc aagaggaacc accaactgac aatcaggata ttgaacctgg acaagagaga    60
gaaggaacac ctccgatcga agaac                                          85

<210> SEQ ID NO 257
<211> LENGTH: 24
<212> TYPE: DNA
<213> ORGANISM: Artificial Sequence
<220> FEATURE:
<223> OTHER INFORMATION: Synthesized DNA

<400> SEQUENCE: 257
agagccagtt gctgtagaac tcaa                                           24

<210> SEQ ID NO 258
<211> LENGTH: 21
<212> TYPE: DNA
<213> ORGANISM: Artificial Sequence
<220> FEATURE:
<223> OTHER INFORMATION: Synthesized DNA

<400> SEQUENCE: 258
ctgggcctac acagtccttc a                                              21

<210> SEQ ID NO 259
<211> LENGTH: 27
<212> TYPE: DNA
<213> ORGANISM: Artificial Sequence
<220> FEATURE:
<223> OTHER INFORMATION: Synthesized DNA

<400> SEQUENCE: 259
tctctgctgg gcaaggatgt tctgttc                                        27
```

<210> SEQ ID NO 260
<211> LENGTH: 74
<212> TYPE: DNA
<213> ORGANISM: Artificial Sequence
<220> FEATURE:
<223> OTHER INFORMATION: Synthesized DNA

<400> SEQUENCE: 260
agagccagtt gctgtagaac tcaaatctct gctgggcaag gatgttctgt tcttgaagga      60
ctgtgtaggc ccag                                                        74

<210> SEQ ID NO 261
<211> LENGTH: 19
<212> TYPE: DNA
<213> ORGANISM: Artificial Sequence
<220> FEATURE:
<223> OTHER INFORMATION: Synthesized DNA

<400> SEQUENCE: 261
acaagcacca tcccagtga                                                   19

<210> SEQ ID NO 262
<211> LENGTH: 22
<212> TYPE: DNA
<213> ORGANISM: Artificial Sequence
<220> FEATURE:
<223> OTHER INFORMATION: Synthesized DNA

<400> SEQUENCE: 262
cacgaagaaa actatgcagc ag                                               22

<210> SEQ ID NO 263
<211> LENGTH: 24
<212> TYPE: DNA
<213> ORGANISM: Artificial Sequence
<220> FEATURE:
<223> OTHER INFORMATION: Synthesized DNA

<400> SEQUENCE: 263
accagggctc cttgagcaaa tcct                                             24

<210> SEQ ID NO 264
<211> LENGTH: 77
<212> TYPE: DNA
<213> ORGANISM: Artificial Sequence
<220> FEATURE:
<223> OTHER INFORMATION: Synthesized DNA

<400> SEQUENCE: 264
acaagcacca tcccagtgat gttctggcag gatttgctca aggagccctg gtggcctgct      60
gcatagtttt cttcgtg                                                     77

<210> SEQ ID NO 265
<211> LENGTH: 20
<212> TYPE: DNA
<213> ORGANISM: Artificial Sequence
<220> FEATURE:
<223> OTHER INFORMATION: Synthesized DNA

<400> SEQUENCE: 265
cggcaagggg ttgatataga                                                  20

<210> SEQ ID NO 266
<211> LENGTH: 19
<212> TYPE: DNA

```
<213> ORGANISM: Artificial Sequence
<220> FEATURE:
<223> OTHER INFORMATION: Synthesized DNA

<400> SEQUENCE: 266
tgcctggcat ctctaagca                                                    19

<210> SEQ ID NO 267
<211> LENGTH: 24
<212> TYPE: DNA
<213> ORGANISM: Artificial Sequence
<220> FEATURE:
<223> OTHER INFORMATION: Synthesized DNA

<400> SEQUENCE: 267
ccgttcttct tcctttcgag ctgc                                              24

<210> SEQ ID NO 268
<211> LENGTH: 68
<212> TYPE: DNA
<213> ORGANISM: Artificial Sequence
<220> FEATURE:
<223> OTHER INFORMATION: Synthesized DNA

<400> SEQUENCE: 268
cggcaagggg ttgatataga agcagctcga aaggaagaag aacggatcat gcttagagat      60
gccaggca                                                                68

<210> SEQ ID NO 269
<211> LENGTH: 21
<212> TYPE: DNA
<213> ORGANISM: Artificial Sequence
<220> FEATURE:
<223> OTHER INFORMATION: Synthesized DNA

<400> SEQUENCE: 269
caagcaatgc gtcatcaatg t                                                 21

<210> SEQ ID NO 270
<211> LENGTH: 20
<212> TYPE: DNA
<213> ORGANISM: Artificial Sequence
<220> FEATURE:
<223> OTHER INFORMATION: Synthesized DNA

<400> SEQUENCE: 270
gtaaatccgc cccctcttct                                                   20

<210> SEQ ID NO 271
<211> LENGTH: 25
<212> TYPE: DNA
<213> ORGANISM: Artificial Sequence
<220> FEATURE:
<223> OTHER INFORMATION: Synthesized DNA

<400> SEQUENCE: 271
cagcctctgc ggaatggatc acact                                             25

<210> SEQ ID NO 272
<211> LENGTH: 70
<212> TYPE: DNA
<213> ORGANISM: Artificial Sequence
<220> FEATURE:
<223> OTHER INFORMATION: Synthesized DNA

<400> SEQUENCE: 272
```

```
caagcaatgc gtcatcaatg tccccagcct ctgcggaatg gatcacactg agaagagggg    60
gcggatttac                                                          70

<210> SEQ ID NO 273
<211> LENGTH: 20
<212> TYPE: DNA
<213> ORGANISM: Artificial Sequence
<220> FEATURE:
<223> OTHER INFORMATION: Synthesized DNA

<400> SEQUENCE: 273
gaaattgacg aggggtgtct                                               20

<210> SEQ ID NO 274
<211> LENGTH: 20
<212> TYPE: DNA
<213> ORGANISM: Artificial Sequence
<220> FEATURE:
<223> OTHER INFORMATION: Synthesized DNA

<400> SEQUENCE: 274
aggagctaac ggagaacctg                                               20

<210> SEQ ID NO 275
<211> LENGTH: 22
<212> TYPE: DNA
<213> ORGANISM: Artificial Sequence
<220> FEATURE:
<223> OTHER INFORMATION: Synthesized DNA

<400> SEQUENCE: 275
ctctgagcgc ctccatccaa gg                                            22

<210> SEQ ID NO 276
<211> LENGTH: 76
<212> TYPE: DNA
<213> ORGANISM: Artificial Sequence
<220> FEATURE:
<223> OTHER INFORMATION: Synthesized DNA

<400> SEQUENCE: 276
gaaattgacg aggggtgtct tgggcagagc tggctctgag cgcctccatc caaggccagg    60
ttctccgtta gctcct                                                   76

<210> SEQ ID NO 277
<211> LENGTH: 18
<212> TYPE: DNA
<213> ORGANISM: Artificial Sequence
<220> FEATURE:
<223> OTHER INFORMATION: Synthesized DNA

<400> SEQUENCE: 277
tacaggatga ggctgggc                                                 18

<210> SEQ ID NO 278
<211> LENGTH: 18
<212> TYPE: DNA
<213> ORGANISM: Artificial Sequence
<220> FEATURE:
<223> OTHER INFORMATION: Synthesized DNA

<400> SEQUENCE: 278
gttgttaggg caaggggc                                                 18
```

<210> SEQ ID NO 279
<211> LENGTH: 24
<212> TYPE: DNA
<213> ORGANISM: Artificial Sequence
<220> FEATURE:
<223> OTHER INFORMATION: Synthesized DNA

<400> SEQUENCE: 279
cctgggacag cctatgtaag gcca                                         24

<210> SEQ ID NO 280
<211> LENGTH: 67
<212> TYPE: DNA
<213> ORGANISM: Artificial Sequence
<220> FEATURE:
<223> OTHER INFORMATION: Synthesized DNA

<400> SEQUENCE: 280
tacaggatga ggctgggcat tgcctgggac agcctatgta aggccatgtg ccccttgccc    60
taacaac                                                            67

<210> SEQ ID NO 281
<211> LENGTH: 20
<212> TYPE: DNA
<213> ORGANISM: Artificial Sequence
<220> FEATURE:
<223> OTHER INFORMATION: Synthesized DNA

<400> SEQUENCE: 281
agcgggtgct agagcttgta                                              20

<210> SEQ ID NO 282
<211> LENGTH: 18
<212> TYPE: DNA
<213> ORGANISM: Artificial Sequence
<220> FEATURE:
<223> OTHER INFORMATION: Synthesized DNA

<400> SEQUENCE: 282
atggcacttc ggtctcca                                                18

<210> SEQ ID NO 283
<211> LENGTH: 25
<212> TYPE: DNA
<213> ORGANISM: Artificial Sequence
<220> FEATURE:
<223> OTHER INFORMATION: Synthesized DNA

<400> SEQUENCE: 283
ccatcactgc caacaagaac acctg                                        25

<210> SEQ ID NO 284
<211> LENGTH: 67
<212> TYPE: DNA
<213> ORGANISM: Artificial Sequence
<220> FEATURE:
<223> OTHER INFORMATION: Synthesized DNA

<400> SEQUENCE: 284
agcgggtgct agagcttgta tccatcactg ccaacaagaa cacctgtcct ggagaccgaa    60
gtgccat                                                            67

<210> SEQ ID NO 285
<211> LENGTH: 20

<212> TYPE: DNA
<213> ORGANISM: Artificial Sequence
<220> FEATURE:
<223> OTHER INFORMATION: Synthesized DNA

<400> SEQUENCE: 285
atcgtcagcg agtttgacct                                          20

<210> SEQ ID NO 286
<211> LENGTH: 18
<212> TYPE: DNA
<213> ORGANISM: Artificial Sequence
<220> FEATURE:
<223> OTHER INFORMATION: Synthesized DNA

<400> SEQUENCE: 286
caggatggct tgggtgag                                            18

<210> SEQ ID NO 287
<211> LENGTH: 24
<212> TYPE: DNA
<213> ORGANISM: Artificial Sequence
<220> FEATURE:
<223> OTHER INFORMATION: Synthesized DNA

<400> SEQUENCE: 287
cagcatccac gcattgacac agac                                     24

<210> SEQ ID NO 288
<211> LENGTH: 66
<212> TYPE: DNA
<213> ORGANISM: Artificial Sequence
<220> FEATURE:
<223> OTHER INFORMATION: Synthesized DNA

<400> SEQUENCE: 288
atcgtcagcg agtttgacct tgtctgtgtc aatgcgtgga tgctggacct cacccaagcc    60
atcctg                                                         66

<210> SEQ ID NO 289
<211> LENGTH: 22
<212> TYPE: DNA
<213> ORGANISM: Artificial Sequence
<220> FEATURE:
<223> OTHER INFORMATION: Synthesized DNA

<400> SEQUENCE: 289
ggacattact ggcctgttca ca                                       22

<210> SEQ ID NO 290
<211> LENGTH: 23
<212> TYPE: DNA
<213> ORGANISM: Artificial Sequence
<220> FEATURE:
<223> OTHER INFORMATION: Synthesized DNA

<400> SEQUENCE: 290
accaatactc aggagcagga tga                                      23

<210> SEQ ID NO 291
<211> LENGTH: 23
<212> TYPE: DNA
<213> ORGANISM: Artificial Sequence
<220> FEATURE:
<223> OTHER INFORMATION: Synthesized DNA

```
<400> SEQUENCE: 291
tgcattccag cctcccattt cca                                           23

<210> SEQ ID NO 292
<211> LENGTH: 76
<212> TYPE: DNA
<213> ORGANISM: Artificial Sequence
<220> FEATURE:
<223> OTHER INFORMATION: Synthesized DNA

<400> SEQUENCE: 292
ggacattact ggcctgttca caatgagctt gcattccagc ctcccatttc caatcatcct   60
gctcctgagt attggt                                                   76

<210> SEQ ID NO 293
<211> LENGTH: 23
<212> TYPE: DNA
<213> ORGANISM: Artificial Sequence
<220> FEATURE:
<223> OTHER INFORMATION: Synthesized DNA

<400> SEQUENCE: 293
tcttccctgt acactggcag ttc                                           23

<210> SEQ ID NO 294
<211> LENGTH: 20
<212> TYPE: DNA
<213> ORGANISM: Artificial Sequence
<220> FEATURE:
<223> OTHER INFORMATION: Synthesized DNA

<400> SEQUENCE: 294
agctcggtgt gggagaggta                                               20

<210> SEQ ID NO 295
<211> LENGTH: 22
<212> TYPE: DNA
<213> ORGANISM: Artificial Sequence
<220> FEATURE:
<223> OTHER INFORMATION: Synthesized DNA

<400> SEQUENCE: 295
tggaccagca ccccattgac gg                                            22

<210> SEQ ID NO 296
<211> LENGTH: 73
<212> TYPE: DNA
<213> ORGANISM: Artificial Sequence
<220> FEATURE:
<223> OTHER INFORMATION: Synthesized DNA

<400> SEQUENCE: 296
tcttccctgt acactggcag ttcggccagc tggaccagca ccccattgac gggtacctct   60
cccacaccga gct                                                      73

<210> SEQ ID NO 297
<211> LENGTH: 23
<212> TYPE: DNA
<213> ORGANISM: Artificial Sequence
<220> FEATURE:
<223> OTHER INFORMATION: Synthesized DNA

<400> SEQUENCE: 297
tgaggagtgg tattttggca aga                                           23
```

<210> SEQ ID NO 298
<211> LENGTH: 21
<212> TYPE: DNA
<213> ORGANISM: Artificial Sequence
<220> FEATURE:
<223> OTHER INFORMATION: Synthesized DNA

<400> SEQUENCE: 298
ctctcgggtt ctctgcattg a                                              21

<210> SEQ ID NO 299
<211> LENGTH: 24
<212> TYPE: DNA
<213> ORGANISM: Artificial Sequence
<220> FEATURE:
<223> OTHER INFORMATION: Synthesized DNA

<400> SEQUENCE: 299
aaccgctctg actcccgtct ggtg                                           24

<210> SEQ ID NO 300
<211> LENGTH: 74
<212> TYPE: DNA
<213> ORGANISM: Artificial Sequence
<220> FEATURE:
<223> OTHER INFORMATION: Synthesized DNA

<400> SEQUENCE: 300
tgaggagtgg tattttggca agatcaccag acgggagtca gagcggttac tgctcaatgc    60
agagaacccg agag                                                      74

<210> SEQ ID NO 301
<211> LENGTH: 20
<212> TYPE: DNA
<213> ORGANISM: Artificial Sequence
<220> FEATURE:
<223> OTHER INFORMATION: Synthesized DNA

<400> SEQUENCE: 301
gtaggtctcc tggcgttctg                                                20

<210> SEQ ID NO 302
<211> LENGTH: 21
<212> TYPE: DNA
<213> ORGANISM: Artificial Sequence
<220> FEATURE:
<223> OTHER INFORMATION: Synthesized DNA

<400> SEQUENCE: 302
tccctggaag ggtaggagta a                                              21

<210> SEQ ID NO 303
<211> LENGTH: 24
<212> TYPE: DNA
<213> ORGANISM: Artificial Sequence
<220> FEATURE:
<223> OTHER INFORMATION: Synthesized DNA

<400> SEQUENCE: 303
agacaccact cagaatcccc aggc                                           24

<210> SEQ ID NO 304
<211> LENGTH: 81
<212> TYPE: DNA

```
<213> ORGANISM: Artificial Sequence
<220> FEATURE:
<223> OTHER INFORMATION: Synthesized DNA

<400> SEQUENCE: 304
gtaggtctcc tggcgttctg ccagctggcc tggggattct gagtggtgtc tgcttagagt      60
ttactcctac ccttccaggg a                                                81

<210> SEQ ID NO 305
<211> LENGTH: 20
<212> TYPE: DNA
<213> ORGANISM: Artificial Sequence
<220> FEATURE:
<223> OTHER INFORMATION: Synthesized DNA

<400> SEQUENCE: 305
ccagtggtgg tgatcgttca                                                  20

<210> SEQ ID NO 306
<211> LENGTH: 21
<212> TYPE: DNA
<213> ORGANISM: Artificial Sequence
<220> FEATURE:
<223> OTHER INFORMATION: Synthesized DNA

<400> SEQUENCE: 306
gcaaaagcat tgtcccagag a                                                21

<210> SEQ ID NO 307
<211> LENGTH: 23
<212> TYPE: DNA
<213> ORGANISM: Artificial Sequence
<220> FEATURE:
<223> OTHER INFORMATION: Synthesized DNA

<400> SEQUENCE: 307
cagccaggac aacaatgcga cgg                                              23

<210> SEQ ID NO 308
<211> LENGTH: 74
<212> TYPE: DNA
<213> ORGANISM: Artificial Sequence
<220> FEATURE:
<223> OTHER INFORMATION: Synthesized DNA

<400> SEQUENCE: 308
ccagtggtgg tgatcgttca tggcagccag gacaacaatg cgacggccac tgttctctgg      60
gacaatgctt ttgc                                                        74

<210> SEQ ID NO 309
<211> LENGTH: 20
<212> TYPE: DNA
<213> ORGANISM: Artificial Sequence
<220> FEATURE:
<223> OTHER INFORMATION: Synthesized DNA

<400> SEQUENCE: 309
gctactttga gcgcttctcg                                                  20

<210> SEQ ID NO 310
<211> LENGTH: 19
<212> TYPE: DNA
<213> ORGANISM: Artificial Sequence
<220> FEATURE:
<223> OTHER INFORMATION: Synthesized DNA
```

<400> SEQUENCE: 310
ggtcaccatc ttgtgtcgg                                              19

<210> SEQ ID NO 311
<211> LENGTH: 24
<212> TYPE: DNA
<213> ORGANISM: Artificial Sequence
<220> FEATURE:
<223> OTHER INFORMATION: Synthesized DNA

<400> SEQUENCE: 311
caagatgtgg cttctgcaac cagc                                        24

<210> SEQ ID NO 312
<211> LENGTH: 68
<212> TYPE: DNA
<213> ORGANISM: Artificial Sequence
<220> FEATURE:
<223> OTHER INFORMATION: Synthesized DNA

<400> SEQUENCE: 312
gctactttga gcgcttctcg ccaagatgtg gcttctgcaa ccagcccatc cgacacaaga    60
tggtgacc                                                          68

<210> SEQ ID NO 313
<211> LENGTH: 28
<212> TYPE: DNA
<213> ORGANISM: Artificial Sequence
<220> FEATURE:
<223> OTHER INFORMATION: Synthesized DNA

<400> SEQUENCE: 313
caagactggc tacatcagag tcttagtg                                    28

<210> SEQ ID NO 314
<211> LENGTH: 25
<212> TYPE: DNA
<213> ORGANISM: Artificial Sequence
<220> FEATURE:
<223> OTHER INFORMATION: Synthesized DNA

<400> SEQUENCE: 314
cagcgtaggt ttggtcatag atagg                                       25

<210> SEQ ID NO 315
<211> LENGTH: 29
<212> TYPE: DNA
<213> ORGANISM: Artificial Sequence
<220> FEATURE:
<223> OTHER INFORMATION: Synthesized DNA

<400> SEQUENCE: 315
tgagtctgcc atgacctgtt ttccttcat                                   29

<210> SEQ ID NO 316
<211> LENGTH: 86
<212> TYPE: DNA
<213> ORGANISM: Artificial Sequence
<220> FEATURE:
<223> OTHER INFORMATION: Synthesized DNA

<400> SEQUENCE: 316
caagactggc tacatcagag tcttagtgca tgaaggaaaa caggtcatgg cagactcagg    60
acctatctat gaccaaacct acgctg                                            86

<210> SEQ ID NO 317
<211> LENGTH: 24
<212> TYPE: DNA
<213> ORGANISM: Artificial Sequence
<220> FEATURE:
<223> OTHER INFORMATION: Synthesized DNA

<400> SEQUENCE: 317
ctctgagaca gtgcttcgat gact                                              24

<210> SEQ ID NO 318
<211> LENGTH: 19
<212> TYPE: DNA
<213> ORGANISM: Artificial Sequence
<220> FEATURE:
<223> OTHER INFORMATION: Synthesized DNA

<400> SEQUENCE: 318
ccatgaggcc caacttcct                                                    19

<210> SEQ ID NO 319
<211> LENGTH: 23
<212> TYPE: DNA
<213> ORGANISM: Artificial Sequence
<220> FEATURE:
<223> OTHER INFORMATION: Synthesized DNA

<400> SEQUENCE: 319
cagacttggt gccctttgac tcc                                               23

<210> SEQ ID NO 320
<211> LENGTH: 84
<212> TYPE: DNA
<213> ORGANISM: Artificial Sequence
<220> FEATURE:
<223> OTHER INFORMATION: Synthesized DNA

<400> SEQUENCE: 320
ctctgagaca gtgcttcgat gactttgcag acttggtgcc ctttgactcc tgggagccgc       60
tcatgaggaa gttgggcctc atgg                                              84

<210> SEQ ID NO 321
<211> LENGTH: 20
<212> TYPE: DNA
<213> ORGANISM: Artificial Sequence
<220> FEATURE:
<223> OTHER INFORMATION: Synthesized DNA

<400> SEQUENCE: 321
aggagatgca gctgaaggag                                                   20

<210> SEQ ID NO 322
<211> LENGTH: 20
<212> TYPE: DNA
<213> ORGANISM: Artificial Sequence
<220> FEATURE:
<223> OTHER INFORMATION: Synthesized DNA

<400> SEQUENCE: 322
ccacctcttc atatttgcgg                                                   20

<210> SEQ ID NO 323
<211> LENGTH: 24

```
<212> TYPE: DNA
<213> ORGANISM: Artificial Sequence
<220> FEATURE:
<223> OTHER INFORMATION: Synthesized DNA

<400> SEQUENCE: 323
ccaagcacat cgctgaggat tcag                                          24

<210> SEQ ID NO 324
<211> LENGTH: 66
<212> TYPE: DNA
<213> ORGANISM: Artificial Sequence
<220> FEATURE:
<223> OTHER INFORMATION: Synthesized DNA

<400> SEQUENCE: 324
aggagatgca gctgaaggag gccaagcaca tcgctgagga ttcagaccgc aaatatgaag   60
aggtgg                                                              66

<210> SEQ ID NO 325
<211> LENGTH: 20
<212> TYPE: DNA
<213> ORGANISM: Artificial Sequence
<220> FEATURE:
<223> OTHER INFORMATION: Synthesized DNA

<400> SEQUENCE: 325
tcagctgtga gctgcggata                                               20

<210> SEQ ID NO 326
<211> LENGTH: 24
<212> TYPE: DNA
<213> ORGANISM: Artificial Sequence
<220> FEATURE:
<223> OTHER INFORMATION: Synthesized DNA

<400> SEQUENCE: 326
acggtcctag gtttgaggtt aaga                                          24

<210> SEQ ID NO 327
<211> LENGTH: 19
<212> TYPE: DNA
<213> ORGANISM: Artificial Sequence
<220> FEATURE:
<223> OTHER INFORMATION: Synthesized DNA

<400> SEQUENCE: 327
caggtcccat tgccgggcg                                                19

<210> SEQ ID NO 328
<211> LENGTH: 65
<212> TYPE: DNA
<213> ORGANISM: Artificial Sequence
<220> FEATURE:
<223> OTHER INFORMATION: Synthesized DNA

<400> SEQUENCE: 328
tcagctgtga gctgcggata ccgcccggca atgggacctg ctcttaacct caaacctagg   60
accgt                                                               65

<210> SEQ ID NO 329
<211> LENGTH: 20
<212> TYPE: DNA
<213> ORGANISM: Artificial Sequence
<220> FEATURE:
```

<223> OTHER INFORMATION: Synthesized DNA

<400> SEQUENCE: 329
cgaggacgag gcttaaaaac                                           20

<210> SEQ ID NO 330
<211> LENGTH: 20
<212> TYPE: DNA
<213> ORGANISM: Artificial Sequence
<220> FEATURE:
<223> OTHER INFORMATION: Synthesized DNA

<400> SEQUENCE: 330
accatgcttg aggacaacag                                           20

<210> SEQ ID NO 331
<211> LENGTH: 29
<212> TYPE: DNA
<213> ORGANISM: Artificial Sequence
<220> FEATURE:
<223> OTHER INFORMATION: Synthesized DNA

<400> SEQUENCE: 331
tctcagatca atcgtgcatc cttagtgaa                                 29

<210> SEQ ID NO 332
<211> LENGTH: 73
<212> TYPE: DNA
<213> ORGANISM: Artificial Sequence
<220> FEATURE:
<223> OTHER INFORMATION: Synthesized DNA

<400> SEQUENCE: 332
cgaggacgag gcttaaaaac ttctcagatc aatcgtgcat ccttagtgaa cttctgttgt   60
cctcaagcat ggt                                                  73

<210> SEQ ID NO 333
<211> LENGTH: 20
<212> TYPE: DNA
<213> ORGANISM: Artificial Sequence
<220> FEATURE:
<223> OTHER INFORMATION: Synthesized DNA

<400> SEQUENCE: 333
tgttctcaaa ttgccaccaa                                           20

<210> SEQ ID NO 334
<211> LENGTH: 20
<212> TYPE: DNA
<213> ORGANISM: Artificial Sequence
<220> FEATURE:
<223> OTHER INFORMATION: Synthesized DNA

<400> SEQUENCE: 334
agaggtcaac acagttgcga                                           20

<210> SEQ ID NO 335
<211> LENGTH: 24
<212> TYPE: DNA
<213> ORGANISM: Artificial Sequence
<220> FEATURE:
<223> OTHER INFORMATION: Synthesized DNA

<400> SEQUENCE: 335
aggtgcttgg agaccatccc tcaa                                      24

<210> SEQ ID NO 336
<211> LENGTH: 67
<212> TYPE: DNA
<213> ORGANISM: Artificial Sequence
<220> FEATURE:
<223> OTHER INFORMATION: Synthesized DNA

<400> SEQUENCE: 336
tgttctcaaa ttgccaccaa aaggtgcttg gagaccatcc ctcaacatcg caactgtgtt    60
gacctct                                                              67

<210> SEQ ID NO 337
<211> LENGTH: 23
<212> TYPE: DNA
<213> ORGANISM: Artificial Sequence
<220> FEATURE:
<223> OTHER INFORMATION: Synthesized DNA

<400> SEQUENCE: 337
gataccacaa ctcccatcaa gct                                            23

<210> SEQ ID NO 338
<211> LENGTH: 19
<212> TYPE: DNA
<213> ORGANISM: Artificial Sequence
<220> FEATURE:
<223> OTHER INFORMATION: Synthesized DNA

<400> SEQUENCE: 338
tccctgttag gcgcatcag                                                 19

<210> SEQ ID NO 339
<211> LENGTH: 18
<212> TYPE: DNA
<213> ORGANISM: Artificial Sequence
<220> FEATURE:
<223> OTHER INFORMATION: Synthesized DNA

<400> SEQUENCE: 339
agtggcagcc acggcgcc                                                  18

<210> SEQ ID NO 340
<211> LENGTH: 68
<212> TYPE: DNA
<213> ORGANISM: Artificial Sequence
<220> FEATURE:
<223> OTHER INFORMATION: Synthesized DNA

<400> SEQUENCE: 340
gataccacaa ctcccatcaa gctgttggca gtggcagcca cggcgcctcc tgatgcgcct    60
aacaggga                                                             68

<210> SEQ ID NO 341
<211> LENGTH: 19
<212> TYPE: DNA
<213> ORGANISM: Artificial Sequence
<220> FEATURE:
<223> OTHER INFORMATION: Synthesized DNA

<400> SEQUENCE: 341
cattaaccca ctccccctga                                                19

<210> SEQ ID NO 342

```
<211> LENGTH: 20
<212> TYPE: DNA
<213> ORGANISM: Artificial Sequence
<220> FEATURE:
<223> OTHER INFORMATION: Synthesized DNA

<400> SEQUENCE: 342
cccccaccat catgaatact                                                   20

<210> SEQ ID NO 343
<211> LENGTH: 23
<212> TYPE: DNA
<213> ORGANISM: Artificial Sequence
<220> FEATURE:
<223> OTHER INFORMATION: Synthesized DNA

<400> SEQUENCE: 343
caggtcccca agtgtgcaag ctc                                               23

<210> SEQ ID NO 344
<211> LENGTH: 75
<212> TYPE: DNA
<213> ORGANISM: Artificial Sequence
<220> FEATURE:
<223> OTHER INFORMATION: Synthesized DNA

<400> SEQUENCE: 344
cattaaccca ctcccctgac ctcacgctgg ggcaggtccc caagtgtgca agctcagtat       60
tcatgatggt ggggg                                                        75
```

GENE EXPRESSION PROFILE ALGORITHM AND TEST FOR DETERMINING PROGNOSIS OF PROSTATE CANCER

RELATED APPLICATIONS

This application is a division of U.S. application Ser. No. 14/221,556, filed Mar. 21, 2014, which is a continuation of U.S. application Ser. No. 13/752,199, filed Jan. 28, 2013, now U.S. Pat. No. 8,725,426, issued May 13, 2014, which claims the benefit of priority of U.S. Provisional Application Nos. 61/593,106, filed Jan. 31, 2012; 61/672,679, filed Jul. 17, 2012; and 61/713,734, filed Oct. 15, 2012, all of which are hereby incorporated by reference in their entirety.

TECHNICAL FIELD

The present disclosure relates to molecular diagnostic assays that provide information concerning gene expression profiles to determine prognostic information for cancer patients. Specifically, the present disclosure provides an algorithm comprising genes, or co-expressed genes, the expression levels of which may be used to determine the likelihood that a prostate cancer patient will experience a positive or a negative clinical outcome.

INTRODUCTION

The introduction of prostate-specific antigen (PSA) screening in 1987 has led to the diagnosis and aggressive treatment of many cases of indolent prostate cancer that would never have become clinically significant or caused death. The reason for this is that the natural history of prostate cancer is unusual among malignancies in that the majority of cases are indolent and even if untreated would not progress during the course of a man's life to cause suffering or death. While approximately half of men develop invasive prostate cancer during their lifetimes (as detected by autopsy studies) (B. Halpert et al, Cancer 16: 737-742 (1963); B. Holund, Scand J Urol Nephrol 14: 29-35 (1980); S. Lundberg et al., Scand J Urol Nephrol 4: 93-97 (1970); M. Yin et al., J Urol 179: 892-895 (2008)), only 17% will be diagnosed with prostate cancer and only 3% will die as a result of prostate cancer. Cancer Facts and Figures. Atlanta, Ga.: American Cancer Society (2010); J E Damber et al., Lancet 371: 1710-1721 (2008).

However, currently, over 90% of men who are diagnosed with prostate cancer, even low-risk prostate cancer, are treated with either immediate radical prostatectomy or definitive radiation therapy. M R Cooperberg et al., J Clin Oncol 28: 1117-1123 (2010); M R Cooperberg et al., J Clin Oncol 23: 8146-8151 (2005). Surgery and radiation therapy reduce the risk of recurrence and death from prostate cancer (AV D'Amico et al., Jama 280: 969-974 (1998); M Han et al., Urol Clin North Am 28: 555-565 (2001); W U Shipley et al., Jama 281: 1598-1604 (1999); A J Stephenson et al., J Clin Oncol 27: 4300-4305 (2009)), however estimates of the number of men that must be treated to prevent one death from prostate cancer range from 12 to 100. A Bill-Axelson et al., J Natl Cancer Inst 100: 1144-1154 (2008); J Hugosson et al., Lancet Oncol 11: 725-732 (2010); L H Klotz et al., Can J Urol 13 Suppl 1: 48-55 (2006); S Loeb et al., J Clin Oncol 29: 464-467 (2011); F H Schroder et al., N Engl J Med 360: 1320-1328 (2009). This over-treatment of prostate cancer comes at a cost of money and toxicity. For example, the majority of men who undergo radical prostatectomy suffer incontinence and impotence as a result of the procedure (M S Litwin et al., Cancer 109: 2239-2247 (2007); M G Sanda et al., N Engl J Med 358: 1250-1261 (2008), and as many as 25% of men regret their choice of treatment for prostate cancer. FR Schroeck et al., Eur Urol 54: 785-793 (2008).

One of the reasons for the over-treatment of prostate cancer is the lack of adequate prognostic tools to distinguish men who need immediate definitive therapy from those who are appropriate candidates to defer immediate therapy and undergo active surveillance instead. For example, of men who appear to have low-risk disease based on the results of clinical staging, pre-treatment PSA, and biopsy Gleason score, and have been managed with active surveillance on protocols, 30-40% experience disease progression (diagnosed by rising PSA, an increased Gleason score on repeat biopsy, or clinical progression) over the first few years of follow-up, and some of them may have lost the opportunity for curative therapy. H B Carter et al., J Urol 178: 2359-2364 and discussion 2364-2355 (2007); M A Dall'Era et al., Cancer 112: 2664-2670 (2008); L Klotz et al., J Clin Oncol 28: 126-131 (2010). Also, of men who appear to be candidates for active surveillance, but who undergo immediate prostatectomy anyway, 30-40% are found at surgery to have higher risk disease than expected as defined by having high-grade (Gleason score of 3+4 or higher) or non-organ-confined disease (extracapsular extension (ECE) or seminal vesicle involvement (SVI)). S L et al., J Urol 181: 1628-1633 and discussion 1633-1624 (2009); C R Griffin et al., J Urol 178: 860-863 (2007); P W Mufarrij et al., J Urol 181: 607-608 (2009).

Estimates of recurrence risk and treatment decisions in prostate cancer are currently based primarily on PSA levels and/or clinical tumor stage. Although clinical tumor stage has been demonstrated to have a significant association with outcome, sufficient to be included in pathology reports, the College of American Pathologists Consensus Statement noted that variations in approach to the acquisition, interpretation, reporting, and analysis of this information exist. C. Compton, et al., Arch Pathol Lab Med 124:979-992 (2000). As a consequence, existing pathologic staging methods have been criticized as lacking reproducibility and therefore may provide imprecise estimates of individual patient risk.

SUMMARY

This application discloses molecular assays that involve measurement of expression level(s) of one or more genes or gene subsets from a biological sample obtained from a prostate cancer patient, and analysis of the measured expression levels to provide information concerning the likelihood of a clinical outcome. For example, the likelihood of a clinical outcome may be described in terms of a quantitative score based on clinical or biochemical recurrence-free interval, overall survival, prostate cancer-specific survival, upstaging/upgrading from biopsy to radical prostatectomy, or presence of high grade or non-organ confined disease at radical prostatectomy.

In addition, this application discloses molecular assays that involve measurement of expression level(s) of one or more genes or gene subsets from a biological sample obtained to identify a risk classification for a prostate cancer patient. For example, patients may be stratified using expression level(s) of one or more genes, positively or negatively, with positive clinical outcome of prostate cancer, or with a prognostic factor. In an exemplary embodiment, the prognostic factor is Gleason score.

The present invention provides a method of predicting the likelihood of a clinical outcome for a patient with prostate cancer comprising determination of a level of one or more RNA transcripts, or an expression product thereof, in a biological sample containing tumor cells obtained from the patient, wherein the RNA transcript, or its expression product, is selected from the 81 genes shown in FIG. 1 and listed in Tables 1A and 1B. The method comprises assigning the one or more RNA transcripts, or an expression product thereof, to one or more gene groups selected from a cellular organization gene group, basal epithelia gene group, a stress response gene group, an androgen gene group, a stromal response gene group, and a proliferation gene group. The method further comprises calculating a quantitative score for the patient by weighting the level of the one or more RNA transcripts or an expression product thereof, by their contribution to a clinical outcome and predicting the likelihood of a clinical outcome for the patient based on the quantitative score. In an embodiment of the invention, an increase in the quantitative score correlates with an increased likelihood of a negative clinical outcome.

In a particular embodiment, the one or more RNA transcripts, or an expression product thereof, is selected from BIN1, IGF1, C7, GSN, DES, TGFB1I1, TPM2, VCL, FLNC, ITGA7, COL6A1, PPP1R12A, GSTM1, GSTM2, PAGE4, PPAP2B, SRD5A2, PRKCA, IGFBP6, GPM6B, OLFML3, HLF, CYP3A5, KRT15, KRT5, LAMB3, SDC1, DUSP1, EGFR1, FOS, JUN, EGR3, GADD45B, ZFP36, FAM13C, KLK2, ASPN, SFRP4, BGN, THBS2, INHBA, COL1A1, COL3A1, COL1A2, SPARC, COL8A1, COL4A1, FN1, FAP, COL5A2, CDC120, TPX2, UBE2T, MYBL2, and CDKN2C. BIN1, IGF1, C7, GSN, DES, TGFB1I1, TPM2, VCL, FLNC, ITGA7, COL6A1, PPP1R12A, GSTM1, GSTM2, PAGE4, PPAP2B, SRD5A2, PRKCA, IGFBP6, GPM6B, OLFML3, and HLF are assigned to the cellular organization gene group. CYP3A5, KRT15, KRT5, LAMB3, and SDC1 are assigned to the basal epithelial gene group. DUSP1, EGFR1, FOS, JUN, EGR3, GADD45B, and ZFP36 are assigned to the stress response gene group. FAM13C, KLK2, AZGP1, and SRD5A2 are assigned to the androgen gene group. ASPN, SFRP4, BGN, THBS2, INHBA, COL1A1, COL3A1, COL1A2, SPARC, COL8A1, COL4A1, FN1, FAP and COL5A2 are assigned to the stromal response gene group. CDC120, TPX2, UBE2T, MYBL2, and CDKN2C are assigned to the proliferation gene group. The method may further comprise determining the level of at least one RNA transcript, or an expression product thereof, selected from STAT5B, NFAT5, AZGP1, ANPEP, IGFBP2, SLC22A3, ERG, AR, SRD5A2, GSTM1, and GSTM2.

In an embodiment of the invention, the level of one or more RNA transcripts, or an expression product thereof, from each of the stromal response gene group and the cellular organization gene group are determined. In another embodiment, the level of one or more RNA transcripts, or expression products thereof, from each of the stromal response gene group and PSA gene group are determined. Additionally, the level of one or more RNA transcripts, or expression products thereof, from the cellular organization gene group and/or proliferation gene group may be determined. In this embodiment, gene(s) to be assayed from the stromal response gene group may be selected from ASPN, BGN, COL1A1, SPARC, FN1, COL3A1, COL4A1, INHBA, THBS2, and SFRP4; gene(s) to be assayed from the androgen gene group may be selected from FAM13C and KLK2; gene(s) to be assayed from the cellular organization gene group may be selected from FLNC, GSN, GSTM2, IGFBP6, PPAP2B, PPP1R12A, BIN1, VCL, IGF1, TPM2, C7, and GSTM1; and gene(s) to be assayed from the proliferation gene group may be selected from TPX2, CDC120, and MYBL2.

In a particular embodiment, the RNA transcripts, or their expression products, are selected from BGN, COL1A1, SFRP4, FLNC, GSN, TPM2, TPX2, FAM13C, KLK2, AZGP1, GSTM2, and SRD5A2. BGN, COL1A1, and SFRP4 are assigned to the stromal response gene group; FLNC, GSN, and TPM2 are assigned to the cellular organization gene group; and FAM13C and KLK2 are assigned to the androgen gene group. The level of the RNA transcripts, or their expression products, comprising at least one of the gene groups selected from the stromal response gene group, cellular organization gene group, and androgen gene group, may be determined for the method of the invention. In any of the embodiments, the androgen gene group may further comprise AZGP1 and SRD5A2.

In addition, the level of any one of the gene combinations show in Table 4 may be determined. For instance, the RS0 model in Table 4 comprises determining the levels of the RNA transcripts, or gene expression products thereof, of ASPN, BGN, COL1A1, SPARC, FLNC, GSN, GSTM2, IGFBP6, PPAP2B, PPP1R12A, TPX2, CDC120, MYBL2, FAM13C, KLK2, STAT5B, and NFAT5. Furthermore, any one of the algorithms shown in Table 4 may be used to calculate the quantitative score for the patient.

BRIEF DESCRIPTION OF THE DRAWING

FIG. 2A: All ECM (stomal response) genes; FIG. 2B: All migration (cellular organization) genes; FIG. 2C: All proliferation genes; FIG. 2D: PSA (androgen) genes; FIG. 2E: other genes from the 81 gene list that do not fall within any of these four gene groups.

FIG. 3A: All ECM (stromal response) genes;

FIG. 3B: All migration (cellular organization) genes; FIG. 3C: All proliferation genes; FIG. 3D: other genes from the 81 gene list that do not fall within any of the gene groups.

FIGS. 5A-5C show examples of cliques and stacks. FIG. 5A is an example of a graph that is not a clique; FIG. 5B is an example of a clique; FIG. 5C is an example of a clique but is not a maximal clique.

FIG. 6 is a graph showing two maximal cliques: 1-2-3-4-5 and 1-2-3-4-6.

FIGS. 7A-7C schematically illustrate stacking (in FIG. 7C) of two maximal cliques (shown in FIGS. 7A and 7B).

DEFINITIONS

Figure 1:
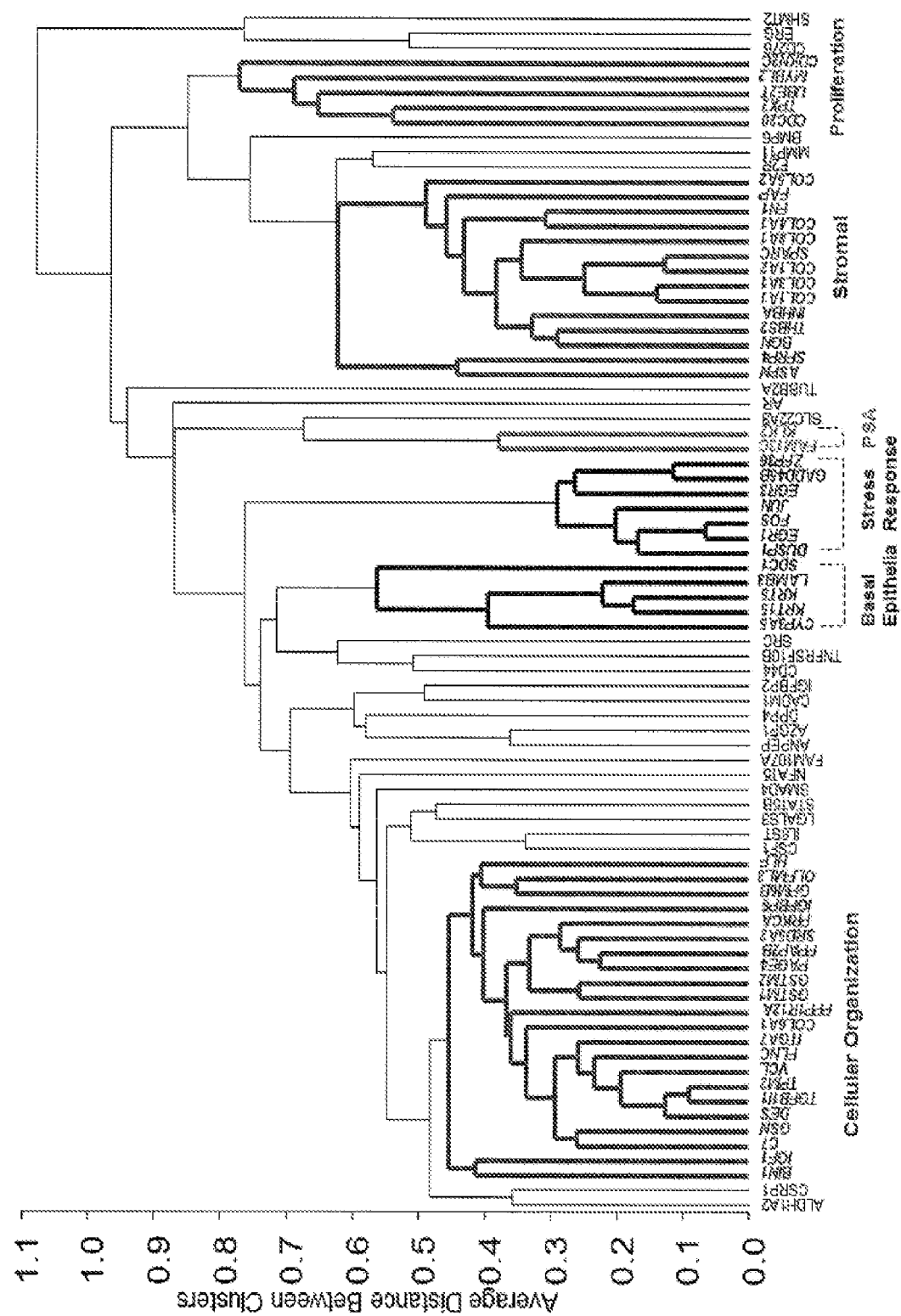
FIG. 1 is a dendrogram depicting the association of the 81 genes selected from the gene identification study.
Figure 2A:
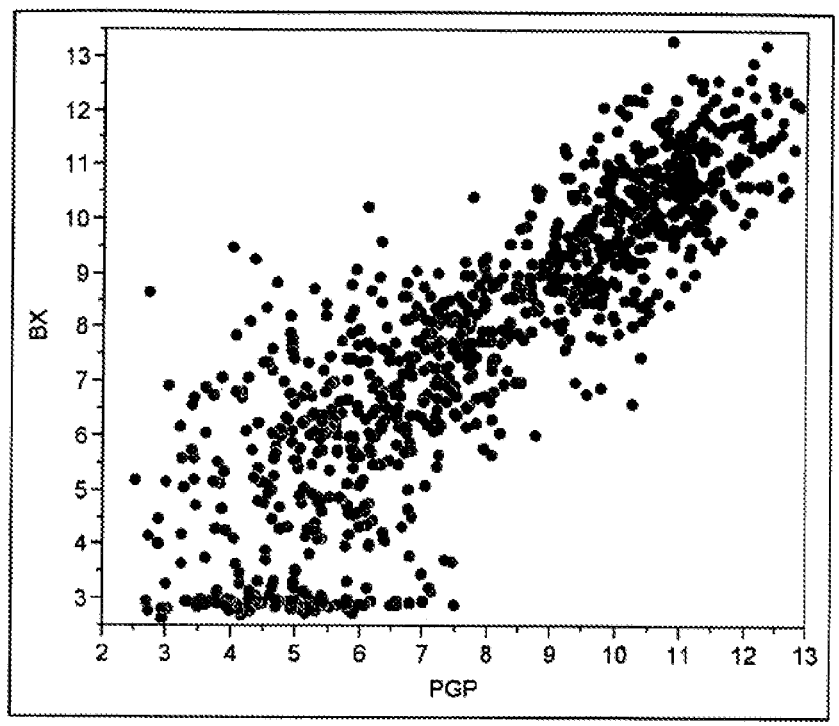
FIGS. 2A-2E are scatter plots showing the comparison of normalized gene expression (Cp) for matched samples from each patient where the x-axis is the gene expression from the primary Gleason pattern RP sample (PGP) and the y-axis is the gene expression from the biopsy (BX) sample.
Figure 2B:
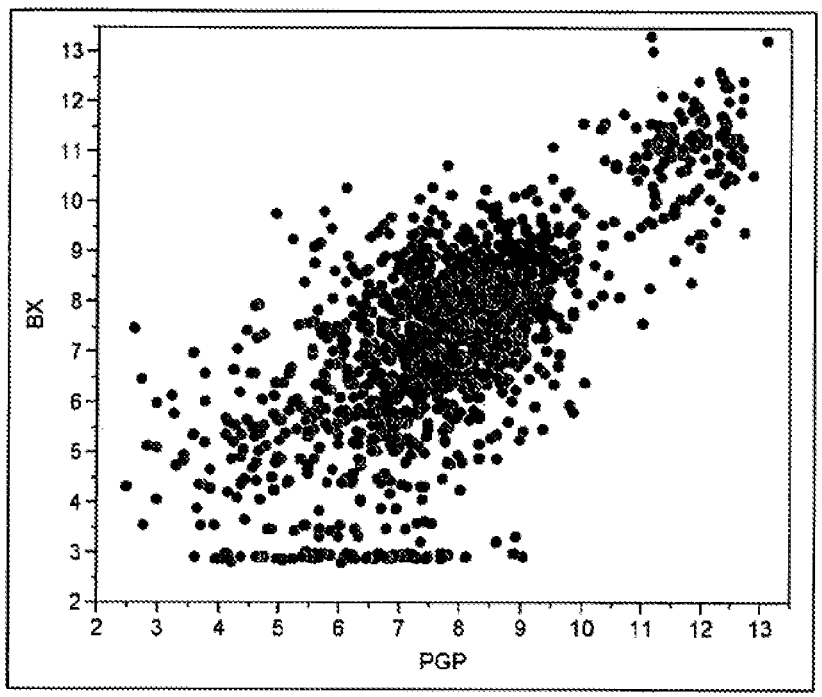
Figure 2C:
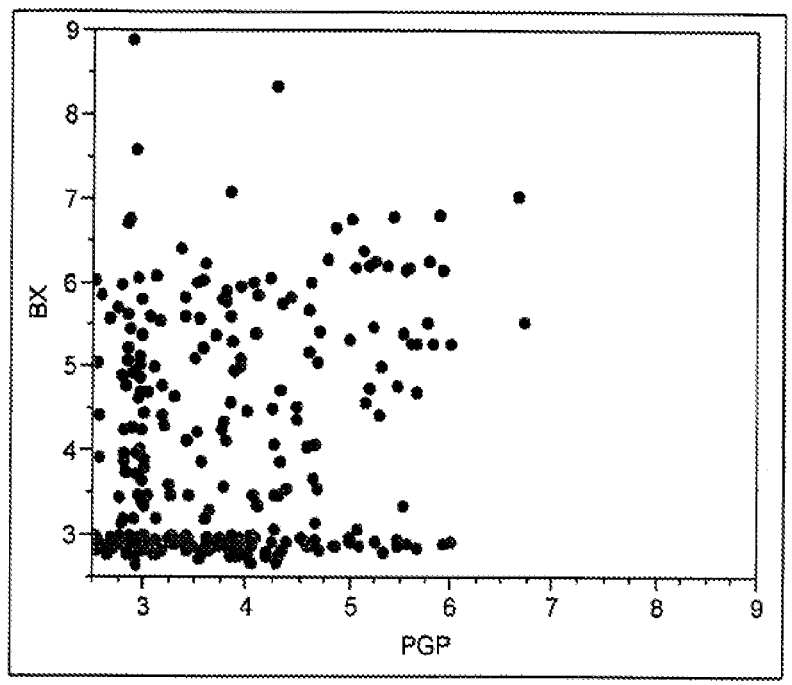
Figure 2D:
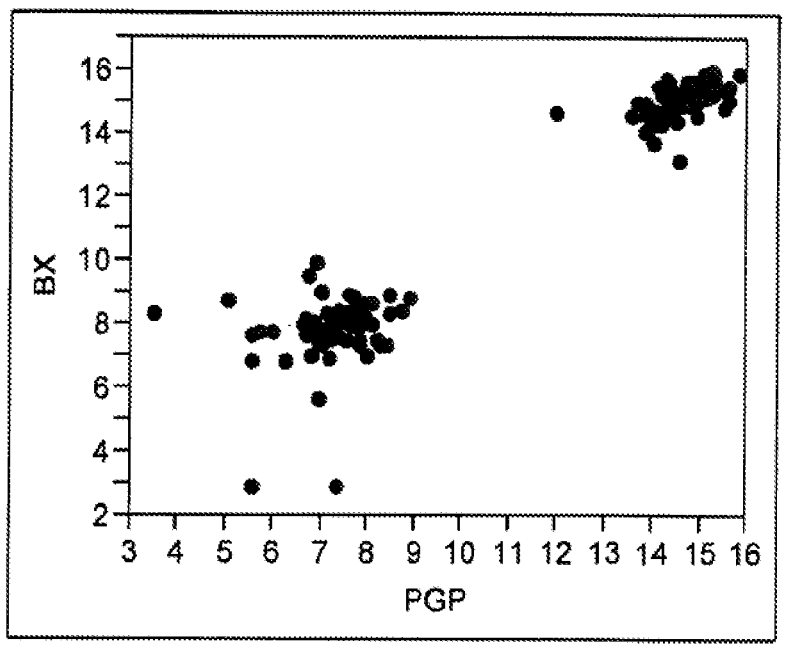
Figure 2E:
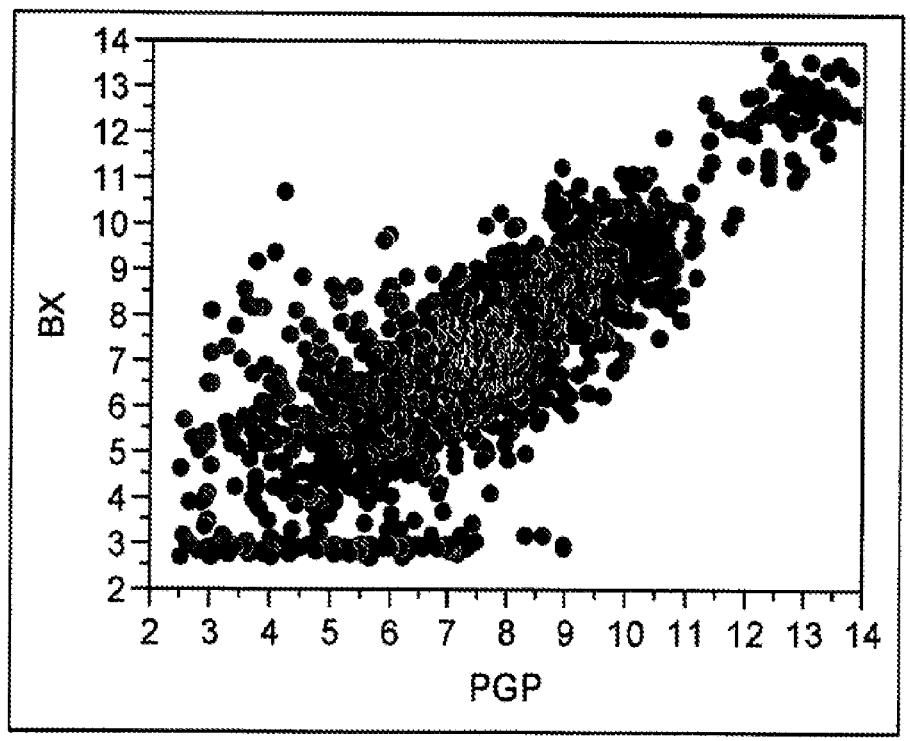
Figure 3A:
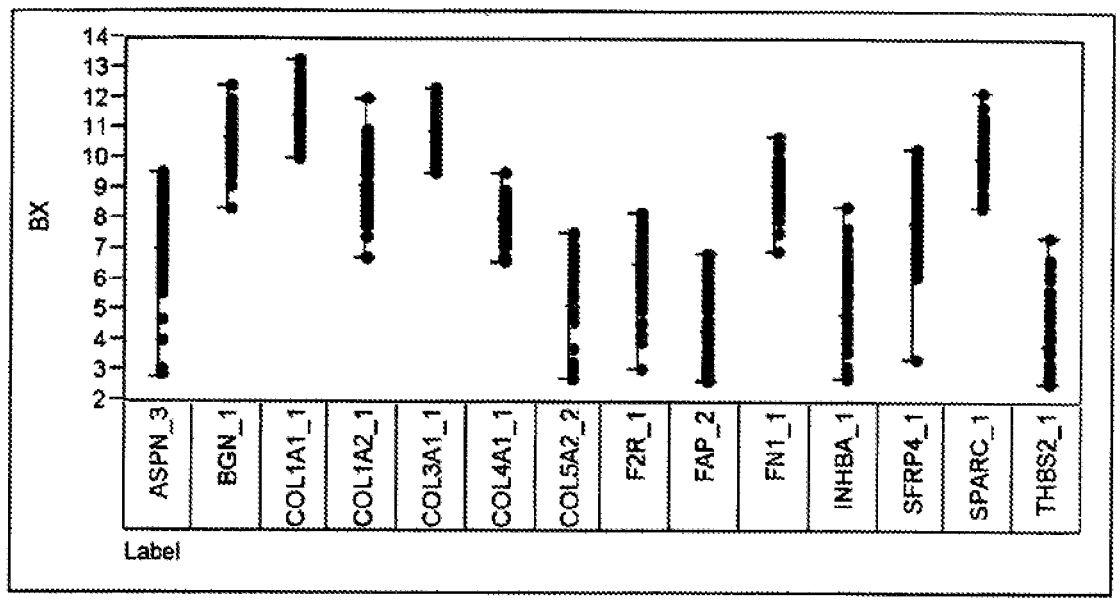
FIGS. 3A-3D are range plots of gene expression of individual genes within each gene group in the biopsy (BX) and PGP RP samples.
Figure 3A:
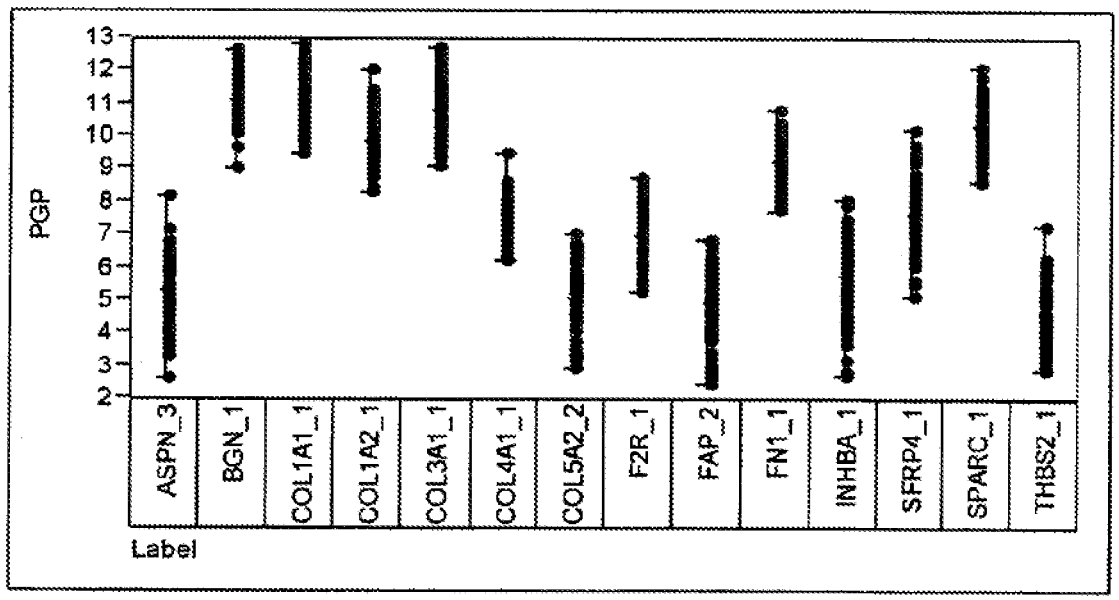
Figure 3B:
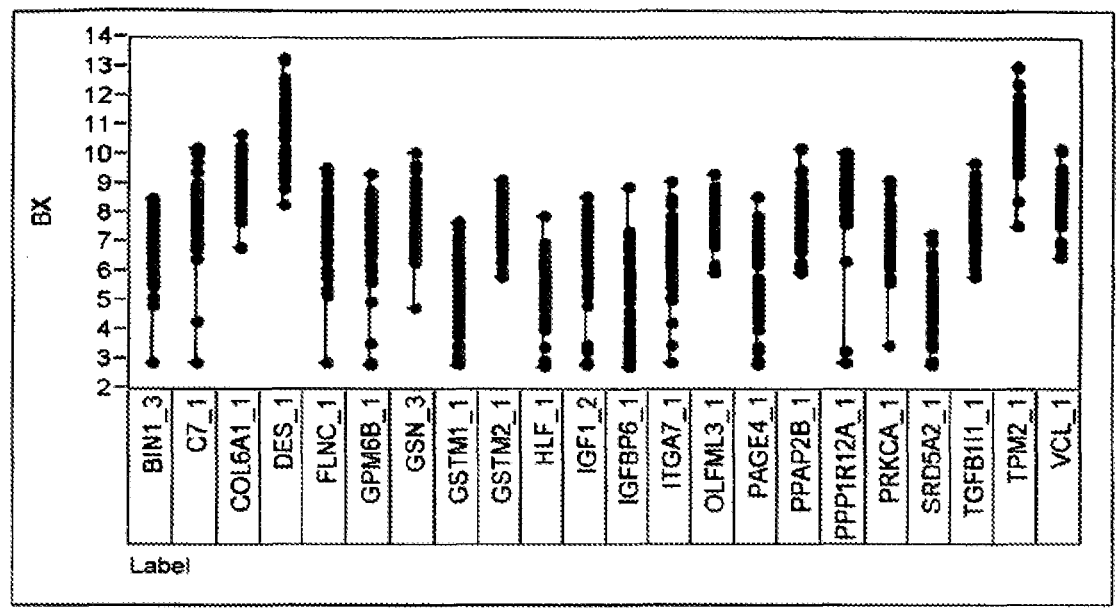
Figure 3B:
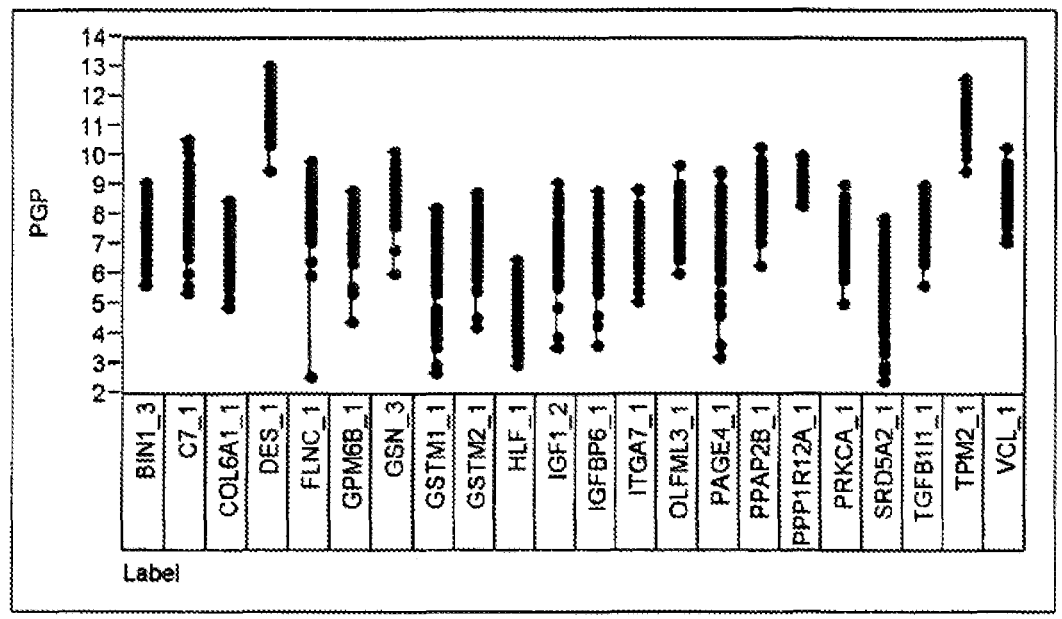
Figure 3C:
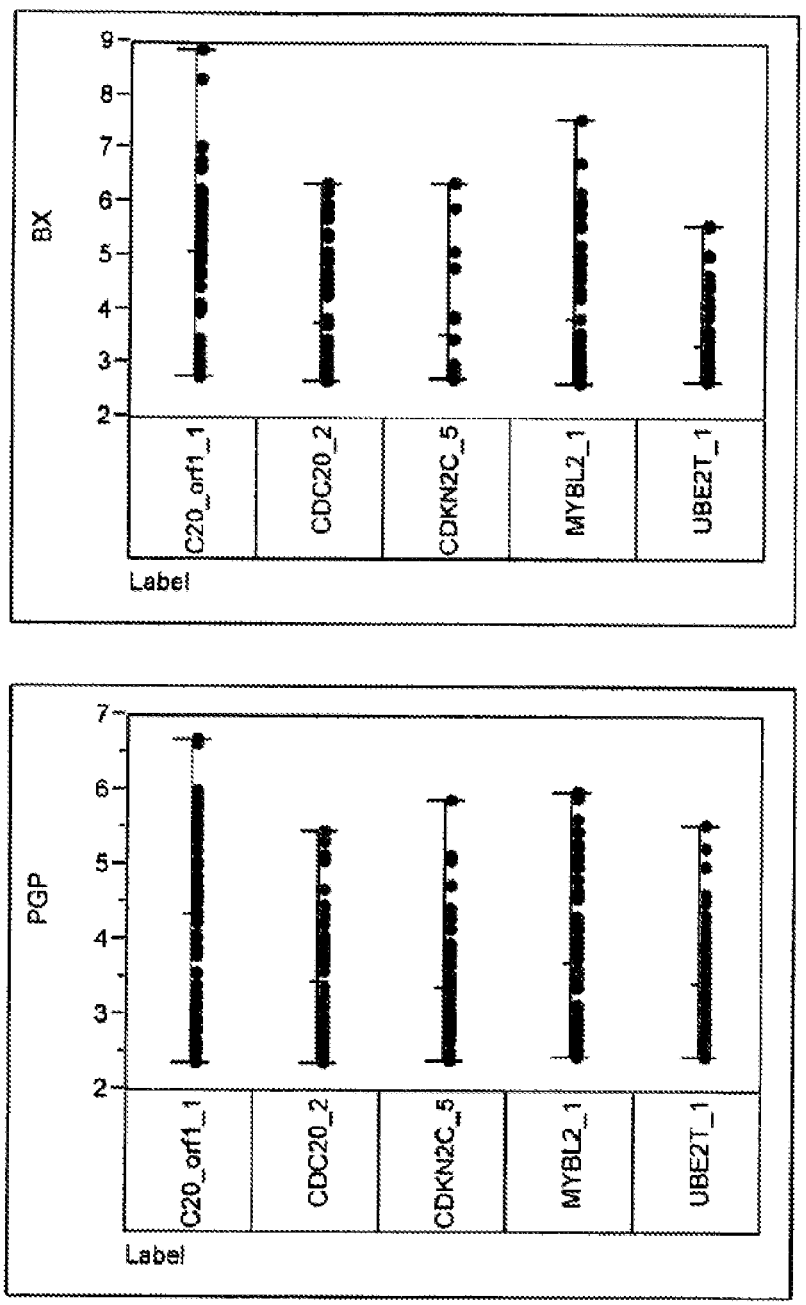
Figure 3D:
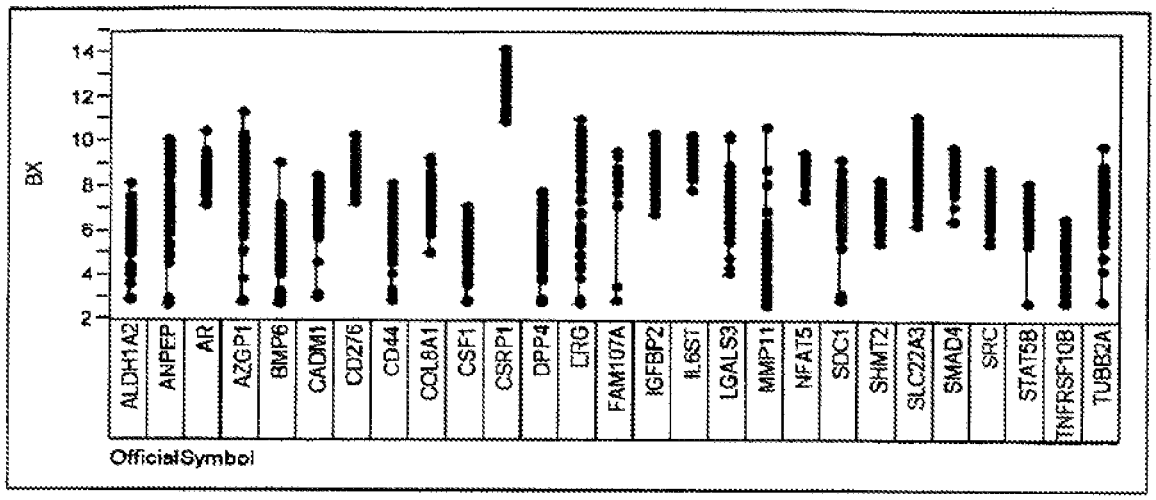
Figure 3D:
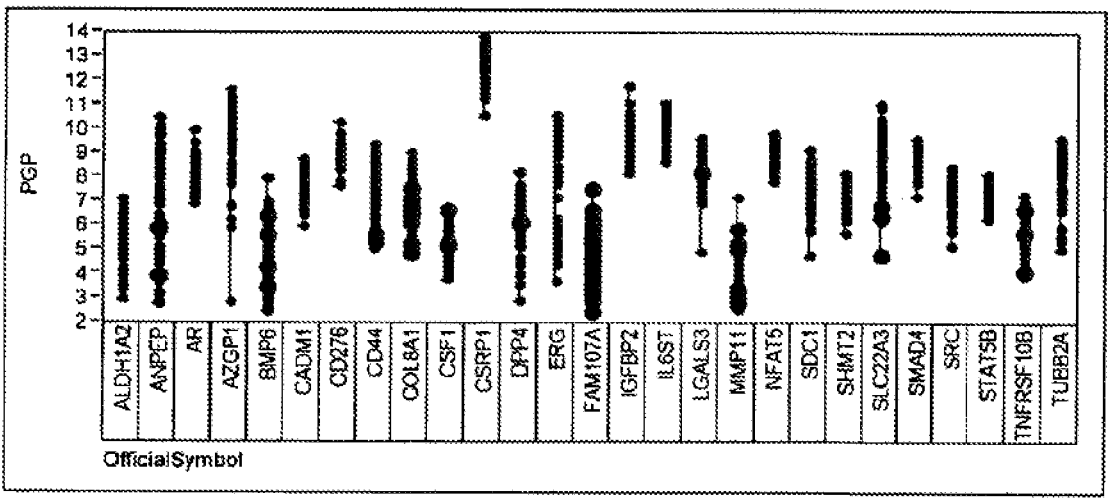

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described herein. For purposes of the invention, the following terms are defined below.

The terms "tumor" and "lesion" as used herein, refer to all neoplastic cell growth and proliferation, whether malignant or benign, and all pre-cancerous and cancerous cells and tissues. Those skilled in the art will realize that a tumor tissue sample may comprise multiple biological elements, such as one or more cancer cells, partial or fragmented cells, tumors in various stages, surrounding histologically normal-appearing tissue, and/or macro or micro-dissected tissue.

The terms "cancer" and "cancerous" refer to or describe the physiological condition in mammals that is typically characterized by unregulated cell growth. Examples of cancer in the present disclosure include cancer of the urogenital tract, such as prostate cancer.

As used herein, the term "prostate cancer" is used in the broadest sense and refers to all stages and all forms of cancer arising from the tissue of the prostate gland.

Staging of the cancer assists a physician in assessing how far the disease has progressed and to plan a treatment for the patient. Staging may be done clinically (clinical staging) by physical examination, blood tests, or response to radiation therapy, and/or pathologically (pathologic staging) based on surgery, such as radical prostatectomy. According to the tumor, node, metastasis (TNM) staging system of the American Joint Committee on Cancer (AJCC), AJCC Cancer Staging Manual (7th Ed., 2010), the various stages of prostate cancer are defined as follows: Tumor: T1: clinically inapparent tumor not palpable or visible by imaging, T1a: tumor incidental histological finding in 5% or less of tissue resected, T1b: tumor incidental histological finding in more than 5% of tissue resected, T1c: tumor identified by needle biopsy; T2: tumor confined within prostate, T2a: tumor involves one half of one lobe or less, T2b: tumor involves more than half of one lobe, but not both lobes, T2c: tumor involves both lobes; T3: tumor extends through the prostatic capsule, T3a: extracapsular extension (unilateral or bilateral), T3b: tumor invades seminal vesicle(s); T4: tumor is fixed or invades adjacent structures other than seminal vesicles (bladder neck, external sphincter, rectum, levator muscles, or pelvic wall). Generally, a clinical T (cT) stage is T1 or T2 and pathologic T (pT) stage is T2 or higher. Node: N0: no regional lymph node metastasis; N1: metastasis in regional lymph nodes. Metastasis: M0: no distant metastasis; M1: distant metastasis present.

The Gleason Grading system is used to help evaluate the prognosis of men with prostate cancer. Together with other parameters, it is incorporated into a strategy of prostate cancer staging, which predicts prognosis and helps guide therapy. A Gleason "score" or "grade" is given to prostate cancer based upon its microscopic appearance. Tumors with a low Gleason score typically grow slowly enough that they may not pose a significant threat to the patients in their lifetimes. These patients are monitored ("watchful waiting" or "active surveillance") over time. Cancers with a higher Gleason score are more aggressive and have a worse prognosis, and these patients are generally treated with surgery (e.g., radical prostatectomy) and, in some cases, therapy (e.g., radiation, hormone, ultrasound, chemotherapy). Gleason scores (or sums) comprise grades of the two most common tumor patterns. These patterns are referred to as Gleason patterns 1-5, with pattern 1 being the most well-differentiated. Most have a mixture of patterns. To obtain a Gleason score or grade, the dominant pattern is added to the second most prevalent pattern to obtain a number between 2 and 10. The Gleason Grades include: G1: well differentiated (slight anaplasia) (Gleason 2-4); G2: moderately differentiated (moderate anaplasia) (Gleason 5-6); G3-4: poorly differentiated/undifferentiated (marked anaplasia) (Gleason 7-10).

Stage groupings: Stage I: T1a N0 M0 G1; Stage II: (T1a N0 M0 G2-4) or (T1b, c, T1, T2, N0 M0 Any G); Stage III: T3 N0 M0 Any G; Stage IV: (T4 N0 M0 Any G) or (Any T N1 M0 Any G) or (Any T Any N M1 Any G).

The term "upgrading" as used herein refers to an increase in Gleason grade determined from biopsy to Gleason grade determined from radical prostatectomy (RP). For example, upgrading includes a change in Gleason grade from 3+3 or 3+4 on biopsy to 3+4 or greater on RP. "Significant upgrading" or "upgrade2" as used herein, refers to a change in Gleason grade from 3+3 or 3+4 determined from biopsy to 4+3 or greater, or seminal vessical involvement (SVI), or extracapsular involvement (ECE) as determined from RP.

The term "high grade" as used herein refers to Gleason score of >=3+4 or >=4+3 on RP. The term "low grade" as used herein refers to a Gleason score of 3+3 on RP. In a particular embodiment, "high grade" disease refers to Gleason score of at least major pattern 4, minor pattern 5, or tertiary pattern 5.

The term "upstaging" as used herein refers to an increase in tumor stage from biopsy to tumor stage at RP. For example, upstaging is a change in tumor stage from clinical T1 or T2 stage at biopsy to pathologic T3 stage at RP.

The term "non organ-confined disease" as used herein refers to having pathologic stage T3 disease at RP. The term "organ-confined" as used herein refers to pathologic stage pT2 at RP.

The term "adverse pathology" as used herein refers to a high grade disease as defined above, or non organ-confined disease as defined above. In a particular embodiment, "adverse pathology" refers to prostate cancer with a Gleason score of >=3+4 or >=4+3 or pathologic stage T3.

In another embodiment, the term "high-grade or non-organ-confined disease" refers to prostate cancer with a Gleason score of at least major pattern 4, minor pattern 5, or tertiary pattern 5, or pathologic stage T3.

As used herein, the terms "active surveillance" and "watchful waiting" mean closely monitoring a patient's condition without giving any treatment until symptoms appear or change. For example, in prostate cancer, watchful waiting is usually used in older men with other medical problems and early-stage disease.

As used herein, the term "surgery" applies to surgical methods undertaken for removal of cancerous tissue, including pelvic lymphadenectomy, radical prostatectomy, transurethral resection of the prostate (TURP), excision, dissection, and tumor biopsy/removal. The tumor tissue or sections used for gene expression analysis may have been obtained from any of these methods.

As used herein, the term "biological sample containing cancer cells" refers to a sample comprising tumor material obtained from a cancer patient. The term encompasses tumor tissue samples, for example, tissue obtained by radical prostatectomy and tissue obtained by biopsy, such as for example, a core biopsy or a fine needle biopsy. The biological sample may be fresh, frozen, or a fixed, wax-embedded tissue sample, such as a formalin-fixed, paraffin-embedded tissue sample. A biological sample also encompasses bodily fluids containing cancer cells, such as blood, plasma, serum, urine, and the like. Additionally, the term "biological sample containing cancer cells" encompasses a sample comprising tumor cells obtained from sites other than the primary tumor, e.g., circulating tumor cells. The term also encompasses cells that are the progeny of the patient's tumor cells, e.g. cell culture samples derived from primary tumor cells or circulating tumor cells. The term further encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

Prognostic factors are those variables related to the natural history of cancer that influence the recurrence rates and outcome of patients once they have developed cancer. Clinical parameters that have been associated with a worse prognosis include, for example, increased tumor stage, high PSA level at presentation, and high Gleason grade or pattern. Prognostic factors are frequently used to categorize patients into subgroups with different baseline relapse risks.

The term "prognosis" is used herein to refer to the likelihood that a cancer patient will have a cancer-attributable death or progression, including recurrence, metastatic spread, and drug resistance, of a neoplastic disease, such as prostate cancer. For example, a "good prognosis" would include long term survival without recurrence and a "bad prognosis" would include cancer recurrence.

A "positive clinical outcome" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down, or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the duration of survival following treatment; and/or (9) decreased mortality at a given point of time following treatment. Positive clinical outcome can also be considered in the context of an individual's outcome relative to an outcome of a population of patients having a comparable clinical diagnosis, and can be assessed using various endpoints such as an increase in the duration of Recurrence-Free Interval (RFI), an increase in survival time (Overall Survival (OS)) or prostate cancer-specific survival time (Prostate Cancer-Specific Survival (PCSS)) in a population, no upstaging or upgrading in tumor stage or Gleason grade between biopsy and radical prostatectomy, presence of 3+3 grade and organ-confined disease at radical prostatectomy, and the like.

The term "risk classification" means a grouping of subjects by the level of risk (or likelihood) that the subject will experience a particular negative clinical outcome. A subject may be classified into a risk group or classified at a level of risk based on the methods of the present disclosure, e.g. high, medium, or low risk. A "risk group" is a group of subjects or individuals with a similar level of risk for a particular clinical outcome.

The term "long-term" survival is used herein to refer to survival for a particular time period, e.g., for at least 5 years, or for at least 10 years.

The term "recurrence" is used herein to refer to local or distant recurrence (i.e., metastasis) of cancer. For example, prostate cancer can recur locally in the tissue next to the prostate or in the seminal vesicles. The cancer may also affect the surrounding lymph nodes in the pelvis or lymph nodes outside this area. Prostate cancer can also spread to tissues next to the prostate, such as pelvic muscles, bones, or other organs. Recurrence can be determined by clinical recurrence detected by, for example, imaging study or biopsy, or biochemical recurrence detected by, for example, sustained follow-up prostate-specific antigen (PSA) levels≥0.4 ng/mL or the initiation of salvage therapy as a result of a rising PSA level.

The term "clinical recurrence-free interval (cRFI)" is used herein as time from surgery to first clinical recurrence or death due to clinical recurrence of prostate cancer. If follow-up ended without occurrence of clinical recurrence, or other primary cancers or death occurred prior to clinical recurrence, time to cRFI is considered censored; when this occurs, the only information known is that up through the censoring time, clinical recurrence has not occurred in this subject. Biochemical recurrences are ignored for the purposes of calculating cRFI.

The term "biochemical recurrence-free interval (bRFI)" is used herein to mean the time from surgery to first biochemical recurrence of prostate cancer. If clinical recurrence occurred before biochemical recurrence, follow-up ended without occurrence of bRFI, or other primary cancers or death occurred prior to biochemical recurrence, time to biochemical recurrence is considered censored at the first of these.

The term "Overall Survival (OS)" is used herein to refer to the time from surgery to death from any cause. If the subject was still alive at the time of last follow-up, survival time is considered censored at the time of last follow-up. Biochemical recurrence and clinical recurrence are ignored for the purposes of calculating OS.

The term "Prostate Cancer-Specific Survival (PCSS)" is used herein to describe the time from surgery to death from prostate cancer. If the patient did not die of prostate cancer before end of followup, or died due to other causes, PCSS is considered censored at this time. Clinical recurrence and biochemical recurrence are ignored for the purposes of calculating PCSS.

In practice, the calculation of the time-to-event measures listed above may vary from study to study depending on the definition of events to be considered censored.

As used herein, the term "expression level" as applied to a gene refers to the normalized level of a gene product, e.g.

the normalized value determined for the RNA level of a gene or for the polypeptide level of a gene.

The term "gene product" or "expression product" are used herein to refer to the RNA (ribonucleic acid) transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The term "RNA transcript" as used herein refers to the RNA transcription products of a gene, including, for example, mRNA, an unspliced RNA, a splice variant mRNA, a microRNA, and a fragmented RNA.

Unless indicated otherwise, each gene name used herein corresponds to the Official Symbol assigned to the gene and provided by Entrez Gene (URL: www.ncbi.nlm.nih.gov/sites/entrez) as of the filing date of this application.

The term "microarray" refers to an ordered arrangement of hybridizable array elements, e.g. oligonucleotide or polynucleotide probes, on a substrate.

The term "polynucleotide" generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons, are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNArDNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "Ct" as used herein refers to threshold cycle, the cycle number in quantitative polymerase chain reaction (qPCR) at which the fluorescence generated within a reaction well exceeds the defined threshold, i.e. the point during the reaction at which a sufficient number of amplicons have accumulated to meet the defined threshold.

The term "Cp" as used herein refers to "crossing point." The Cp value is calculated by determining the second derivatives of entire qPCR amplification curves and their maximum value. The Cp value represents the cycle at which the increase of fluorescence is highest and where the logarithmic phase of a PCR begins.

The terms "threshold" or "thresholding" refer to a procedure used to account for non-linear relationships between gene expression measurements and clinical response as well as to further reduce variation in reported patient scores. When thresholding is applied, all measurements below or above a threshold are set to that threshold value. A non-linear relationship between gene expression and outcome could be examined using smoothers or cubic splines to model gene expression on recurrence free interval using Cox PH regression or on adverse pathology status using logistic regression. D. Cox, Journal of the Royal Statistical Society, Series B 34:187-220 (1972). Variation in reported patient scores could be examined as a function of variability in gene expression at the limit of quantitation and/or detection for a particular gene.

As used herein, the term "amplicon," refers to pieces of DNA that have been synthesized using amplification techniques, such as polymerase chain reactions (PCR) and ligase chain reactions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology* (Wiley Interscience Publishers, 1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide, followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-500 C. The skilled artisan will recognize how to adjust the temperature, ionic strength, etc. as necessary to accommodate factors such as probe length and the like.

The terms "splicing" and "RNA splicing" are used interchangeably and refer to RNA processing that removes introns and joins exons to produce mature mRNA with continuous coding sequence that moves into the cytoplasm of an eukaryotic cell.

As used herein, the term "TMPRSS fusion" and "TMPRSS2 fusion" are used interchangeably and refer to a fusion of the androgen-driven TMPRSS2 gene with the ERG oncogene, which has been demonstrated to have a significant association with prostate cancer. S. Perner, et al., Urologe A. 46(7):754-760 (2007); S. A. Narod, et al., Br J Cancer 99(6):847-851 (2008). As used herein, positive TMPRSS fusion status indicates that the TMPRSS fusion is present in a tissue sample, whereas negative TMPRSS fusion status indicates that the TMPRSS fusion is not present in a tissue sample. Experts skilled in the art will recognize that there are numerous ways to determine TMPRSS fusion status, such as real-time, quantitative PCR or high-throughput sequencing. See, e.g., K. Mertz, et al., Neoplasis 9(3): 200-206 (2007); C. Maher, Nature 458(7234):97-101 (2009).

The terms "correlated" and "associated" are used interchangeably herein to refer to the association between two measurements (or measured entities). The disclosure provides genes or gene subsets, the expression levels of which are associated with clinical outcome. For example, the increased expression level of a gene may be positively correlated (positively associated) with a good or positive clinical outcome. Such a positive correlation may be demonstrated statistically in various ways, e.g. by a cancer recurrence hazard ratio less than one or by a cancer upgrading or upstaging odds ratio of less than one. In another example, the increased expression level of a gene may be negatively correlated (negatively associated) with a good or positive clinical outcome. In that case, for example, the patient may experience a cancer recurrence or upgrading/upstaging of the cancer, and this may be demonstrated statistically in various ways, e.g., a hazard ratio greater than 1 or an odds ratio greater than one. "Correlation" is also used herein to refer to the strength of association between the expression levels of two different genes, such that the expression level of a first gene can be substituted with an expression level of a second gene in a given algorithm if their expression levels are highly correlated. Such "correlated expression" of two genes that are substitutable in an algorithm are usually gene expression levels that are positively correlated with one another, e.g., if increased expression of a first gene is positively correlated with an outcome (e.g., increased likelihood of good clinical outcome), then the second gene that is co-expressed and exhibits correlated expression with the first gene is also positively correlated with the same outcome.

The terms "co-express" and "co-expressed", as used herein, refer to a statistical correlation between the amounts of different transcript sequences across a population of different patients. Pairwise co-expression may be calculated by various methods known in the art, e.g., by calculating Pearson correlation coefficients or Spearman correlation coefficients. Co-expressed gene cliques may also be identified by seeding and stacking the maximal clique enumeration (MCE) described in Example 4 herein. An analysis of co-expression may be calculated using normalized expression data. Genes within the same gene subset are also considered to be co-expressed.

A "computer-based system" refers to a system of hardware, software, and data storage medium used to analyze information. The minimum hardware of a patient computer-based system comprises a central processing unit (CPU), and hardware for data input, data output (e.g., display), and data storage. An ordinarily skilled artisan can readily appreciate that any currently available computer-based systems and/or components thereof are suitable for use in connection with the methods of the present disclosure. The data storage medium may comprise any manufacture comprising a recording of the present information as described above, or a memory access device that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Algorithm-Based Methods and Gene Subsets

The present invention provides an algorithm-based molecular diagnostic assay for predicting a clinical outcome for a patient with prostate cancer. The expression level of one or more genes may be used alone or arranged into functional gene subsets to calculate a quantitative score that can be used to predict the likelihood of a clinical outcome. The algorithm-based assay and associated information provided by the practice of the methods of the present invention facilitate optimal treatment decision-making in prostate cancer. For example, such a clinical tool would enable physicians to identify patients who have a low likelihood of having an aggressive cancer and therefore would not need RP, or who have a high likelihood of having an aggressive cancer and therefore would need RP.

As used herein, a "quantitative score" is an arithmetically or mathematically calculated numerical value for aiding in simplifying or disclosing or informing the analysis of more complex quantitative information, such as the correlation of certain expression levels of the disclosed genes or gene subsets to a likelihood of a clinical outcome of a prostate cancer patient. A quantitative score may be determined by the application of a specific algorithm. The algorithm used to calculate the quantitative score in the methods disclosed herein may group the expression level values of genes. The grouping of genes may be performed at least in part based on knowledge of the relative contribution of the genes according to physiologic functions or component cellular characteristics, such as in the groups discussed herein. A quantitative score may be determined for a gene group ("gene group score"). The formation of groups, in addition, can facilitate the mathematical weighting of the contribution of various expression levels of genes or gene subsets to the quantitative score. The weighting of a gene or gene group representing a physiological process or component cellular characteristic can reflect the contribution of that process or characteristic to the pathology of the cancer and clinical outcome, such as recurrence or upgrading/upstaging of the cancer. The present invention provides a number of algorithms for calculating the quantitative scores, for example, as set forth in Table 4. In an embodiment of the invention, an increase in the quantitative score indicates an increased likelihood of a negative clinical outcome.

In an embodiment, a quantitative score is a "recurrence score," which indicates the likelihood of a cancer recurrence, upgrading or upstaging of a cancer, adverse pathology, non-organ-confined disease, high-grade disease, and/or highgrade or non-organ-confined disease. An increase in the recurrence score may correlate with an increase in the likelihood of cancer recurrence, upgrading or upstaging of a cancer, adverse pathology, non-organ-confined disease, high-grade disease, and/or highgrade or non-organ-confined disease.

The gene subsets of the present invention include an ECM gene group, migration gene group, androgen gene group, proliferation gene group, epithelia gene group, and stress gene group.

The gene subsets referred to herein as the "ECM gene group," "stromal gene group," and "stromal response gene group" are used interchangeably and include genes that are synthesized predominantly by stromal cells and are involved in stromal response and genes that co-express with the genes of the ECM gene group. "Stromal cells" are referred to herein as connective tissue cells that make up the support structure of biological tissues. Stromal cells include fibroblasts, immune cells, pericytes, endothelial cells, and inflammatory cells. "Stromal response" refers to a desmoplastic response of the host tissues at the site of a primary tumor or invasion. See, e.g., E. Rubin, J. Farber, Pathology, 985-986 (end Ed. 1994). The ECM gene group includes, for example, ASPN, SFRP4, BGN, THBS2, INHBA, COL1A1, COL3A1, COL1A2, SPARC, COL8A1, COL4A1, FN1, FAP, and COL5A2, and co-expressed genes thereof. Exemplary co-expressed genes include the genes and/or gene cliques shown in Table 8.

The gene subsets referred to herein as the "migration gene group" or "migration regulation gene group" or "cytoskeletal gene group" or "cellular organization gene group" are used interchangeably and include genes and co-expressed genes that are part of a dynamic microfilament network of actin and accessory proteins and that provide intracellular support to cells, generate the physical forces for cell movement and cell division, as well as facilitate intracellular transport of vesicles and cellular organelle. The migration gene group includes, for example, BIN1, IGF1, C7, GSN, DES, TGFB1I1, TPM2, VCL, FLNC, ITGA7, COL6A1, PPP1R12A, GSTM1, GSTM2, PAGE4, PPAP2B, SRD5A2, PRKCA, IGFBP6, GPM6B, OLFML3, and HLF, and co-expressed genes thereof. Exemplary co-expressed genes and/or gene cliques are provided in Table 9.

The gene subset referred to herein as the "androgen gene group," "PSA gene group," and "PSA regulation gene group" are used interchangeably and include genes that are members of the kallikrein family of serine proteases (e.g. kallikrein 3 [PSA]), and genes that co-express with genes of the androgen gene group. The androgen gene group includes, for example, FAM13C and KLK2, and co-expressed genes thereof. The androgen gene group may further comprise AZGP1 and SRD5A2, and co-expressed genes thereof.

The gene subsets referred to herein as the "proliferation gene group" and "cell cycle gene group" are used interchangeably and include genes that are involved with cell cycle functions and genes that co-express with genes of the proliferation gene group. "Cell cycle functions" as used herein refers to cell proliferation and cell cycle control, e.g., checkpoint/G1 to S phase transition. The proliferation gene group thus includes, for example, CDC120, TPX2, UBE2T, MYBL2, and CDKN2C, and co-expressed genes thereof. Exemplary co-expressed genes and/or gene cliques are provided in Table 10.

The gene subsets referred to herein as the "epithelia gene group" and "basal epithelia gene group" are used interchangeably and include genes that are expressed during the differentiation of a polarized epithelium and that provide intracellular structural integrity to facilitate physical interactions with neighboring epithelial cells, and genes that co-express with genes of the epithelia gene group. The epithelia gene group includes, for example, CYP3A5, KRT15, KRT5, LAMB3, and SDC1 and co-expressed genes thereof.

The gene subset referred to herein as the "stress gene group," "stress response gene group," and "early response gene group" are used interchangeably and includes genes and co-expressed genes that are transcription factors and DNA-binding proteins activated rapidly and transiently in response to cellular stress and other extracellular signals. These factors, in turn, regulate the transcription of a diverse range of genes. The stress gene group includes, for example, DUSP1, EGR1, FOS, JUN, EGR3, GADD45B, and ZFP36, and co-expressed genes thereof. Exemplary co-expressed genes and/or gene cliques are provided in Table 11.

Expression levels of other genes and their co-expressed genes may be used with one more of the above gene subsets to predict a likelihood of a clinical outcome of a prostate cancer patient. For example, the expression level of one or more genes selected from the 81 genes of FIG. 1 or Table 1A or 1B that do not fall within any of the disclosed gene subsets may be used with one or more of the disclosed gene subsets. In an embodiment of the invention, one or more of STAT5B, NFAT5, AZGP1, ANPEP, IGFBP2, SLC22A3, ERG, AR, SRD5A2, GSTM1, and GSTM2 may be used in one or more gene subsets described above to predict a likelihood of a clinical outcome.

The present invention also provides methods to determine a threshold expression level for a particular gene. A threshold expression level may be calculated for a specific gene. A threshold expression level for a gene may be based on a normalized expression level. In one example, a $C_p$ threshold expression level may be calculated by assessing functional forms using logistic regression or Cox proportional hazards regression.

The present invention further provides methods to determine genes that co-express with particular genes identified by, e.g., quantitative RT-PCR (qRT-PCR), as validated biomarkers relevant to a particular type of cancer. The co-expressed genes are themselves useful biomarkers. The co-expressed genes may be substituted for the genes with which they co-express. The methods can include identifying gene cliques from microarray data, normalizing the microarray data, computing a pairwise Spearman correlation matrix for the array probes, filtering out significant co-expressed probes across different studies, building a graph, mapping the probe to genes, and generating a gene clique report. An exemplary method for identifying co-expressed genes is described in Example 3 below, and co-expressed genes identified using this method are provided in Tables 8-11. The expression levels of one or more genes of a gene clique may be used to calculate the likelihood that a patient with prostate cancer will experience a positive clinical outcome, such as a reduced likelihood of a cancer recurrence.

Any one or more combinations of gene groups may be assayed in the method of the present invention. For example, a stromal response gene group may be assayed, alone or in combination, with a cellular organization gene group, a proliferation gene group, and/or an androgen gene group. In addition, any number of genes within each gene group may be assayed.

In a specific embodiment of the invention, a method for predicting a clinical outcome for a patient with prostate cancer comprises measuring an expression level of at least one gene from a stromal response gene group, or a co-expressed gene thereof, and at least one gene from a cellular organization gene group, or a co-expressed gene thereof. In another embodiment, the expression level of at least two genes from a stromal response gene group, or a co-expressed gene thereof, and at least two genes from a cellular organization gene group, or a co-expressed gene thereof, are measured. In yet another embodiment, the expression levels of at least three genes are measured from each of the stromal response gene group and the cellular organization gene group. In a further embodiment, the expression levels of at least four genes are measured from each of the stromal response gene group and the cellular organization gene group. In another embodiment, the expression levels of at least five genes are measured from each of the stromal response gene group and the cellular organization gene group. In yet a further embodiment, the expression levels of at least six genes are measured from each of the stromal response gene group and the cellular organization gene group.

In another specific embodiment, the expression level of at least one gene from the stromal response gene group, or a co-expressed gene thereof, may be measured in addition to the expression level of at least one gene from an androgen gene group, or a co-expressed gene thereof. In a particular embodiment, the expression levels of at least three genes, or co-expressed genes thereof, from the stromal response gene group, and the expression level of at least one gene, or co-expressed gene thereof, from the androgen gene group may be measured.

In a further embodiment, the expression level of at least one gene each from the stromal response gene group, the androgen gene group, and the cellular organization gene group, or co-expressed genes thereof, may be measured. In a particular embodiment, the level of at least three genes from the stromal resonse gene group, at least one gene from the androgen gene group, and at least three genes from the cellular organization gene group may be measured. In another embodiment, the expression level of at least one gene each from the stromal response gene group, the androgen gene group, and the proliferation gene group, or co-expressed genes thereof, may be measured. In a particular embodiment, the level of at least three genes from the stromal response gene group, at least one gene from the androgen gene group, and at least one gene from the proliferation gene group may be measured. In either of these combinations, at least two genes from the androgen gene group may also be measured. In any of the combinations, at least four genes from the androgen gene group may also be measured.

In another embodiment, the expression level of at least one gene each from the stromal response gene group, the androgen gene group, the cellular organization gene group, and the proliferation gene group, or co-expressed genes thereof, may be measured. In a particular embodiment, the level of at least three genes from the stromal response gene group, at least three genes from the cellular organization gene group, at least one gene from the proliferation gene group, and at least two genes from the androgen gene group may be measured. In any of the embodiments, at least four genes from the androgen gene group may be measured.

Additionally, expression levels of one or more genes that do not fall within the gene subsets described herein may be measured with any of the combinations of the gene subsets described herein. Alternatively, any gene that falls within a gene subset may be analyzed separately from the gene subset, or in another gene subset. For example, the expression levels of at least one, at least two, at least three, or at least 4 genes may be measured in addition to the gene subsets described herein. In an embodiment of the invention, the additional gene(s) are selected from STAT5B, NFAT5, AZGP1, ANPEP, IGFBP2, SLC22A3, ERG, AR, SRD5A2, GSTM1, and GSTM2.

In a specific embodiment, the method of the invention comprises measuring the expression levels of the specific combinations of genes and gene subsets shown in Table 4. In a further embodiment, gene group score(s) and quantitative score(s) are calculated according to the algorithm(s) shown in Table 4.

Various technological approaches for determination of expression levels of the disclosed genes are set forth in this specification, including, without limitation, RT-PCR, microarrays, high-throughput sequencing, serial analysis of gene expression (SAGE) and Digital Gene Expression (DGE), which will be discussed in detail below. In particular aspects, the expression level of each gene may be determined in relation to various features of the expression products of the gene including exons, introns, protein epitopes and protein activity.

The expression product that is assayed can be, for example, RNA or a polypeptide. The expression product may be fragmented. For example, the assay may use primers that are complementary to target sequences of an expression product and could thus measure full transcripts as well as those fragmented expression products containing the target sequence. Further information is provided in Table A.

The RNA expression product may be assayed directly or by detection of a cDNA product resulting from a PCR-based amplification method, e.g., quantitative reverse transcription polymerase chain reaction (qRT-PCR). (See e.g., U.S. Pat. No. 7,587,279). Polypeptide expression product may be assayed using immunohistochemistry (IHC) by proteomics techniques. Further, both RNA and polypeptide expression products may also be assayed using microarrays.

Methods of Assaying Expression Levels of a Gene Product

Methods of gene expression profiling include methods based on hybridization analysis of polynucleotides, methods based on sequencing of polynucleotides, and proteomics-based methods. Exemplary methods known in the art for the quantification of RNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription PCR (RT-PCR) (Weis et al., Trends in Genetics 8:263-264 (1992)). Antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). Other methods known in the art may be used.

Reverse Transcription PCR (RT-PCR)

Typically, mRNA is isolated from a test sample. The starting material is typically total RNA isolated from a human tumor, usually from a primary tumor. Optionally, normal tissues from the same patient can be used as an internal control. Such normal tissue can be histologically-appearing normal tissue adjacent to a tumor. mRNA can be extracted from a tissue sample, e.g., from a sample that is fresh, frozen (e.g. fresh frozen), or paraffin-embedded and fixed (e.g. formalin-fixed).

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The sample containing the RNA is then subjected to reverse transcription to produce cDNA from the RNA template, followed by exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

PCR-based methods use a thermostable DNA-dependent DNA polymerase, such as a Taq DNA polymerase. For example, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction product. A third oligonucleotide, or probe, can be designed to facilitate detection of a nucleotide sequence of the amplicon located between the hybridization sites the two PCR primers. The probe can be detectably labeled, e.g., with a reporter dye, and can further be provided with both a fluorescent dye, and a quencher fluorescent dye, as in a Taqman® probe configuration. Where a Taqman® probe is used, during the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, high-throughput platforms such as the ABI PRISM 7700 Sequence Detection System® (Perkin-Elmer-Applied Biosystems, Foster City, Calif., USA), or Lightcycler (Roche Molecular Biochemicals, Mannheim, Germany). In a preferred embodiment, the procedure is run on a LightCycler® 480 (Roche Diagnostics) real-time PCR system, which is a microwell plate-based cycler platform.

5'-Nuclease assay data are commonly initially expressed as a threshold cycle ("Ct"). Fluorescence values are recorded during every cycle and represent the amount of product amplified to that point in the amplification reaction. The threshold cycle (Ct) is generally described as the point when the fluorescent signal is first recorded as statistically significant. Alternatively, data may be expressed as a crossing point ("Cp"). The Cp value is calculated by determining the second derivatives of entire qPCR amplification curves and their maximum value. The Cp value represents the cycle at which the increase of fluorescence is highest and where the logarithmic phase of a PCR begins.

To minimize errors and the effect of sample-to-sample variation, RT-PCR is usually performed using an internal standard. The ideal internal standard gene (also referred to as a reference gene) is expressed at a quite constant level among cancerous and non-cancerous tissue of the same origin (i.e., a level that is not significantly different among normal and cancerous tissues), and is not significantly affected by the experimental treatment (i.e., does not exhibit a significant difference in expression level in the relevant tissue as a result of exposure to chemotherapy), and expressed at a quite constant level among the same tissue taken from different patients. For example, reference genes useful in the methods disclosed herein should not exhibit significantly different expression levels in cancerous prostate as compared to normal prostate tissue. Exemplary reference genes used for normalization comprise one or more of the following genes: AAMP, ARF1, ATP5E, CLTC, GPS1, and PGK1. Gene expression measurements can be normalized relative to the mean of one or more (e.g., 2, 3, 4, 5, or more) reference genes. Reference-normalized expression measurements can range from 2 to 15, where a one unit increase generally reflects a 2-fold increase in RNA quantity.

Real time PCR is compatible both with quantitative competitive PCR, where an internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

The steps of a representative protocol for use in the methods of the present disclosure use fixed, paraffin-embedded tissues as the RNA source. For example, mRNA isolation, purification, primer extension and amplification can be performed according to methods available in the art. (see, e.g., Godfrey et al. J. Molec. Diagnostics 2: 84-91 (2000); Specht et al., Am. J. Pathol. 158: 419-29 (2001)). Briefly, a representative process starts with cutting about 10 µm thick sections of paraffin-embedded tumor tissue samples. The RNA is then extracted, and protein and DNA depleted from the RNA-containing sample. After analysis of the RNA concentration, RNA is reverse transcribed using gene-specific primers followed by RT-PCR to provide for cDNA amplification products.

Design of Intron-Based PCR Primers and Probes

PCR primers and probes can be designed based upon exon or intron sequences present in the mRNA transcript of the gene of interest. Primer/probe design can be performed using publicly available software, such as the DNA BLAT software developed by Kent, W. J., Genome Res. 12(4):656-64 (2002), or by the BLAST software including its variations.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. See S. Rrawetz, S. Misener, Bioinformatics Methods and Protocols: Methods in Molecular Biology, pp. 365-386 (Humana Press).

Other factors that can influence PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases, and exhibit Tm's between 50 and 80 OC, e.g. about 50 to 70° C.

For further guidelines for PCR primer and probe design see, e.g. Dieffenbach, C W. et al, "General Concepts for PCR Primer Design" in: PCR Primer, A Laboratory Manual, Cold Spring Harbor Laboratory Press. New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods MoI. Biol. 70:520-527 (1997), the entire disclosures of which are hereby expressly incorporated by reference.

Table A provides further information concerning the primer, probe, and amplicon sequences associated with the Examples disclosed herein.

MassARRAY® System

In MassARRAY-based methods, such as the exemplary method developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivarion of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059-3064 (2003).

Other PCR-Based Methods

Further PCR-based techniques that can find use in the methods disclosed herein include, for example, BeadArray® technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression® (BADGE), using the commercially available LuminexlOO LabMAP® system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003).

Microarrays

Expression levels of a gene or microArray of interest can also be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from RNA of a test sample. As in the RT-PCR method, the source of RNA typically is total RNA isolated from a tumor sample, and optionally from normal tissue of the same patient as an internal control or cell lines. RNA can be extracted, for example, from frozen or archived paraffin-embedded and fixed (e.g. formalin-fixed) tissue samples.

For example, PCR amplified inserts of cDNA clones of a gene to be assayed are applied to a substrate in a dense array. Usually at least 10,000 nucleotide sequences are applied to the substrate. For example, the microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After washing under stringent conditions to remove non-specifically bound probes, the chip is scanned by confocal laser microscopy or by another detection method, such as a CCD camera. Quantitation of hybridization of each arrayed element allows for assessment of corresponding RNA abundance.

With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et at, Proc. Natl. Acad. ScL USA 93(2):106-149 (1996)). Microarray analysis can be performed by commercially available equipment, following manufacturer's protocols, such as by using the Affymetrix GenChip® technology, or Incyte's microarray technology.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484-487 (1995); and Velculescu et al., Cell 88:243-51 (1997).

Gene Expression Analysis by Nucleic Acid Sequencing

Nucleic acid sequencing technologies are suitable methods for analysis of gene expression. The principle underlying these methods is that the number of times a cDNA sequence is detected in a sample is directly related to the relative expression of the RNA corresponding to that sequence. These methods are sometimes referred to by the term Digital Gene Expression (DGE) to reflect the discrete numeric property of the resulting data. Early methods applying this principle were Serial Analysis of Gene Expression (SAGE) and Massively Parallel Signature Sequencing (MPSS). See, e.g., S. Brenner, et al., Nature Biotechnology 18(6):630-634 (2000). More recently, the advent of "next-generation" sequencing technologies has made DGE simpler, higher throughput, and more affordable. As a result, more laboratories are able to utilize DGE to screen the expression of more genes in more individual patient samples than previously possible. See, e.g., J. Marioni, Genome Research 18(9):1509-1517 (2008); R. Morin, Genome Research 18(4):610-621 (2008); A. Mortazavi, Nature Methods 5(7):621-628 (2008); N. Cloonan, Nature Methods 5(7):613-619 (2008).

Isolating RNA from Body Fluids

Methods of isolating RNA for expression analysis from blood, plasma and serum (see, e.g., K. Enders, et al., Clin Chem 48, 1647-53 (2002) (and references cited therein) and from urine (see, e.g., R. Boom, et al., J Clin Microbiol. 28, 495-503 (1990) and references cited therein) have been described.

Immunohistochemistry

Immunohistochemistry methods are also suitable for detecting the expression levels of genes and applied to the method disclosed herein. Antibodies (e.g., monoclonal antibodies) that specifically bind a gene product of a gene of interest can be used in such methods. The antibodies can be detected by direct labeling of the antibodies themselves, for example, with radioactive labels, fluorescent labels, hapten' labels such as, biotin, or an enzyme such as horse radish peroxidase or alkaline phosphatase. Alternatively, unlabeled primary antibody can be used in conjunction with a labeled secondary antibody specific for the primary antibody. Immunohistochemistry protocols and kits are well known in the art and are commercially available.

Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics.

General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles. (See, e.g., T. E. Godfrey, et al. J. Molec. Diagnostics 2: 84-91 (2000); K. Specht et al., Am. J. Pathol. 158: 419-29 (2001), M. Cronin, et al., Am J Pathol 164:35-42 (2004)). Briefly, a representative process starts with cutting a tissue sample section (e.g. about 10 μm thick sections of a paraffin-embedded tumor tissue sample). The RNA is then extracted, and protein and DNA are removed. After analysis of the RNA concentration, RNA repair is performed if desired. The sample can then be subjected to analysis, e.g., by reverse transcribed using gene specific promoters followed by RT-PCR.

Statistical Analysis of Expression Levels in Identification of Genes

One skilled in the art will recognize that there are many statistical methods that may be used to determine whether there is a significant relationship between a clinical outcome of interest (e.g., recurrence) and expression levels of a marker gene as described here. In an exemplary embodiment, the present invention includes three studies. The first study is a stratified cohort sampling design (a form of case-control sampling) using tissue and data from prostate cancer patients. Selection of specimens was stratified by clinical T-stage (T1, T2), year of surgery (<1993, ≥1993), and prostatectomy Gleason Score (low/intermediate, high). All patients with clinical recurrence were selected and a stratified random sample of patients who did not experience a clinical recurrence was selected. For each patient, up to two enriched tumor specimens and one normal-appearing tissue sample were assayed. The second study used a subset of 70 patients from the first study from whom matched prostate biopsy tumor tissue was assayed. The third study includes all patients (170 evaluable patients) who had surgery for their prostate cancer between 1999 and 2010 at the Cleveland Clinic (CC) and had Low or Intermediate risk (by AUA) clinically localized prostate cancer who might have been reasonable candidates for active surveillance but who underwent RP at CC within 6 months of the diagnosis of prostate cancer by biopsy. Biopsy tumor tissue from these patients was assayed.

All hypothesis tests were reported using two-sided p-values. To investigate if there is a significant relationship of outcomes (eg. clinical recurrence-free interval (cRFI), biochemical recurrence-free interval (bRFI), prostate cancer-specific survival (PCSS), overall survival (OS)) with individual genes, and demographic or clinical covariates), Cox Proportional Hazards (PH) models using maximum weighted pseudo partial-likelihood estimators were used and p-values from Wald tests of the null hypothesis that the hazard ratio (HR) is one are reported. To investigate if there is a significant relationship between individual genes and Gleason pattern of a particular sample, ordinal logistic regression models using maximum weighted pseudolikelihood methods were used and p-values from Wald tests of the null hypothesis that the odds ratio (OR) is one are reported. To investigate if there is a significant relationship between individual genes and upgrading and/or upstaging or adverse pathology at RP, logistic regression models using maximum weighted pseudolikelihood methods were used and p-values from Wald tests of the null hypothesis that the odds ratio (OR) is one are reported.

Coexpression Analysis

In an exemplary embodiment, the joint correlation of gene expression levels among prostate cancer specimens under study may be assessed. For this purpose, the correlation structures among genes and specimens may be examined through hierarchical cluster methods. This information may be used to confirm that genes that are known to be highly correlated in prostate cancer specimens cluster together as expected. Only genes exhibiting a nominally significant (unadjusted p<0.05) relationship with cRFI in the univariate Cox PH regression analysis are included in these analyses.

One skilled in the art will recognize that many co-expression analysis methods now known or later developed will fall within the scope and spirit of the present invention. These methods may incorporate, for example, correlation coefficients, co-expression network analysis, clique analysis, etc., and may be based on expression data from RT-PCR, microarrays, sequencing, and other similar technologies. For example, gene expression clusters can be identified using pair-wise analysis of correlation based on Pearson or Spearman correlation coefficients. (See, e.g., Pearson K. and Lee A., Biometrika 2, 357 (1902); C. Spearman, Amer. J. Psychol 15:72-101 (1904); J. Myers, A. Well, Research Design and Statistical Analysis, p. 508 (2nd Ed., 2003).) An exemplary method for identifying co-expressed genes is described in Example 3 below.

Normalization of Expression Levels

The expression data used in the methods disclosed herein can be normalized. Normalization refers to a process to correct for (normalize away), for example, differences in the amount of RNA assayed and variability in the quality of the RNA used, to remove unwanted sources of systematic variation in Ct or Cp measurements, and the like. With respect to RT-PCR experiments involving archived fixed paraffin embedded tissue samples, sources of systematic variation are known to include the degree of RNA degradation relative to the age of the patient sample and the type of fixative used to store the sample. Other sources of systematic variation are attributable to laboratory processing conditions.

Assays can provide for normalization by incorporating the expression of certain normalizing genes, which do not significantly differ in expression levels under the relevant conditions. Exemplary normalization genes disclosed herein include housekeeping genes. (See, e.g., E. Eisenberg, et al., Trends in Genetics 19(7):362-365 (2003).) Normalization can be based on the mean or median signal (Ct or Cp) of all of the assayed genes or a large subset thereof (global normalization approach). In general, the normalizing genes, also referred to as reference genes, are typically genes that are known not to exhibit meaningfully different expression in prostate cancer as compared to non-cancerous prostate tissue, and track with various sample and process conditions, thus provide for normalizing away extraneous effects.

In exemplary embodiments, one or more of the following genes are used as references by which the mRNA expression data is normalized: AAMP, ARF1, ATP5E, CLTC, GPS1, and PGK1. The calibrated weighted average CT or Cp measurements for each of the prognostic and predictive genes may be normalized relative to the mean of five or more reference genes.

Those skilled in the art will recognize that normalization may be achieved in numerous ways, and the techniques described above are intended only to be exemplary, not exhaustive.

Standardization of Expression Levels

The expression data used in the methods disclosed herein can be standardized. Standardization refers to a process to effectively put all the genes on a comparable scale. This is performed because some genes will exhibit more variation (a broader range of expression) than others. Standardization is performed by dividing each expression value by its standard deviation across all samples for that gene. Hazard ratios are then interpreted as the proportional change in the hazard for the clinical endpoint (clinical recurrence, biological recurrence, death due to prostate cancer, or death due to any cause) per 1 standard deviation increase in expression.

Kits of the Invention

The materials for use in the methods of the present invention are suited for preparation of kits produced in accordance with well-known procedures. The present disclosure thus provides kits comprising agents, which may include gene-specific or gene-selective probes and/or primers, for quantifying the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microliter plates suitable for use in an automated implementation of the method), each with one or more of the various materials or reagents (typically in concentrated form) utilized in the methods, including, for example, chromatographic columns, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase). Mathematical algorithms used to estimate or quantify prognostic or predictive information are also properly potential components of kits.

Reports

The methods of this invention, when practiced for commercial diagnostic purposes, generally produce a report or summary of information obtained from the herein-described methods. For example, a report may include information concerning expression levels of one or more genes, classification of the tumor or the patient's risk of recurrence, the patient's likely prognosis or risk classification, clinical and pathologic factors, and/or other information. The methods and reports of this invention can further include storing the report in a database. The method can create a record in a database for the subject and populate the record with data. The report may be a paper report, an auditory report, or an electronic record. The report may be displayed and/or stored on a computing device (e.g., handheld device, desktop computer, smart device, website, etc.). It is contemplated that the report is provided to a physician and/or the patient. The receiving of the report can further include establishing a network connection to a server computer that includes the data and report and requesting the data and report from the server computer.

Computer Program

The values from the assays described above, such as expression data, can be calculated and stored manually. Alternatively, the above-described steps can be completely or partially performed by a computer program product. The present invention thus provides a computer program product including a computer readable storage medium having a computer program stored on it. The program can, when read by a computer, execute relevant calculations based on values obtained from analysis of one or more biological samples from an individual (e.g., gene expression levels, normalization, standardization, thresholding, and conversion of values from assays to a score and/or text or graphical depiction of tumor stage and related information). The computer program product has stored therein a computer program for performing the calculation.

The present disclosure provides systems for executing the program described above, which system generally includes: a) a central computing environment; b) an input device, operatively connected to the computing environment, to receive patient data, wherein the patient data can include, for example, expression level or other value obtained from an assay using a biological sample from the patient, or microarray data, as described in detail above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates an expression score, thresholding, or other functions described herein. The methods provided by the present invention may also be automated in whole or in part.

Having described the invention, the same will be more readily understood through reference to the following Examples, which are provided by way of illustration, and are not intended to limit the invention in any way.

EXAMPLES

Example 1: Selection of 81 Genes for Algorithm Development

A gene identification study to identify genes associated with clinical recurrence, biochemical recurrence and/or death from prostate cancer is described in U.S. Provisional Application Nos. 61/368,217, filed Jul. 27, 2010; 61/414,310, filed Nov. 16, 2010; and 61/485,536, filed May 12, 2011, and in U.S. Pub. No. 20120028264, filed Jul. 25, 2011, and published Feb. 2, 2012 (all of which are hereby incorporated by reference). RT-PCR analysis was used to determine RNA expression levels for 732 genes and reference genes in prostate cancer tissue and surrounding normal appearing tissue (NAT) in patients with early-stage prostate cancer treated with radical prostatectomy. Genes significantly associated ($p<0.05$) with clinical recurrence-free interval (cRFI), biochemical recurrence-free interval (bRFI), prostate cancer-specific survival (PCSS), and upgrading/upstaging were determined.

From the genes that were identified as being associated with outcome, 81 genes were selected for subsequent algorithm development. The primers, probes, and amplicon sequences of the 81 genes (and 5 reference genes) are listed in Table A. The genes selected were among the most prognostic with respect to cRFI and other properties and shown in Tables 1A-1B. Other properties considered were: 1) Strongest genes with respect to the regression to the mean corrected standardized hazard ratio for the association of gene expression and cRFI in the primary Gleason pattern tumor; 2) Consistency in association (hazard ratio) with cRFI using the highest Gleason pattern tumor; 3) Associated with prostate-cancer specific survival (PCSS); 4) Strong hazard ratio after adjustment for The University of San Francisco Cancer of the Prostate Risk Assessment (CAPRA) (Cooperberg et al., J. Urol. 173:1983-1942, 2005); 5) Statistically significant odds ratio for the association between gene expression and surgical Gleason pattern of the tumor; 6) Large overall variability with greater between-patient variability than within-patient variability preferable; and 7) Highly expressed.

The true discovery rate degree of association (TDRDA) method (Crager, Stat Med. 2010 January 15; 29(1):33-45.) was used in the analysis of gene expression and cRFI and results are shown in Table 1A. The true discovery rate is the counterpart to the false discovery rate. Univariate Cox PH regression models were fit and the TDRDA method was used to correct estimated standardized hazard ratios for regression to the mean (RM) and and assess false discovery rates for identification of genes with absolute standardized hazard ratio of at least a specified level. The false discovery rates were controlled at 10%. The TDRDA method identifies sets of genes among which a specified proportion are expected to have an absolute association (here, the absolute standardized hazard ratio) of a specified degree or more. This leads to a gene ranking method that uses the maximum lower bound (MLB) degree of association for which each gene belongs to a TDRDA set. Estimates of each gene's actual degree of association with approximate correction for "selection bias" due to regression to the mean can be derived using simple bivariate normal theory and Efron and Tibshirani's empirical Bayes approach. Efron, *Annals of Applied Statistics* 2:197-223 (2008); Efron and Tibshirani. *Genetic Epidemiology* 23: 70-86. Table 1A shows the RM-corrected estimate of the standardized hazard ratio and the MLB for each gene using either the primary Gleason pattern (PGP) or highest Gleason pattern (HGP) sample gene expression. Genes marked with a direction of association of −1 are associated with a reduced likelihood of clinical recurrence, while those marked with a direction of association of 1 are associated with an increased likelihood of clinical recurrence.

Within patient and between patient variance components were estimated using a mixed model treating the patient effect as random. The overall mean and standard deviation of normalized gene expression as well as within- and between-patient components of variance are shown in Table 1A.

Univariate Cox PH regression models using maximum weighted partial pseudolikelihood estimation were used to estimate the association between gene expression and prostate cancer specific-survival (PCSS). The standardized hazard ratio (HR), p-value and q-value using Storey's FDR method are reported in Table 1B. Storey, *Journal of the Royal Statistical Society*, Series B 64:479-498 (2002). The q-value can be interpreted as the empirical Bayes posterior probability given the data that the gene identified is a false discovery, that is, the probability that it has no association with clinical recurrence.

Univariate ordinal logistic regression models were used to estimate the association between gene expression and the Gleason pattern of the primary Gleason pattern tumor (3, 4, 5). The standardized odds ratio (OR), p-value and q-value using Storey's FDR method are reported in Table 1B.

FIG. 1 shows an example of a dendrogram depicting the association of the 81 genes. The y-axis corresponds to the average distance between clusters measured as 1-Pearson r.

The smaller the number (distance measure), the more highly correlated the genes. The amalgamation method is weighted pair-group average. Genes that were co-expressed were identified from the dendrogram and are grouped into gene groups. Based on FIG. 1, the genes from the Gene Identification study were formed into the following gene groups or subsets:

Cellular organization gene group (BIN1; IGF1; C7; GSN; DES; TGFB1I1; TPM2; VCL; FLNC; ITGA7; COL6A1; PPP1R12A; GSTM1; GSTM2; PAGE4; PPAP2B; SRD5A2; PRKCA; IGFBP6; GPM6B; OLFML3; HLF)

Basal epithelia gene group (CYP3A5; KRT15; KRT5; LAMB3; SDC1)

Stress response gene group (DUSP1; EGR1; FOS; JUN; EGR3; GADD45B; ZFP36)

Androgen gene group (FAM13C; KLK2; AZGP1; SRD5A2)

Stromal gene group (ASPN; SFRP4; BGN; THBS2; INHBA; COL1A1; COL3A1; COL1A2; SPARC; COL8A1; COL4A1; FN1; FAP; COL5A2)

Proliferation gene group (CDC120; TPX2; UBE2T; MYBL2; CDKN2C)

TABLE 1A

| GENE | Mean normalized cp | SD normalized CP | Between-patient variance | Within-patient variance | Total variance | Association with cR in PGP sample | | | Association with cR in HGP sample | | |
|---|---|---|---|---|---|---|---|---|---|---|---|
| | | | | | | Direction of Association | Absolute RM Corrected HR | MLB | Direction of Association | Absolute RM Corrected HR | MLB |
| ARF1 | 11.656805 | 0.2475574 | 0.04488 | 0.01646 | 0.0613399 | −1 | 1.0849132 | — | −1 | 1.2006385 | 1.0397705 |
| ATP5E | 10.896515 | 0.2667133 | 0.05141 | 0.01979 | 0.0711992 | 1 | 1.2599111 | 1.0908967 | 1 | 1.3877428 | 1.165325 |
| CLTC | 10.597008 | 0.1780634 | 0.01554 | 0.01619 | 0.0317257 | 1 | 1.0896793 | 1.002002 | 1 | 1.2292343 | 1.0554846 |
| GPS1 | 9.2927019 | 0.2169116 | 0.03181 | 0.01528 | 0.0470897 | 1 | 1.0064191 | — | −1 | 1.1089053 | — |
| PGK1 | 8.3680642 | 0.2655009 | 0.04957 | 0.02099 | 0.0705517 | 1 | 1.1174152 | 1.0151131 | 1 | 1.2149168 | 1.0607752 |
| ASPN | 5.4846081 | 1.1701993 | 0.4981 | 0.8719 | 1.3699944 | 1 | 1.7716283 | 1.4276075 | 1 | 1.7114564 | 1.4007391 |
| BGN | 11.299746 | 0.7357491 | 0.3259 | 0.2159 | 0.5417276 | 1 | 1.6133066 | 1.3271052 | 1 | 1.7312777 | 1.4007391 |
| COL1A1 | 11.325411 | 0.8840402 | 0.4748 | 0.3073 | 0.7821127 | 1 | 1.6162028 | 1.3284329 | 1 | 1.7982985 | 1.4304656 |
| COL1A2 | 10.093055 | 0.8232027 | 0.4321 | 0.2461 | 0.6781941 | 1 | 1.1319748 | 1.0222438 | 1 | 1.3449362 | 1.136553 |
| COL3A1 | 11.007109 | 0.7944239 | 0.352 | 0.2795 | 0.6315424 | 1 | 1.5695255 | 1.2969301 | 1 | 1.7133767 | 1.4007391 |
| COL4A1 | 7.8408604 | 0.6731713 | 0.2393 | 0.2142 | 0.4534598 | 1 | 1.3297169 | 1.14225 | 1 | 1.4292283 | 1.1996142 |
| COL5A2 | 5.2708574 | 0.9571692 | 0.4 | 0.5166 | 0.9166661 | 1 | 1.1715343 | 1.0408108 | 1 | 1.1822568 | 1.0408108 |
| F2R | 7.0775127 | 1.0110657 | 0.5529 | 0.47 | 1.022934 | 1 | 1.5019815 | 1.2636445 | 1 | 1.4888813 | 1.2361479 |
| FAP | 5.0493366 | 1.1898915 | 0.6577 | 0.759 | 1.4166546 | 1 | 1.3007869 | 1.1162781 | 1 | 1.3882726 | 1.1641602 |
| FN1 | 9.5176438 | 0.7224014 | 0.3059 | 0.2163 | 0.5222401 | 1 | 1.0505668 | — | 1 | 1.1524617 | 1.0253151 |
| INHBA | 5.8059993 | 1.2653019 | 0.9629 | 0.6392 | 1.6021763 | 1 | 1.896185 | 1.4858693 | 1 | 2.1859455 | 1.7177237 |
| SFRP4 | 7.8225007 | 1.2053184 | 0.7997 | 0.6541 | 1.4537934 | 1 | 1.5382115 | 1.2763443 | 1 | 1.5692525 | 1.2969301 |
| SPARC | 10.544556 | 0.7978856 | 0.4311 | 0.206 | 0.6371517 | 1 | 1.3683299 | 1.1711662 | 1 | 1.6187451 | 1.3324242 |
| THBS2 | 4.7779897 | 1.0825934 | 0.7121 | 0.4608 | 1.1728864 | 1 | 1.5523887 | 1.2904616 | 1 | 1.6829249 | 1.3785056 |
| BIN1 | 7.8741434 | 0.840604 | 0.4445 | 0.2627 | 0.7071728 | −1 | 1.5631385 | 1.2930451 | −1 | 1.3294226 | 1.1185129 |
| C7 | 8.4895479 | 1.1083704 | 0.6917 | 0.5377 | 1.2293358 | −1 | 1.5658393 | 1.2687092 | −1 | 1.4724885 | 1.220182 |
| COL6A1 | 7.3615421 | 0.848837 | 0.3381 | 0.3828 | 0.7209474 | −1 | 1.5439152 | 1.2687092 | −1 | 1.2634411 | 1.0746553 |
| DES | 11.967287 | 0.896286 | 0.4101 | 0.3938 | 0.8038418 | −1 | 1.5007183 | 1.2386227 | −1 | 1.3032825 | 1.0963648 |
| FLNC | 8.6795128 | 1.0679528 | 0.572 | 0.5692 | 1.1412391 | −1 | 1.2696693 | 1.0650268 | −1 | 1.2353942 | 1.0491707 |
| GPM6B | 7.9402089 | 0.9453416 | 0.4441 | 0.4501 | 0.8942266 | −1 | 1.4471085 | 1.2056273 | −1 | 1.4931412 | 1.2386227 |
| GSN | 8.8308175 | 0.7789199 | 0.3756 | 0.2316 | 0.6071864 | −1 | 1.6223835 | 1.3073471 | −1 | 1.3639212 | 1.136553 |
| GSTM1 | 6.4175398 | 1.2720365 | 1.0519 | 0.5675 | 1.619374 | −1 | 1.5226009 | 1.2560853 | −1 | 1.5822193 | 1.2969301 |
| GSTM2 | 7.2950478 | 1.0014875 | 0.5069 | 0.4967 | 1.0036007 | −1 | 1.6694102 | 1.3284329 | −1 | 1.4815895 | 1.220182 |
| HLF | 5.0774106 | 0.9618562 | 0.4516 | 0.4741 | 0.9257242 | −1 | 1.6225351 | 1.2956338 | −1 | 1.5817614 | 1.2891718 |
| IGF1 | 7.6180418 | 1.1441945 | 0.7925 | 0.5177 | 1.3101729 | −1 | 1.4732764 | 1.2165269 | −1 | 1.6861196 | 1.359341 |
| IGFBP6 | 7.0089783 | 1.0816262 | 0.6302 | 0.5405 | 1.1707038 | −1 | 1.5534588 | 1.257342 | −1 | 1.1860594 | 1.0273678 |
| ITGA7 | 7.3299653 | 0.8913845 | 0.4034 | 0.3916 | 0.7950725 | −1 | 1.5556326 | 1.2636445 | −1 | 1.3587711 | 1.1308844 |
| OLFML3 | 8.1932023 | 0.8189012 | 0.4 | 0.2711 | 0.6710997 | −1 | 1.5254982 | 1.2649088 | −1 | 1.3364894 | 1.1263699 |
| PAGE4 | 7.406255 | 1.4889881 | 1.3023 | 0.9164 | 2.2187195 | −1 | 1.6316984 | 1.2969301 | −1 | 1.5178657 | 1.2435871 |
| PPAP2B | 8.8879191 | 0.7884647 | 0.3841 | 0.238 | 0.6221573 | −1 | 1.5664582 | 1.2649088 | −1 | 1.4703629 | 1.2068335 |
| PPP1R12A | 9.369152 | 0.5056735 | 0.1361 | 0.1198 | 0.2558759 | −1 | 1.4273047 | 1.1711662 | −1 | 1.3719705 | 1.1297541 |
| PRKCA | 7.4654299 | 0.7936779 | 0.2984 | 0.3319 | 0.6302916 | −1 | 1.4498244 | 1.1960207 | −1 | 1.2221961 | 1.0554846 |
| SRD5A2 | 5.7878904 | 1.2691925 | 0.8776 | 0.7343 | 1.6119317 | −1 | 1.8236528 | 1.4276075 | −1 | 1.723879 | 1.4007391 |
| VCL | 8.9766979 | 0.720267 | 0.2667 | 0.2524 | 0.5191126 | −1 | 1.526093 | 1.2423441 | −1 | 1.4080433 | 1.1525766 |
| TGFB1I1 | 8.2191469 | 0.7816114 | 0.3143 | 0.297 | 0.6113098 | −1 | 1.4793989 | 1.2104595 | −1 | 1.3608249 | 1.1229959 |
| TPM2 | 11.83198 | 0.8626062 | 0.4118 | 0.3328 | 0.7446062 | −1 | 1.5739312 | 1.2687092 | −1 | 1.4709656 | 1.2116705 |
| TPX2 | 4.552336 | 1.0856094 | 0.4888 | 0.6903 | 1.1791549 | 1 | 1.6454619 | 1.3444702 | 1 | 1.886703 | 1.4829005 |
| CDC20 | 3.5608774 | 0.7971167 | 0.1978 | 0.4378 | 0.6356438 | 1 | 1.431589 | 1.232445 | 1 | 1.568564 | 1.3271052 |
| CDKN2C | 3.5214932 | 0.6898842 | 0.137 | 0.3391 | 0.476113 | 1 | 1.4751885 | 1.257342 | 1 | 1.6210275 | 1.3485096 |
| MYBL2 | 3.7669784 | 0.981064 | 0.4061 | 0.5569 | 0.9629897 | 1 | 1.5421274 | 1.2969301 | 1 | 1.5553089 | 1.3086551 |
| UBE2T | 3.5015369 | 0.7220453 | 0.1927 | 0.3289 | 0.5215967 | 1 | 1.5156185 | 1.272521 | 1 | 1.2186754 | 1.0618365 |
| CYP3A5 | 4.5549862 | 1.3365744 | 0.5786 | 1.2085 | 1.7871462 | −1 | 1.851997 | 1.4276075 | −1 | 1.8669598 | 1.4304656 |
| KRT15 | 8.1889409 | 1.8188542 | 1.3539 | 1.956 | 3.3098961 | −1 | 1.4985779 | 1.2423441 | −1 | 1.7380356 | 1.4007391 |
| KRT5 | 7.046586 | 1.528426 | 0.8388 | 1.4983 | 2.3371203 | −1 | 1.4656121 | 1.2140963 | −1 | 1.6810573 | 1.3702593 |
| LAMB3 | 6.3356958 | 1.3451305 | 0.6358 | 1.1744 | 1.8101739 | −1 | 1.435434 | 1.1996142 | −1 | 1.5003356 | 1.2287532 |
| EGR1 | 12.925851 | 1.0521413 | 0.7737 | 0.3343 | 1.1079529 | −1 | 1.5840317 | 1.2687092 | −1 | 1.5773643 | 1.2801791 |
| FOS | 12.383619 | 1.1226481 | 0.8869 | 0.3746 | 1.2614295 | −1 | 1.580311 | 1.2687092 | −1 | 1.655218 | 1.3310925 |
| GADD45B | 8.8760029 | 1.2001535 | 0.893 | 0.5485 | 1.4414667 | −1 | 1.5331503 | 1.2460767 | −1 | 1.490302 | 1.220182 |
| JUN | 11.184249 | 1.027684 | 0.8099 | 0.2473 | 1.0571304 | −1 | 1.5816073 | 1.2649088 | −1 | 1.5652799 | 1.2649088 |
| ZFP36 | 12.472841 | 1.1025865 | 0.8095 | 0.4072 | 1.2167102 | −1 | 1.5169178 | 1.2423441 | −1 | 1.580749 | 1.2840254 |
| DUSP1 | 11.51936 | 0.8297195 | 0.439 | 0.25 | 0.6889744 | −1 | 1.3986201 | 1.1502738 | −1 | 1.40278 | 1.1525766 |

TABLE 1A-continued

| GENE | Mean normalized cp | SD normalized CP | Between-patient variance | Within-patient variance | Total variance | Association with cR in PGP sample | | | Association with cR in HGP sample | | |
|---|---|---|---|---|---|---|---|---|---|---|---|
| | | | | | | Direction of Association | Absolute RM Corrected HR | MLB | Direction of Association | Absolute RM Corrected HR | MLB |
| EGR3 | 9.7545461 | 1.3366461 | 1.2104 | 0.5778 | 1.7881414 | −1 | 1.5114362 | 1.2349124 | −1 | 1.4927024 | 1.2226248 |
| FAM13C | 7.4923611 | 0.9318455 | 0.58 | 0.2891 | 0.8690619 | −1 | 1.678403 | 1.3716303 | −1 | 1.7981441 | 1.4520843 |
| KLK2 | 14.718412 | 0.6677811 | 0.3087 | 0.1376 | 0.4463114 | −1 | 1.4443314 | 1.1936311 | −1 | 1.4966995 | 1.2361479 |
| ALDH1A2 | 5.8436909 | 1.0515294 | 0.4984 | 0.6079 | 1.1063379 | −1 | 1.5394232 | 1.2649088 | −1 | 1.817606 | 1.4304656 |
| AZGP1 | 9.3508493 | 1.4900096 | 1.6597 | 0.5625 | 2.2222058 | −1 | 1.6202418 | 1.329762 | −1 | 1.4723607 | 1.2398619 |
| ANPEP | 7.1080338 | 2.3433136 | 3.865 | 1.6309 | 5.4959682 | −1 | 1.5469141 | 1.257342 | −1 | 1.7787926 | 1.4035433 |
| AR | 8.3681098 | 0.5094853 | 0.1629 | 0.09684 | 0.2597757 | −1 | 1.0685968 | — | −1 | 1.1146402 | 1.004008 |
| BMP6 | 4.7641658 | 1.1079887 | 0.5639 | 0.6645 | 1.2283377 | 1 | 1.5010706 | 1.2649088 | 1 | 1.7140049 | 1.4007391 |
| CD276 | 8.9879201 | 0.5574321 | 0.168 | 0.1429 | 0.3109408 | 1 | 1.459777 | 1.2398619 | 1 | 1.6372299 | 1.3525612 |
| CD44 | 7.5506865 | 1.1157404 | 0.8611 | 0.3849 | 1.2459543 | −1 | 1.6840393 | 1.3444702 | −1 | 1.5715077 | 1.3008267 |
| COL8A1 | 7.1807327 | 0.9924731 | 0.529 | 0.4566 | 0.9856651 | 1 | 1.4782028 | 1.251071 | 1 | 1.6302371 | 1.3337573 |
| CSF1 | 5.604685 | 0.806592 | 0.2828 | 0.3678 | 0.6506271 | −1 | 1.4727627 | 1.2092496 | −1 | 1.3423853 | 1.1162781 |
| SRC | 7.4585136 | 0.6681318 | 0.2723 | 0.1745 | 0.446735 | −1 | 1.4782469 | 1.2435871 | −1 | 1.5104712 | 1.2687092 |
| CSRP1 | 12.967068 | 0.8434745 | 0.267 | 0.4448 | 0.711785 | −1 | 1.2323596 | 1.0607752 | −1 | 1.2436215 | 1.0639623 |
| DPP4 | 6.5096496 | 1.228945 | 0.9313 | 0.5802 | 1.5114514 | −1 | 1.5818046 | 1.2930451 | −1 | 1.539425 | 1.2788996 |
| TNFRSF10B | 5.8731042 | 0.836448 | 0.3338 | 0.3663 | 0.7000558 | −1 | 1.5759506 | 1.2687092 | −1 | 1.4449471 | 1.2032184 |
| ERG | 7.2194906 | 2.2910776 | 4.1737 | 1.0805 | 5.2541704 | 1 | 1.0907212 | 1.0030045 | 1 | 1.0828357 | — |
| FAM107A | 4.9863267 | 1.128037 | 0.6041 | 0.6691 | 1.2732255 | −1 | 1.7326232 | 1.3539145 | −1 | 1.5773305 | 1.2801791 |
| IGFBP2 | 9.855496 | 0.7862553 | 0.4734 | 0.1454 | 0.6187898 | −1 | 1.6368294 | 1.2982277 | −1 | 1.4976178 | 1.2287532 |
| CADM1 | 7.5914375 | 0.7603875 | 0.3308 | 0.2478 | 0.5785959 | −1 | 1.6923754 | 1.3539145 | −1 | 1.7428282 | 1.4035433 |
| IL6ST | 10.355178 | 0.5509714 | 0.1851 | 0.1187 | 0.3038017 | −1 | 1.5709644 | 1.2687092 | −1 | 1.470333 | 1.217744 |
| LGALS3 | 8.5926121 | 0.7862207 | 0.3442 | 0.2743 | 0.6185665 | −1 | 1.5048215 | 1.2411024 | −1 | 1.3574436 | 1.1320159 |
| SMAD4 | 8.902039 | 0.4085988 | 0.1025 | 0.06456 | 0.1670791 | −1 | 1.669624 | 1.329762 | −1 | 1.6100555 | 1.3112751 |
| NFAT5 | 9.2271297 | 0.5003181 | 0.1647 | 0.08587 | 0.2505217 | −1 | 1.7299501 | 1.3539145 | −1 | 1.5858292 | 1.2995265 |
| SDC1 | 7.2405046 | 0.9486094 | 0.4431 | 0.4573 | 0.9004048 | 1 | 1.1878437 | 1.0502204 | 1 | 1.0110389 | — |
| SHMT2 | 7.3818144 | 0.5716985 | 0.1376 | 0.1894 | 0.3270085 | 1 | 1.5185392 | 1.2687092 | 1 | 1.494364 | 1.2448313 |
| SLC22A3 | 8.8366285 | 1.3865065 | 1.3128 | 0.6112 | 1.9240432 | −1 | 1.6100215 | 1.2930451 | −1 | 1.6531341 | 1.3271052 |
| STAT5B | 7.443638 | 0.479107 | 0.09118 | 0.1385 | 0.2296576 | −1 | 1.4932136 | 1.2435871 | −1 | 1.4376605 | 1.1948253 |
| MMP11 | 4.0974635 | 1.1790067 | 0.6512 | 0.7396 | 1.3908598 | 1 | 1.4849754 | 1.257342 | 1 | 1.3586058 | 1.1514246 |
| TUBB2A | 8.3247821 | 0.9300317 | 0.553 | 0.3126 | 0.8656511 | −1 | 1.4310473 | 1.1699956 | −1 | 1.4520775 | 1.1817543 |

TABLE 1B

| GENE | Association with PCSS Endpoint | | | Association with cRFI, CAPRA Adjusted | | | Association with primary Gleason pattern | | |
|---|---|---|---|---|---|---|---|---|---|
| | Std. HR | Wald p-value | Storey q-value | Std. HR | Wald p-value | Storey q-value | Std. OR | Wald p-value | Storey q-value |
| ARF1 | 0.9976193 | 0.9892903 | 0.5842039 | 1.13407667 | 0.83255536 | 0.4298654 | 0.982273 | 0.907845 | 0.3887901 |
| ATP5E | 1.7881176 | 0.0115817 | 0.0404889 | 2.78746082 | 0.07918786 | 0.0876892 | 1.3546007 | 0.0347604 | 0.0377781 |
| CLTC | 1.026701 | 0.8673167 | 0.5533326 | 1.95450035 | 0.43611016 | 0.2800117 | 1.293925 | 0.4450274 | 0.2418238 |
| GPS1 | 0.849428 | 0.3590422 | 0.3461617 | 1.04907052 | 0.93720193 | 0.4574281 | 0.8271353 | 0.1863038 | 0.1358186 |
| PGK1 | 0.9801478 | 0.9057919 | 0.5657924 | 2.40228939 | 0.08542284 | 0.0920345 | 0.9775945 | 0.8943649 | 0.3866666 |
| ASPN | 3.0547166 | 1.85E−08 | 3.97E−06 | 1.98680704 | 3.75E−07 | 8.71E−06 | 2.6178187 | 3.32E−07 | 2.89E−06 |
| BGN | 2.6395972 | 2.34E−06 | 0.000144 | 2.65751131 | 3.29E−07 | 8.71E−06 | 2.5773715 | 1.19E−07 | 1.34E−06 |
| COL1A1 | 2.5740243 | 1.16E−07 | 0.0000124 | 2.43783149 | 3.46E−07 | 8.71E−06 | 2.2304742 | 2.40E−07 | 0.0000138 |
| COL1A2 | 1.6067045 | 0.0108778 | 0.0393063 | 1.30239373 | 0.14922155 | 0.1339808 | 1.1226733 | 0.4115421 | 0.2324622 |
| COL3A1 | 2.3815758 | 7.22E−06 | 0.0002217 | 2.52337548 | 6.28E−08 | 3.29E−06 | 1.9034844 | 0.0001218 | 0.0003527 |
| COL4A1 | 1.9704368 | 0.0008215 | 0.006465 | 2.14028481 | 0.00036078 | 0.0014267 | 1.0893045 | 0.5143164 | 0.2654536 |
| COL5A2 | 1.9382474 | 0.0018079 | 0.0111059 | 1.20272948 | 0.23650362 | 0.1864598 | 1.1234816 | 0.4230095 | 0.2350912 |
| F2R | 2.1687429 | 0.000107 | 0.0016437 | 1.62196106 | 0.00161154 | 0.0046735 | 2.3718651 | 0.00000433 | 0.0000227 |
| FAP | 1.9932031 | 0.0015781 | 0.0098344 | 1.37558042 | 0.00581828 | 0.0124219 | 2.3624961 | 2.06E−07 | 2.16E−06 |
| FN1 | 1.5366589 | 0.0242031 | 0.0667138 | 1.46470831 | 0.06004749 | 0.0723063 | 0.9406955 | 0.6630807 | 0.3149629 |
| INHBA | 3.0596839 | 1.07E−07 | 0.0000124 | 1.98607554 | 4.28E−09 | 3.73E−07 | 2.5487503 | 5.65E−06 | 0.0000273 |
| SFRP4 | 2.3836087 | 0.0000248 | 0.0005927 | 1.67750397 | 1.87E−05 | 0.0001515 | 2.6895594 | 6.50E−11 | 1.80E−09 |
| SPARC | 2.249132 | 0.0000652 | 0.0012192 | 1.81223384 | 0.00166372 | 0.0047457 | 1.4031045 | 0.0236369 | 0.0279596 |
| THBS2 | 2.5760475 | 2.97E−07 | 0.0000256 | 1.89140939 | 7.54E−07 | 0.0000146 | 1.8704603 | 0.0000261 | 0.0000967 |
| BIN1 | 0.6582912 | 0.0008269 | 0.006465 | 0.53215394 | 1.35E−07 | 4.02E−06 | 0.4346961 | 2.11E−09 | 4.27E−08 |
| C7 | 0.5305767 | 4.96E−06 | 0.0001778 | 0.61660218 | 1.43E−05 | 0.0001297 | 0.3687542 | 3.26E−12 | 1.24E−10 |
| COL6A1 | 0.6814495 | 0.0146421 | 0.0470118 | 0.59821729 | 8.17E−05 | 0.0004585 | 0.4431674 | 2.65E−07 | 2.52E−06 |
| DES | 0.730098 | 0.0532354 | 0.1095273 | 0.61335977 | 0.00103514 | 0.0033666 | 0.3442483 | 2.78E−08 | 3.52E−07 |
| FLNC | 0.741509 | 0.0356714 | 0.0847442 | 0.85002893 | 0.23258502 | 0.1843763 | 0.3263553 | 4.74E−09 | 8.68E−08 |
| GPM6B | 0.6663529 | 0.0048803 | 0.0233566 | 0.60320026 | 0.00006446 | 0.0003935 | 0.4814972 | 2.01E−06 | 0.0000117 |
| GSN | 0.6464018 | 0.0057152 | 0.0257736 | 0.45512167 | 1.29E−07 | 4.02E−06 | 0.463566 | 3.08E−07 | 2.84E−06 |
| GSTM1 | 0.6720834 | 0.0063399 | 0.0269917 | 0.61970734 | 4.44E−06 | 0.000058 | 0.4449932 | 1.22E−09 | 2.65E−08 |
| GSTM2 | 0.514483 | 0.0000907 | 0.0015002 | 0.52721579 | 4.50E−06 | 0.000058 | 0.2939022 | 3.94E−13 | 2.00E−11 |
| HLF | 0.5812615 | 0.0004971 | 0.0047504 | 0.52096012 | 2.14E−06 | 0.0000338 | 0.4179279 | 8.18E−09 | 1.31E−07 |

TABLE 1B-continued

| | Association with PCSS Endpoint | | | Association with cRFI, CAPRA Adjusted | | | Association with primary Gleason pattern | | |
|---|---|---|---|---|---|---|---|---|---|
| GENE | Std. HR | Wald p-value | Storey q-value | Std. HR | Wald p-value | Storey q-value | Std. OR | Wald p-value | Storey q-value |
| IGF1 | 0.6118674 | 0.0001721 | 0.0022429 | 0.62158322 | 7.65E−06 | 0.0000807 | 0.3470943 | 2.24E−13 | 1.36E−11 |
| IGFBP6 | 0.5776972 | 0.003161 | 0.0172052 | 0.60163498 | 7.96E−05 | 0.0004543 | 0.4536368 | 1.44E−08 | 2.18E−07 |
| ITGA7 | 0.6760378 | 0.0331669 | 0.0810327 | 0.54167205 | 2.10E−05 | 0.0001661 | 0.3682462 | 4.07E−10 | 1.03E−08 |
| OLFML3 | 0.6460637 | 0.0011279 | 0.0080836 | 0.57873289 | 0.00001453 | 0.0001297 | 0.4154584 | 1.88E−08 | 2.64E−07 |
| PAGE4 | 0.5182669 | 5.75E−06 | 0.0001903 | 0.66287751 | 2.46E−06 | 0.0000357 | 0.2677212 | 2.80E−17 | 8.51E−15 |
| PPAP2B | 0.5680087 | 0.0006371 | 0.0055913 | 0.45475585 | 6.81E−06 | 0.0000765 | 0.4140322 | 4.85E−09 | 8.68E−08 |
| PPP1R12A | 0.6937407 | 0.0165382 | 0.0496415 | 0.46377868 | 0.00149833 | 0.0044262 | 0.4793933 | 0.0000198 | 0.0000772 |
| PRKCA | 0.6323113 | 0.0014455 | 0.0092768 | 0.52602482 | 6.68E−05 | 0.0004008 | 0.3682007 | 6.36E−09 | 1.07E−07 |
| SRD5A2 | 0.4878954 | 2.93E−06 | 0.0001573 | 0.53197502 | 1.48E−09 | 2.58E−07 | 0.2848852 | 1.63E−14 | 1.45E−12 |
| VCL | 0.6936282 | 0.4610739 | 0.3983524 | 0.48920691 | 0.00010426 | 0.0005415 | 0.4393103 | 7.90E−06 | 0.0000369 |
| TGEB1I1 | 0.6700491 | 0.0291804 | 0.0749233 | 0.58638267 | 0.00360838 | 0.0089058 | 0.3711508 | 1.96E−08 | 2.64E−07 |
| TPM2 | 0.6225776 | 0.0050533 | 0.0236188 | 0.55889674 | 0.00020286 | 0.0008936 | 0.3008674 | 1.04E−09 | 2.44E−08 |
| TPX2 | 2.07392 | 0.0416277 | 0.0942101 | 1.80670715 | 7.56E−08 | 3.29E−06 | 2.1153062 | 4.98E−06 | 0.0000248 |
| CDC20 | 1.7300441 | 0.0000725 | 0.0012988 | 1.94643748 | 4.81E−06 | 0.0000598 | 1.6858143 | 0.000045 | 0.0001519 |
| CDKN2C | 1.99305 | 0.0125796 | 0.0432737 | 2.2133602 | 1.45E−05 | 0.0001297 | 1.6207388 | 0.00039 | 0.0009879 |
| MYBL2 | 1.7372773 | 0.012916 | 0.0440786 | 1.64874559 | 6.39E−06 | 0.0000745 | 1.4091306 | 0.0068668 | 0.0098934 |
| UBE2T | 1.898363 | 0.0847937 | 0.1462198 | 1.87982565 | 0.00012433 | 0.0005929 | 1.594593 | 0.0006065 | 0.0014404 |
| CYP3A5 | 0.5067698 | 0.0003008 | 0.0032333 | 0.56312246 | 1.39E−07 | 4.02E−06 | 0.5204925 | 9.40E−06 | 0.0000426 |
| KRT15 | 0.6841526 | 0.0052343 | 0.0242015 | 0.7687095 | 7.50E−05 | 0.000435 | 0.5603937 | 0.0000173 | 0.0000713 |
| KRT5 | 0.6729884 | 0.0041853 | 0.0216827 | 0.7264908 | 0.0002245 | 0.0009645 | 0.6401711 | 0.000719 | 0.0016558 |
| LAMB3 | 0.7403354 | 0.0266386 | 0.0724973 | 0.76722056 | 0.00366663 | 0.0089858 | 0.730357 | 0.0177696 | 0.0219488 |
| EGR1 | 0.4902253 | 0.0003344 | 0.0034238 | 0.60204599 | 1.58E−05 | 0.0001377 | 0.5936819 | 0.0007056 | 0.0016501 |
| FOS | 0.5555161 | 0.0045741 | 0.0223508 | 0.6374611 | 5.34E−05 | 0.0003316 | 0.5788589 | 0.0002156 | 0.0005851 |
| GADD45B | 0.5541679 | 0.0021788 | 0.0124919 | 0.64836478 | 3.81E−05 | 0.0002707 | 0.6176176 | 0.002403 | 0.0043482 |
| JUN | 0.505934 | 0.0013437 | 0.0088891 | 0.54410296 | 1.78E−05 | 0.00015 | 0.4795161 | 3.99E−07 | 3.37E−06 |
| ZFP36 | 0.5757824 | 0.001207 | 0.0083714 | 0.66520845 | 0.00023482 | 0.0009966 | 0.6470667 | 0.0043499 | 0.0068874 |
| DUSP1 | 0.6603212 | 0.0498518 | 0.1055975 | 0.63670824 | 0.00347613 | 0.0086407 | 0.586205 | 0.0007564 | 0.0017289 |
| EGR3 | 0.5613678 | 0.0009351 | 0.0071803 | 0.72134117 | 0.0008831 | 0.002955 | 0.7186042 | 0.0260364 | 0.0300953 |
| FAM13C | 0.5260925 | 4.01E−09 | 1.72E−06 | 0.52541845 | 6.04E−10 | 2.10E−07 | 0.3709836 | 5.73E−11 | 1.74E−09 |
| KLK2 | 0.5808923 | 0.0001686 | 0.0022429 | 0.56994638 | 0.00194411 | 0.0053697 | 0.5968229 | 0.0002289 | 0.0006158 |
| ALDH1A2 | 0.5608861 | 0.0000177 | 0.0004751 | 0.65303146 | 0.00010806 | 0.000545 | 0.2822456 | 4.34E−07 | 3.57E−06 |
| AZGP1 | 0.6167537 | 3.96E−06 | 0.0001778 | 0.6708779 | 4.29E−07 | 9.33E−06 | 0.5150783 | 1.17E−06 | 7.43E−06 |
| ANPEP | 0.5313085 | 0.0008229 | 0.006465 | 0.80509148 | 0.00011244 | 0.000559 | 0.6761885 | 0.0081251 | 0.0114354 |
| AR | 0.9479643 | 0.7435374 | 0.510526 | 0.77328075 | 0.35466409 | 0.244458 | 0.9337631 | 0.6073904 | 0.295812 |
| BMP6 | 1.4900185 | 0.0210638 | 0.060383 | 1.44999312 | 0.00201534 | 0.0054792 | 2.3713254 | 6.85E−07 | 4.86E−06 |
| CD276 | 1.6684232 | 0.0049028 | 0.0233566 | 2.16998768 | 0.00057532 | 0.0020641 | 2.1955258 | 2.75E−06 | 0.0000155 |
| CD44 | 0.6866428 | 0.0155666 | 0.0485038 | 0.5502693 | 1.06E−07 | 4.02E−06 | 0.7793905 | 0.0682278 | 0.0654298 |
| COL8A1 | 2.2449967 | 0.0000271 | 0.0006141 | 1.91011656 | 4.90E−05 | 0.0003216 | 1.8755907 | 9.13E−06 | 0.0000421 |
| CSF1 | 0.6749873 | 0.0193771 | 0.0562984 | 0.44321491 | 5.01E−07 | 0.0000103 | 0.9573718 | 0.7643438 | 0.3461448 |
| SRC | 0.6670294 | 0.0040025 | 0.0212478 | 0.47320013 | 1.67E−06 | 0.0000307 | 0.766355 | 0.0813478 | 0.0758976 |
| CSRP1 | 0.7112339 | 0.0067019 | 0.0277098 | 0.89239013 | 0.2633928 | 0.1994666 | 0.4248705 | 0.0058729 | 0.0088825 |
| DPP4 | 0.5441442 | 1.12E−06 | 0.00008 | 0.68915455 | 0.00013991 | 0.0006492 | 0.4140282 | 1.92E−06 | 0.0000114 |
| TNFRSF10B | 0.6852925 | 0.0143692 | 0.0468086 | 0.53054603 | 4.04E−05 | 0.0002757 | 0.7430912 | 0.0304132 | 0.0339912 |
| ERG | 1.0765349 | 0.6794217 | 0.4926667 | 1.12737455 | 0.0349341 | 0.0496809 | 0.8943961 | 0.4148417 | 0.2324622 |
| FAM107A | 0.540565 | 0.0000605 | 0.0011827 | 0.57090059 | 6.82E−08 | 3.29E−06 | 0.3476335 | 1.99E−08 | 2.64E−07 |
| IGFBP2 | 0.6977969 | 0.0532257 | 0.1095273 | 0.45025927 | 6.42E−06 | 0.0000745 | 0.6063083 | 0.0001586 | 0.0004465 |
| CADM1 | 0.6456383 | 0.0150546 | 0.0472518 | 0.40819615 | 3.14E−08 | 2.19E−06 | 0.5598139 | 0.0001184 | 0.000346 |
| IL6ST | 0.5740052 | 0.0003647 | 0.0036466 | 0.33440325 | 2.36E−06 | 0.0000357 | 0.5462964 | 0.0040541 | 0.0065556 |
| LGALS3 | 0.6782394 | 0.0071303 | 0.0283525 | 0.53406803 | 5.18E−05 | 0.0003278 | 0.5903729 | 0.0030449 | 0.0052894 |
| SMAD4 | 0.5277628 | 4.87E−06 | 0.0001778 | 0.24376793 | 2.03E−06 | 0.0000336 | 0.3346823 | 1.85E−06 | 0.0000112 |
| NFAT5 | 0.5361732 | 0.0000856 | 0.0014722 | 0.20926313 | 3.51E−07 | 8.71E−06 | 0.5518236 | 0.0000356 | 0.000126 |
| SDC1 | 1.7097015 | 0.007187 | 0.0283525 | 1.43080815 | 0.02325931 | 0.0359744 | 1.6597668 | 0.0010445 | 0.002268 |
| SHMT2 | 1.9491131 | 0.0031065 | 0.0171257 | 1.94514573 | 0.00591315 | 0.0124714 | 1.6896076 | 0.0074605 | 0.0105488 |
| SLC22A3 | 0.5168636 | 0.000117 | 0.001706 | 0.65464678 | 7.32E−06 | 0.0000796 | 0.2293355 | 1.91E−14 | 1.45E−12 |
| STAT5B | 0.7002104 | 0.0396042 | 0.0914258 | 0.44673718 | 0.00045662 | 0.0017462 | 0.5417213 | 0.0000465 | 0.0001553 |
| MMP11 | 1.8691119 | 0.0001041 | 0.0016437 | 1.62300343 | 1.23E−05 | 0.0001222 | 2.3250222 | 7.87E−07 | 5.44E−06 |
| TUBB2A | 0.6134538 | 0.0026235 | 0.0148438 | 0.56476388 | 1.81E−05 | 0.00015 | 0.9566513 | 0.7630842 | 0.3461448 |

Example 2: Algorithm Development Based on Data from A Companion Study

The Cleveland Clinic ("CC") Companion study consists of three patient cohorts and separate analyses for each cohort as described in Table 2. The first cohort (Table 2) includes men with low to high risk (based on AUA criteria) prostate cancer from Gene ID study 09-002 who underwent RP at CC between 1987 and 2004 and had diagnostic biopsy tissue available at CC. Cohorts 2 and 3 include men with clinically localized Low and Intermediate Risk (based on AUA criteria) prostate cancer, respectively, who might have been reasonable candidates for active surveillance but who underwent radical prostatectomy (RP) within 6 months of the diagnosis of prostate cancer by biopsy. The main objective of Cohort 1 was to compare the molecular profile from biopsy tissue with that from radical prostatectomy tissue. The main objective of Cohorts 2 and 3 was to develop a multigene predictor of upgrading/upstaging at RP using biopsy tissue in low to intermediate risk patients at diagnosis.

Matched biopsy samples were obtained for a subset of the patients (70 patients) from the gene identification study. Gene expression of the 81 selected genes and the 5 reference genes (ARF1, ATP5E, CLTC, GPS1, PGK1) were compared in the RP specimens and the biopsy tissue obtained from these 70 patients.

The 81 genes were evaluated in Cohorts 2 and 3 for association with upgrading and upstaging. The association between these 81 genes and upgrading and upstaging in Cohorts 2 and 3 are shown in Table 3. P values and standardized odds ratio are provided.

In this context, "upgrade" refers to an increase in Gleason grade from 3+3 or 3+4 at the time of biopsy to greater than or equal to 3+4 at the time of RP. "Upgrade2" refers to an increase in Gleason grade from 3+3 or 3+4 at the time of biopsy to greater than or equal to 4+3 at the time of RP.

Several different models were explored to compare expression between the RP and biopsy specimens. Genes were chosen based on consistency of expression between the RP and biopsy specimens. FIGS. 2A-2E are the scatter plots showing the comparison of normalized gene expression (Cp) for matched samples from each patient where the x-axis is the normalized gene expression from the PGP RP sample (PGP) and the y-axis is the normalized gene expression from the biopsy sample (BX). FIGS. 3A-3D show range plots of gene expression of individual genes within each gene group in the biopsy (BX) and PGP RP samples.

After evaluating the concordance of gene expression in biopsy and RP samples, the following algorithms (RS models) shown in Table 4 were developed where the weights are determined using non-standardized, but normalized data. Some genes, such as SRD5A2 and GSTM2, which fall within the cellular organization gene group, were also evaluated separately and independent coefficients were assigned (see the "other" category in Table 4). In other instances, GSTM1 and GSMT2 were grouped as an oxidative "stress" group and a coefficient was assigned to this "stress" group (see RS20 and RS22 models). Other genes, such as AZGP1 and SLC22A3, which did not fall within any of the gene groups, were also included in certain algorithms (see the "other" category in Table 4). Furthermore, the androgen gene group was established to include FAM13C, KLK2, AZGP1, and SRD5A2. Some genes such as BGN, SPARC, FLNC, GSN, TPX2 and SRD5A2 were thresholded before being evaluated in models. For example, normalized expression values below 4.5 were set to 4.5 for TPX2 and normalized expression values below 5.5 were set to 5.5 for SRD5A2.

TABLE 2

| Cohort # | Cohort Description | # of Patients | Objectives |
|---|---|---|---|
| 1 | Subset of patients from Gene ID study 09-002 who underwent RP at CC between 1987 and 2004 and had diagnostic biopsy tissue available at CC. Patients from the original stratified cohort sample with available biopsy tissue blocks | 70 | Comparison of gene expression from biopsy sample with gene expression from RP specimen (Co-Primary Objective) Explore association of risk of recurrence after RP with gene expression from biopsy sample and gene expression from RP sample Explore association of risk of recurrence after RP with gene expression from RP samples |
| 2 | Low Risk Patients from CC database of patients who were biopsied, and then underwent RP at CC between 1999 and 2010 All patients in database who meet minimum tumor tissue criteria | 92 | Association between gene expression from biopsy sample and likelihood of upgrading/upstaging in tissue obtained at prostatectomy (Co-Primary Objective) |
| 3 | Intermediate Risk Patients from CC database of patients who were biopsied, and then underwent RP at CC between 1999 and 2010 All patients in database who meet minimum tumor tissue criteria | 75 | Association between gene expression from biopsy sample and likelihood of upgrading/upstaging in tissue obtained at prostatectomy |

TABLE 3

Association between the 81 genes and Upgrading and Upstaging in Cohorts 2/3

| Gene | N | p-value UpGrade | Std OR Upgrade | 95% CI Upgrade | p-value Upgrade2 | Std OR Upgrade2 | 95% CI Upgrade2 | p-value Upstage | Std OR Upstage | 95% CI Upstage |
|---|---|---|---|---|---|---|---|---|---|---|
| ALDH1A2 | 167 | 0.501 | 1.11 | (0.82, 1.52) | 0.932 | 1.02 | (0.70, 1.47) | 0.388 | 0.86 | (0.61, 1.22) |
| ANPEP | 167 | 0.054 | 1.36 | (0.99, 1.87) | 0.933 | 0.98 | (0.68, 1.42) | 0.003 | 0.58 | (0.40, 0.83) |
| AR | 167 | 0.136 | 1.27 | (0.93, 1.74) | 0.245 | 0.81 | (0.56, 1.16) | 0.005 | 0.60 | (0.42, 0.86) |
| ARF1 | 167 | 0.914 | 0.98 | (0.72, 1.34) | 0.051 | 1.45 | (1.00, 2.11) | 0.371 | 1.17 | (0.83, 1.66) |
| ASPN | 167 | 0.382 | 1.15 | (0.84, 1.56) | 0.040 | 1.60 | (1.02, 2.51) | 0.069 | 1.46 | (0.97, 2.19) |
| ATP5E | 167 | 0.106 | 1.30 | (0.95, 1.77) | 0.499 | 0.88 | (0.61, 1.27) | 0.572 | 0.90 | (0.64, 1.28) |
| AZGP1 | 167 | 0.192 | 1.23 | (0.90, 1.68) | 0.190 | 0.79 | (0.55, 1.13) | 0.005 | 0.59 | (0.41, 0.85) |
| BGN | 167 | 0.568 | 0.91 | (0.67, 1.25) | 0.001 | 2.15 | (1.39, 3.33) | 0.020 | 1.56 | (1.07, 2.28) |
| BIN1 | 167 | 0.568 | 1.09 | (0.80, 1.49) | 0.634 | 0.92 | (0.64, 1.32) | 0.104 | 0.75 | (0.54, 1.06) |
| BMP6 | 167 | 0.509 | 0.90 | (0.66, 1.23) | 0.015 | 1.59 | (1.09, 2.30) | 0.650 | 1.08 | (0.77, 1.54) |
| C7 | 167 | 0.677 | 1.07 | (0.78, 1.46) | 0.013 | 1.66 | (1.11, 2.47) | 0.223 | 0.80 | (0.56, 1.14) |
| CADM1 | 167 | 0.082 | 0.74 | (0.52, 1.04) | 0.235 | 0.81 | (0.57, 1.15) | 0.039 | 0.69 | (0.48, 0.98) |
| CD276 | 167 | 0.454 | 0.89 | (0.65, 1.21) | 0.362 | 0.84 | (0.58, 1.22) | 0.214 | 1.25 | (0.88, 1.78) |
| CD44 | 167 | 0.122 | 1.28 | (0.94, 1.75) | 0.305 | 1.23 | (0.83, 1.81) | 0.876 | 0.97 | (0.69, 1.38) |
| CDC20 | 166 | 0.567 | 1.10 | (0.80, 1.50) | 0.298 | 1.21 | (0.84, 1.75) | 0.279 | 1.21 | (0.86, 1.71) |
| CDKN2C | 152 | 0.494 | 0.89 | (0.64, 1.24) | 0.908 | 0.98 | (0.67, 1.43) | 0.834 | 1.04 | (0.72, 1.49) |
| CLTC | 167 | 0.102 | 0.76 | (0.55, 1.06) | 0.300 | 0.82 | (0.57, 1.19) | 0.264 | 0.82 | (0.58, 1.16) |
| COL1A1 | 167 | 0.732 | 1.06 | (0.77, 1.44) | 0.000 | 3.04 | (1.93, 4.79) | 0.006 | 1.65 | (1.15, 2.36) |
| COL1A2 | 167 | 0.574 | 0.91 | (0.67, 1.25) | 0.017 | 1.65 | (1.09, 2.50) | 0.521 | 0.89 | (0.63, 1.26) |
| COL3A1 | 167 | 0.719 | 0.94 | (0.69, 1.29) | 0.000 | 2.98 | (1.88, 4.71) | 0.020 | 1.53 | (1.07, 2.20) |
| COL4A1 | 167 | 0.682 | 0.94 | (0.69, 1.28) | 0.000 | 2.12 | (1.39, 3.22) | 0.762 | 0.95 | (0.67, 1.35) |
| COL5A2 | 167 | 0.499 | 1.11 | (0.82, 1.52) | 0.009 | 1.81 | (1.16, 2.83) | 0.516 | 0.89 | (0.63, 1.26) |
| COL6A1 | 167 | 0.878 | 0.98 | (0.72, 1.33) | 0.001 | 2.14 | (1.37, 3.34) | 0.883 | 1.03 | (0.72, 1.46) |
| COL8A1 | 165 | 0.415 | 0.88 | (0.64, 1.20) | 0.000 | 3.24 | (1.88, 5.61) | 0.044 | 1.51 | (1.01, 2.25) |
| CSF1 | 167 | 0.879 | 1.02 | (0.75, 1.40) | 0.187 | 1.31 | (0.88, 1.96) | 0.110 | 0.76 | (0.54, 1.07) |
| CSRP1 | 165 | 0.258 | 1.20 | (0.87, 1.65) | 0.226 | 1.26 | (0.87, 1.82) | 0.641 | 0.92 | (0.65, 1.31) |
| CYP3A5 | 167 | 0.989 | 1.00 | (0.73, 1.36) | 0.188 | 1.28 | (0.88, 1.87) | 0.937 | 1.01 | (0.71, 1.44) |
| DES | 167 | 0.776 | 1.05 | (0.77, 1.43) | 0.088 | 1.40 | (0.95, 2.05) | 0.242 | 0.81 | (0.57, 1.15) |
| DPP4 | 167 | 0.479 | 0.89 | (0.65, 1.22) | 0.005 | 0.60 | (0.42, 0.85) | 0.000 | 0.51 | (0.36, 0.74) |
| DUSP1 | 167 | 0.295 | 0.84 | (0.61, 1.16) | 0.262 | 0.82 | (0.58, 1.16) | 0.427 | 0.87 | (0.62, 1.22) |
| EGR1 | 167 | 0.685 | 0.94 | (0.69, 1.28) | 0.217 | 1.27 | (0.87, 1.85) | 0.370 | 1.18 | (0.83, 1.68) |
| EGR3 | 166 | 0.025 | 0.69 | (0.50, 0.95) | 0.539 | 0.89 | (0.62, 1.29) | 0.735 | 1.06 | (0.75, 1.51) |
| ERG | 166 | 0.002 | 0.58 | (0.42, 0.81) | 0.000 | 0.42 | (0.28, 0.64) | 0.768 | 1.05 | (0.74, 1.50) |
| F2R | 160 | 0.324 | 0.85 | (0.62, 1.17) | 0.009 | 1.77 | (1.16, 2.70) | 0.000 | 2.39 | (1.52, 3.76) |
| FAM107A | 143 | 0.832 | 1.04 | (0.74, 1.45) | 0.088 | 1.42 | (0.95, 2.11) | 0.687 | 1.08 | (0.74, 1.58) |
| FAM13C | 167 | 0.546 | 1.10 | (0.81, 1.50) | 0.041 | 0.68 | (0.47, 0.98) | 0.003 | 0.58 | (0.40, 0.83) |
| FAP | 167 | 0.540 | 0.91 | (0.67, 1.24) | 0.093 | 1.37 | (0.95, 1.97) | 0.001 | 1.85 | (1.28, 2.68) |
| FLNC | 167 | 0.963 | 1.01 | (0.74, 1.37) | 0.254 | 1.26 | (0.85, 1.87) | 0.030 | 0.68 | (0.48, 0.96) |
| FN1 | 167 | 0.530 | 0.91 | (0.66, 1.23) | 0.005 | 1.73 | (1.18, 2.53) | 0.364 | 1.17 | (0.83, 1.66) |
| FOS | 167 | 0.649 | 0.93 | (0.68, 1.27) | 0.071 | 1.38 | (0.97, 1.97) | 0.015 | 1.53 | (1.09, 2.16) |
| GADD45B | 167 | 0.978 | 1.00 | (0.73, 1.36) | 0.105 | 1.38 | (0.94, 2.04) | 0.876 | 0.97 | (0.69, 1.38) |
| GPM6B | 159 | 0.944 | 0.99 | (0.72, 1.36) | 0.002 | 1.95 | (1.27, 2.97) | 0.266 | 0.81 | (0.57, 1.17) |
| GPS1 | 167 | 0.404 | 1.14 | (0.84, 1.56) | 0.609 | 0.91 | (0.62, 1.32) | 0.125 | 1.31 | (0.93, 1.86) |
| GSN | 167 | 0.272 | 0.84 | (0.61, 1.15) | 0.309 | 0.83 | (0.57, 1.19) | 0.027 | 0.67 | (0.47, 0.96) |
| GSTM1 | 167 | 0.178 | 1.24 | (0.91, 1.69) | 0.762 | 0.95 | (0.66, 1.36) | 0.000 | 0.50 | (0.34, 0.72) |
| GSTM2 | 167 | 0.145 | 1.26 | (0.92, 1.73) | 0.053 | 1.48 | (1.00, 2.20) | 0.654 | 0.92 | (0.65, 1.31) |
| HLF | 167 | 0.979 | 1.00 | (0.73, 1.36) | 0.602 | 1.11 | (0.76, 1.62) | 0.030 | 0.69 | (0.49, 0.96) |
| IGF1 | 167 | 0.313 | 1.17 | (0.86, 1.60) | 0.878 | 0.97 | (0.67, 1.40) | 0.146 | 0.77 | (0.55, 1.09) |
| IGFBP2 | 167 | 0.253 | 1.20 | (0.88, 1.64) | 0.493 | 0.88 | (0.61, 1.27) | 0.051 | 0.70 | (0.49, 1.00) |
| IGFBP6 | 167 | 0.336 | 0.86 | (0.62, 1.17) | 0.510 | 1.14 | (0.78, 1.66) | 0.204 | 0.80 | (0.57, 1.13) |
| IL6ST | 167 | 0.774 | 1.05 | (0.77, 1.43) | 0.541 | 1.12 | (0.77, 1.63) | 0.235 | 0.81 | (0.57, 1.15) |
| INHBA | 167 | 0.104 | 1.30 | (0.95, 1.78) | 0.002 | 1.89 | (1.26, 2.84) | 0.077 | 1.38 | (0.97, 1.97) |
| ITGA7 | 167 | 0.990 | 1.00 | (0.73, 1.36) | 0.780 | 1.05 | (0.73, 1.53) | 0.470 | 0.88 | (0.62, 1.25) |
| JUN | 167 | 0.586 | 1.09 | (0.80, 1.48) | 0.538 | 0.89 | (0.62, 1.28) | 0.259 | 0.82 | (0.59, 1.15) |
| KLK2 | 167 | 0.267 | 0.84 | (0.61, 1.15) | 0.003 | 0.56 | (0.38, 0.82) | 0.007 | 0.61 | (0.42, 0.87) |
| KRT15 | 167 | 0.500 | 0.90 | (0.65, 1.23) | 0.738 | 0.94 | (0.65, 1.35) | 0.987 | 1.00 | (0.71, 1.42) |
| KRT5 | 152 | 0.834 | 0.97 | (0.70, 1.34) | 0.632 | 1.10 | (0.74, 1.63) | 0.908 | 0.98 | (0.68, 1.40) |
| LAMB3 | 167 | 0.090 | 1.31 | (0.96, 1.79) | 0.013 | 1.73 | (1.12, 2.68) | 0.132 | 1.33 | (0.92, 1.94) |
| LGALS3 | 166 | 0.345 | 1.16 | (0.85, 1.59) | 0.405 | 1.18 | (0.80, 1.72) | 0.208 | 0.80 | (0.57, 1.13) |
| MMP11 | 167 | 0.715 | 1.06 | (0.78, 1.45) | 0.080 | 1.37 | (0.96, 1.96) | 0.257 | 1.22 | (0.87, 1.71) |
| MYBL2 | 167 | 0.235 | 1.21 | (0.88, 1.67) | 0.868 | 1.03 | (0.71, 1.49) | 0.266 | 1.21 | (0.86, 1.70) |
| NFAT5 | 167 | 0.514 | 0.90 | (0.66, 1.23) | 0.058 | 0.70 | (0.48, 1.01) | 0.530 | 0.89 | (0.63, 1.27) |
| OLFML3 | 167 | 0.448 | 0.89 | (0.65, 1.21) | 0.056 | 1.50 | (0.99, 2.28) | 0.129 | 0.77 | (0.54, 1.08) |
| PAGE4 | 167 | 0.914 | 0.98 | (0.72, 1.34) | 0.211 | 0.80 | (0.56, 1.14) | 0.005 | 0.61 | (0.43, 0.86) |
| PGK1 | 167 | 0.138 | 0.78 | (0.56, 1.08) | 0.666 | 0.92 | (0.64, 1.33) | 0.292 | 0.83 | (0.59, 1.17) |
| PPAP2B | 167 | 0.952 | 0.99 | (0.73, 1.35) | 0.989 | 1.00 | (0.69, 1.44) | 0.221 | 0.80 | (0.56, 1.14) |
| PPP1R12A | 167 | 0.547 | 0.91 | (0.66, 1.24) | 0.563 | 0.90 | (0.63, 1.29) | 0.001 | 0.55 | (0.38, 0.79) |
| PRKCA | 167 | 0.337 | 1.17 | (0.85, 1.59) | 0.141 | 1.35 | (0.90, 2.03) | 0.029 | 0.67 | (0.46, 0.96) |
| SDC1 | 167 | 0.064 | 1.36 | (0.98, 1.87) | 0.013 | 1.83 | (1.14, 2.96) | 0.037 | 1.58 | (1.03, 2.42) |
| SFRP4 | 166 | 0.986 | 1.00 | (0.73, 1.37) | 0.047 | 1.47 | (1.01, 2.14) | 0.031 | 1.49 | (1.04, 2.14) |
| SHMT2 | 167 | 0.133 | 0.78 | (0.56, 1.08) | 0.147 | 0.77 | (0.53, 1.10) | 0.715 | 0.94 | (0.66, 1.33) |
| SLC22A3 | 167 | 0.828 | 1.03 | (0.76, 1.41) | 0.044 | 0.69 | (0.48, 0.99) | 0.050 | 0.71 | (0.50, 1.00) |
| SMAD4 | 167 | 0.165 | 1.25 | (0.91, 1.71) | 0.333 | 0.83 | (0.58, 1.21) | 0.021 | 0.65 | (0.45, 0.94) |
| SPARC | 167 | 0.810 | 0.96 | (0.71, 1.31) | 0.000 | 2.15 | (1.40, 3.30) | 0.154 | 1.30 | (0.91, 1.86) |
| SRC | 167 | 0.083 | 1.34 | (0.96, 1.86) | 0.750 | 1.06 | (0.72, 1.56) | 0.550 | 0.90 | (0.64, 1.26) |

TABLE 3-continued

Association between the 81 genes and Upgrading and Upstaging in Cohorts 2/3

| Gene | N | p-value UpGrade | Std OR Upgrade | 95% CI Upgrade | p-value Upgrade2 | Std OR Upgrade2 | 95% CI Upgrade2 | p-value Upstage | Std OR Upstage | 95% CI Upstage |
|---|---|---|---|---|---|---|---|---|---|---|
| SRD5A2 | 167 | 0.862 | 0.97 | (0.71, 1.33) | 0.122 | 0.75 | (0.53, 1.08) | 0.010 | 0.63 | (0.45, 0.90) |
| STAT5B | 167 | 0.298 | 0.84 | (0.62, 1.16) | 0.515 | 0.89 | (0.62, 1.27) | 0.016 | 0.65 | (0.46, 0.92) |
| TGFB1I1 | 167 | 0.985 | 1.00 | (0.74, 1.37) | 0.066 | 1.45 | (0.98, 2.14) | 0.131 | 0.76 | (0.54, 1.08) |
| THBS2 | 167 | 0.415 | 1.14 | (0.83, 1.56) | 0.001 | 1.91 | (1.30, 2.80) | 0.288 | 1.21 | (0.85, 1.70) |
| TNFRSF10B | 167 | 0.214 | 1.22 | (0.89, 1.66) | 0.805 | 0.95 | (0.66, 1.38) | 0.118 | 0.76 | (0.54, 1.07) |
| TPM2 | 167 | 0.996 | 1.00 | (0.73, 1.36) | 0.527 | 1.13 | (0.78, 1.64) | 0.094 | 0.74 | (0.52, 1.05) |
| TPX2 | 167 | 0.017 | 1.48 | (1.07, 2.04) | 0.002 | 1.89 | (1.26, 2.83) | 0.001 | 1.91 | (1.30, 2.80) |
| TUBB2A | 167 | 0.941 | 0.99 | (0.73, 1.35) | 0.182 | 0.78 | (0.54, 1.12) | 0.111 | 0.75 | (0.53, 1.07) |
| UBE2T | 167 | 0.095 | 1.36 | (0.95, 1.96) | 0.009 | 1.58 | (1.12, 2.23) | 0.084 | 1.33 | (0.96, 1.84) |
| VCL | 167 | 0.954 | 0.99 | (0.73, 1.35) | 0.165 | 1.31 | (0.90, 1.91) | 0.265 | 0.82 | (0.57, 1.16) |
| ZFP36 | 167 | 0.685 | 1.07 | (0.78, 1.45) | 0.784 | 0.95 | (0.66, 1.37) | 0.610 | 0.91 | (0.64, 1.29) |

TABLE 4

| RS Model | ECM (Stromal Response) | Migration (Cellular Organization) | Prolif. | Androgen (PSA) | Other | Algorithm |
|---|---|---|---|---|---|---|
| RS0 | (ASPN + BGN + COL1A1 + SPARC)/4 | (FLNC + GSN + GSTM2 + IGFBP6 + PPAP2B + PPP1R12A)/6 | (TPX2 + CDC20 + MYBL2)/3 | (FAM13C + KLK2)/2 | STAT5B, NFAT5 | 1.05 * ECM – 0.58 * Migration – 0.30 * PSA + 0.08 * Prolif – 0.16 * STAT5B – 0.23 * NFAT5 |
| RS1 | (BGN + COL1A1 + FN1 + SPARC)/4 | (FLNC + GSN + GSTM2 + PPAP2B + PPP1R12A)/6 | | (FAM13C + KLK2)/2 | STAT5B, NFAT5 | 1.15 * ECM – 0.72 * Migration – 0.56 * PSA – 0.45 * STAT5B – 0.56 * NFAT5 |
| RS2 | (BGN + COL1A1 + FN1 + SPARC)/4 | (BIN1 + FLNC + GSN + GSTM2 + PPAP2B + PPP1R12A + VCL)/7 | | (FAM13C + KLK2)/2 | STAT5B, NFAT5 | 1.16 * ECM – 0.75 * Migration – 0.57 * PSA – 0.47 * STAT5B – 0.50 * NFAT5 |
| RS3 | (BGN + COL1A1 + COL3A1 + COL4A1 + FN1 + SPARC)/6 | (FLNC + GSN + GSTM2 + PPAP2B + PPP1R12A)/5 | | (FAM13C + KLK2)/2 | STAT5B, NFAT5 | 1.18 * ECM – 0.75 * Migration – 0.56 * PSA – 0.40 * STAT5B – 0.48 * NFAT5 |
| RS4 | (BGN + COL1A1 + COL3A1 + COL4A1 + FN1 + SPARC)/6 | (BIN1 + FLNC + GSN + GSTM2 + PPAP2B + PPP1R12A + VCL)/7 | | (FAM13C + KLK2)/2 | STAT5B, NFAT5 | 1.18 * ECM – 0.76 * Migration – 0.58 * PSA – 0.43 * STAT5B – 0.43 * NFAT5 |
| RS5 | (COL4A1 (thresholded) + INHBA + SPARC + THBS2)/4 | (BIN1 + IGF1 (thresholded) + VCL)/3 | | KLK2 | AZGP1, ANPEP, IGFBP2 (thresholded) | 1.20 * ECM – 0.91 * Migration – 0.29 * KLK2 – 0.14 * AZGP1 + 0.05 * ANPEP – 0.56 * IGFBP2 |
| RS6 | (BGN + COL3A1 + INHBA + SPARC)/4 | Migratn1: (FLNC + GSN + TPM2)/3 Migratn2: (GSTM2 + PPAP2B)/2 | TPX2 | (FAM13C + KLK2)/2 | AZGP1, SLC22A3 | 1.09 * ECM – 0.44 * Migration1 – 0.23 * Migratn2 – 0.36 * PSA + 0.15 * TPX2 – 0.16 * AZGP1 – 0.08 * SLC22A3 |
| RS7 | (BGN + COL3A1 + INHBA + SPARC)/4 | Migratn1: (FLNC + GSN + TPM2)/3 Migratn2: (GSTM2 + PPAP2B)/2 | | (FAM13C + KLK2)/2 | AZGP1, SLC22A3 | 1.16 * ECM – 0.53 * Migration1 – 0.24 * Migratn2 – 0.42 * PSA – 0.14 * AZGP1 – 0.08 * SLC22A3 |
| RS8 | (BGN + COL3A1 + SPARC)/3 | Migratn1: (FLNC + GSN + TPM2)/3 Migratn2: (GSTM2 + PPAP2B)/2 | | KLK2 | AZGP1, SLC22A3 | 1.37 * ECM – 0.56 * Migration1 – 0.49 * Migratn2 – 0.52 * KLK2 – 0.16 * AZGP1 – 0.00 * SLC22A3 |
| RS9 | (BGN (thresholded) + COL3A1 + INHBA + SPARC (thresholded))/4 | Migratn1: (FLNC (thresholded) + GSN (thresholded) + TPM2)/3 Migratn2: (GSTM2 + PPAP2B)/2 | | (FAM13C + KLK2)/2 | AZGP1, SLC22A3 | 1.28 * ECM – 1.11 * Migration1 – 0.00 * Migratn2 – 0.34 * PSA – 0.16 * AZGP1 – 0.08 * SLC22A3 |
| RS10 | (BGN + COL3A1 + INHBA + SPARC)/4 | (FLNC + GSN + GSTM2 + PPAP2B + TPM2)/5 | TPX2 | (FAM13C + KLK2)/2 | AZGP1, SLC22A3 | 1.09 * ECM – 0.68 * Migration – 0.37 * PSA + 0.16 * TPX2 – 0.16 * AZGP1 – 0.08 * SLC22A3 |
| RS11 | (BGN (thresholded) + COL3A1 + INHBA + SPARC (thresholded))/4 | (FLNC (thresholded) + GSN (thresholded) + GSTM2 + PPAP2B + TPM2)/5 | | (FAM13C + KLK2)/2 | AZGP1, SLC22A3 | 1.19 * ECM – 0.96 * Migration – 0.39 * PSA – 0.14 * AZGP1 – 0.09 * SLC22A3 |
| RS12 | (BGN (thresholded) + COL3A1 + INHBA + SPARC (thresholded))/4 | (FLNC (thresholded) + GSN (thresholded) + GSTM2 + PPAP2B + TPM2)/5 | TPX2 | (FAM13C + KLK2)/2 | AZGP1, SLC22A3 | 1.13 * ECM – 0.85 * Migration – 0.34 * PSA + 0.15 * TPX2 – 0.15 * AZGP1 – 0.08 * SLC22A3 |
| RS13 | (BGN (thresholded) + COL3A1 + INHBA + SPARC (thresholded))/4 | (FLNC (thresholded) + GSN (thresholded) + GSTM2 + PPAP2B + TPM2)/5 | TPX2 | (FAM13C + KLK2)/2 | AZGP1, ERG, SLC22A3 | 1.12 * ECM – 0.83 * Migration – 0.33 * PSA + 0.17 * TPX2 – 0.14 * AZGP1 + 0.04 * ERG – 0.10 * SLC22A3 |

TABLE 4-continued

| RS Model | ECM (Stromal Response) | Migration (Cellular Organization) | Prolif. | Androgen (PSA) | Other | Algorithm |
|---|---|---|---|---|---|---|
| RS14 | (BGN (thresholded) + COL3A1 + INHBA + SPARC(thresholded))/4 | (FLNC(thresholded) + GSN(thresholded) + GSTM2 + PPAP2B + TPM2)/5 | TPX2 | (FAM13C + KLK2)/2 | AR, AZGP1, ERG, SLC22A3 | 1.13 * ECM − 0.83 * Migration − 0.35 * PSA + 0.16 * TPX2 + 0.15 * AR − 0.15 * AZGP1 + 0.03 * ERG − 0.10 * SLC22A3 |
| RS15 | (BGN (thresholded) + COL3A1 + INHBA + SPARC(thresholded))/4 | (FLNC(thresholded) + GSN(thresholded) + GSTM2 + PPAP2B + TPM2)/5 | — | KLK2 | AR, ERG, SLC22A3 | 1.30 * ECM − 1.20 * Migration − 0.52 * KLK2 + 0.09 * AR + 0.05 * ERG − 0.06 * SLC22A3 |
| RS16 | (BGN (thresholded) + COL3A1 + INHBA + SPARC(thresholded))/4 | (C7 + FLNC(thresholded) + GSN(thresholded) + GSTM1)/4 | — | KLK2 | AR, ERG, SLC22A3 | 1.23 * ECM − 1.02 * Migration − 0.46 * KLK2 + 0.09 * AR + 0.07 * ERG − 0.09 * SLC22A3 |
| RS17 | (BGN + COL1A1 + SFRP4)/3 | (FLNC + GSN + GSTM1 + TPM2)/4 | TPX2 | (FAM13C + KLK2)/2 | AR, AZGP1, ERG, SLC22A3, SRD5A2 | 0.63 * ECM − 0.12 * Migration − 0.44 * PSA + 0.19 * TPX2 − 0.02 * AR − 0.15 * AZGP1 + 0.06 * ERG − 0.13 * SLC22A3 − 0.33 * SRD5A2 |
| RS18 | (BGN + COL1A1 + SFRP4)/3 | (FLNC + GSN + GSTM1 + TPM2)/4 | TPX2 | (FAM13C + KLK2)/2 | AR, ERG, SLC22A3, SRD5A2 | 0.63 * ECM − 0.17 * Migration − 0.52 * PSA + 0.19 * TPX2 − 0.07 * AR + 0.09 * ERG − 0.14 * SLC22A3 − 0.36 * SRD5A2 |
| RS19 | (BGN + COL1A1 + SFRP4)/3 | (FLNC + GSN + GSTM1 + TPM2)/4 | — | (FAM13C + KLK2)/2 | AR, AZGP1, ERG, SLC22A3, SRD5A2 | 0.72 * ECM − 0.24 * Migration − 0.51 * PSA + 0.03 * AR − 0.15 * AZGP1 + 0.04 * ERG − 0.12 * SLC22A3 − 0.32 * SRD5A2 |
| RS20 | (BGN + COL1A1 + SFRP4)/3 | (FLNC + GSN + PPAP2B + TPM2)/4 | TPX2 | (FAM13C + KLK2)/2 | (Stress: GSTM1 + GSTM2) AZGP1, SLC22A3, SRD5A2 | 0.72 * ECM − 0.26 * Migration − 0.45 * PSA + 0.15 * TPX2 + 0.02 * Stress − 0.16 * AZGP1 − 0.06 * SLC22A3 − 0.30 * SRD5A2 |
| RS21 | (BGN + COL1A1 + SFRP4)/3 | (FLNC + GSN + PPAP2B + TPM2)/4 | TPX2 | (FAM13C + KLK2)/2 | AZGP1, SLC22A3, SRD5A2 | 0.68 * ECM − 0.19 * Migration − 0.43 * PSA + 0.16 * TPX2 − 0.18 * AZGP1 − 0.07 * SLC22A3 − 0.31 * SRD5A2 |
| RS22 | (BGN + COL1A1 + SFRP4)/3 | | TPX2 | (FAM13C + KLK2)/2 | (Stress: GSTM1 + GSTM2) AZGP1, SLC22A3, SRD5A2 | 0.62 * ECM − 0.46 * PSA + 0.18 * TPX2 − 0.07 * Stress − 0.18 * AZGP1 − 0.08 * SLC22A3 − 0.34 * SRD5A2 |
| RS23 | (BGN + COL1A1 + SFRP4)/3 | (FLNC + GSN + GSTM2 + TPM2)/4 | TPX2 | (FAM13C + KLK2)/2 | AR, AZGP1, ERG, SRD5A2 | 0.73 * ECM − 0.26 * Migration − 0.45 * PSA + 0.17 * TPX2 + 0.02 * AR − 0.17 * AZGP1 + 0.03 * ERG − 0.29 * SRD5A2 |
| RS24 | (BGN + COL1A1 + SFRP4)/3 | (FLNC + GSN + GSTM1 + GSTM2 + PPAP2B + TPM2)/6 | TPX2 | (FAM13C + KLK2)/2 | AZGP1, SLC22A3, SRD5A2 | 0.52 * ECM − 0.23 * Migration − 0.30 * PSA + 0.14 * TPX2 − 0.17 * AZGP1 − 0.07 * SLC22A3 − 0.27 * SRD5A2 |
| RS25 | (BGN + COL1A1 + SFRP4)/3 | (FLNC + GSN + TPM2)/3 | TPX2 | (FAM13C + KLK2)/2 | AZGP1, GSTM2, SRD5A2 | 0.72 * ECM − 0.14 * Migration − 0.45 * PSA + 0.16 * TPX2 − 0.17 * AZGP11 − 0.14 * GSTM2 − 0.28 * SRD5A2 |

TABLE 4-continued

| RS Model | ECM (Stromal Response) | Migration (Cellular Organization) | Prolif. | Androgen (PSA) | Other | Algorithm |
|---|---|---|---|---|---|---|
| RS26 | (1.581 * BGN + 1.371 * COL1A1 + 0.469 * SFRP4)/3 | (0.489 * FLNC + 1.512 * GSN + 1.264 * TPM2)/3 | TPX2 (thresholded) | (1.267 * FAM13C + 2.158 * KLK2)/2 | AZGP1, GSTM2, SRD5A2 (thresholded) | 0.735 * ECM − 0.368 * Migration − 0.352 * PSA + 0.094 * TPX2 − 0.226 * AZGP11 − 0.145 * GSTM2 − 0.351 * SRD5A2 |
| RS27 | (1.581 * BGN + 1.371 * COL1A1 + 0.469 * SFRP4)/3 = 0.527 * BGN + 0.457 * COL1A1 + 0.156 * SFRP4 | [(0.489 * FLNC + 1.512 * GSN + 1.264 * TPM2)/3] + (0.145 * GSTM2/0.368) = 0.163 * FLNC + 0.504 * GSN + 0.421 * TPM2 + 0.394 * GSTM2 | TPX2 (thresholded) | [(1.267 * FAM13C + 2.158 * KLK2)/2] + (0.226 * AZGP1/0.352) + (0.351 * SRD5A2Thresh/0.352) = 0.634 * FAM13C + 1.079 * KLK2 + 0.642 * AZGP1 + 0.997SRD5A2Thresh | | 0.735 * ECM − 0.368 * Migration − 0.352 * PSA + 0.095 * TPX2 |

Table 5A shows the standardized odds ratio of each of the RS models using the data from the original Gene ID study described in Example 1 for time to cR and for upgrading and upstaging and the combination of significant upgrading and upstaging. Table 5B shows the performance of each of the RS models using the data from the CC Companion (Cohorts 2 and 3) study for upgrading and upstaging and the combination of significant upgrading and upstaging. In this context, "upgrading" refers to an increase in Gleason grade from 3+3 or 3+4 at biopsy to greater than or equal to 3+4 at radical prostatectomy. "Significant upgrading" in this context refers to upgrading from Gleason grade 3+3 or 3+4 at biopsy to equal to or greater than 4+3 at radical prostatectomy.

In addition, the gene groups used in the RS25 model were evaluated alone and in various combinations. Table 6A shows the results of this analysis using the data from the Gene Identification study and Table 6B shows the results of this analysis using the data from Cohorts 2 and 3 of the CC Companion Study.

The gene expression for some genes may be thresholded, for example SRD5A2 Thresh=5.5 if SRD5A2<5.5 or SRD5A2 if SRD5A2≥ 5.5 and TPX2 Thresh=5.0 if TPX2<5.0 or TPX2 if TPX2≥ 5.0, wherein the gene symbols represent normalized gene expression values.

The unscaled RS scores derived from Table 4 can also be rescaled to be between 0 and 100. For example, RS27 can be rescaled to be between 0 and 100 as follows:

RS (scaled)=0 if 13.4×(RSu+10.5)<0; 13.4×(RSu+10.5) if 0≤13.4×(RSu+10.5)≤100; or 100 if 13.4×(RSu+10.5)>100.

Using the scaled RS, patients can be classified into low, intermediate, and high RS groups using pre-specified cut-points defined below in Table B. These cut-points define the boundaries between low and intermediate RS groups and between intermediate and high RS groups. The cutpoints were derived from the discovery study with the intent of identifying substantial proportions of patients who on average had clinically meaningful low or high risk of aggressive disease. The scaled RS is rounded to the nearest integer before the cut-points defining RS groups are applied.

TABLE B

| RS Group | Risk Score |
| --- | --- |
| Low | Less than 16 |
| Intermediate | Greater than or equal to 16 and less than 30 |
| High | Greater than or equal to 30 |

TABLE 5A

| RS | N | Upgrading | | Significant Upgrading | | Upstaging | | Significant Upgrading or Upstaging | |
| --- | --- | --- | --- | --- | --- | --- | --- | --- | --- |
| | | OR | 95% CI | OR | 95% CI | OR | 95% CI | OR | 95% CI |
| RS0 | 280 | 1.72 | (1.22, 2.41) | 7.51 | (4.37, 12.9) | 2.01 | (1.41, 2.88) | 2.91 | (1.95, 4.34) |
| RS1 | 287 | 1.73 | (1.21, 2.48) | 5.98 | (3.30, 10.8) | 1.99 | (1.40, 2.82) | 2.68 | (1.80, 3.97) |
| RS2 | 287 | 1.72 | (1.19, 2.48) | 5.89 | (3.18, 10.9) | 2.02 | (1.42, 2.86) | 2.67 | (1.80, 3.95) |
| RS3 | 287 | 1.71 | (1.20, 2.45) | 6.30 | (3.66, 10.8) | 1.96 | (1.38, 2.80) | 2.69 | (1.84, 3.93) |
| RS4 | 287 | 1.69 | (1.18, 2.42) | 6.06 | (3.48, 10.5) | 1.99 | (1.40, 2.82) | 2.65 | (1.82, 3.86) |
| RS5 | 288 | 1.78 | (1.21, 2.62) | 5.60 | (3.56, 8.81) | 2.24 | (1.59, 3.15) | 2.87 | (1.93, 4.28) |
| RS6 | 287 | 1.94 | (1.37, 2.74) | 10.16 | (5.82, 17.8) | 2.07 | (1.48, 2.91) | 3.11 | (2.07, 4.67) |
| RS7 | 288 | 1.91 | (1.34, 2.71) | 9.34 | (5.25, 16.6) | 2.06 | (1.47, 2.89) | 3.01 | (2.02, 4.48) |
| RS8 | 289 | 1.80 | (1.27, 2.55) | 7.49 | (4.02, 14.0) | 2.09 | (1.49, 2.92) | 2.86 | (1.97, 4.14) |
| RS9 | 288 | 2.00 | (1.39, 2.89) | 9.56 | (5.06, 18.0) | 1.99 | (1.42, 2.79) | 3.09 | (2.08, 4.60) |
| RS10 | 287 | 1.94 | (1.37, 2.75) | 10.12 | (5.79, 17.7) | 2.09 | (1.49, 2.94) | 3.14 | (2.08, 4.74) |
| RS11 | 288 | 2.09 | (1.43, 3.05) | 9.46 | (5.18, 17.3) | 2.17 | (1.54, 3.05) | 3.42 | (2.24, 5.23) |
| RS12 | 287 | 2.10 | (1.45, 3.04) | 10.41 | (5.92, 18.3) | 2.17 | (1.55, 3.06) | 3.52 | (2.30, 5.40) |
| RS13 | 287 | 2.10 | (1.44, 3.05) | 9.40 | (5.50, 16.1) | 2.20 | (1.55, 3.13) | 3.50 | (2.25, 5.43) |
| RS14 | 287 | 2.06 | (1.42, 2.99) | 9.71 | (5.65, 16.7) | 2.18 | (1.55, 3.08) | 3.53 | (2.29, 5.44) |
| RS15 | 288 | 1.92 | (1.32, 2.78) | 7.93 | (4.56, 13.8) | 2.12 | (1.51, 2.99) | 3.25 | (2.20, 4.80) |
| RS16 | 288 | 1.76 | (1.23, 2.52) | 7.10 | (4.12, 12.2) | 1.99 | (1.41, 2.82) | 2.94 | (1.98, 4.38) |
| RS17 | 286 | 2.23 | (1.52, 3.27) | 7.52 | (4.18, 13.5) | 2.91 | (1.93, 4.38) | 4.48 | (2.72, 7.38) |
| RS18 | 286 | 2.12 | (1.46, 3.08) | 7.04 | (3.87, 12.8) | 2.89 | (1.91, 4.37) | 4.30 | (2.62, 7.06) |
| RS19 | 287 | 2.14 | (1.46, 3.13) | 6.90 | (3.80, 12.5) | 2.88 | (1.96, 4.23) | 4.20 | (2.66, 6.63) |
| RS20 | 286 | 2.30 | (1.55, 3.42) | 8.41 | (4.65, 15.2) | 2.90 | (1.98, 4.25) | 4.78 | (3.00, 7.61) |
| RS21 | 287 | 2.36 | (1.59, 3.52) | 8.83 | (4.87, 16.0) | 2.63 | (1.76, 3.94) | 4.93 | (3.06, 7.93) |
| RS22 | 286 | 2.16 | (1.48, 3.15) | 7.57 | (4.14, 13.8) | 2.90 | (1.96, 4.27) | 4.39 | (2.75, 7.01) |
| RS23 | 287 | 2.26 | (1.53, 3.35) | 7.46 | (4.24, 13.1) | 2.80 | (1.85, 4.24) | 4.79 | (2.98, 7.68) |
| RS24 | 286 | 2.21 | (1.50, 3.24) | 8.01 | (4.38, 14.7) | 2.93 | (1.99, 4.31) | 4.62 | (2.89, 7.39) |
| RS25 | 287 | 2.25 | (1.53, 3.31) | 7.70 | (4.25, 14.0) | 2.76 | (1.83, 4.16) | 4.76 | (2.99, 7.58) |
| RS26 | 287 | 2.23 | (1.51, 3.29) | 6.67 | (3.52, 12.7) | 2.64 | (1.81, 3.86) | 4.01 | (2.56, 6.28) |
| RS27 | 287 | 2.23 | (1.51, 3.29) | 6.67 | (3.52, 12.7) | 2.64 | (1.81, 3.86) | 4.01 | (2.56, 6.28) |

TABLE 5B

| Model | N | Upgrading Std OR | 95% CI | Significant Upgrading Std OR | 95% CI | Upstaging Std OR | 95% CI | Significant Upgrading or Upstaging Std OR | 95% CI |
|---|---|---|---|---|---|---|---|---|---|
| RS0 | 166 | 1.16 | (0.84, 1.58) | 2.45 | (1.61, 3.73) | 2.42 | (1.61, 3.62) | 3 | (1.98, 4.56) |
| RS1 | 167 | 1.05 | (0.77, 1.43) | 2.46 | (1.63, 3.71) | 2.38 | (1.61, 3.53) | 3.36 | (2.18, 5.18) |
| RS2 | 167 | 1.04 | (0.76, 1.42) | 2.45 | (1.63, 3.69) | 2.34 | (1.58, 3.46) | 3.25 | (2.12, 4.99) |
| RS3 | 167 | 1.04 | (0.76, 1.41) | 2.56 | (1.69, 3.89) | 2.28 | (1.55, 3.36) | 3.27 | (2.13, 5.03) |
| RS4 | 167 | 1.03 | (0.75, 1.40) | 2.54 | (1.68, 3.86) | 2.23 | (1.52, 3.27) | 3.16 | (2.07, 4.82) |
| RS5 | 167 | 1.02 | (0.75, 1.39) | 1.89 | (1.28, 2.78) | 1.77 | (1.23, 2.55) | 2.21 | (1.52, 3.20) |
| RS6 | 167 | 1.08 | (0.79, 1.48) | 2.49 | (1.64, 3.79) | 2.42 | (1.62, 3.62) | 3.22 | (2.09, 4.96) |
| RS7 | 167 | 1.03 | (0.75, 1.40) | 2.31 | (1.54, 3.48) | 2.28 | (1.54, 3.38) | 2.97 | (1.96, 4.51) |
| RS8 | 167 | 0.94 | (0.69, 1.28) | 2.34 | (1.55, 3.53) | 2.31 | (1.56, 3.43) | 2.87 | (1.91, 4.30) |
| RS9 | 167 | 1.02 | (0.75, 1.39) | 2.19 | (1.47, 3.27) | 2.22 | (1.51, 3.27) | 2.77 | (1.85, 4.14) |
| RS10 | 167 | 1.08 | (0.79, 1.48) | 2.49 | (1.63, 3.78) | 2.41 | (1.61, 3.61) | 3.22 | (2.09, 4.95) |
| RS11 | 167 | 0.99 | (0.73, 1.35) | 2.18 | (1.46, 3.24) | 2.17 | (1.48, 3.19) | 2.83 | (1.88, 4.25) |
| RS12 | 167 | 1.06 | (0.78, 1.45) | 2.36 | (1.57, 3.56) | 2.34 | (1.57, 3.48) | 3.12 | (2.04, 4.78) |
| RS13 | 166 | 1.01 | (0.74, 1.37) | 2.17 | (1.45, 3.23) | 2.41 | (1.61, 3.60) | 2.99 | (1.97, 4.54) |
| RS14 | 166 | 1.03 | (0.76, 1.41) | 2.22 | (1.48, 3.31) | 2.33 | (1.57, 3.46) | 2.95 | (1.94, 4.47) |
| RS15 | 166 | 1 | (0.73, 1.36) | 1.98 | (1.34, 2.92) | 2.12 | (1.44, 3.12) | 2.58 | (1.74, 3.84) |
| RS16 | 166 | 0.94 | (0.69, 1.28) | 1.7 | (1.16, 2.48) | 2.07 | (1.41, 3.03) | 2.24 | (1.54, 3.25) |
| RS17 | 165 | 0.98 | (0.72, 1.34) | 1.96 | (1.33, 2.89) | 2.63 | (1.73, 3.98) | 3.02 | (1.99, 4.60) |
| RS18 | 165 | 0.97 | (0.71, 1.33) | 1.86 | (1.26, 2.73) | 2.71 | (1.78, 4.13) | 3.01 | (1.98, 4.56) |
| RS19 | 165 | 0.93 | (0.68, 1.27) | 1.86 | (1.27, 2.72) | 2.4 | (1.61, 3.58) | 2.75 | (1.84, 4.10) |
| RS20 | 166 | 1.07 | (0.78, 1.46) | 2.2 | (1.48, 3.29) | 2.47 | (1.65, 3.69) | 3.1 | (2.04, 4.72) |
| RS21 | 166 | 1.06 | (0.77, 1.45) | 2.2 | (1.47, 3.28) | 2.48 | (1.65, 3.71) | 3.11 | (2.04, 4.74) |
| RS22 | 166 | 1.04 | (0.76, 1.43) | 2.21 | (1.48, 3.29) | 2.47 | (1.65, 3.70) | 3.14 | (2.05, 4.79) |
| RS23 | 165 | 1.02 | (0.75, 1.40) | 2.01 | (1.36, 2.97) | 2.52 | (1.67, 3.79) | 2.94 | (1.95, 4.44) |
| RS24 | 166 | 1.04 | (0.76, 1.42) | 2.18 | (1.46, 3.26) | 2.52 | (1.68, 3.78) | 3.14 | (2.06, 4.80) |
| RS25 | 166 | 1.04 | (0.76, 1.42) | 2.11 | (1.42, 3.13) | 2.45 | (1.64, 3.67) | 3 | (1.98, 4.54) |
| RS26 | 166 | 0.99 | (0.72, 1.35) | 2.05 | (1.38, 3.04) | 2.43 | (1.63, 3.65) | 2.82 | (1.88, 4.21) |
| RS27 | 166 | 0.99 | (0.72, 1.35) | 2.05 | (1.38, 3.04) | 2.43 | (1.63, 3.65) | 2.82 | (1.88, 4.21) |

TABLE 6A

| Model | Time to cR N | Std HR | Upgrading N | Std OR | 95% CI | Significant Upgrading Std OR | 95% CI | Upstaging Std OR | 95% CI | Significant Upgrading or Upstaging Std OR | 95% CI |
|---|---|---|---|---|---|---|---|---|---|---|---|
| RS25 | 428 | 2.82 | 232 | 2.09 | (1.41, 3.10) | 7.35 | (3.87, 14.0) | 2.55 | (1.63, 4.00) | 4.46 | (2.72, 7.32) |
| Stromal | 430 | 2.05 | 234 | 1.32 | (0.95, 1.84) | 3.08 | (1.84, 5.14) | 1.6 | (1.12, 2.30) | 1.95 | (1.35, 2.82) |
| Cellular Organization | 430 | 1.67 | 234 | 1.67 | (1.16, 2.39) | 2.83 | (1.63, 4.90) | 1.38 | (0.96, 1.99) | 2.06 | (1.37, 3.10) |
| PSA | 430 | 1.89 | 234 | 0.96 | (0.70, 1.32) | 1.38 | (0.72, 2.63) | 1.47 | (1.06, 2.03) | 1.25 | (0.83, 1.88) |
| ECM Cellular Organization | 430 | 2.6 | 234 | 2 | (1.37, 2.93) | 11.5 | (5.84, 22.7) | 1.98 | (1.34, 2.93) | 4.01 | (2.44, 6.58) |
| ECM PSA | 430 | 2.45 | 234 | 1.17 | (0.85, 1.61) | 2.46 | (1.44, 4.21) | 1.7 | (1.21, 2.39) | 1.76 | (1.22, 2.53) |
| Cellular Organization PSA | 430 | 2.04 | 234 | 1.3 | (0.92, 1.82) | 2.52 | (1.23, 5.16) | 1.63 | (1.13, 2.36) | 1.85 | (1.19, 2.87) |
| ECM Cellular Organization TPX2 | 429 | 2.61 | 233 | 1.89 | (1.31, 2.72) | 11.3 | (5.46, 23.5) | 1.94 | (1.31, 2.87) | 3.99 | (2.44, 6.54) |
| ECM PSA TPX2 | 429 | 2.42 | 233 | 1.24 | (0.90, 1.71) | 3.25 | (1.91, 5.51) | 1.75 | (1.22, 2.49) | 2.08 | (1.45, 2.98) |
| Cellular Organization PSA TPX2 | 429 | 2.04 | 233 | 1.33 | (0.95, 1.86) | 3.2 | (1.74, 5.90) | 1.69 | (1.17, 2.44) | 2.21 | (1.45, 3.37) |
| ECM Cellular Organization GSTM2 | 430 | 2.67 | 234 | 2.03 | (1.39, 2.96) | 11.3 | (5.72, 22.3) | 2.17 | (1.43, 3.30) | 4.35 | (2.50, 7.58) |
| ECM PSA GSTM2 | 430 | 2.86 | 234 | 1.48 | (1.05, 2.09) | 4.45 | (2.03, 9.76) | 2.2 | (1.45, 3.34) | 2.66 | (1.64, 4.31) |
| Cellular Organization PSA GSTM2 | 430 | 2.25 | 234 | 1.34 | (0.94, 1.90) | 2.52 | (1.18, 5.38) | 1.92 | (1.29, 2.84) | 2.02 | (1.20, 3.39) |
| ECM Cellular Organization GSTM2 TPX2 AZGP1 SRD5A2 | 428 | 2.72 | 232 | 2.38 | (1.58, 3.57) | 11.5 | (6.02, 21.8) | 2.48 | (1.58, 3.87) | 5.22 | (2.97, 9.17) |
| ECM PSA GSTM2 TPX2 AZGP1 SRD5A2 | 428 | 2.8 | 232 | 2.03 | (1.38, 3.00) | 6.65 | (3.52, 12.6) | 2.6 | (1.65, 4.09) | 4.26 | (2.58, 7.02) |
| Cellular Organization PSA GSTM2 TPX2 AZGP1 SRD5A2 | 428 | 2.38 | 232 | 1.92 | (1.28, 2.88) | 3.63 | (2.14, 6.15) | 2.6 | (1.64, 4.12) | 3.49 | (2.08, 5.83) |

TABLE 6B

| Model | Upgrading | | Significant Upgrading | | Upstaging | | Significant Upgrading or Upstaging | |
|---|---|---|---|---|---|---|---|---|
| | N | Std OR | 95% CI | Std OR | 95% CI | Std OR | 95% CI | Std OR | 95% CI |
| RS25 | 166 | 1.04 | (0.76, 1.42) | 2.11 | (1.42, 3.13) | 2.45 | (1.64, 3.67) | 3 | (1.98, 4.54) |
| Stromal | 166 | 0.99 | (0.73, 1.35) | 2.19 | (1.45, 3.32) | 1.65 | (1.15, 2.38) | 1.86 | (1.31, 2.65) |
| Cellular Organization | 167 | 1.06 | (0.77, 1.44) | 0.93 | (0.64, 1.36) | 1.49 | (1.04, 2.13) | 1.44 | (1.03, 2.00) |
| PSA | 167 | 1.04 | (0.76, 1.42) | 1.68 | (1.16, 2.44) | 1.78 | (1.24, 2.57) | 1.96 | (1.37, 2.81) |
| ECM Cellular Organization | 166 | 1.04 | (0.76, 1.42) | 1.96 | (1.32, 2.91) | 2.32 | (1.55, 3.45) | 2.6 | (1.76, 3.85) |
| ECM PSA | 166 | 1.02 | (0.75, 1.39) | 2.14 | (1.44, 3.20) | 1.84 | (1.28, 2.67) | 2.11 | (1.47, 3.04) |
| Cellular Organization PSA | 167 | 1.07 | (0.78, 1.46) | 1.36 | (0.94, 1.97) | 2.06 | (1.40, 3.04) | 2.12 | (1.47, 3.06) |
| ECM Cellular Organization TPX2 | 166 | 1.15 | (0.84, 1.58) | 2.24 | (1.49, 3.37) | 2.55 | (1.69, 3.85) | 2.95 | (1.96, 4.45) |
| ECM PSA TPX2 | 166 | 1.2 | (0.88, 1.65) | 2.66 | (1.71, 4.13) | 2.28 | (1.53, 3.40) | 2.72 | (1.82, 4.07) |
| Cellular Organization PSA TPX2 | 167 | 1.3 | (0.95, 1.79) | 1.77 | (1.21, 2.60) | 2.42 | (1.62, 3.63) | 2.65 | (1.79, 3.92) |
| ECM Cellular Organization GSTM2 | 166 | 0.96 | (0.70, 1.30) | 1.76 | (1.20, 2.57) | 2.12 | (1.44, 3.12) | 2.34 | (1.60, 3.42) |
| ECM PSA GSTM2 | 166 | 0.91 | (0.67, 1.24) | 1.69 | (1.16, 2.46) | 1.85 | (1.28, 2.67) | 2.05 | (1.42, 2.94) |
| Cellular Organization PSA GSTM2 | 167 | 0.89 | (0.65, 1.22) | 1.13 | (0.78, 1.62) | 1.72 | (1.19, 2.48) | 1.75 | (1.23, 2.48) |
| ECM Cellular Organization GSTM2 TPX2 AZGP1 SRD5A2 | 166 | 1.04 | (0.76, 1.42) | 2.14 | (1.44, 3.20) | 2.47 | (1.65, 3.70) | 2.94 | (1.95, 4.44) |
| ECM PSA GSTM2 TPX2 AZGP1 SRD5A2 | 166 | 1.03 | (0.75, 1.41) | 2.11 | (1.42, 3.13) | 2.39 | (1.61, 3.57) | 2.94 | (1.95, 4.45) |
| Cellular Organization PSA GSTM2 TPX2 AZGP1 SRD5A2 | 167 | 1.07 | (0.78, 1.46) | 1.84 | (1.26, 2.68) | 2.22 | (1.51, 3.27) | 2.73 | (1.83, 4.09) |

Example 3: Clique Stack Analysis to Identify Co-Expressed Genes

Figure 4:
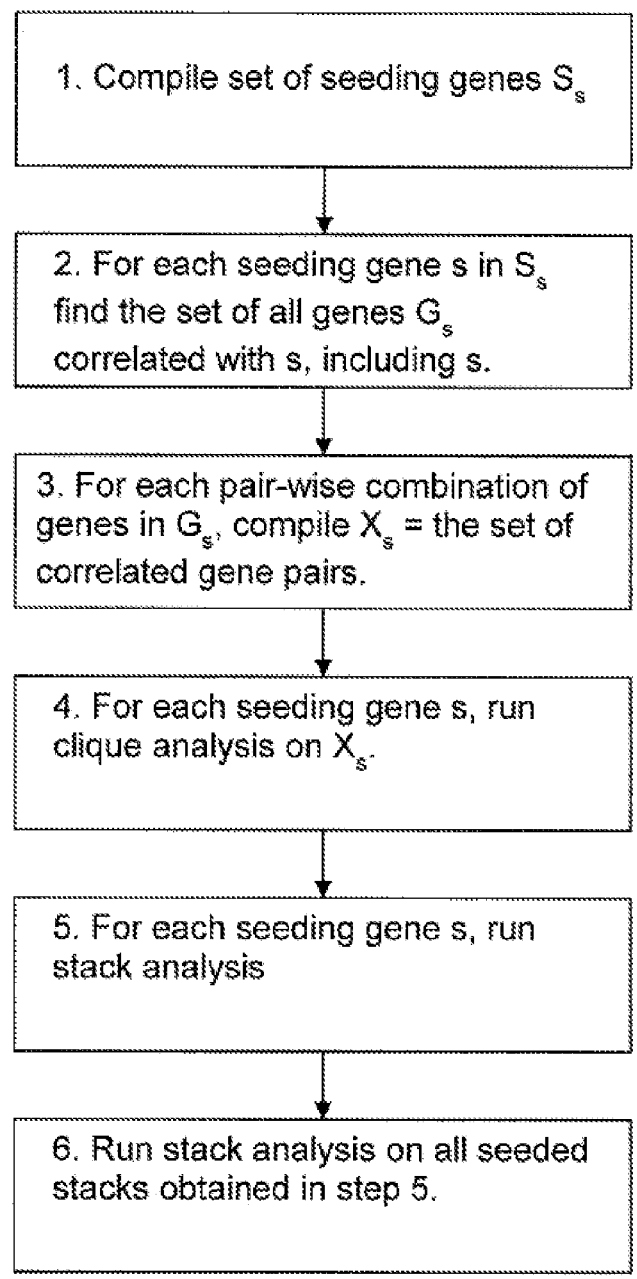
FIG. 4 is a schematic illustration of the clique-stack method used to identify co-expressed genes.

The purpose of the gene clique stacks method described in this Example was to find a set of co-expressed (or surrogate) biomarkers that can be used to reliably predict outcome as well or better than the genes disclosed above. The method used to identify the co-expressed markers is illustrated in FIG. 4. The set of co-expressed biomarkers were obtained by seeding the maximal clique enumeration (MCE) with curated biomarkers extracted from the scientific literature. The maximal clique enumeration (MCE) method [Bron et al, 1973] aggregates genes into tightly co-expressed groups such that all of the genes in the group have a similar expression profile. When all of the genes in a group satisfy a minimal similarity condition, the group is called a clique. When a clique is as large as possible without admitting any 'dissimilar' genes into the clique, then the clique is said to be maximal. Using the MCE method, all maximal cliques are searched within a dataset. Using this method, almost any degree of overlap between the maximal cliques can be found, as long as the overlap is supported by the data. Maximal clique enumeration has been shown [Borate et al, 2009] to be an effective way of identifying co-expressed gene modules (CGMs).

1. Definitions

The following table defines a few terms commonly used in the gene clique stack analyses.

TABLE 7

| Term | Definition |
|---|---|
| Node | The abundance of a gene (for the purposes of CGM analysis) |
| Edge | A line connecting two nodes, indicating co-expression of the two nodes |

TABLE 7-continued

| Term | Definition |
|---|---|
| Graph | A collection of nodes and edges |
| Clique | A graph with an edge connecting all pair-wise combinations of nodes in the graph |
| maximal clique | A clique that is not contained in any other clique |
| Stack | A graph obtained by merging at least two cliques or stacks such that the overlap between the two cliques or stacks exceeds some user-defined threshold. |
| gene expression profile | A two-dimensional matrix, with genes listed down the rows and samples listed across the columns. Each (i, j) entry in the matrix corresponds to relative mRNA abundance for gene i and sample j. |

2. Examples of Cliques and Stacks

FIG. 5 shows a family of three different graphs. A graph consists of nodes (numbered) and connecting edges (lines). FIG. 5(a) is not a clique because there is no edge connecting nodes 3 and 4. FIG. 5(b) is a clique because there is an edge connecting all pair-wise combinations of nodes in the graph. FIG. 5(c) is a clique, but not a maximal clique because it is contained in clique (b). Given a graph with connecting edges, the MCE algorithm will systematically list all of maximal cliques with 3 or more nodes. For example, the graph in FIG. 6 has two maximal cliques: 1-2-3-4-5 and 1-2-3-4-6.

When based on gene expression data, there are typically large numbers of maximal cliques that are very similar to one another. These maximal cliques can be merged into stacks of maximal cliques. The stacks are the final gene modules of interest and generally are far fewer in number than are the maximal cliques. FIG. 7A-C schematically illustrates stacking of two maximal cliques.

3. Seeding

For the purposes of finding surrogate co-expressed markers, biomarkers from the literature can be identified and then used to seed the MCE and stacking algorithms. The basic idea is as follows: for each seed, compute a set of maximal cliques (using the parallel MCE algorithm). Then stack the maximal cliques obtained for each seed, yielding a set of seeded stacks. Finally, stack the seeded stacks to obtain a "stack of seeded stacks." The stack of seeded stacks is an approximation to the stacks that would be obtained by using the conventional (i.e. unseeded) MCE/stacking algorithms. The method used to identify genes that co-express with the genes disclosed above illustrated in FIG. 4 and is described in more detail below.

3.1 Seeded MCE Algorithm (Steps 1-4)

1. The process begins by identifying an appropriate set, $S_s$, of seeding genes. In the instant case, the seeding genes were selected from the gene subsets disclosed above.
2. With the seeding genes specified, select a measure of correlation, $R(g_1,g_2)$, between the gene expression profiles of any two genes, $g_1,g_2$, along with a correlation threshold below which $g_1,g_2$, can be considered uncorrelated. For each seeding gene s in the seeding set $S_s$, find all gene pairs (s,g) in the dataset such that $R(s,g)$ is greater than or equal to the correlation threshold. Let $G_s$ be the union of s and the set of all genes correlated with s. For the instant study, the Spearman coefficient was used as the measure of correlation and 0.7 as the correlation threshold.
3. Compute the correlation coefficient for each pair-wise combination of genes $(g_i,g_j)$ in $G_s$. Let $X_s$ be the set of all gene pairs for which $R(g_i,g_j)$ is greater than or equal to the correlation threshold. If the genes were plotted as in FIG. 5, there would be an edge (line) between each pair of genes in $X_s$.
4. Run the MCE algorithm, as described in Schmidt et al (J. Parallel Distrib. Comput. 69 (2009) 417-428) on the gene pairs $X_s$ for each seeding gene.

3.2 Seeded Stacking Algorithm (Steps 5-6)

The purpose of stacking is to reduce the number of cliques down to a manageable number of gene modules (stacks). Continuing with steps 5 and 6 of FIG. 4:

5. For each seeding gene, sort cliques from largest to smallest, i.e. most number of nodes to smallest number of nodes. From the remaining cliques, find the clique with the greatest overlap. If the overlap exceeds a user-specified threshold T, merge the two cliques together to form the first stack. Resort the cliques and stack(s) from largest to smallest and repeat the overlap test and merging. Repeat the process until no new merges occur.
6. One now has a set of stacks for each seeding gene. In the final step, all of the seeded stacks are combined into one set of stacks, a. As the final computation, all of the stacks in a are stacked, just as in step 5. This stack of stacks is the set of gene modules used for the instant study.

Genes that were shown to co-express with genes identified by this method are shown in Tables 8-11. "Stack ID" in the Tables is simply an index to enumerate the stacks and "probeWt" refers to the probe weight, or the number of times a probe (gene) appears in the stack.

TABLE 8

| StackID | Coexpressed Gene | ProbeWt | SeedingGene | StackID | Coexpressed Gene | ProbeWt | SeedingGene | StackID | Coexpressed Gene | ProbeWt | SeedingGene |
|---|---|---|---|---|---|---|---|---|---|---|---|
| 1 | SLCO2B1 | 1 | BGN | 1 | SPARC | 1 | SPARC | 1 | SPARC | 1 | COL4A1 |
| 1 | LHFP | 1 | BGN | 1 | COL4A1 | 1 | SPARC | 1 | COL4A1 | 1 | COL4A1 |
| 1 | ENG | 1 | BGN | 1 | COL4A2 | 1 | SPARC | 1 | HTRA1 | 1 | COL4A1 |
| 2 | LHFP | 1 | BGN | 2 | COL3A1 | 1 | SPARC | 2 | COL4A1 | 3 | COL4A1 |
| 2 | THY1 | 1 | BGN | 2 | SPARC | 1 | SPARC | 2 | NID1 | 3 | COL4A1 |
| 2 | ENG | 1 | BGN | 2 | COL4A1 | 1 | SPARC | 2 | CD93 | 2 | COL4A1 |
| 3 | COL1A1 | 1 | BGN | 2 | VCAN | 1 | SPARC | 2 | FBN1 | 2 | COL4A1 |
| 3 | THY1 | 1 | BGN | 2 | FN1 | 1 | SPARC | 2 | COL1A1 | 1 | COL4A1 |
| 3 | ENG | 1 | BGN | 3 | HEG1 | 3 | SPARC | 2 | MCAM | 1 | COL4A1 |
| 4 | COL1A1 | 1 | BGN | 3 | MEF2C | 3 | SPARC | 2 | SPARC | 1 | COL4A1 |
| 4 | PDGFRB | 1 | BGN | 3 | RGS5 | 2 | SPARC | 3 | COL1A2 | 4 | COL4A1 |
| 4 | FMNL3 | 1 | BGN | 3 | KDR | 2 | SPARC | 3 | COL4A1 | 4 | COL4A1 |
| 5 | SLCO2B1 | 1 | BGN | 3 | LAMA4 | 1 | SPARC | 3 | VCAN | 2 | COL4A1 |
| 5 | LHFP | 1 | BGN | 3 | SPARC | 1 | SPARC | 3 | FN1 | 2 | COL4A1 |
| 5 | COL3A1 | 1 | BGN | 4 | COL3A1 | 5 | SPARC | 3 | COL1A1 | 2 | COL4A1 |
| 6 | THY1 | 1 | BGN | 4 | SPARC | 5 | SPARC | 3 | NID1 | 2 | COL4A1 |
| 6 | LHFP | 1 | BGN | 4 | COL1A1 | 3 | SPARC | 3 | HTRA1 | 1 | COL4A1 |
| 6 | COL3A1 | 1 | BGN | 4 | COL1A2 | 2 | SPARC | 3 | COL6A3 | 1 | COL4A1 |
| 7 | THY1 | 1 | BGN | 4 | BGN | 2 | SPARC | | | | |
| 7 | COL1A1 | 1 | BGN | 4 | PDGFRB | 2 | SPARC | 1 | INHBA | 1 | INHBA |
| 7 | COL3A1 | 1 | BGN | 4 | COL4A1 | 1 | SPARC | 1 | STMN2 | 1 | INHBA |
| 8 | BGN | 7 | BGN | 4 | IGFBP7 | 1 | SPARC | 1 | COL10A1 | 1 | INHBA |
| 8 | COL1A1 | 4 | BGN | 4 | FBN1 | 1 | SPARC | | | | |
| 8 | COL3A1 | 4 | BGN | 5 | SPARC | 4 | SPARC | 1 | THBS2 | 1 | THBS2 |
| 8 | FMNL3 | 4 | BGN | 5 | PDGFRB | 4 | SPARC | 1 | COL3A1 | 1 | THBS2 |
| 8 | SLCO2B1 | 3 | BGN | 5 | DPYSL2 | 3 | SPARC | 1 | VCAN | 1 | THBS2 |
| 8 | SPARC | 3 | BGN | 5 | FBN1 | 3 | SPARC | | | | |
| 8 | ENG | 3 | BGN | 5 | HEG1 | 2 | SPARC | | | | |
| 8 | PDGFRB | 3 | BGN | 5 | CDH11 | 2 | SPARC | | | | |
| 8 | THBS2 | 1 | BGN | 5 | FBLN5 | 2 | SPARC | | | | |
| 1 | THBS2 | 1 | COL3A1 | 5 | LAMA2 | 2 | SPARC | | | | |
| 1 | COL3A1 | 1 | COL3A1 | 5 | IGFBP7 | 2 | SPARC | | | | |
| 1 | VCAN | 1 | COL3A1 | 5 | LAMA4 | 2 | SPARC | | | | |
| 2 | COL3A1 | 3 | COL3A1 | 5 | RGS5 | 1 | SPARC | | | | |
| 2 | SPARC | 3 | COL3A1 | 5 | COL4A2 | 1 | SPARC | | | | |
| 2 | FN1 | 2 | COL3A1 | 5 | COL1A2 | 1 | SPARC | | | | |
| 2 | COL4A1 | 2 | COL3A1 | 6 | FBN1 | 7 | SPARC | | | | |
| 2 | VCAN | 1 | COL3A1 | 6 | LAMA4 | 6 | SPARC | | | | |
| 2 | COL1A1 | 1 | COL3A1 | 6 | SGK269 | 5 | SPARC | | | | |

TABLE 8-continued

| StackID | Coexpressed Gene | ProbeWt | SeedingGene | StackID | Coexpressed Gene | ProbeWt | SeedingGene | StackID | Coexpressed Gene | ProbeWt | SeedingGene |
|---|---|---|---|---|---|---|---|---|---|---|---|
| 2 | FBN1 | 1 | COL3A1 | 6 | CDH11 | 5 | SPARC | | | | |
| 3 | COL1A2 | 3 | COL3A1 | 6 | DPYSL2 | 5 | SPARC | | | | |
| 3 | PDGFRB | 3 | COL3A1 | 6 | LAMA2 | 5 | SPARC | | | | |
| 3 | IGFBP7 | 3 | COL3A1 | 6 | SPARC | 4 | SPARC | | | | |
| 3 | FBN1 | 3 | COL3A1 | 6 | SULF1 | 4 | SPARC | | | | |
| 3 | CDH11 | 2 | COL3A1 | 6 | FBLN5 | 3 | SPARC | | | | |
| 3 | AEBP1 | 2 | COL3A1 | 6 | LTBP1 | 3 | SPARC | | | | |
| 3 | COL3A1 | 1 | COL3A1 | 6 | EPB41L2 | 3 | SPARC | | | | |
| 3 | SPARC | 1 | COL3A1 | 6 | MEF2C | 3 | SPARC | | | | |
| 4 | COL3A1 | 5 | COL3A1 | 6 | FN1 | 2 | SPARC | | | | |
| 4 | BGN | 4 | COL3A1 | 6 | EDIL3 | 2 | SPARC | | | | |
| 4 | COL1A1 | 3 | COL3A1 | 6 | COL3A1 | 1 | SPARC | | | | |
| 4 | SPARC | 3 | COL3A1 | 6 | IGFBP7 | 1 | SPARC | | | | |
| 4 | FMNL3 | 2 | COL3A1 | 6 | HEG1 | 1 | SPARC | | | | |
| 4 | PDGFRB | 2 | COL3A1 | | | | | | | | |
| 4 | COL1A2 | 1 | COL3A1 | | | | | | | | |
| 4 | THY1 | 1 | COL3A1 | | | | | | | | |
| 4 | THBS2 | 1 | COL3A1 | | | | | | | | |

TABLE 9

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 1 | DDR2 | 26870 | C7 | 1 | MYH11 | 168 | GSTM2 | 1 | PPAP2B | 15794 | SRD5A2 |
| 1 | SPARCL1 | 25953 | C7 | 1 | TGFBR3 | 163 | GSTM2 | 1 | VWA5A | 12616 | SRD5A2 |
| 1 | FAT4 | 24985 | C7 | 1 | RBMS3 | 162 | GSTM2 | 1 | SPON1 | 12395 | SRD5A2 |
| 1 | SYNE1 | 24825 | C7 | 1 | FHL1 | 161 | GSTM2 | 1 | FAT4 | 12218 | SRD5A2 |
| 1 | SLC8A1 | 24327 | C7 | 1 | MYLK | 158 | GSTM2 | 1 | SSPN | 12126 | SRD5A2 |
| 1 | MEIS1 | 23197 | C7 | 1 | CACHD1 | 155 | GSTM2 | 1 | MKX | 11552 | SRD5A2 |
| 1 | PRRX1 | 22847 | C7 | 1 | TIMP3 | 154 | GSTM2 | 1 | PRRX1 | 11061 | SRD5A2 |
| 1 | CACHD1 | 22236 | C7 | 1 | SYNM | 152 | GSTM2 | 1 | LOC645954 | 10811 | SRD5A2 |
| 1 | DPYSL3 | 20623 | C7 | 1 | NEXN | 147 | GSTM2 | 1 | SYNM | 10654 | SRD5A2 |
| 1 | LTBP1 | 20345 | C7 | 1 | MYL9 | 142 | GSTM2 | 1 | ANXA6 | 10330 | SRD5A2 |
| 1 | SGK269 | 19461 | C7 | 1 | CRYAB | 141 | GSTM2 | 1 | PDE5A | 10011 | SRD5A2 |
| 1 | EDNRA | 19280 | C7 | 1 | VWA5A | 131 | GSTM2 | 1 | TSHZ3 | 9588 | SRD5A2 |
| 1 | TRPC4 | 18689 | C7 | 1 | AOX1 | 130 | GSTM2 | 1 | GSN | 9505 | SRD5A2 |
| 1 | TIMP3 | 18674 | C7 | 1 | FLNC | 127 | GSTM2 | 1 | NID2 | 9503 | SRD5A2 |
| 1 | TGFBR3 | 18367 | C7 | 1 | PPAP2B | 125 | GSTM2 | 1 | CLU | 9304 | SRD5A2 |
| 1 | ZEB1 | 18355 | C7 | 1 | GSTM2 | 118 | GSTM2 | 1 | TPM2 | 8659 | SRD5A2 |
| 1 | C1S | 16871 | C7 | 1 | C21orf63 | 101 | GSTM2 | 1 | FBLN1 | 8068 | SRD5A2 |
| 1 | ABCC9 | 16562 | C7 | 1 | POPDC2 | 72 | GSTM2 | 1 | PARVA | 7949 | SRD5A2 |
| 1 | PCDH18 | 14936 | C7 | 1 | TPM2 | 66 | GSTM2 | 1 | SPOCK3 | 7772 | SRD5A2 |
| 1 | C7 | 14789 | C7 | 1 | CDC42EP3 | 60 | GSTM2 | 1 | PCDH18 | 7514 | SRD5A2 |
| 1 | PDGFC | 14748 | C7 | 1 | CCDC69 | 58 | GSTM2 | 1 | ILK | 7078 | SRD5A2 |
| 1 | PTPLAD2 | 13590 | C7 | 1 | CRISPLD2 | 52 | GSTM2 | 1 | ITIH5 | 6903 | SRD5A2 |
| 1 | VCL | 13332 | C7 | 1 | GBP2 | 47 | GSTM2 | 1 | ADCY5 | 6374 | SRD5A2 |
| 1 | MMP2 | 13107 | C7 | 1 | ADCY5 | 44 | GSTM2 | 1 | CRYAB | 6219 | SRD5A2 |
| 1 | FERMT2 | 12681 | C7 | 1 | MATN2 | 40 | GSTM2 | 1 | RBMS3 | 6108 | SRD5A2 |
| 1 | EPB41L2 | 12335 | C7 | 1 | AOC3 | 38 | GSTM2 | 1 | AOX1 | 4943 | SRD5A2 |
| 1 | PRNP | 12133 | C7 | 1 | ACACB | 36 | GSTM2 | 1 | WWTR1 | 4789 | SRD5A2 |
| 1 | FBN1 | 11965 | C7 | 1 | RND3 | 28 | GSTM2 | 1 | AOC3 | 4121 | SRD5A2 |
| 1 | GLT8D2 | 11954 | C7 | 1 | CLIP4 | 26 | GSTM2 | 1 | CAP2 | 4091 | SRD5A2 |
| 1 | DSE | 11888 | C7 | 1 | APOBEC3C | 20 | GSTM2 | 1 | MAP1B | 3917 | SRD5A2 |
| 1 | SCN7A | 11384 | C7 | 1 | CAV2 | 18 | GSTM2 | 1 | OGN | 3893 | SRD5A2 |
| 1 | PPAP2B | 11121 | C7 | 1 | TRIP10 | 17 | GSTM2 | 1 | PLN | 3581 | SRD5A2 |
| 1 | PGR | 10566 | C7 | 1 | TCF21 | 11 | GSTM2 | 1 | CFL2 | 2857 | SRD5A2 |
| 1 | PALLD | 10240 | C7 | 1 | CAMK2G | 11 | GSTM2 | 1 | MATN2 | 2808 | SRD5A2 |
| 1 | CNTN1 | 10113 | C7 | 1 | GSTM5P1 | 9 | GSTM2 | 1 | ADRA1A | 2694 | SRD5A2 |
| 1 | SERPING1 | 9800 | C7 | 1 | ACSS3 | 9 | GSTM2 | 1 | BOC | 2401 | SRD5A2 |
| 1 | DKK3 | 9279 | C7 | 1 | GSTM4 | 7 | GSTM2 | 1 | ANGPT1 | 2290 | SRD5A2 |
| 1 | CCND2 | 9131 | C7 | 1 | GSTP1 | 5 | GSTM2 | 1 | POPDC2 | 2205 | SRD5A2 |
| 1 | MSRB3 | 8502 | C7 | 1 | GSTM1 | 3 | GSTM2 | 1 | FGF2 | 2162 | SRD5A2 |
| 1 | LAMA4 | 8477 | C7 | 1 | GSTM3 | 2 | GSTM2 | 1 | TCF21 | 1996 | SRD5A2 |
| 1 | RBMS3 | 8425 | C7 | 1 | GSTM2P1 | 2 | GSTM2 | 1 | LOC283904 | 1983 | SRD5A2 |
| 1 | FBLN1 | 7968 | C7 | 1 | TGFB3 | 1 | GSTM2 | 1 | DNAJB5 | 1773 | SRD5A2 |
| 1 | EPHA3 | 6930 | C7 | 1 | FTO | 1 | IGF1 | 1 | TSPAN2 | 1731 | SRD5A2 |
| 1 | ACTA2 | 6824 | C7 | 1 | UTP11L | 1 | IGF1 | 1 | GSTM5 | 1635 | SRD5A2 |
| 1 | ADAM22 | 6791 | C7 | 1 | SGCB | 1 | IGF1 | 1 | RGN | 1594 | SRD5A2 |
| 1 | WWTR1 | 6611 | C7 | 2 | CHP | 14 | IGF1 | 1 | PDLIM7 | 1503 | SRD5A2 |
| 1 | HEPH | 6406 | C7 | 2 | RP2 | 14 | IGF1 | 1 | MITF | 1481 | SRD5A2 |
| 1 | TIMP2 | 6219 | C7 | 2 | SPRYD4 | 14 | IGF1 | 1 | BNC2 | 1300 | SRD5A2 |
| 1 | CLIC4 | 6151 | C7 | 2 | SGCB | 13 | IGF1 | 1 | SCN7A | 1274 | SRD5A2 |
| 1 | ATP2B4 | 5897 | C7 | 2 | INMT | 13 | IGF1 | 1 | GPM6B | 1202 | SRD5A2 |

TABLE 9-continued

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 1 | TNS1 | 5842 | C7 | 2 | IGF1 | 12 | IGF1 | 1 | ARHGAP20 | 1193 | SRD5A2 |
| 1 | PDGFRA | 5802 | C7 | 2 | ARPP19 | 9 | IGF1 | 1 | PDZRN4 | 1190 | SRD5A2 |
| 1 | ITGA1 | 5781 | C7 | 2 | MOCS3 | 9 | IGF1 | 1 | PCP4 | 1107 | SRD5A2 |
| 1 | RHOJ | 5103 | C7 | 2 | KATNAL1 | 8 | IGF1 | 1 | ANO5 | 987 | SRD5A2 |
| 1 | COL14A1 | 5063 | C7 | 2 | C3orf33 | 8 | IGF1 | 1 | C6orf186 | 930 | SRD5A2 |
| 1 | CALD1 | 4828 | C7 | 2 | SLC16A4 | 7 | IGF1 | 1 | ARHGAP10 | 793 | SRD5A2 |
| 1 | DCN | 4825 | C7 | 2 | FTO | 7 | IGF1 | 1 | CLIP4 | 775 | SRD5A2 |
| 1 | IRAK3 | 4476 | C7 | 2 | SNX27 | 6 | IGF1 | 1 | CCDC69 | 733 | SRD5A2 |
| 1 | MATN2 | 4448 | C7 | 2 | C1orf55 | 5 | IGF1 | 1 | SLC24A3 | 673 | SRD5A2 |
| 1 | KIT | 4329 | C7 | 2 | C1orf174 | 4 | IGF1 | 1 | ACSS3 | 668 | SRD5A2 |
| 1 | NEXN | 4257 | C7 | 2 | SNTN | 4 | IGF1 | 1 | IL33 | 611 | SRD5A2 |
| 1 | ZEB2 | 3798 | C7 | 2 | MCART6 | 4 | IGF1 | 1 | CAMK2G | 519 | SRD5A2 |
| 1 | COL6A3 | 3679 | C7 | 2 | OTUD3 | 4 | IGF1 | 1 | PTPLA | 505 | SRD5A2 |
| 1 | NID2 | 3678 | C7 | 2 | ADAMTS4 | 4 | IGF1 | 1 | EFEMP1 | 493 | SRD5A2 |
| 1 | PRICKLE2 | 3671 | C7 | 2 | FEZ1 | 4 | IGF1 | 1 | KIT | 470 | SRD5A2 |
| 1 | OGN | 3418 | C7 | 2 | SPATA5 | 4 | IGF1 | 1 | ODZ3 | 428 | SRD5A2 |
| 1 | SSPN | 3142 | C7 | 2 | ZNRF3 | 4 | IGF1 | 1 | MRGPRF | 390 | SRD5A2 |
| 1 | SORBS1 | 3126 | C7 | 2 | C1orf229 | 4 | IGF1 | 1 | C21orf63 | 383 | SRD5A2 |
| 1 | PDE5A | 2963 | C7 | 2 | STX2 | 4 | IGF1 | 1 | CRISPLD2 | 322 | SRD5A2 |
| 1 | LOC732446 | 2925 | C7 | 2 | PURB | 4 | IGF1 | 1 | MYADM | 314 | SRD5A2 |
| 1 | FCHSD2 | 2741 | C7 | 2 | BVES | 4 | IGF1 | 1 | C7 | 278 | SRD5A2 |
| 1 | PMP22 | 2609 | C7 | 2 | DTX3L | 4 | IGF1 | 1 | PDGFRA | 219 | SRD5A2 |
| 1 | TRPC1 | 2519 | C7 | 2 | ZNF713 | 4 | IGF1 | 1 | EYA1 | 199 | SRD5A2 |
| 1 | ANXA6 | 2353 | C7 | 2 | DSCR3 | 4 | IGF1 | 1 | ATP1A2 | 174 | SRD5A2 |
| 1 | SPON1 | 2278 | C7 | 2 | SLC35F1 | 4 | IGF1 | 1 | ACACB | 173 | SRD5A2 |
| 1 | FBLN5 | 2115 | C7 | 2 | C22orf25 | 4 | IGF1 | 1 | NT5E | 168 | SRD5A2 |
| 1 | CHRDL1 | 1996 | C7 | 2 | STK4 | 4 | IGF1 | 1 | GPR124 | 166 | SRD5A2 |
| 1 | MEF2C | 1980 | C7 | 2 | EIF5A2 | 4 | IGF1 | 1 | LOC652799 | 165 | SRD5A2 |
| 1 | EFEMP1 | 1939 | C7 | 2 | SUPT7L | 4 | IGF1 | 1 | LRCH2 | 123 | SRD5A2 |
| 1 | JAZF1 | 1748 | C7 | 2 | C10orf78 | 4 | IGF1 | 1 | PYGM | 100 | SRD5A2 |
| 1 | DNAJB4 | 1636 | C7 | 2 | ANKS4B | 4 | IGF1 | 1 | GSTM2 | 92 | SRD5A2 |
| 1 | ARHGEF6 | 1594 | C7 | 2 | C1orf151 | 4 | IGF1 | 1 | KCNAB1 | 90 | SRD5A2 |
| 1 | MFAP4 | 1503 | C7 | 2 | RPL32P3 | 4 | IGF1 | 1 | HHIP | 82 | SRD5A2 |
| 1 | LOC652799 | 1470 | C7 | 2 | SEC62 | 4 | IGF1 | 1 | ALDH1A2 | 70 | SRD5A2 |
| 1 | PREX2 | 1464 | C7 | 2 | DBR1 | 4 | IGF1 | 1 | PRDM5 | 63 | SRD5A2 |
| 1 | MAN1A1 | 1433 | C7 | 2 | FLJ39639 | 4 | IGF1 | 1 | ABCA8 | 59 | SRD5A2 |
| 1 | TCF21 | 1224 | C7 | 2 | ZNF543 | 4 | IGF1 | 1 | MAML2 | 51 | SRD5A2 |
| 1 | CRIM1 | 1181 | C7 | 2 | FRRS1 | 4 | IGF1 | 1 | PAK3 | 38 | SRD5A2 |
| 1 | A2M | 1168 | C7 | 2 | TATDN3 | 4 | IGF1 | 1 | SNAI2 | 35 | SRD5A2 |
| 1 | DPYSL2 | 1029 | C7 | 2 | WDR55 | 4 | IGF1 | 1 | UST | 27 | SRD5A2 |
| 1 | GPM6B | 993 | C7 | 2 | KIAA1737 | 4 | IGF1 | 1 | TMLHE | 21 | SRD5A2 |
| 1 | PLN | 970 | C7 | 2 | APOBEC3F | 4 | IGF1 | 1 | ACTC1 | 15 | SRD5A2 |
| 1 | IL33 | 942 | C7 | 2 | RNF7 | 4 | IGF1 | 1 | C5orf4 | 8 | SRD5A2 |
| 1 | CCDC80 | 889 | C7 | 2 | SIKE1 | 4 | IGF1 | 1 | GSTM5P1 | 4 | SRD5A2 |
| 1 | LMO3 | 852 | C7 | 2 | HSP90B3P | 4 | IGF1 | 1 | GSTM4 | 3 | SRD5A2 |
| 1 | SEC23A | 765 | C7 | 2 | GNS | 4 | IGF1 | 1 | PDK4 | 2 | SRD5A2 |
| 1 | MOXD1 | 708 | C7 | 2 | C1orf212 | 4 | IGF1 | 1 | TGFB3 | 2 | SRD5A2 |
| 1 | SPOCK3 | 622 | C7 | 2 | ZNF70 | 4 | IGF1 | 1 | GSTM1 | 1 | SRD5A2 |
| 1 | HEG1 | 608 | C7 | 2 | TMEM127 | 4 | IGF1 | 1 | LOC728846 | 1 | TGFB1I1 |
| 1 | LUM | 589 | C7 | 2 | ALDH1B1 | 4 | IGF1 | 1 | CLIP3 | 1 | TGFB1I1 |
| 1 | C7orf58 | 566 | C7 | 2 | HP1BP3 | 4 | IGF1 | 1 | EMILIN1 | 1 | TGFB1I1 |
| 1 | CDC42EP3 | 539 | C7 | 2 | APOL6 | 4 | IGF1 | 2 | CLIP3 | 1 | TGFB1I1 |
| 1 | CPVL | 524 | C7 | 2 | MALL | 4 | IGF1 | 2 | MRC2 | 1 | TGFB1I1 |
| 1 | CPA3 | 421 | C7 | 2 | C11orf17 | 4 | IGF1 | 2 | MEG3 | 1 | TGFB1I1 |
| 1 | SLIT2 | 417 | C7 | 2 | LOC729199 | 4 | IGF1 | 3 | MRC2 | 1 | TGFB1I1 |
| 1 | KLHL5 | 376 | C7 | 2 | RELL1 | 4 | IGF1 | 3 | LCAT | 1 | TGFB1I1 |
| 1 | HLF | 322 | C7 | 2 | PELI1 | 4 | IGF1 | 3 | MEG3 | 1 | TGFB1I1 |
| 1 | PLXDC2 | 313 | C7 | 2 | ASB6 | 4 | IGF1 | 4 | LDB3 | 18 | TGFB1I1 |
| 1 | CAP2 | 301 | C7 | 2 | C2orf18 | 4 | IGF1 | 4 | TGFB1I1 | 15 | TGFB1I1 |
| 1 | FXYD6 | 291 | C7 | 2 | PSTPIP2 | 4 | IGF1 | 4 | ASB2 | 11 | TGFB1I1 |
| 1 | ECM2 | 272 | C7 | 2 | CLEC7A | 4 | IGF1 | 4 | CLIP3 | 11 | TGFB1I1 |
| 1 | SRD5A2 | 245 | C7 | 2 | RAB22A | 4 | IGF1 | 4 | ITGA7 | 10 | TGFB1I1 |
| 1 | MBNL1 | 245 | C7 | 2 | LOC643770 | 4 | IGF1 | 4 | JPH2 | 10 | TGFB1I1 |
| 1 | LAMA2 | 169 | C7 | 2 | LOC100129502 | 4 | IGF1 | 4 | RUSC2 | 10 | TGFB1I1 |
| 1 | IL6ST | 166 | C7 | 2 | ZCCHC4 | 4 | IGF1 | 4 | HRNBP3 | 8 | TGFB1I1 |
| 1 | PODN | 112 | C7 | 2 | PNMA2 | 4 | IGF1 | 4 | LIMS2 | 8 | TGFB1I1 |
| 1 | ATRNL1 | 110 | C7 | 2 | PIGW | 4 | IGF1 | 4 | CSPG4 | 7 | TGFB1I1 |
| 1 | DOCK11 | 60 | C7 | 2 | SLC25A32 | 4 | IGF1 | 4 | NLGN3 | 5 | TGFB1I1 |
| 1 | FGL2 | 56 | C7 | 2 | CLCC1 | 4 | IGF1 | 4 | ADAM33 | 3 | TGFB1I1 |
| 1 | SPRY2 | 12 | C7 | 2 | KIAA0513 | 4 | IGF1 | 4 | NHSL2 | 3 | TGFB1I1 |
| 1 | OLFML1 | 12 | C7 | 2 | SS18 | 4 | IGF1 | 4 | SYDE1 | 2 | TGFB1I1 |
| 1 | NEGR1 | 4 | C7 | 2 | CECR1 | 4 | IGF1 | 4 | RASL12 | 2 | TGFB1I1 |
| 1 | IGFBP5 | 1 | C7 | 2 | ZNF490 | 4 | IGF1 | 4 | LOC90586 | 2 | TGFB1I1 |
| 1 | SORBS1 | 1 | DES | 2 | PDE12 | 4 | IGF1 | 4 | GNAZ | 1 | TGFB1I1 |
| 1 | CACNA1C | 1 | DES | 2 | C10orf76 | 4 | IGF1 | 4 | TMEM35 | 1 | TGFB1I1 |
| 1 | DES | 1 | DES | 2 | CCL22 | 4 | IGF1 | 4 | LCAT | 1 | TGFB1I1 |
| 2 | ITIH5 | 1 | DES | 2 | RRN3P1 | 4 | IGF1 | 4 | LOC728846 | 1 | TGFB1I1 |

TABLE 9-continued

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 2 | ANXA6 | 1 | DES | 2 | LOC100127925 | 4 | IGF1 | 4 | SLC24A3 | 1 | TGFB1I1 |
| 2 | ATP1A2 | 1 | DES | 2 | SC4MOL | 4 | IGF1 | 5 | MRGPRF | 381 | TGFB1I1 |
| 3 | ITIH5 | 1 | DES | 2 | AP4E1 | 4 | IGF1 | 5 | PDLIM7 | 362 | TGFB1I1 |
| 3 | DES | 1 | DES | 2 | APOLD1 | 4 | IGF1 | 5 | AOC3 | 321 | TGFB1I1 |
| 3 | ANXA6 | 1 | DES | 2 | ARSB | 4 | IGF1 | 5 | ADCY5 | 317 | TGFB1I1 |
| 4 | TPM1 | 1 | DES | 2 | ZNF264 | 4 | IGF1 | 5 | KANK2 | 306 | TGFB1I1 |
| 4 | DES | 1 | DES | 2 | SLC30A6 | 4 | IGF1 | 5 | SLC24A3 | 292 | TGFB1I1 |
| 4 | CES1 | 1 | DES | 2 | METTL7A | 4 | IGF1 | 5 | MYL9 | 287 | TGFB1I1 |
| 5 | TAGLN | 72309 | DES | 2 | PARD6B | 4 | IGF1 | 5 | FLNC | 275 | TGFB1I1 |
| 5 | FLNA | 72305 | DES | 2 | STOM | 4 | IGF1 | 5 | TGFB1I1 | 253 | TGFB1I1 |
| 5 | TNS1 | 72049 | DES | 2 | CYP20A1 | 4 | IGF1 | 5 | ITGA7 | 222 | TGFB1I1 |
| 5 | CNN1 | 69837 | DES | 2 | LYZ | 4 | IGF1 | 5 | DES | 216 | TGFB1I1 |
| 5 | ACTA2 | 68389 | DES | 2 | ATP1B4 | 4 | IGF1 | 5 | FLNA | 214 | TGFB1I1 |
| 5 | CHRDL1 | 67725 | DES | 2 | SCD5 | 4 | IGF1 | 5 | EFEMP2 | 206 | TGFB1I1 |
| 5 | DPYSL3 | 67225 | DES | 2 | CEP170L | 4 | IGF1 | 5 | TAGLN | 184 | TGFB1I1 |
| 5 | MSRB3 | 66488 | DES | 2 | NUDT19 | 4 | IGF1 | 5 | RASL12 | 163 | TGFB1I1 |
| 5 | VCL | 65707 | DES | 2 | TXNL4B | 4 | IGF1 | 5 | GAS6 | 163 | TGFB1I1 |
| 5 | CCND2 | 65291 | DES | 2 | APPL1 | 4 | IGF1 | 5 | KCNMB1 | 163 | TGFB1I1 |
| 5 | SLC8A1 | 65217 | DES | 2 | OSBPL2 | 4 | IGF1 | 5 | SMTN | 157 | TGFB1I1 |
| 5 | MEIS1 | 65097 | DES | 2 | VMA21 | 4 | IGF1 | 5 | GPR124 | 140 | TGFB1I1 |
| 5 | ATP2B4 | 64428 | DES | 2 | NF2 | 4 | IGF1 | 5 | COL6A1 | 133 | TGFB1I1 |
| 5 | DDR2 | 64293 | DES | 2 | ZNF772 | 4 | IGF1 | 5 | DNAJB5 | 127 | TGFB1I1 |
| 5 | LMOD1 | 64271 | DES | 2 | LOC646973 | 4 | IGF1 | 5 | COL6A2 | 124 | TGFB1I1 |
| 5 | SORBS1 | 63359 | DES | 2 | LOC100128096 | 4 | IGF1 | 5 | TPM2 | 121 | TGFB1I1 |
| 5 | KCNMB1 | 61499 | DES | 2 | MOAP1 | 4 | IGF1 | 5 | WFDC1 | 121 | TGFB1I1 |
| 5 | PGR | 60803 | DES | 2 | HIGD1A | 4 | IGF1 | 5 | TNS1 | 112 | TGFB1I1 |
| 5 | RBPMS | 59947 | DES | 2 | DISC2 | 4 | IGF1 | 5 | DKK3 | 111 | TGFB1I1 |
| 5 | FLNC | 59840 | DES | 2 | CYCS | 4 | IGF1 | 5 | HSPB8 | 108 | TGFB1I1 |
| 5 | MYLK | 58329 | DES | 2 | ZSCAN22 | 4 | IGF1 | 5 | TSPAN18 | 103 | TGFB1I1 |
| 5 | FHL1 | 58303 | DES | 2 | LOC646127 | 4 | IGF1 | 5 | MYH11 | 102 | TGFB1I1 |
| 5 | FZD7 | 56889 | DES | 2 | RRP15 | 4 | IGF1 | 5 | GEFT | 90 | TGFB1I1 |
| 5 | EDNRA | 56620 | DES | 2 | LOC100130357 | 4 | IGF1 | 5 | ITIH5 | 81 | TGFB1I1 |
| 5 | DKK3 | 56591 | DES | 2 | YES1 | 4 | IGF1 | 5 | PYGM | 81 | TGFB1I1 |
| 5 | DES | 54990 | DES | 2 | MTFMT | 4 | IGF1 | 5 | MCAM | 78 | TGFB1I1 |
| 5 | PGM5 | 54713 | DES | 2 | JOSD1 | 4 | IGF1 | 5 | MRVI1 | 75 | TGFB1I1 |
| 5 | LOC729468 | 53979 | DES | 2 | RHOF | 4 | IGF1 | 5 | MYLK | 68 | TGFB1I1 |
| 5 | SYNE1 | 53386 | DES | 2 | LIN54 | 4 | IGF1 | 5 | CNN1 | 63 | TGFB1I1 |
| 5 | PGM5P2 | 53378 | DES | 2 | LOC729142 | 4 | IGF1 | 5 | RBPMS2 | 63 | TGFB1I1 |
| 5 | SPARCL1 | 52082 | DES | 2 | GNG4 | 4 | IGF1 | 5 | ATP1A2 | 58 | TGFB1I1 |
| 5 | ACTG2 | 51556 | DES | 2 | H6PD | 4 | IGF1 | 5 | LIMS2 | 58 | TGFB1I1 |
| 5 | TRPC4 | 51205 | DES | 2 | FBXW2 | 4 | IGF1 | 5 | LMOD1 | 56 | TGFB1I1 |
| 5 | CAV1 | 49615 | DES | 2 | NUP43 | 4 | IGF1 | 5 | GNAO1 | 46 | TGFB1I1 |
| 5 | GNAL | 49292 | DES | 2 | WDR5B | 4 | IGF1 | 5 | LGALS1 | 43 | TGFB1I1 |
| 5 | TIMP3 | 48293 | DES | 2 | ANGEL2 | 4 | IGF1 | 5 | DAAM2 | 41 | TGFB1I1 |
| 5 | ABCC9 | 46190 | DES | 2 | SGTB | 4 | IGF1 | 5 | MRC2 | 39 | TGFB1I1 |
| 5 | MRVI1 | 44926 | DES | 2 | MAPK1IP1L | 4 | IGF1 | 5 | HRNBP3 | 38 | TGFB1I1 |
| 5 | ACTN1 | 44120 | DES | 2 | ZSCAN29 | 4 | IGF1 | 5 | ASB2 | 36 | TGFB1I1 |
| 5 | PALLD | 43624 | DES | 2 | FXC1 | 4 | IGF1 | 5 | CLIP3 | 25 | TGFB1I1 |
| 5 | SERPINF1 | 43602 | DES | 2 | NQO1 | 4 | IGF1 | 5 | C16orf45 | 22 | TGFB1I1 |
| 5 | JAZF1 | 42715 | DES | 2 | MOBKL1A | 4 | IGF1 | 5 | DBNDD2 | 20 | TGFB1I1 |
| 5 | KANK2 | 42364 | DES | 2 | ANAPC16 | 4 | IGF1 | 5 | RUSC2 | 19 | TGFB1I1 |
| 5 | HSPB8 | 41435 | DES | 2 | C16orf63 | 4 | IGF1 | 5 | RARRES2 | 18 | TGFB1I1 |
| 5 | MYL9 | 37460 | DES | 2 | TBCCD1 | 4 | IGF1 | 5 | ADRA1A | 18 | TGFB1I1 |
| 5 | PRNP | 33800 | DES | 2 | DLEU2 | 4 | IGF1 | 5 | TINAGL1 | 17 | TGFB1I1 |
| 5 | TSPAN18 | 33287 | DES | 2 | CARD8 | 4 | IGF1 | 5 | SYNM | 17 | TGFB1I1 |
| 5 | FRMD6 | 32935 | DES | 2 | LOC100130236 | 4 | IGF1 | 5 | TMEM35 | 14 | TGFB1I1 |
| 5 | CSRP1 | 32471 | DES | 2 | LOC100130442 | 4 | IGF1 | 5 | COPZ2 | 12 | TGFB1I1 |
| 5 | HEPH | 32337 | DES | 2 | CAMLG | 4 | IGF1 | 5 | LTBP4 | 12 | TGFB1I1 |
| 5 | NEXN | 29867 | DES | 2 | ZBTB3 | 4 | IGF1 | 5 | SCARA3 | 11 | TGFB1I1 |
| 5 | PRICKLE2 | 29746 | DES | 2 | ZNF445 | 4 | IGF1 | 5 | NR2F1 | 11 | TGFB1I1 |
| 5 | PPAP2B | 28983 | DES | 2 | CASP8 | 4 | IGF1 | 5 | PCDH10 | 11 | TGFB1I1 |
| 5 | MYH11 | 28923 | DES | 2 | RAB21 | 4 | IGF1 | 5 | RAB34 | 10 | TGFB1I1 |
| 5 | PDGFC | 28732 | DES | 2 | ZC3HAV1L | 4 | IGF1 | 5 | FOXF1 | 8 | TGFB1I1 |
| 5 | TPM1 | 27766 | DES | 2 | SC5DL | 4 | IGF1 | 5 | TCF7L1 | 7 | TGFB1I1 |
| 5 | SVIL | 27521 | DES | 2 | KILLIN | 4 | IGF1 | 5 | KIRREL | 6 | TGFB1I1 |
| 5 | LOC732446 | 27335 | DES | 2 | MTX3 | 4 | IGF1 | 5 | DACT1 | 6 | TGFB1I1 |
| 5 | MEIS2 | 25944 | DES | 2 | KCNE4 | 4 | IGF1 | 5 | ZNF516 | 5 | TGFB1I1 |
| 5 | CALD1 | 25386 | DES | 2 | GM2A | 4 | IGF1 | 5 | EMILIN1 | 4 | TGFB1I1 |
| 5 | CNTN1 | 25377 | DES | 2 | LOC401588 | 4 | IGF1 | 5 | DCHS1 | 4 | TGFB1I1 |
| 5 | FERMT2 | 25146 | DES | 2 | C8orf79 | 4 | IGF1 | 5 | EHBP1L1 | 3 | TGFB1I1 |
| 5 | CLU | 24888 | DES | 2 | KIAA0754 | 4 | IGF1 | 5 | SYDE1 | 2 | TGFB1I1 |
| 5 | SPON1 | 23171 | DES | 2 | SMU1 | 4 | IGF1 | 5 | PPP1R14A | 2 | TGFB1I1 |
| 5 | TGFBR3 | 23018 | DES | 2 | TSPYL1 | 4 | IGF1 | 5 | SMOC1 | 2 | TGFB1I1 |
| 5 | CACHD1 | 22496 | DES | 2 | SPRED1 | 4 | IGF1 | 5 | JPH2 | 1 | TGFB1I1 |
| 5 | TPM2 | 22108 | DES | 2 | LOC100128997 | 4 | IGF1 | 5 | MICALL1 | 1 | TGFB1I1 |
| 5 | GSN | 22102 | DES | 2 | LOC729652 | 4 | IGF1 | 5 | LCAT | 1 | TGFB1I1 |
| 5 | NID2 | 21240 | DES | 2 | TRAPPC2 | 4 | IGF1 | 5 | HSPB6 | 1 | TGFB1I1 |

TABLE 9-continued

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 5 | MYOCD | 21178 | DES | 2 | KCTD10 | 4 | IGF1 | 1 | FLNA | 33418 | TPM2 |
| 5 | MKX | 20028 | DES | 2 | DUSP19 | 4 | IGF1 | 1 | TAGLN | 33391 | TPM2 |
| 5 | EYA4 | 19967 | DES | 2 | CCDC122 | 4 | IGF1 | 1 | TNS1 | 32975 | TPM2 |
| 5 | LOC100127983 | 18208 | DES | 2 | NXN | 4 | IGF1 | 1 | CNN1 | 32489 | TPM2 |
| 5 | ANXA6 | 16600 | DES | 2 | ZNF283 | 4 | IGF1 | 1 | CHRDL1 | 31765 | TPM2 |
| 5 | HLF | 16262 | DES | 2 | SPATS2L | 4 | IGF1 | 1 | LMOD1 | 31568 | TPM2 |
| 5 | VWA5A | 16175 | DES | 2 | TRIM5 | 4 | IGF1 | 1 | MYLK | 31444 | TPM2 |
| 5 | SRD5A2 | 16145 | DES | 2 | HAUS3 | 4 | IGF1 | 1 | ACTA2 | 31310 | TPM2 |
| 5 | SYNM | 15943 | DES | 2 | UTP11L | 4 | IGF1 | 1 | ACTG2 | 30665 | TPM2 |
| 5 | CDC42EP3 | 14001 | DES | 2 | SLC30A5 | 4 | IGF1 | 1 | KCNMB1 | 30331 | TPM2 |
| 5 | AOC3 | 13787 | DES | 2 | MBOAT1 | 4 | IGF1 | 1 | MSRB3 | 30007 | TPM2 |
| 5 | TIMP2 | 13760 | DES | 2 | TERF2 | 4 | IGF1 | 1 | SORBS1 | 29926 | TPM2 |
| 5 | ILK | 13444 | DES | 2 | VPS33A | 4 | IGF1 | 1 | DPYSL3 | 29802 | TPM2 |
| 5 | ADCY5 | 13346 | DES | 2 | SENP5 | 4 | IGF1 | 1 | DES | 29158 | TPM2 |
| 5 | PARVA | 13266 | DES | 2 | EVI5 | 4 | IGF1 | 1 | VCL | 29088 | TPM2 |
| 5 | FBLN1 | 12617 | DES | 2 | NDUFC2 | 4 | IGF1 | 1 | SLC8A1 | 29075 | TPM2 |
| 5 | LOC645954 | 12259 | DES | 2 | ZBTB8A | 4 | IGF1 | 1 | CCND2 | 28780 | TPM2 |
| 5 | FAT4 | 12247 | DES | 2 | ST8SIA4 | 4 | IGF1 | 1 | MEIS1 | 28764 | TPM2 |
| 5 | ITIH5 | 11490 | DES | 2 | C7orf64 | 4 | IGF1 | 1 | PGM5 | 28584 | TPM2 |
| 5 | COL6A3 | 10595 | DES | 2 | MED18 | 4 | IGF1 | 1 | ATP2B4 | 28495 | TPM2 |
| 5 | TSHZ3 | 10118 | DES | 2 | MPV17L | 4 | IGF1 | 1 | LOC729468 | 28204 | TPM2 |
| 5 | MCAM | 8671 | DES | 2 | C1orf210 | 4 | IGF1 | 1 | FHL1 | 28101 | TPM2 |
| 5 | MAP1B | 8478 | DES | 2 | LIN7C | 4 | IGF1 | 1 | FLNC | 27926 | TPM2 |
| 5 | WFDC1 | 7000 | DES | 2 | KCNJ11 | 4 | IGF1 | 1 | PGM5P2 | 27789 | TPM2 |
| 5 | PDE5A | 6648 | DES | 2 | COX18 | 4 | IGF1 | 1 | HSPB8 | 27438 | TPM2 |
| 5 | TLN1 | 5948 | DES | 2 | PCBD2 | 4 | IGF1 | 1 | DDR2 | 26679 | TPM2 |
| 5 | PDLIM7 | 5715 | DES | 2 | SPAST | 4 | IGF1 | 1 | PGR | 26409 | TPM2 |
| 5 | SPOCK3 | 5657 | DES | 2 | CYP4V2 | 4 | IGF1 | 1 | MRVI1 | 25979 | TPM2 |
| 5 | BOC | 5611 | DES | 2 | LRTOMT | 4 | IGF1 | 1 | DKK3 | 25603 | TPM2 |
| 5 | CRYAB | 5555 | DES | 2 | IMPAD1 | 3 | IGF1 | 1 | RBPMS | 24576 | TPM2 |
| 5 | PMP22 | 4795 | DES | 2 | UBXN2B | 3 | IGF1 | 1 | MYH11 | 24353 | TPM2 |
| 5 | ADRA1A | 4611 | DES | 2 | C5orf33 | 3 | IGF1 | 1 | FZD7 | 24298 | TPM2 |
| 5 | FGF2 | 4439 | DES | 2 | FOXJ3 | 3 | IGF1 | 1 | TPM2 | 23458 | TPM2 |
| 5 | CELF2 | 4392 | DES | 2 | PPP1R15B | 3 | IGF1 | 1 | GNAL | 23091 | TPM2 |
| 5 | MMP2 | 4243 | DES | 2 | GNAI3 | 2 | IGF1 | 1 | MYL9 | 22987 | TPM2 |
| 5 | WWTR1 | 3966 | DES | 2 | SAR1B | 2 | IGF1 | 1 | JAZF1 | 21665 | TPM2 |
| 5 | CAP2 | 3592 | DES | 2 | SERPINB9 | 2 | IGF1 | 1 | CAV1 | 21569 | TPM2 |
| 5 | LOC100129846 | 3236 | DES | 2 | PTGIS | 2 | IGF1 | 1 | KANK2 | 21564 | TPM2 |
| 5 | RBMS3 | 3165 | DES | 2 | C3orf70 | 2 | IGF1 | 1 | EDNRA | 20876 | TPM2 |
| 5 | AOX1 | 3042 | DES | 2 | RUNDC2B | 2 | IGF1 | 1 | SPARCL1 | 20468 | TPM2 |
| 5 | MFAP4 | 3011 | DES | 2 | SYT11 | 1 | IGF1 | 1 | TRPC4 | 19698 | TPM2 |
| 5 | TCF21 | 2881 | DES | 1 | CPXM2 | 1 | ITGA7 | 1 | TSPAN18 | 18763 | TPM2 |
| 5 | MATN2 | 2851 | DES | 1 | MRVI1 | 1 | ITGA7 | 1 | ACTN1 | 18284 | TPM2 |
| 5 | MRGPRF | 2724 | DES | 1 | ITGA7 | 1 | ITGA7 | 1 | TIMP3 | 18017 | TPM2 |
| 5 | POPDC2 | 2704 | DES | 2 | ADCY5 | 661 | ITGA7 | 1 | ABCC9 | 17793 | TPM2 |
| 5 | CFL2 | 2404 | DES | 2 | MRGPRF | 652 | ITGA7 | 1 | SYNE1 | 17659 | TPM2 |
| 5 | LOC283904 | 2374 | DES | 2 | PDLIM7 | 649 | ITGA7 | 1 | SERPINF1 | 17306 | TPM2 |
| 5 | PRELP | 2253 | DES | 2 | FLNC | 627 | ITGA7 | 1 | PALLD | 16659 | TPM2 |
| 5 | CCDC69 | 2088 | DES | 2 | KANK2 | 624 | ITGA7 | 1 | PRICKLE2 | 16570 | TPM2 |
| 5 | PLN | 2046 | DES | 2 | MYL9 | 611 | ITGA7 | 1 | CSRP1 | 15853 | TPM2 |
| 5 | DNAJB5 | 1956 | DES | 2 | AOC3 | 602 | ITGA7 | 1 | HEPH | 14646 | TPM2 |
| 5 | GPR124 | 1851 | DES | 2 | FLNA | 540 | ITGA7 | 1 | NEXN | 13548 | TPM2 |
| 5 | GAS6 | 1830 | DES | 2 | TAGLN | 527 | ITGA7 | 1 | MYOCD | 13479 | TPM2 |
| 5 | TSPAN2 | 1830 | DES | 2 | KCNMB1 | 492 | ITGA7 | 1 | MEIS2 | 13043 | TPM2 |
| 5 | ANGPT1 | 1797 | DES | 2 | DES | 491 | ITGA7 | 1 | TPM1 | 12988 | TPM2 |
| 5 | MFGE8 | 1766 | DES | 2 | ITGA7 | 481 | ITGA7 | 1 | SPON1 | 12334 | TPM2 |
| 5 | ITGA1 | 1682 | DES | 2 | SLC24A3 | 434 | ITGA7 | 1 | EYA4 | 12112 | TPM2 |
| 5 | GSTM5 | 1596 | DES | 2 | TNS1 | 423 | ITGA7 | 1 | HLF | 11972 | TPM2 |
| 5 | MYADM | 1579 | DES | 2 | TSPAN18 | 364 | ITGA7 | 1 | SYNM | 11833 | TPM2 |
| 5 | CES1 | 1511 | DES | 2 | MCAM | 351 | ITGA7 | 1 | SVIL | 11249 | TPM2 |
| 5 | CAMK2G | 1453 | DES | 2 | TPM2 | 322 | ITGA7 | 1 | FRMD6 | 10974 | TPM2 |
| 5 | PCP4 | 1361 | DES | 2 | MYLK | 322 | ITGA7 | 1 | CNTN1 | 10796 | TPM2 |
| 5 | SLC24A3 | 1275 | DES | 2 | HSPB8 | 317 | ITGA7 | 1 | CLU | 10687 | TPM2 |
| 5 | RGN | 1215 | DES | 2 | MYH11 | 317 | ITGA7 | 1 | LOC100127983 | 10582 | TPM2 |
| 5 | KCNMA1 | 1050 | DES | 2 | MRVI1 | 314 | ITGA7 | 1 | PRNP | 10088 | TPM2 |
| 5 | PDZRN4 | 876 | DES | 2 | LMOD1 | 301 | ITGA7 | 1 | MKX | 9903 | TPM2 |
| 5 | ARHGAP10 | 867 | DES | 2 | CNN1 | 288 | ITGA7 | 1 | CALD1 | 9712 | TPM2 |
| 5 | C6orf186 | 841 | DES | 2 | ITIH5 | 287 | ITGA7 | 1 | FERMT2 | 9315 | TPM2 |
| 5 | ARHGAP20 | 828 | DES | 2 | DNAJB5 | 282 | ITGA7 | 1 | NID2 | 9290 | TPM2 |
| 5 | FXYD6 | 826 | DES | 2 | CHRDL1 | 264 | ITGA7 | 1 | ITIH5 | 8936 | TPM2 |
| 5 | PTGER2 | 802 | DES | 2 | EFEMP2 | 256 | ITGA7 | 1 | PDGFC | 8919 | TPM2 |
| 5 | SLC12A4 | 721 | DES | 2 | ATP1A2 | 239 | ITGA7 | 1 | LOC732446 | 8793 | TPM2 |
| 5 | NID1 | 670 | DES | 2 | SMTN | 238 | ITGA7 | 1 | LOC645954 | 8764 | TPM2 |
| 5 | ITGA9 | 568 | DES | 2 | GAS6 | 231 | ITGA7 | 1 | ADCY5 | 8698 | TPM2 |
| 5 | SMTN | 558 | DES | 2 | WFDC1 | 222 | ITGA7 | 1 | AOC3 | 8557 | TPM2 |
| 5 | TCEAL2 | 557 | DES | 2 | TGFB1I1 | 220 | ITGA7 | 1 | SRD5A2 | 8415 | TPM2 |
| 5 | COL6A1 | 499 | DES | 2 | GPR124 | 206 | ITGA7 | 1 | GSN | 7427 | TPM2 |

TABLE 9-continued

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 5 | ITGA5 | 475 | DES | 2 | NID2 | 204 | ITGA7 | 1 | WFDC1 | 6345 | TPM2 |
| 5 | ATP1A2 | 417 | DES | 2 | ADRA1A | 197 | ITGA7 | 1 | VWA5A | 6297 | TPM2 |
| 5 | C21orf63 | 408 | DES | 2 | PYGM | 189 | ITGA7 | 1 | ILK | 6243 | TPM2 |
| 5 | EFEMP2 | 389 | DES | 2 | RASL12 | 186 | ITGA7 | 1 | TGFBR3 | 5718 | TPM2 |
| 5 | PTPLA | 366 | DES | 2 | BOC | 184 | ITGA7 | 1 | CDC42EP3 | 5544 | TPM2 |
| 5 | ST5 | 364 | DES | 2 | FZD7 | 174 | ITGA7 | 1 | TSHZ3 | 5478 | TPM2 |
| 5 | JAM3 | 350 | DES | 2 | ACTG2 | 172 | ITGA7 | 1 | FAT4 | 4923 | TPM2 |
| 5 | ITGA7 | 333 | DES | 2 | PRICKLE2 | 157 | ITGA7 | 1 | PARVA | 4922 | TPM2 |
| 5 | LPP | 320 | DES | 2 | GEFT | 156 | ITGA7 | 1 | MCAM | 4880 | TPM2 |
| 5 | COL6A2 | 302 | DES | 2 | COL6A1 | 142 | ITGA7 | 1 | PDLIM7 | 4753 | TPM2 |
| 5 | ODZ3 | 294 | DES | 2 | PGM5 | 133 | ITGA7 | 1 | ADRA1A | 4540 | TPM2 |
| 5 | PLEKHO1 | 266 | DES | 2 | SYNM | 132 | ITGA7 | 1 | ANXA6 | 4499 | TPM2 |
| 5 | PYGM | 249 | DES | 2 | FHL1 | 126 | ITGA7 | 1 | FBLN1 | 4133 | TPM2 |
| 5 | TINAGL1 | 239 | DES | 2 | HEPH | 112 | ITGA7 | 1 | BOC | 3515 | TPM2 |
| 5 | PCDH10 | 238 | DES | 2 | COL6A2 | 110 | ITGA7 | 1 | COL6A3 | 3490 | TPM2 |
| 5 | PNMA1 | 232 | DES | 2 | LOC729468 | 109 | ITGA7 | 1 | CRYAB | 3436 | TPM2 |
| 5 | ACACB | 221 | DES | 2 | MYOCD | 101 | ITGA7 | 1 | SPOCK3 | 3141 | TPM2 |
| 5 | RASL12 | 213 | DES | 2 | ACTA2 | 66 | ITGA7 | 1 | PDE5A | 2530 | TPM2 |
| 5 | LARGE | 182 | DES | 2 | RBPMS2 | 62 | ITGA7 | 1 | MAP1B | 2406 | TPM2 |
| 5 | GEFT | 181 | DES | 2 | LIMS2 | 53 | ITGA7 | 1 | FGF2 | 2375 | TPM2 |
| 5 | NCS1 | 176 | DES | 2 | GNAO1 | 45 | ITGA7 | 1 | LOC100129846 | 2231 | TPM2 |
| 5 | TRANK1 | 173 | DES | 2 | ASB2 | 44 | ITGA7 | 1 | MRGPRF | 2029 | TPM2 |
| 5 | FGFR1 | 166 | DES | 2 | HRNBP3 | 43 | ITGA7 | 1 | DNAJB5 | 2029 | TPM2 |
| 5 | AHNAK2 | 164 | DES | 2 | POPDC2 | 41 | ITGA7 | 1 | LOC283904 | 2007 | TPM2 |
| 5 | LGALS1 | 156 | DES | 2 | DAAM2 | 38 | ITGA7 | 1 | POPDC2 | 1965 | TPM2 |
| 5 | RRAS | 133 | DES | 2 | ODZ3 | 34 | ITGA7 | 1 | TCF21 | 1785 | TPM2 |
| 5 | C2orf40 | 132 | DES | 2 | PDZRN4 | 33 | ITGA7 | 1 | TLN1 | 1720 | TPM2 |
| 5 | TGFB1I1 | 126 | DES | 2 | C6orf186 | 30 | ITGA7 | 1 | CELF2 | 1700 | TPM2 |
| 5 | RAB34 | 95 | DES | 2 | ITGA9 | 28 | ITGA7 | 1 | AOX1 | 1459 | TPM2 |
| 5 | PTRF | 94 | DES | 2 | NID1 | 27 | ITGA7 | 1 | SLC24A3 | 1296 | TPM2 |
| 5 | SCHIP1 | 91 | DES | 2 | C16orf45 | 22 | ITGA7 | 1 | CCDC69 | 1287 | TPM2 |
| 5 | GSTM2 | 87 | DES | 2 | RUSC2 | 22 | ITGA7 | 1 | ANGPT1 | 1256 | TPM2 |
| 5 | MAOB | 49 | DES | 2 | TMEM35 | 19 | ITGA7 | 1 | PCP4 | 1226 | TPM2 |
| 5 | MASP1 | 48 | DES | 2 | CLIP3 | 19 | ITGA7 | 1 | BNC2 | 1170 | TPM2 |
| 5 | TRIP10 | 45 | DES | 2 | MRC2 | 19 | ITGA7 | 1 | PDZRN4 | 1069 | TPM2 |
| 5 | RARRES2 | 40 | DES | 2 | TINAGL1 | 17 | ITGA7 | 1 | RGN | 1065 | TPM2 |
| 5 | RBPMS2 | 37 | DES | 2 | DBNDD2 | 17 | ITGA7 | 1 | CES1 | 1060 | TPM2 |
| 5 | APOBEC3C | 30 | DES | 2 | ITGB3 | 11 | ITGA7 | 1 | GPR124 | 917 | TPM2 |
| 5 | COPZ2 | 29 | DES | 2 | LDB3 | 9 | ITGA7 | 1 | GAS6 | 888 | TPM2 |
| 5 | CACNA1C | 21 | DES | 2 | ITGA5 | 9 | ITGA7 | 1 | CFL2 | 871 | TPM2 |
| 5 | GNAO1 | 16 | DES | 2 | NCS1 | 9 | ITGA7 | 1 | CAMK2G | 869 | TPM2 |
| 5 | UST | 12 | DES | 2 | FOXF1 | 8 | ITGA7 | 1 | ARHGAP20 | 850 | TPM2 |
| 5 | ACTC1 | 12 | DES | 2 | DACT1 | 7 | ITGA7 | 1 | GSTM5 | 794 | TPM2 |
| 5 | CES4 | 11 | DES | 2 | CSPG4 | 6 | ITGA7 | 1 | CAP2 | 752 | TPM2 |
| 5 | ID4 | 11 | DES | 2 | JPH2 | 6 | ITGA7 | 1 | PRELP | 693 | TPM2 |
| 5 | C16orf45 | 10 | DES | 2 | ZNF516 | 6 | ITGA7 | 1 | SMTN | 540 | TPM2 |
| 5 | LIMS2 | 9 | DES | 2 | KIRREL | 3 | ITGA7 | 1 | FXYD6 | 533 | TPM2 |
| 5 | GSTM5P1 | 6 | DES | 2 | NHSL2 | 3 | ITGA7 | 1 | TSPAN2 | 500 | TPM2 |
| 5 | GSTM4 | 5 | DES | 2 | LCAT | 2 | ITGA7 | 1 | KCNMA1 | 488 | TPM2 |
| 5 | CBX7 | 3 | DES | 2 | FABP3 | 2 | ITGA7 | 1 | PTGER2 | 429 | TPM2 |
| 5 | PPP1R14A | 3 | DES | 2 | GNAZ | 1 | ITGA7 | 1 | TCEAL2 | 425 | TPM2 |
| 5 | FABP3 | 3 | DES | 2 | P2RX1 | 1 | ITGA7 | 1 | MYADM | 402 | TPM2 |
| 5 | GSTM1 | 2 | DES | 1 | SLC8A1 | 47139 | SRD5A2 | 1 | JAM3 | 360 | TPM2 |
| 5 | GSTM2P1 | 2 | DES | 1 | LOC729468 | 47056 | SRD5A2 | 1 | COL6A1 | 354 | TPM2 |
| 5 | HSPB6 | 1 | DES | 1 | DPYSL3 | 47002 | SRD5A2 | 1 | ATP1A2 | 339 | TPM2 |
| 1 | GSTM5P1 | 4 | GSTM1 | 1 | ACTA2 | 46967 | SRD5A2 | 1 | SLC12A4 | 327 | TPM2 |
| 1 | GSTM2 | 4 | GSTM1 | 1 | PGM5 | 46874 | SRD5A2 | 1 | ITGA5 | 325 | TPM2 |
| 1 | GSTM4 | 4 | GSTM1 | 1 | MEIS1 | 46871 | SRD5A2 | 1 | ITGA9 | 301 | TPM2 |
| 1 | GSTM5 | 4 | GSTM1 | 1 | ACTG2 | 46703 | SRD5A2 | 1 | ITGA7 | 300 | TPM2 |
| 1 | SPOCK3 | 3 | GSTM1 | 1 | PGM5P2 | 46699 | SRD5A2 | 1 | EFEMP2 | 298 | TPM2 |
| 1 | PGM5 | 3 | GSTM1 | 1 | MSRB3 | 46428 | SRD5A2 | 1 | PYGM | 254 | TPM2 |
| 1 | HSPB8 | 3 | GSTM1 | 1 | TAGLN | 46404 | SRD5A2 | 1 | COL6A2 | 248 | TPM2 |
| 1 | AOX1 | 2 | GSTM1 | 1 | FLNA | 46365 | SRD5A2 | 1 | ARHGAP10 | 227 | TPM2 |
| 1 | CSRP1 | 2 | GSTM1 | 1 | VCL | 46278 | SRD5A2 | 1 | PNMA1 | 211 | TPM2 |
| 1 | FLNC | 2 | GSTM1 | 1 | CNN1 | 45892 | SRD5A2 | 1 | RASL12 | 207 | TPM2 |
| 1 | DES | 2 | GSTM1 | 1 | CHRDL1 | 45879 | SRD5A2 | 1 | GEFT | 194 | TPM2 |
| 1 | GSTM2P1 | 2 | GSTM1 | 1 | TNS1 | 45774 | SRD5A2 | 1 | PTPLA | 183 | TPM2 |
| 1 | GSTM1 | 2 | GSTM1 | 1 | ATP2B4 | 45519 | SRD5A2 | 1 | CRISPLD2 | 181 | TPM2 |
| 1 | CAV1 | 1 | GSTM1 | 1 | LMOD1 | 44299 | SRD5A2 | 1 | ACSS3 | 177 | TPM2 |
| 1 | SRD5A2 | 1 | GSTM1 | 1 | PGR | 44126 | SRD5A2 | 1 | AHNAK2 | 175 | TPM2 |
| 1 | GSTM3 | 1 | GSTM1 | 1 | SORBS1 | 43839 | SRD5A2 | 1 | ST5 | 175 | TPM2 |
| 1 | LOC729468 | 1 | GSTM1 | 1 | CCND2 | 43401 | SRD5A2 | 1 | PLEKHO1 | 165 | TPM2 |
| 1 | EYA4 | 1 | GSTM1 | 1 | DDR2 | 43389 | SRD5A2 | 1 | LARGE | 164 | TPM2 |
| 1 | PGM5P2 | 1 | GSTM1 | 1 | EDNRA | 42947 | SRD5A2 | 1 | C21orf63 | 151 | TPM2 |
| 1 | CSRP1 | 364 | GSTM2 | 1 | FHL1 | 41382 | SRD5A2 | 1 | TINAGL1 | 150 | TPM2 |
| 1 | CAV1 | 358 | GSTM2 | 1 | KCNMB1 | 41204 | SRD5A2 | 1 | ACACB | 138 | TPM2 |
| 1 | TNS1 | 358 | GSTM2 | 1 | TRPC4 | 40884 | SRD5A2 | 1 | LGALS1 | 136 | TPM2 |

TABLE 9-continued

| StackID | Coexpressed Gene | Probe-Wt | Seeding Gene | StackID | Coexpressed Gene | Probe-Wt | Seeding Gene | StackID | Coexpressed Gene | ProbeWt | Seeding Gene |
|---|---|---|---|---|---|---|---|---|---|---|---|
| 1 | ATP2B4 | 356 | GSTM2 | 1 | SYNE1 | 40118 | SRD5A2 | 1 | TGFB1I1 | 126 | TPM2 |
| 1 | MEIS2 | 352 | GSTM2 | 1 | CAV1 | 39836 | SRD5A2 | 1 | ITGB3 | 123 | TPM2 |
| 1 | FLNA | 350 | GSTM2 | 1 | SPARCL1 | 39359 | SRD5A2 | 1 | RRAS | 123 | TPM2 |
| 1 | TAGLN | 350 | GSTM2 | 1 | RBPMS | 38414 | SRD5A2 | 1 | NCS1 | 107 | TPM2 |
| 1 | GNAL | 350 | GSTM2 | 1 | FZD7 | 34246 | SRD5A2 | 1 | PTRF | 94 | TPM2 |
| 1 | DPYSL3 | 348 | GSTM2 | 1 | SRD5A2 | 33968 | SRD5A2 | 1 | LPP | 91 | TPM2 |
| 1 | MEIS1 | 347 | GSTM2 | 1 | DKK3 | 33963 | SRD5A2 | 1 | C2orf40 | 90 | TPM2 |
| 1 | TRPC4 | 345 | GSTM2 | 1 | JAZF1 | 33635 | SRD5A2 | 1 | MAOB | 59 | TPM2 |
| 1 | CCND2 | 325 | GSTM2 | 1 | MYLK | 33158 | SRD5A2 | 1 | GSTM2 | 51 | TPM2 |
| 1 | SYNE1 | 321 | GSTM2 | 1 | ABCC9 | 33072 | SRD5A2 | 1 | TRIP10 | 48 | TPM2 |
| 1 | EDNRA | 317 | GSTM2 | 1 | GNAL | 32392 | SRD5A2 | 1 | ALDH1A2 | 43 | TPM2 |
| 1 | ACTA2 | 313 | GSTM2 | 1 | PALLD | 31713 | SRD5A2 | 1 | RARRES2 | 36 | TPM2 |
| 1 | PALLD | 310 | GSTM2 | 1 | FLNC | 29309 | SRD5A2 | 1 | COPZ2 | 34 | TPM2 |
| 1 | FRMD6 | 309 | GSTM2 | 1 | PRICKLE2 | 29168 | SRD5A2 | 1 | APOBEC3C | 34 | TPM2 |
| 1 | PGM5 | 301 | GSTM2 | 1 | MRVI1 | 28467 | SRD5A2 | 1 | RBPMS2 | 33 | TPM2 |
| 1 | HSPB8 | 293 | GSTM2 | 1 | TIMP3 | 28313 | SRD5A2 | 1 | DBNDD2 | 31 | TPM2 |
| 1 | ACTG2 | 287 | GSTM2 | 1 | FRMD6 | 28108 | SRD5A2 | 1 | GNAO1 | 19 | TPM2 |
| 1 | CNN1 | 286 | GSTM2 | 1 | PRNP | 28106 | SRD5A2 | 1 | ACTC1 | 15 | TPM2 |
| 1 | PGM5P2 | 285 | GSTM2 | 1 | HSPB8 | 26756 | SRD5A2 | 1 | CES4 | 11 | TPM2 |
| 1 | SLC8A1 | 282 | GSTM2 | 1 | PDGFC | 26571 | SRD5A2 | 1 | C16orf45 | 10 | TPM2 |
| 1 | LOC729468 | 276 | GSTM2 | 1 | CNTN1 | 26148 | SRD5A2 | 1 | GSTP1 | 8 | TPM2 |
| 1 | PRICKLE2 | 275 | GSTM2 | 1 | EYA4 | 26129 | SRD5A2 | 1 | UST | 5 | TPM2 |
| 1 | SRD5A2 | 275 | GSTM2 | 1 | MEIS2 | 25616 | SRD5A2 | 1 | GSTM4 | 4 | TPM2 |
| 1 | RBPMS | 275 | GSTM2 | 1 | MYOCD | 25477 | SRD5A2 | 1 | GSTM5P1 | 4 | TPM2 |
| 1 | PDGFC | 270 | GSTM2 | 1 | NEXN | 25068 | SRD5A2 | 1 | CBX7 | 3 | TPM2 |
| 1 | EYA4 | 270 | GSTM2 | 1 | CACHD1 | 25049 | SRD5A2 | 1 | PPP1R14A | 3 | TPM2 |
| 1 | MYOCD | 262 | GSTM2 | 1 | FERMT2 | 24208 | SRD5A2 | 1 | FABP3 | 3 | TPM2 |
| 1 | CALD1 | 255 | GSTM2 | 1 | LOC100127983 | 23635 | SRD5A2 | 1 | C15orf51 | 1 | TPM2 |
| 1 | KCNMB1 | 250 | GSTM2 | 1 | TPM1 | 22943 | SRD5A2 | 1 | GSTM2P1 | 1 | TPM2 |
| 1 | ACTN1 | 227 | GSTM2 | 1 | CALD1 | 22765 | SRD5A2 | | | | |
| 1 | FZD7 | 216 | GSTM2 | 1 | SERPINF1 | 22186 | SRD5A2 | | | | |
| 1 | LOC100127983 | 216 | GSTM2 | 1 | CSRP1 | 21728 | SRD5A2 | | | | |
| 1 | DKK3 | 209 | GSTM2 | 1 | ACTN1 | 21590 | SRD5A2 | | | | |
| 1 | GSTM5 | 207 | GSTM2 | 1 | HLF | 21402 | SRD5A2 | | | | |
| 1 | CHRDL1 | 204 | GSTM2 | 1 | DES | 20952 | SRD5A2 | | | | |
| 1 | SORBS1 | 202 | GSTM2 | 1 | MYL9 | 19970 | SRD5A2 | | | | |
| 1 | SPOCK3 | 202 | GSTM2 | 1 | HEPH | 19688 | SRD5A2 | | | | |
| 1 | JAZF1 | 189 | GSTM2 | 1 | TSPAN18 | 19099 | SRD5A2 | | | | |
| 1 | LMOD1 | 180 | GSTM2 | 1 | SVIL | 18819 | SRD5A2 | | | | |
| 1 | DES | 172 | GSTM2 | 1 | TGFBR3 | 18423 | SRD5A2 | | | | |
| | | | | 1 | MYH11 | 18066 | SRD5A2 | | | | |
| | | | | 1 | KANK2 | 17638 | SRD5A2 | | | | |
| | | | | 1 | CDC42EP3 | 16173 | SRD5A2 | | | | |

TABLE 10

| StackID | Coexpressed Gene | ProbeWt | Seeding Gene |
|---|---|---|---|
| 1 | NCAPH | 9758 | CDC20 |
| 1 | CDC20 | 9758 | CDC20 |
| 1 | IQGAP3 | 9758 | CDC20 |
| 1 | ESPL1 | 9674 | CDC20 |
| 1 | CENPA | 9671 | CDC20 |
| 1 | POC1A | 9671 | CDC20 |
| 1 | KIF18B | 9328 | CDC20 |
| 1 | WDR62 | 9316 | CDC20 |
| 1 | TROAP | 9178 | CDC20 |
| 1 | ADAMTS7 | 8987 | CDC20 |
| 1 | PKMYT1 | 8875 | CDC20 |
| 1 | SLC2A6 | 8875 | CDC20 |
| 1 | FNDC1 | 8554 | CDC20 |
| 1 | FAM64A | 8346 | CDC20 |
| 1 | FAM131B | 8322 | CDC20 |
| 1 | PNLDC1 | 8135 | CDC20 |
| 1 | KIFC1 | 7598 | CDC20 |
| 1 | C9orf100 | 7547 | CDC20 |
| 1 | RPS6KL1 | 7527 | CDC20 |
| 1 | MRAP | 7521 | CDC20 |
| 1 | AURKB | 7224 | CDC20 |
| 1 | C2orf54 | 7150 | CDC20 |
| 1 | TMEM163 | 6853 | CDC20 |
| 1 | KRBA1 | 6846 | CDC20 |
| 1 | ZMYND10 | 6825 | CDC20 |
| 1 | LOC541473 | 6824 | CDC20 |
| 1 | SLC6A1 | 6669 | CDC20 |
| 1 | DQX1 | 6601 | CDC20 |
| 1 | BAI2 | 6583 | CDC20 |
| 1 | EME1 | 6533 | CDC20 |
| 1 | CICP3 | 6481 | CDC20 |
| 1 | PPFIA4 | 6480 | CDC20 |
| 1 | PADI1 | 6458 | CDC20 |
| 1 | SSPO | 6431 | CDC20 |
| 1 | GABRB2 | 6422 | CDC20 |
| 1 | IRF5 | 6399 | CDC20 |
| 1 | NXPH1 | 6399 | CDC20 |
| 1 | ZIC1 | 6346 | CDC20 |
| 1 | SLC6A20 | 6336 | CDC20 |
| 1 | PKD1L1 | 6281 | CDC20 |
| 1 | BIRC5 | 6278 | CDC20 |
| 1 | AQP10 | 6251 | CDC20 |
| 1 | ABCA4 | 6216 | CDC20 |
| 1 | TFR2 | 6181 | CDC20 |
| 1 | LOC646070 | 6179 | CDC20 |
| 1 | CSPG5 | 6165 | CDC20 |
| 1 | CENPM | 6124 | CDC20 |
| 1 | EFNA3 | 6100 | CDC20 |
| 1 | GPC2 | 6078 | CDC20 |
| 1 | HYAL3 | 6047 | CDC20 |
| 1 | CELA3B | 6031 | CDC20 |
| 1 | LOC100287112 | 6015 | CDC20 |

TABLE 10-continued

| StackID | Coexpressed Gene | ProbeWt | Seeding Gene |
|---|---|---|---|
| 1 | SRCRB4D | 5999 | CDC20 |
| 1 | DNAJB3 | 5993 | CDC20 |
| 1 | PADI3 | 5989 | CDC20 |
| 1 | PAX8 | 5971 | CDC20 |
| 1 | AIM1L | 5971 | CDC20 |
| 1 | FAM131C | 5915 | CDC20 |
| 1 | PRRT4 | 5915 | CDC20 |
| 1 | MLXIPL | 5915 | CDC20 |
| 1 | E2F1 | 5912 | CDC20 |
| 1 | E2F7 | 5893 | CDC20 |
| 1 | RAD54L | 5888 | CDC20 |
| 1 | C1orf81 | 5813 | CDC20 |
| 1 | NFKBIL2 | 5742 | CDC20 |
| 1 | LOC729061 | 5728 | CDC20 |
| 1 | TAS1R3 | 5671 | CDC20 |
| 1 | VWA3B | 5643 | CDC20 |
| 1 | MYBL2 | 5565 | CDC20 |
| 1 | TTLL6 | 5531 | CDC20 |
| 1 | LOC100130097 | 5525 | CDC20 |
| 1 | CHRNG | 5491 | CDC20 |
| 1 | TTBK1 | 5491 | CDC20 |
| 1 | TRIM46 | 5491 | CDC20 |
| 1 | MST1R | 5491 | CDC20 |
| 1 | EXOC3L | 5474 | CDC20 |
| 1 | TH | 5474 | CDC20 |
| 1 | CHST1 | 5474 | CDC20 |
| 1 | LOC442676 | 5439 | CDC20 |
| 1 | CNTN2 | 5435 | CDC20 |
| 1 | DPYSL5 | 5435 | CDC20 |
| 1 | C3orf20 | 5368 | CDC20 |
| 1 | NPC1L1 | 5291 | CDC20 |
| 1 | CICP5 | 5281 | CDC20 |
| 1 | KLRG2 | 5275 | CDC20 |
| 1 | CCDC108 | 5275 | CDC20 |
| 1 | IL28B | 5217 | CDC20 |
| 1 | CELSR3 | 5166 | CDC20 |
| 1 | RNFT2 | 5138 | CDC20 |
| 1 | C17orf53 | 5114 | CDC20 |
| 1 | TRPC2 | 5095 | CDC20 |
| 1 | KCNA1 | 5078 | CDC20 |
| 1 | C8G | 4946 | CDC20 |
| 1 | COL11A1 | 4685 | CDC20 |
| 1 | C1orf222 | 4673 | CDC20 |
| 1 | SLC6A12 | 4633 | CDC20 |
| 1 | HCN3 | 4608 | CDC20 |
| 1 | GTSE1 | 4528 | CDC20 |
| 1 | ORC1L | 4497 | CDC20 |
| 1 | STX1A | 4475 | CDC20 |
| 1 | MFSD2A | 4451 | CDC20 |
| 1 | BEST4 | 4389 | CDC20 |
| 1 | CACNA1E | 4299 | CDC20 |
| 1 | KLHDC7A | 4297 | CDC20 |
| 1 | MAPK15 | 4272 | CDC20 |
| 1 | GHRHR | 4211 | CDC20 |
| 1 | KEL | 4155 | CDC20 |
| 1 | C2orf62 | 4113 | CDC20 |
| 1 | ANXA9 | 4063 | CDC20 |
| 1 | RAET1G | 4059 | CDC20 |
| 1 | GPR88 | 3913 | CDC20 |
| 1 | F12 | 3749 | CDC20 |
| 1 | LYPD1 | 3681 | CDC20 |
| 1 | C2orf70 | 3665 | CDC20 |
| 1 | ABCB9 | 3638 | CDC20 |
| 1 | MSLNL | 3589 | CDC20 |
| 1 | CDC25C | 3573 | CDC20 |
| 1 | CELA3A | 3551 | CDC20 |
| 1 | AQP12B | 3551 | CDC20 |
| 1 | NEU4 | 3551 | CDC20 |
| 1 | KIF2C | 3541 | CDC20 |
| 1 | NEIL3 | 3426 | CDC20 |
| 1 | NUDT17 | 3399 | CDC20 |
| 1 | ULBP2 | 3395 | CDC20 |
| 1 | KIF17 | 3341 | CDC20 |
| 1 | ARHGEF19 | 3340 | CDC20 |
| 1 | CYP4A22 | 3317 | CDC20 |
| 1 | CYP4A11 | 3317 | CDC20 |
| 1 | SCNN1D | 3311 | CDC20 |
| 1 | FRMD1 | 3219 | CDC20 |
| 1 | FAM179A | 3194 | CDC20 |
| 1 | NDUFA4L2 | 3109 | CDC20 |
| 1 | LCE2D | 2984 | CDC20 |
| 1 | ODZ4 | 2936 | CDC20 |
| 1 | ABCC12 | 2809 | CDC20 |
| 1 | DPF1 | 2750 | CDC20 |
| 1 | CDH24 | 2653 | CDC20 |
| 1 | LOC154449 | 2641 | CDC20 |
| 1 | KIF21B | 2534 | CDC20 |
| 1 | SEMA5B | 2499 | CDC20 |
| 1 | PSORS1C2 | 2497 | CDC20 |
| 1 | FCRL4 | 2434 | CDC20 |
| 1 | FUT6 | 2313 | CDC20 |
| 1 | TRAIP | 2258 | CDC20 |
| 1 | E2F8 | 2232 | CDC20 |
| 1 | SLC38A3 | 2199 | CDC20 |
| 1 | CBX2 | 2174 | CDC20 |
| 1 | CDCA5 | 2130 | CDC20 |
| 1 | DUSP5P | 2080 | CDC20 |
| 1 | GPAT2 | 1997 | CDC20 |
| 1 | AVPR1B | 1991 | CDC20 |
| 1 | MGC50722 | 1990 | CDC20 |
| 1 | AQP12A | 1983 | CDC20 |
| 1 | C6orf222 | 1965 | CDC20 |
| 1 | PRAMEF19 | 1965 | CDC20 |
| 1 | PRAMEF18 | 1965 | CDC20 |
| 1 | SLC5A9 | 1965 | CDC20 |
| 1 | FCN3 | 1955 | CDC20 |
| 1 | GCM2 | 1910 | CDC20 |
| 1 | ADORA3 | 1862 | CDC20 |
| 1 | PLA2G2F | 1821 | CDC20 |
| 1 | C6orf25 | 1765 | CDC20 |
| 1 | CDC45 | 1681 | CDC20 |
| 1 | AGXT | 1529 | CDC20 |
| 1 | KIF25 | 1507 | CDC20 |
| 1 | ZDHHC19 | 1507 | CDC20 |
| 1 | APLNR | 1374 | CDC20 |
| 1 | TACC3 | 1220 | CDC20 |
| 1 | TK1 | 1063 | CDC20 |
| 1 | C15orf42 | 1052 | CDC20 |
| 1 | FANCA | 990 | CDC20 |
| 1 | GINS4 | 932 | CDC20 |
| 1 | MCM10 | 757 | CDC20 |
| 1 | CYB561D1 | 748 | CDC20 |
| 1 | FUT5 | 687 | CDC20 |
| 1 | POLQ | 632 | CDC20 |
| 1 | LOC643988 | 621 | CDC20 |
| 1 | RAD51 | 601 | CDC20 |
| 1 | DGAT2 | 582 | CDC20 |
| 1 | KIF24 | 566 | CDC20 |
| 1 | CDCA3 | 442 | CDC20 |
| 1 | CLSPN | 381 | CDC20 |
| 1 | ESYT3 | 356 | CDC20 |
| 1 | EXO1 | 278 | CDC20 |
| 1 | CDCA2 | 186 | CDC20 |
| 1 | CKAP2L | 159 | CDC20 |
| 1 | FOXM1 | 157 | CDC20 |
| 1 | FEN1 | 136 | CDC20 |
| 1 | UHRF1 | 125 | CDC20 |
| 1 | KIF20A | 110 | CDC20 |
| 1 | ESCO2 | 107 | CDC20 |
| 1 | CA2 | 100 | CDC20 |
| 1 | PLK1 | 84 | CDC20 |
| 1 | PTTG1 | 64 | CDC20 |
| 1 | KIF14 | 53 | CDC20 |
| 1 | CIT | 42 | CDC20 |
| 1 | FAM54A | 39 | CDC20 |
| 1 | CDCA8 | 28 | CDC20 |
| 1 | DEPDC1B | 12 | CDC20 |
| 1 | MYBL2 | 12208 | MYBL2 |
| 1 | BIRC5 | 12208 | MYBL2 |
| 1 | TROAP | 12208 | MYBL2 |
| 1 | ESPL1 | 12190 | MYBL2 |
| 1 | WDR62 | 12032 | MYBL2 |
| 1 | KIF18B | 12015 | MYBL2 |
| 1 | FAM64A | 11915 | MYBL2 |
| 1 | PKMYT1 | 11774 | MYBL2 |
| 1 | SLC2A6 | 11774 | MYBL2 |

TABLE 10-continued

| StackID | Coexpressed Gene | ProbeWt | Seeding Gene |
|---|---|---|---|
| 1 | GTSE1 | 11356 | MYBL2 |
| 1 | E2F1 | 11062 | MYBL2 |
| 1 | AURKB | 11010 | MYBL2 |
| 1 | RNFT2 | 10720 | MYBL2 |
| 1 | CENPM | 10651 | MYBL2 |
| 1 | CENPA | 10628 | MYBL2 |
| 1 | POC1A | 10289 | MYBL2 |
| 1 | FDXR | 10285 | MYBL2 |
| 1 | NFKBIL2 | 10214 | MYBL2 |
| 1 | E2F7 | 10195 | MYBL2 |
| 1 | C9orf100 | 10103 | MYBL2 |
| 1 | CDH24 | 10094 | MYBL2 |
| 1 | ABCB9 | 10079 | MYBL2 |
| 1 | NDUFA4L2 | 9961 | MYBL2 |
| 1 | ADAMTS7 | 9614 | MYBL2 |
| 1 | MAST1 | 9313 | MYBL2 |
| 1 | GABBR2 | 9262 | MYBL2 |
| 1 | MYH7B | 8759 | MYBL2 |
| 1 | DNAH3 | 8637 | MYBL2 |
| 1 | TTLL6 | 8619 | MYBL2 |
| 1 | ZFHX2 | 8592 | MYBL2 |
| 1 | CDC20 | 8589 | MYBL2 |
| 1 | RASAL1 | 8452 | MYBL2 |
| 1 | NCAPH | 8273 | MYBL2 |
| 1 | IQGAP3 | 8245 | MYBL2 |
| 1 | DNAH2 | 8219 | MYBL2 |
| 1 | LOC400499 | 8151 | MYBL2 |
| 1 | CHST1 | 8037 | MYBL2 |
| 1 | ATP4A | 7868 | MYBL2 |
| 1 | TH | 7731 | MYBL2 |
| 1 | EXOC3L | 7603 | MYBL2 |
| 1 | E2F8 | 7590 | MYBL2 |
| 1 | MMP11 | 7465 | MYBL2 |
| 1 | CELP | 7344 | MYBL2 |
| 1 | CDCA5 | 7024 | MYBL2 |
| 1 | FAM131B | 6981 | MYBL2 |
| 1 | C14orf73 | 6896 | MYBL2 |
| 1 | FBXW9 | 6802 | MYBL2 |
| 1 | PLEKHG6 | 6725 | MYBL2 |
| 1 | FNDC1 | 6720 | MYBL2 |
| 1 | SEZ6 | 6515 | MYBL2 |
| 1 | FCHO1 | 6413 | MYBL2 |
| 1 | APLNR | 6402 | MYBL2 |
| 1 | ALAS2 | 6382 | MYBL2 |
| 1 | VSX1 | 6360 | MYBL2 |
| 1 | LOC197350 | 6312 | MYBL2 |
| 1 | DPF1 | 6205 | MYBL2 |
| 1 | CDC45 | 6026 | MYBL2 |
| 1 | C11orf9 | 6020 | MYBL2 |
| 1 | EME1 | 6010 | MYBL2 |
| 1 | ADAMTS13 | 5896 | MYBL2 |
| 1 | TMEM145 | 5896 | MYBL2 |
| 1 | C8G | 5840 | MYBL2 |
| 1 | CBX2 | 5838 | MYBL2 |
| 1 | TMEM210 | 5659 | MYBL2 |
| 1 | CCDC135 | 5593 | MYBL2 |
| 1 | ADAMTS14 | 5571 | MYBL2 |
| 1 | ITGA2B | 5337 | MYBL2 |
| 1 | POLD1 | 5286 | MYBL2 |
| 1 | PNLDC1 | 5146 | MYBL2 |
| 1 | UCP3 | 5123 | MYBL2 |
| 1 | FANCA | 5068 | MYBL2 |
| 1 | MSLNL | 5061 | MYBL2 |
| 1 | TEPP | 4930 | MYBL2 |
| 1 | LRRC16B | 4901 | MYBL2 |
| 1 | CACNA1F | 4901 | MYBL2 |
| 1 | EFNB3 | 4887 | MYBL2 |
| 1 | MYBPC2 | 4851 | MYBL2 |
| 1 | FUT6 | 4847 | MYBL2 |
| 1 | CDH15 | 4847 | MYBL2 |
| 1 | HAL | 4809 | MYBL2 |
| 1 | PGA3 | 4720 | MYBL2 |
| 1 | PGA4 | 4720 | MYBL2 |
| 1 | C17orf53 | 4717 | MYBL2 |
| 1 | UMODL1 | 4713 | MYBL2 |
| 1 | OTOG | 4690 | MYBL2 |
| 1 | DBH | 4661 | MYBL2 |
| 1 | POM121L9P | 4629 | MYBL2 |
| 1 | DNAJB13 | 4394 | MYBL2 |
| 1 | TK1 | 4360 | MYBL2 |
| 1 | C9orf117 | 4336 | MYBL2 |
| 1 | RHBDL1 | 4308 | MYBL2 |
| 1 | MUC5B | 4283 | MYBL2 |
| 1 | SPAG4 | 4276 | MYBL2 |
| 1 | GOLGA7B | 4111 | MYBL2 |
| 1 | APOB48R | 4107 | MYBL2 |
| 1 | IQCD | 3984 | MYBL2 |
| 1 | FUT5 | 3977 | MYBL2 |
| 1 | AIFM3 | 3973 | MYBL2 |
| 1 | LOC390595 | 3868 | MYBL2 |
| 1 | CYP27B1 | 3833 | MYBL2 |
| 1 | SUSD2 | 3824 | MYBL2 |
| 1 | TGM6 | 3767 | MYBL2 |
| 1 | CDCA3 | 3765 | MYBL2 |
| 1 | C20orf151 | 3706 | MYBL2 |
| 1 | C11orf41 | 3650 | MYBL2 |
| 1 | C9orf98 | 3636 | MYBL2 |
| 1 | KRT24 | 3589 | MYBL2 |
| 1 | ABCC12 | 3582 | MYBL2 |
| 1 | B3GNT4 | 3569 | MYBL2 |
| 1 | AZI1 | 3556 | MYBL2 |
| 1 | RLTPR | 3427 | MYBL2 |
| 1 | KIF24 | 3264 | MYBL2 |
| 1 | DERL3 | 3232 | MYBL2 |
| 1 | LIPE | 3221 | MYBL2 |
| 1 | TTLL9 | 3196 | MYBL2 |
| 1 | SEC1 | 3196 | MYBL2 |
| 1 | ADAM8 | 3185 | MYBL2 |
| 1 | SLC25A19 | 3136 | MYBL2 |
| 1 | PRSS27 | 3136 | MYBL2 |
| 1 | ODF3L2 | 3094 | MYBL2 |
| 1 | ODZ4 | 3034 | MYBL2 |
| 1 | RAD54L | 2936 | MYBL2 |
| 1 | KCNE1L | 2936 | MYBL2 |
| 1 | SBF1P1 | 2915 | MYBL2 |
| 1 | AIPL1 | 2868 | MYBL2 |
| 1 | UNC13A | 2862 | MYBL2 |
| 1 | REM2 | 2832 | MYBL2 |
| 1 | KIFC1 | 2808 | MYBL2 |
| 1 | TSNAXIP1 | 2799 | MYBL2 |
| 1 | LOC390660 | 2767 | MYBL2 |
| 1 | SLC6A12 | 2762 | MYBL2 |
| 1 | WDR16 | 2723 | MYBL2 |
| 1 | ACR | 2710 | MYBL2 |
| 1 | TMPRSS13 | 2672 | MYBL2 |
| 1 | C15orf42 | 2659 | MYBL2 |
| 1 | DNMT3B | 2649 | MYBL2 |
| 1 | UNC13D | 2610 | MYBL2 |
| 1 | SYT5 | 2544 | MYBL2 |
| 1 | PAX2 | 2462 | MYBL2 |
| 1 | PRCD | 2426 | MYBL2 |
| 1 | PPFIA3 | 2421 | MYBL2 |
| 1 | GCGR | 2338 | MYBL2 |
| 1 | CACNG3 | 2289 | MYBL2 |
| 1 | LAIR2 | 2233 | MYBL2 |
| 1 | MCM10 | 2178 | MYBL2 |
| 1 | C2orf54 | 2172 | MYBL2 |
| 1 | LOC400419 | 2138 | MYBL2 |
| 1 | RINL | 2136 | MYBL2 |
| 1 | DKFZp451A211 | 2118 | MYBL2 |
| 1 | LAMA1 | 2060 | MYBL2 |
| 1 | C9orf169 | 2060 | MYBL2 |
| 1 | CATSPER1 | 2001 | MYBL2 |
| 1 | OPCML | 1896 | MYBL2 |
| 1 | C9orf50 | 1852 | MYBL2 |
| 1 | DOC2GP | 1760 | MYBL2 |
| 1 | TACC3 | 1665 | MYBL2 |
| 1 | APOBEC3A | 1632 | MYBL2 |
| 1 | LOC728307 | 1606 | MYBL2 |
| 1 | PDIA2 | 1572 | MYBL2 |
| 1 | LTB4R2 | 1419 | MYBL2 |
| 1 | OIP5 | 1393 | MYBL2 |
| 1 | ORC1L | 1340 | MYBL2 |
| 1 | GSG2 | 1268 | MYBL2 |
| 1 | FSD1 | 1256 | MYBL2 |
| 1 | CDC25C | 1228 | MYBL2 |

TABLE 10-continued

| StackID | Coexpressed Gene | ProbeWt | Seeding Gene |
|---|---|---|---|
| 1 | KSR2 | 1183 | MYBL2 |
| 1 | DGAT2 | 1183 | MYBL2 |
| 1 | KIF2C | 1180 | MYBL2 |
| 1 | RAD51 | 1178 | MYBL2 |
| 1 | FNDC8 | 1178 | MYBL2 |
| 1 | RAB3IL1 | 991 | MYBL2 |
| 1 | UHRF1 | 936 | MYBL2 |
| 1 | ENO4 | 855 | MYBL2 |
| 1 | C10orf105 | 780 | MYBL2 |
| 1 | NEIL3 | 733 | MYBL2 |
| 1 | PPBP | 672 | MYBL2 |
| 1 | PROCA1 | 671 | MYBL2 |
| 1 | TMEM132A | 647 | MYBL2 |
| 1 | DHRS2 | 548 | MYBL2 |
| 1 | PLK1 | 523 | MYBL2 |
| 1 | GINS4 | 485 | MYBL2 |
| 1 | CEL | 480 | MYBL2 |
| 1 | ZNF367 | 406 | MYBL2 |
| 1 | FOXM1 | 402 | MYBL2 |
| 1 | POLQ | 319 | MYBL2 |
| 1 | ADAM12 | 312 | MYBL2 |
| 1 | SEMA7A | 284 | MYBL2 |
| 1 | HOXB5 | 137 | MYBL2 |
| 1 | EXO1 | 115 | MYBL2 |
| 1 | KIF4A | 114 | MYBL2 |
| 1 | FEN1 | 112 | MYBL2 |
| 1 | CLSPN | 107 | MYBL2 |
| 1 | CIT | 94 | MYBL2 |
| 1 | CDCA2 | 85 | MYBL2 |
| 1 | KIF4B | 68 | MYBL2 |
| 1 | PIK3R5 | 56 | MYBL2 |
| 1 | KIF20A | 52 | MYBL2 |
| 1 | ZWINT | 31 | MYBL2 |
| 1 | SPAG5 | 19 | MYBL2 |
| 1 | ERCC6L | 17 | MYBL2 |
| 1 | TPX2 | 11 | TPX2 |
| 1 | TOP2A | 11 | TPX2 |
| 1 | NUSAP1 | 10 | TPX2 |
| 1 | MELK | 7 | TPX2 |
| 1 | RACGAP1 | 6 | TPX2 |
| 1 | NCAPG | 4 | TPX2 |
| 1 | MKI67 | 4 | TPX2 |
| 1 | CDKN3 | 4 | TPX2 |
| 1 | PRC1 | 4 | TPX2 |
| 1 | ARHGAP11B | 3 | TPX2 |
| 1 | KIAA0101 | 3 | TPX2 |
| 1 | ANLN | 3 | TPX2 |
| 1 | FAM111B | 2 | TPX2 |
| 1 | RRM2 | 1 | TPX2 |
| 1 | KIF11 | 1 | TPX2 |
| 1 | PRR11 | 1 | TPX2 |
| 1 | CENPF | 1 | TPX2 |
| 2 | MKI67 | 41 | TPX2 |
| 2 | CASC5 | 39 | TPX2 |
| 2 | ASPM | 38 | TPX2 |
| 2 | KIF4A | 36 | TPX2 |
| 2 | DLGAP5 | 36 | TPX2 |
| 2 | KIF4B | 36 | TPX2 |
| 2 | TPX2 | 33 | TPX2 |
| 2 | KIF14 | 31 | TPX2 |
| 2 | EXO1 | 31 | TPX2 |
| 2 | SKA3 | 30 | TPX2 |
| 2 | SPAG5 | 27 | TPX2 |
| 2 | CIT | 27 | TPX2 |
| 2 | BUB1 | 26 | TPX2 |
| 2 | CDKN3 | 26 | TPX2 |
| 2 | CENPF | 25 | TPX2 |
| 2 | MELK | 20 | TPX2 |
| 2 | ANLN | 19 | TPX2 |
| 2 | BUB1B | 18 | TPX2 |
| 2 | UBE2C | 17 | TPX2 |
| 2 | CEP55 | 16 | TPX2 |
| 2 | KIF20A | 15 | TPX2 |
| 2 | DEPDC1B | 15 | TPX2 |
| 2 | DTL | 14 | TPX2 |
| 2 | UBE2T | 13 | TPX2 |
| 2 | NCAPG | 13 | TPX2 |
| 2 | PBK | 13 | TPX2 |
| 2 | DIAPH3 | 10 | TPX2 |
| 2 | KIF23 | 6 | TPX2 |
| 2 | FOXM1 | 5 | TPX2 |
| 2 | RRM2 | 3 | TPX2 |
| 2 | SGOL1 | 2 | TPX2 |
| 2 | PLK1 | 2 | TPX2 |
| 2 | CCNA2 | 2 | TPX2 |
| 2 | CDK1 | 2 | TPX2 |
| 2 | NUSAP1 | 1 | TPX2 |

TABLE 11

| StackID | Coexpressed Gene | ProbeWt | Seeding Gene |
|---|---|---|---|
| 1 | NNT | 1 | DUSP1 |
| 1 | RNF180 | 1 | DUSP1 |
| 1 | PCDH18 | 1 | DUSP1 |
| 2 | RNF180 | 1 | DUSP1 |
| 2 | DUSP1 | 1 | DUSP1 |
| 2 | PCDH18 | 1 | DUSP1 |
| 3 | ACTB | 1 | DUSP1 |
| 3 | RHOB | 1 | DUSP1 |
| 3 | DUSP1 | 1 | DUSP1 |
| 4 | ACTB | 1 | DUSP1 |
| 4 | DUSP1 | 1 | DUSP1 |
| 4 | CRTAP | 1 | DUSP1 |
| 5 | RNF180 | 1 | DUSP1 |
| 5 | DUSP1 | 1 | DUSP1 |
| 5 | CRTAP | 1 | DUSP1 |
| 5 | PAM | 1 | DUSP1 |
| 6 | DUSP1 | 8 | DUSP1 |
| 6 | NR4A1 | 7 | DUSP1 |
| 6 | FOS | 7 | DUSP1 |
| 6 | EGR1 | 5 | DUSP1 |
| 6 | BTG2 | 5 | DUSP1 |
| 6 | FOSB | 5 | DUSP1 |
| 6 | JUN | 4 | DUSP1 |
| 6 | NR4A2 | 3 | DUSP1 |
| 6 | TIPARP | 3 | DUSP1 |
| 6 | CYR61 | 3 | DUSP1 |
| 6 | ATF3 | 2 | DUSP1 |
| 6 | RHOB | 2 | DUSP1 |
| 6 | NEDD9 | 2 | DUSP1 |
| 6 | MCL1 | 1 | DUSP1 |
| 6 | RASD1 | 1 | DUSP1 |
| 1 | JUNB | 1 | EGR1 |
| 1 | TIPARP | 1 | EGR1 |
| 1 | BTG2 | 1 | EGR1 |
| 2 | JUNB | 1 | EGR1 |
| 2 | BTG2 | 1 | EGR1 |
| 2 | EGR1 | 1 | EGR1 |
| 3 | KLF4 | 1 | EGR1 |
| 3 | FOSB | 1 | EGR1 |
| 3 | EGR1 | 1 | EGR1 |
| 4 | FOSB | 1 | EGR1 |
| 4 | CSRNP1 | 1 | EGR1 |
| 4 | EGR1 | 1 | EGR1 |
| 5 | EGR1 | 35 | EGR1 |
| 5 | FOS | 30 | EGR1 |
| 5 | NR4A1 | 25 | EGR1 |
| 5 | FOSB | 23 | EGR1 |
| 5 | BTG2 | 22 | EGR1 |
| 5 | CYR61 | 20 | EGR1 |
| 5 | ZFP36 | 18 | EGR1 |
| 5 | CSRNP1 | 17 | EGR1 |
| 5 | NR4A3 | 13 | EGR1 |
| 5 | EGR3 | 13 | EGR1 |
| 5 | KLF6 | 12 | EGR1 |
| 5 | RHOB | 11 | EGR1 |
| 5 | DUSP1 | 10 | EGR1 |
| 5 | ATF3 | 9 | EGR1 |
| 5 | JUN | 9 | EGR1 |
| 5 | TIPARP | 8 | EGR1 |
| 5 | NFKBIZ | 7 | EGR1 |
| 5 | NR4A2 | 7 | EGR1 |

TABLE 11-continued

| StackID | Coexpressed Gene | ProbeWt | Seeding Gene |
|---|---|---|---|
| 5 | JUNB | 7 | EGR1 |
| 5 | IER2 | 7 | EGR1 |
| 5 | MCL1 | 4 | EGR1 |
| 5 | KLF4 | 4 | EGR1 |
| 5 | EGR2 | 4 | EGR1 |
| 5 | NEDD9 | 2 | EGR1 |
| 5 | SRF | 2 | EGR1 |
| 5 | GADD45B | 1 | EGR1 |
| 5 | TRIB1 | 1 | EGR1 |
| 1 | FOS | 14 | FOS |
| 1 | BTG2 | 14 | FOS |
| 1 | CSRNP1 | 13 | FOS |
| 1 | ZFP36 | 13 | FOS |
| 1 | JUNB | 9 | FOS |
| 1 | NR4A3 | 7 | FOS |
| 1 | FOSB | 7 | FOS |
| 1 | SIK1 | 6 | FOS |
| 1 | BHLHE40 | 6 | FOS |
| 1 | RHOB | 5 | FOS |
| 1 | TIPARP | 5 | FOS |
| 1 | KLF6 | 5 | FOS |
| 1 | MCL1 | 5 | FOS |
| 1 | NR4A1 | 4 | FOS |
| 1 | EGR1 | 4 | FOS |
| 1 | NR4A2 | 4 | FOS |
| 1 | GADD45B | 3 | FOS |
| 1 | SOCS3 | 2 | FOS |
| 1 | NFKBIZ | 1 | FOS |
| 2 | FOS | 24 | FOS |
| 2 | FOSB | 22 | FOS |
| 2 | EGR1 | 20 | FOS |
| 2 | NR4A1 | 19 | FOS |
| 2 | BTG2 | 18 | FOS |
| 2 | ZFP36 | 12 | FOS |
| 2 | CSRNP1 | 11 | FOS |
| 2 | CYR61 | 10 | FOS |
| 2 | DUSP1 | 8 | FOS |
| 2 | ATF3 | 8 | FOS |
| 2 | IER2 | 7 | FOS |
| 2 | RHOB | 6 | FOS |
| 2 | TIPARP | 6 | FOS |
| 2 | NR4A2 | 6 | FOS |
| 2 | JUN | 6 | FOS |
| 2 | JUNB | 6 | FOS |
| 2 | EGR3 | 5 | FOS |
| 2 | NR4A3 | 4 | FOS |
| 2 | KLF6 | 3 | FOS |
| 2 | PPP1R15A | 2 | FOS |
| 2 | NEDD9 | 2 | FOS |
| 2 | KLF4 | 2 | FOS |
| 2 | EGR2 | 2 | FOS |
| 2 | MCL1 | 1 | FOS |
| 1 | EMP1 | 7 | GADD45B |
| 1 | BHLHE40 | 7 | GADD45B |
| 1 | SOCS3 | 7 | GADD45B |
| 1 | NR4A3 | 4 | GADD45B |
| 1 | FOSL2 | 3 | GADD45B |
| 1 | GADD45B | 3 | GADD45B |
| 1 | RNF122 | 3 | GADD45B |
| 1 | KLF10 | 3 | GADD45B |
| 1 | CSRNP1 | 3 | GADD45B |
| 1 | SLC2A3 | 2 | GADD45B |
| 1 | ZFP36 | 1 | GADD45B |
| 2 | FOSB | 2 | GADD45B |
| 2 | NR4A1 | 2 | GADD45B |
| 2 | FOS | 2 | GADD45B |
| 2 | GADD45B | 2 | GADD45B |
| 2 | BTG2 | 2 | GADD45B |
| 2 | NR4A3 | 2 | GADD45B |
| 2 | JUNB | 2 | GADD45B |
| 2 | EGR1 | 2 | GADD45B |
| 2 | CSRNP1 | 2 | GADD45B |
| 2 | ZFP36 | 2 | GADD45B |
| 2 | RHOB | 1 | GADD45B |
| 2 | EGR3 | 1 | GADD45B |
| 2 | ATF3 | 1 | GADD45B |
| 3 | GADD45B | 4 | GADD45B |
| 3 | JUNB | 4 | GADD45B |
| 3 | CSRNP1 | 4 | GADD45B |
| 3 | ZFP36 | 4 | GADD45B |
| 3 | SOCS3 | 4 | GADD45B |
| 3 | RHOB | 3 | GADD45B |
| 3 | BHLHE40 | 3 | GADD45B |
| 3 | FOS | 2 | GADD45B |
| 3 | FOSL2 | 2 | GADD45B |
| 3 | BTG2 | 2 | GADD45B |
| 3 | NR4A3 | 2 | GADD45B |
| 3 | FOSB | 1 | GADD45B |
| 3 | IRF1 | 1 | GADD45B |
| 1 | FOSL2 | 1 | ZFP36 |
| 1 | HBEGF | 1 | ZFP36 |
| 1 | BHLHE40 | 1 | ZFP36 |
| 2 | HBEGF | 1 | ZFP36 |
| 2 | NR4A3 | 1 | ZFP36 |
| 2 | BHLHE40 | 1 | ZFP36 |
| 3 | CSRNP1 | 53 | ZFP36 |
| 3 | ZFP36 | 49 | ZFP36 |
| 3 | JUNB | 29 | ZFP36 |
| 3 | FOS | 26 | ZFP36 |
| 3 | BHLHE40 | 24 | ZFP36 |
| 3 | BTG2 | 24 | ZFP36 |
| 3 | FOSB | 20 | ZFP36 |
| 3 | NR4A3 | 18 | ZFP36 |
| 3 | SOCS3 | 18 | ZFP36 |
| 3 | EGR1 | 16 | ZFP36 |
| 3 | RHOB | 16 | ZFP36 |
| 3 | FOSL2 | 15 | ZFP36 |
| 3 | NR4A1 | 15 | ZFP36 |
| 3 | GADD45B | 10 | ZFP36 |
| 3 | MYADM | 9 | ZFP36 |
| 3 | KLF6 | 8 | ZFP36 |
| 3 | CYR61 | 8 | ZFP36 |
| 3 | EGR3 | 8 | ZFP36 |
| 3 | EMP1 | 8 | ZFP36 |
| 3 | LMNA | 7 | ZFP36 |
| 3 | TIPARP | 7 | ZFP36 |
| 3 | NR4A2 | 7 | ZFP36 |
| 3 | MCL1 | 6 | ZFP36 |
| 3 | SIK1 | 6 | ZFP36 |
| 3 | ATF3 | 6 | ZFP36 |
| 3 | CEBPD | 5 | ZFP36 |
| 3 | IER3 | 5 | ZFP36 |
| 3 | IER2 | 5 | ZFP36 |
| 3 | MAFF | 4 | ZFP36 |
| 3 | IRF1 | 4 | ZFP36 |
| 3 | RNF122 | 4 | ZFP36 |
| 3 | SRF | 3 | ZFP36 |
| 3 | ERRFI1 | 2 | ZFP36 |
| 3 | SLC25A25 | 2 | ZFP36 |
| 3 | CDKN1A | 2 | ZFP36 |
| 3 | EGR2 | 2 | ZFP36 |
| 3 | KLF4 | 1 | ZFP36 |

Example 4: Prospective Validation Study of RS27

Study Design and Statistical Methods

The algorithm RS27 in Table 4 was tested in a prospective clinical validation study that included 395 evaluable patients who had surgery for their prostate cancer between 1997 and 2010 at the University of California, San Francisco (UCSF). The patients had Low or Intermediate risk (by CAPRA) for clinically localized prostate cancer who might have been reasonable candidates for active surveillance but underwent RP at UCSF within 6 months of the diagnosis of prostate cancer by biopsy. No randomization for patient selection was performed. For each patient, prostate biopsy samples from one fixed, paraffin-embedded tissue (FPET) block containing one or more tumor-containing needle cores was evaluated.

To investigate if there is a significant relationship between RS27 or any component of RS27 and adverse pathology at RP, multivariable and univariable multinomial logistic regression models were used and p-values from likelihood-ratio (LR) tests of the null hypothesis that the odds ratio (OR) is one were reported. The multinomial logistic model was also used to calculate estimates with 95% confidence intervals of the probability of high-grade or non-organ confined disease. To evaluate the relationship between RS27, baseline covariates, and combinations of these factors with high grade or non-organ confined disease, multivariable and univariable binary logistic regression models were used and p-values from likelihood-ratio tests of the null hypothesis that the odds ratio (OR) is one were reported.

The primary endpoint was formulated as follows:

TABLE 12

Clinical Endpoint-RP Grade and Stage

| RP Gleason Score | Pathologic T2 Stage | Pathologic T3 Stage |
| --- | --- | --- |
| ≤3 + 3 | 1 | 2 |
| 3 + 4 | 3 | 4 |
| Major pattern 4 or minor pattern 5, or tertiary pattern 5 | 5 | 6 | where Gleason Score≤3+3 and pT2 (denoted "1") is the reference category and all other categories (2-6) are compared to the reference category.

Cell combinations of Table 12 evaluated in binary logistic regression models include the following:
 Cells 2, 4, 6 vs. 1, 3, 5: Non-organ-confined disease
 Cells 5, 6 vs. 1, 2, 3, 4: High-grade disease
 Cells 2, 4, 5, 6 vs. 1 and 3: High-grade or non-organ-confined disease RS27 Algorithm RS27 on a scale from 0 to 100 was derived from reference-normalized gene expression measurements as follows. Unscaled RS27 (RS27u) was defined as in Table 4:

$RS27u = 0.735*ECM$ (Stromal Response) group−
 $0.368*$Migration (Cellular Organization) group−
 $0.352*PSA$ (Androgen) group+$0.095*$Proliferation ($TPX2$)

Where:

$ECM$ (Stromal Response) group score=$0.527*BGN+$
 $0.457*COL1A1+0.156*SFRP4$

Migration (Cellular Organization) group
 score=$0.163*FLNC+0.504*GSN+0.421*TPM2+$
 $0.394*GSTM2$ $PSA$ (Androgen) group score=$0.634*FAM13C+$
 $1.079*KLK2+0.642*AZGP1+0.997*SRD5A2$ Thresh Proliferation ($TPX2$) score=$TPX2$ Thresh where the thresholded gene scores for SRD5A2 and TPX2 are calculated as follows:

$$SRD5A2\ Thresh = \begin{cases} 5.5 & \text{if } SRD5A2 < 5.5 \\ SRD5A2 & \text{otherwise} \end{cases}$$

$$TPX2\ Thresh = \begin{cases} 5.0 & \text{if } TPX2 < 5.0 \\ TPX2 & \text{otherwise} \end{cases}$$

RS27u is then rescaled to be between 0 and 100 as follows:

$$RS27(\text{scaled}) = \begin{cases} 0 & \text{if } 13.4 \times (RS27u + 10.5) < 0 \\ 13.4 \times (RS27u + 10.5) & \text{if } 0 \leq 13.4 \times (RS27u + 10.5) \leq 100 \\ 100 & \text{if } 13.4 \times (RS27u + 10.5) > 100 \end{cases}$$

Patients were classified into low, intermediate, and high RS27 groups using pre-specified cut-points defined in Table 13 below. These cut-points defined the boundaries between low and intermediate RS27 groups and between intermediate and high RS27 groups. The cutpoints were derived from the discovery study with the intent of identifying substantial proportions of patients who on average had clinically meaningful low or high risk of adverse pathology. The RS27 was rounded to the nearest integer before the cut-points defining the RS27 groups were applied.

TABLE 13

| RS27 Group | Score |
| --- | --- |
| Low | Less than 16 |
| Intermediate | Greater than or equal to 16 and less than 30 |
| High | Greater than or equal to 30 |

Assay Methods

Paraffin from the samples was removed with Shandon Xylene substitute (Thermo Scientific, Kalamazoo, Mich.). Nucleic acids were isolated using the Agencourt® FormaPure® XP kit (Beckman Coulter, Beverly, Mass.).

The amount of RNA was determined using the Quant-iT™ RiboGreen® RNA Assay kit (Invitrogen™, Carlsbad, Calif.). Quantitated RNA was convereted to complementary DNA using the Omniscript® RT kit (Qiagen, Valencia, Calif.) and combined with the reverse primers for the 12 genes of RS27 and 5 normalization genes (ARF1, ATP5E, CLTC, GPS1, PGK1) as shown in Table A. The reaction was incubated at 37° C. for 60 minutes and then inactivated at 93° C. for 5 minutes.

The cDNA was preamplified using a custom TaqMan® PreAmp Master Mix made for Genomic Health, Inc. by Life Technologies (Carlsbad, Calif.) and the forward and reverse primers for all targets as shown in Table A. The reaction was placed in a thermocycler (DNA Engine® PTC 200G, Bio-Rad, Hercules, Calif.) and incubated under the following conditions: A) 95° C. for 15 sec; B) 60° C. for 4 min; C) 95° C. for 15 sec; and D) steps B and C were repeated 8 times. The amplified product was then mixed with the forward and reverse primers and probes for each of the targets as shown in Table A and the QuantiTect® Primer Assay master mix (Qiagen, Valencia, Calif.) and amplified for 45 cycles in a LightCycler® 480 (Roche Applied Science, Indianapolis, Ind.). The level of expression was calculated using the crossing-point (Cp) method.

Results

RS27 significantly predicted for adverse pathology, non-organ-confined disease, high-grade disease, and high-grade or non-organ-confined disease, and adds value beyond biopsy Gleason Score as shown in Tables 14, 15, 16, and 17, respectively.

TABLE 14

Prediction of Adverse Pathology

| Variable | LR Chi-Square | DF | P-value |
|---|---|---|---|
| RS27 Score | 19.31 | 5 | 0.002 |
| Central Biopsy Gleason Score 3 + 4 vs 3 + 3 | 32.86 | 5 | <0.001 |

Results obtained from the multivariable multinomial logistic model for cells 2, 3, 4, 5, and 6 vs 1 in Table 12.
DF = degrees of freedom

TABLE 15

Prediction of Non-organ-confined disease

| Model | Variables | Odds Ratio | 95% Confidence Interval | DF | LR Chi-Square | P-value |
|---|---|---|---|---|---|---|
| Univariable Model | RS27 | 2.20 | (1.46, 3.31) | 1 | 14.44 | <0.001 |
| Multivariable Model | RS27 | 1.93 | (1.25, 2.96) | 1 | 8.97 | 0.003 |
| | Central Biopsy Gleason Score 3 + 4 vs 3 + 3 | 1.79 | (1.04, 3.10) | 1 | 4.23 | 0.040 |

Results obtained from univariable and multivariable binary logistic regression models for cells 2, 4, 6 vs. 1, 3, 5 in Table 12
Odds ratio for RS27 was per 20 unit increase

TABLE 16

Prediction of high-grade disease

| Model | Variables | Odds Ratio | 95% Confidence Interval | DF | LR Chi-Square | P-value |
|---|---|---|---|---|---|---|
| Univariable Model | RS27 | 2.48 | (1.60, 3.85) | 1 | 16.78 | <0.001 |
| Multivariable Model | RS27 | 2.32 | (1.46, 3.67) | 1 | 12.92 | <0.001 |
| | Central Biopsy Gleason Score 3 + 4 vs 3 + 3 | 1.36 | (0.75, 2.47) | 1 | 0.98 | 0.322 |

Results obtained from univariable and multivariable binary logistic regression models for cells 5, 6 vs. 1-4 in Table 12
Odds ratio for RS27 was per 20 unit increase

TABLE 17

Prediction of high-grade or non-organ-confined disease

| Model | Variables | Odds Ratio | 95% Confidence Interval | DF | LR Chi-Square | P-value |
|---|---|---|---|---|---|---|
| Univariable Model | RS27 | 2.23 | (1.52, 3.27) | 1 | 17.77 | <0.001 |
| Multivariable Model | RS27 | 1.93 | (1.30, 2.88) | 1 | 10.70 | 0.001 |
| | Central Biopsy Gleason Score 3 + 4 vs 3 + 3 | 1.94 | (1.17, 3.21) | 1 | 6.45 | 0.011 |

*Results obtained from univariable and multivariable binary logistic regression models for cells 2, 4, 5, 6 vs. 1, 3 in Table 12
Odds ratio for RS17 was per 20 unit increase In addition, RS27 predicted adverse pathology beyond conventional clinical/pathology treatment factors as shown in Table 18.

TABLE 18

Prediction of Adverse Pathology Beyond Conventional Clinical/Pathology Treatment Factors

| Variable | LR Chi-Square | DF | P-value |
|---|---|---|---|
| RS27 | 21.46 | 5 | <0.001 |
| Original Biopsy Gleason Score | 22.77 | 5 | <0.001 |
| RS27 | 19.31 | 5 | 0.002 |
| Central Biopsy Gleason Score | 32.86 | 5 | <0.001 |
| RS27 | 30.09 | 5 | <0.001 |
| Clin T2 v. T1 | 11.94 | 5 | 0.036 |
| RS27 | 30.17 | 5 | <0.001 |
| Baseline PSA (ng/ml) <10 v. >= 10 | 10.44 | 5 | 0.064 |
| RS27 | 30.75 | 5 | <0.001 |
| Continuous PSA | 15.17 | 5 | 0.010 |
| RS27 | 26.36 | 5 | <0.001 |
| Age | 19.05 | 5 | 0.002 |
| RS27 | 29.20 | 5 | <0.001 |
| Pct Core Positive | 4.75 | 5 | 0.447 |

Figure 8:
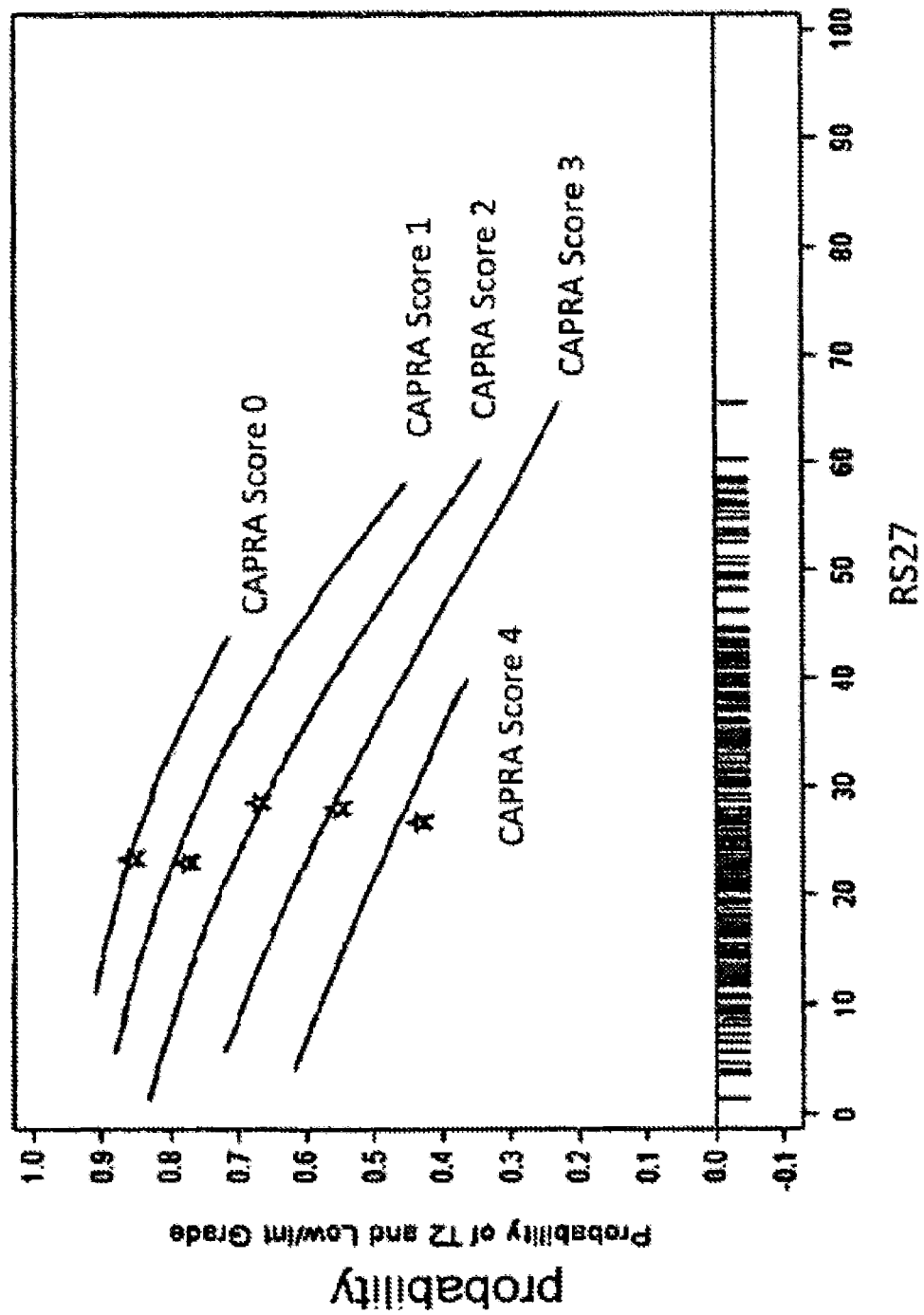
FIG. 8 is a graph showing that RS27 and CAPRA risk groups predict freedom from high-grade or non-organ-confined disease.

When added to conventional clinical/pathology tools such as CAPRA, RS27 further refined the risk of high grade or non-organ-confined disease. Using CAPRA alone, 5% of patients were identified as having greater than 85% probability of being free from high-grade or non-organ-confined disease compared to 22% of patients identified of being free from high-grade or non-organ-confined disease using RS27 in addition to CAPRA (FIG. 8).

Figure 9:
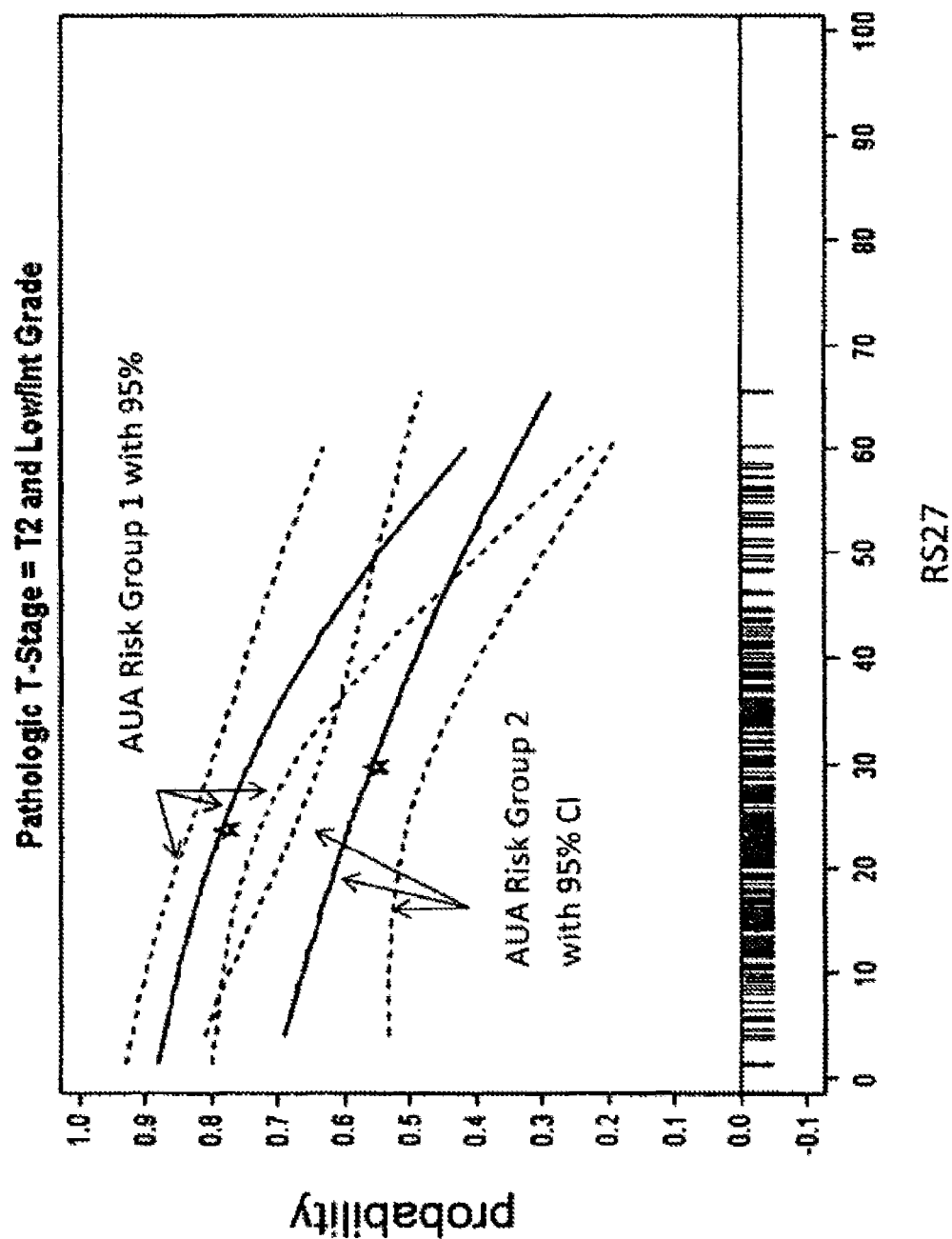
FIG. 9 is a graph showing that RS27 and AUA risk groups predict freedom from high-grade or non-organ-confined disease.

When added to conventional clinical/pathology tools such as AUA (D'Amico et al., *JAMA* 280:969-974, 1998), RS27 further refined the risk of high grade or non-organ-confined disease. As shown in FIG. 9, using AUA alone, 0% of patients are identified as having greater than 80% probability of being free from high-grade or non-organ-confined disease compared to 27% of patients identified of being free from high-grade or non-organ-confined disease using GPS in addition to AUA.

Individual genes and gene groups of RS27 were also associated with adverse pathology, high-grade disease, non-organ-confined disease, and high-grade or non-organ-confined disease, in univariable analyses as shown in Tables 19, 20, 21, and 22, respectively.

TABLE 19

Association of Genes and Gene Groups with Adverse Pathology, Univariable Analyses

| Genes and Gene Groups | LR Chi-Square | DF | P-value |
|---|---|---|---|
| BGN | 7.11 | 5 | 0.213 |
| COL1A1 | 7.88 | 5 | 0.163 |
| SFRP4 | 8.87 | 5 | 0.114 |
| FLNC | 12.26 | 5 | 0.031 |
| GSN | 5.73 | 5 | 0.333 |
| GSTM2 | 1.84 | 5 | 0.870 |
| TPM2 | 18.33 | 5 | 0.003 |
| AZGP1 | 22.87 | 5 | <0.001 |
| KLK2 | 5.97 | 5 | 0.309 |
| FAM13C1 | 21.55 | 5 | <0.001 |
| SRD5A2 | 9.10 | 5 | 0.105 |
| SRD5A2 Thresholded | 9.25 | 5 | 0.099 |
| TPX2 | 14.26 | 5 | 0.014 |
| TPX2 Thresholded | 23.34 | 5 | <0.001 |
| Ref Gene Average | 3.27 | 5 | 0.659 |
| Stromal Group Score | 9.84 | 5 | 0.080 |
| Cellular Organization Group Score | 8.04 | 5 | 0.154 |
| Androgen Group Score | 29.46 | 5 | <0.001 |
| Proliferation Group Score | 23.34 | 5 | <0.001 |
| GPS | 29.98 | 5 | <0.001 |

TABLE 20

Association of Genes and Gene Groups with High-Grade Disease, Univariable Analyses

| Gene | Chi-Square | DF | P-value | OR | (95% CI) |
|---|---|---|---|---|---|
| BGN | 3.67 | 1 | 0.055 | 1.46 | (0.99, 2.15) |
| COL1A1 | 2.33 | 1 | 0.127 | 1.32 | (0.93, 1.87) |
| SFRP4 | 6.08 | 1 | 0.014 | 1.33 | (1.06, 1.67) |
| FLNC | 3.04 | 1 | 0.081 | 0.77 | (0.57, 1.03) |
| GSN | 0.14 | 1 | 0.710 | 0.94 | (0.67, 1.32) |
| GSTM2 | 0.03 | 1 | 0.870 | 0.97 | (0.69, 1.37) |
| TPM2 | 2.85 | 1 | 0.091 | 0.76 | (0.56, 1.04) |
| AZGP1 | 12.69 | 1 | <0.001 | 0.58 | (0.42, 0.79) |
| KLK2 | 3.50 | 1 | 0.061 | 0.62 | (0.38, 1.02) |
| FAM13C1 | 9.29 | 1 | 0.002 | 0.51 | (0.33, 0.79) |
| SRD5A2 | 3.26 | 1 | 0.071 | 0.76 | (0.56, 1.02) |
| SRD5A2 Thresholded | 2.70 | 1 | 0.100 | 0.75 | (0.53, 1.06) |
| TPX2 | 1.72 | 1 | 0.190 | 1.21 | (0.91, 1.59) |
| TPX2 Thresholded | 7.38 | 1 | 0.007 | 1.93 | (1.20, 3.11) |
| Ref Gene Average | 1.18 | 1 | 0.277 | 0.86 | (0.65, 1.14) |
| Stromal Response Group Score | 4.92 | 1 | 0.027 | 1.49 | (1.05, 2.12) |
| Cellular Organization Group Score | 1.12 | 1 | 0.290 | 0.87 | (0.66, 1.13) |
| Androgen Group Score | 15.07 | 1 | <0.001 | 0.69 | (0.58, 0.83) |
| Proliferation Group Score | 7.38 | 1 | 0.007 | 1.93 | (1.20, 3.11) |

TABLE 21

Association of Genes and Gene Groups with Non-Organ-Confined Disease, Univariable Analyses

| Gene | Chi-Square | DF | p-value | Odds Ratio | 95% CI |
|---|---|---|---|---|---|
| BGN | 2.58 | 1 | 0.109 | 1.34 | (0.94, 1.91) |
| COL1A1 | 2.90 | 1 | 0.089 | 1.33 | (0.96, 1.83) |
| SFRP4 | 4.39 | 1 | 0.036 | 1.25 | (1.01, 1.54) |
| FLNC | 0.34 | 1 | 0.560 | 0.92 | (0.70, 1.21) |
| GSN | 0.27 | 1 | 0.603 | 0.92 | (0.67, 1.26) |
| GSTM2 | 0.16 | 1 | 0.693 | 0.94 | (0.68, 1.29) |
| TPM2 | 0.51 | 1 | 0.473 | 0.9 | (0.67, 1.20) |
| AZGP1 | 12.48 | 1 | <0.001 | 0.59 | (0.44, 0.80) |
| KLK2 | 2.10 | 1 | 0.148 | 0.71 | (0.45, 1.12) |
| FAM13C1 | 12.42 | 1 | 0.000 | 0.48 | (0.32, 0.73) |
| SRD5A2 | 2.42 | 1 | 0.120 | 0.8 | (0.60, 1.06) |
| SRD5A2 Thresholded | 2.65 | 1 | 0.103 | 0.77 | (0.56, 1.06) |
| TPX2 | 6.38 | 1 | 0.012 | 1.39 | (1.08, 1.81) |
| TPX2 Thresholded | 6.51 | 1 | 0.011 | 1.82 | (1.14, 2.89) |
| Ref Gene Average | 0.33 | 1 | 0.563 | 0.93 | (0.73, 1.19) |
| Stromal Response Group Score | 4.24 | 1 | 0.040 | 1.41 | (1.02, 1.95) |
| Cellular Organization Group Score | 0.45 | 1 | 0.504 | 0.92 | (0.72, 1.18) |
| Androgen Group Score | 14.64 | 1 | <0.001 | 0.71 | (0.60, 0.85) |
| Proliferation Group Score | 6.51 | 1 | 0.011 | 1.82 | (1.14, 2.89) |

TABLE 22

Association of Genes and Gene Groups with High-Grade or Non-Organ-Confined Disease, Univariable Analyses

| Gene | Chi-Square | DF | p-value | Odds Ratio | 95% CI |
|---|---|---|---|---|---|
| BGN | 3.15 | 1 | 0.076 | 1.33 | (0.97, 1.84) |
| COL1A1 | 1.96 | 1 | 0.162 | 1.23 | (0.92, 1.65) |
| SFRP4 | 7.08 | 1 | 0.008 | 1.29 | (1.07, 1.55) |
| FLNC | 2.36 | 1 | 0.125 | 0.83 | (0.65, 1.06) |
| GSN | 0.45 | 1 | 0.503 | 0.91 | (0.68, 1.20) |
| GSTM2 | 0.49 | 1 | 0.484 | 0.9 | (0.68, 1.20) |
| TPM2 | 2.24 | 1 | 0.135 | 0.82 | (0.63, 1.06) |
| AZGP1 | 12.20 | 1 | 0.001 | 0.61 | (0.46, 0.82) |
| KLK2 | 2.18 | 1 | 0.140 | 0.73 | (0.48, 1.11) |
| FAM13C1 | 11.13 | 1 | 0.001 | 0.53 | (0.37, 0.78) |
| SRD5A2 | 4.36 | 1 | 0.037 | 0.76 | (0.59, 0.98) |

TABLE 22-continued

Association of Genes and Gene Groups with High-Grade or Non-Organ-Confined Disease, Univariable Analyses

| Gene | Chi-Square | DF | p-value | Odds Ratio | 95% CI |
|---|---|---|---|---|---|
| SRD5A2 Thresholded | 4.63 | 1 | 0.032 | 0.73 | (0.55, 0.98) |
| TPX2 | 3.50 | 1 | 0.062 | 1.25 | (0.99, 1.58) |
| TPX2 Thresholded | 5.86 | 1 | 0.016 | 1.73 | (1.09, 2.74) |
| Ref Gene Average | 0.68 | 1 | 0.041 | 0.91 | (0.73, 1.14) |
| Stromal Response Group Score | 4.59 | 1 | 0.032 | 1.37 | (1.03, 1.84) |
| Cellular Organization Group Score | 1.54 | 1 | 0.215 | 0.87 | (0.70, 1.08) |
| Androgen Group Score | 16.56 | 1 | <0.001 | 0.72 | (0.61, 0.84) |
| Proliferation Group Score | 5.86 | 1 | 0.016 | 1.73 | (1.09, 2.74) |

Example 5: RS27 Adds Value Beyond PTEN/TMPRSS2-ERG Status in Predicting Clinical Recurrence PTEN mutation and TMPRSS2-ERG fusion genes are commonly associated with poor prognosis in prostate cancer. Here, RS27 was analyzed to determine whether it can provide value beyond PTEN/TMPRSS2-ERG status in predicting clinical recurrence.

PTEN and TMPRSS2-ERG fusion expression levels obtained in the gene identification study described in Example 1 above and in U.S. Pub. No. 20120028264 were used to stratify patients into PTEN low and PTEN normal groups. PTEN and TMPRSS2-ERG ("T2-ERG") status of the patients were found as follows:

TABLE 23

Distribution of PTEN Expression by T2-ERG Status

|  | T2-ERG Negative (53%) | T2-ERG Positive (47%) |
|---|---|---|
| Median PTEN | 8.9 | 8.7 |
| 25% PTEN | 8.7 | 8.4 |

A cutpoint for "PTEN low" was made at <=8.5, which included approximately 13% of T2-ERG negative patients and 28% of T2-ERG positive patients. PTEN normal was defined as >8.5.

Figure 10:
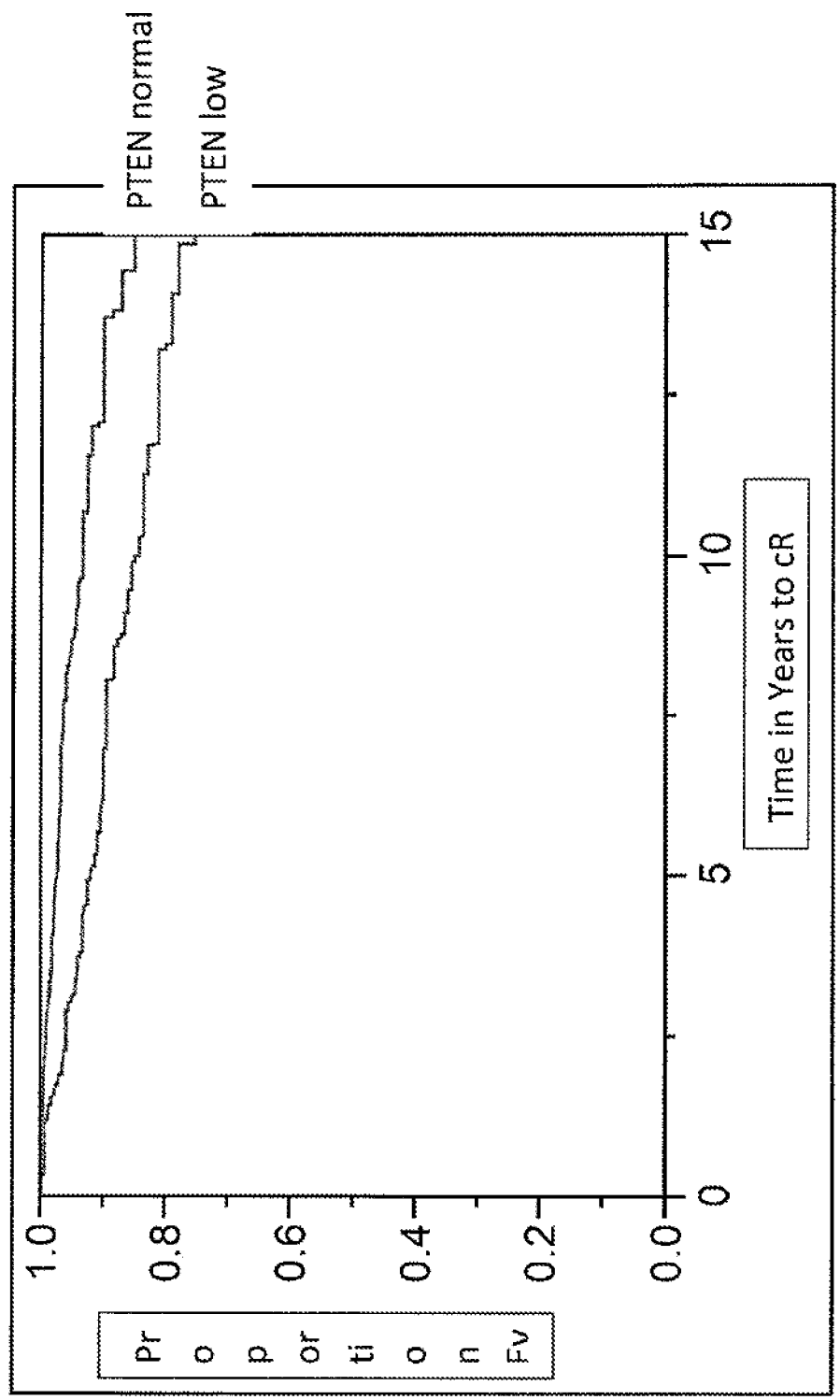
FIG. 10 is a graph showing time to clinical recurrence of PTEN low and PTEN normal patients from the gene identification study.

Univaraible Cox Proportional Hazards was applied to evaluate the association between PTEN status and time to clinical recurrence (cR). FIG. 10 and Table 24 show that PTEN low patients have a higher risk of recurrence compared to PTEN normal patients.

TABLE 24

| Chi Sq | P-value | HR | 95% CI |
|---|---|---|---|
| 12.44 | <0.001 | 0.38 | (0.22, 0.65) |

Figure 11:
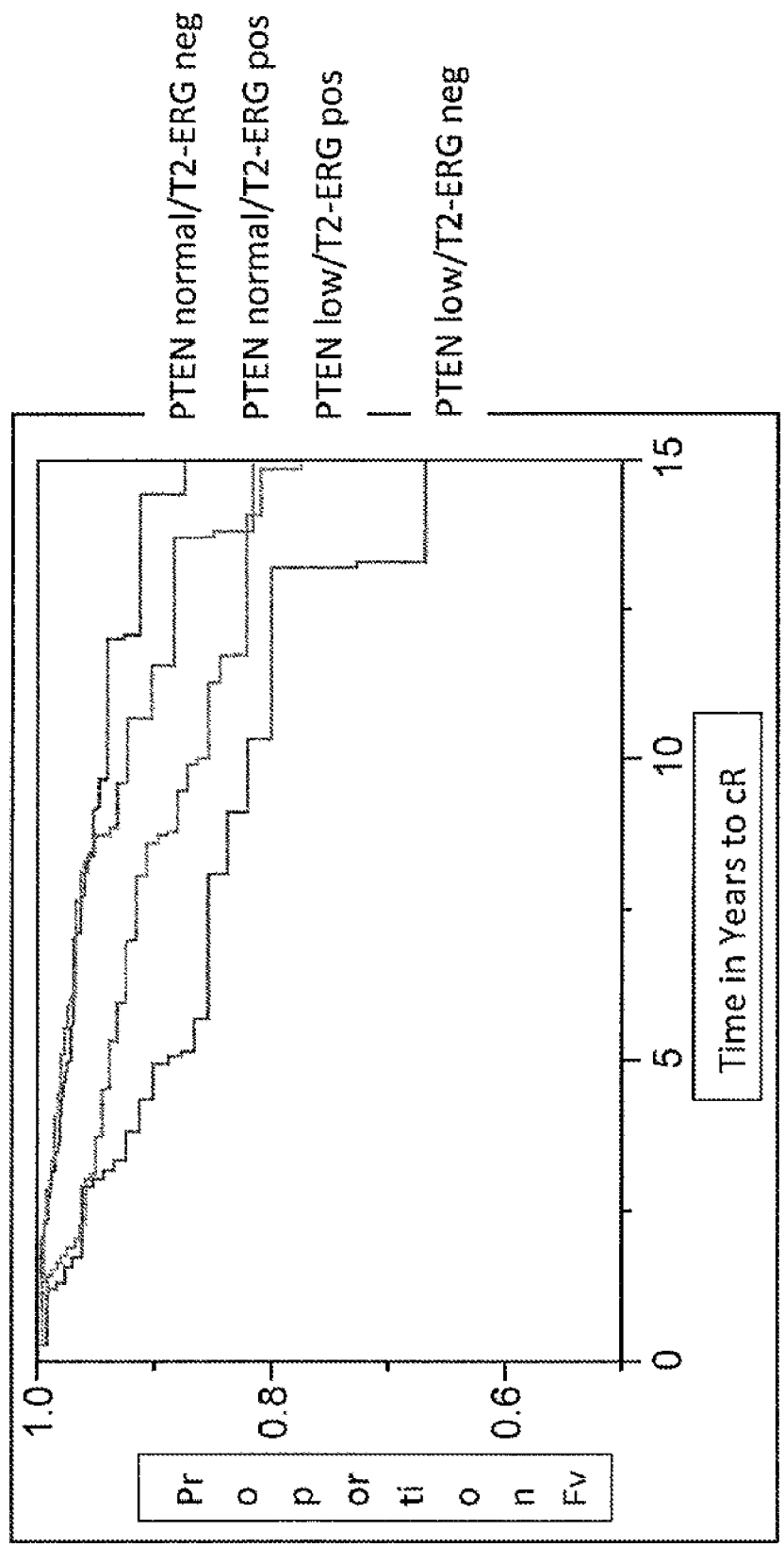
FIG. 11 is a graph showing time to clinical recurrence of patients from the gene identification study stratified into PTEN low/normal and TMPRSS-ERG negative/positive.

When the patients were further stratified into PTEN low/T2-ERG negative ("category 0"), PTEN low/T2-ERG positive ("category 1"), PTEN normal/T2-ERG negative ("category 2"), and PTEN normal/T2-ERG positive ("category 3"), both PTEN low categories had the lowest recurrence rates compared to PTEN normal patients as shown in FIG. 11 and Table 25.

TABLE 25

| PTEN/T2-ERG categories | CHISQ | P-VALUE | 95% CI |
|---|---|---|---|
| Cat 1 v 0 | 0.93 | 0.34 | (0.28, 1.55) |
| Cat 2 v 0 | 11.80 | <0.01 | (0.12, 0.56) |
| Cat 3 v 0 | 7.05 | 0.01 | (0.16, 0.76) |

The tables below summarize the results of a multivariable model with PTEN/T2-ERG status (Table 26) or PTEN status (Table 27), RS27, and biopsy Gleason Score (Bx GS), demonstrating that RS27 adds value beyond PTEN and T2-ERG markers and Biopsy GS in predicting clinical recurrence.

TABLE 26

| VARIABLE | DF | CHISQ | P-VALUE | HR | 95% CI |
|---|---|---|---|---|---|
| RS27 | 1 | 64.13 | <0.01 | 1.07 | (1.05, 1.09) |
| PTEN/T2-ERG Status | 3 | 1.59 | 0.66 |  |  |
| PTEN/T2-ERG (Cat 1 v. 0) | 1 | 0.06 | 0.80 | 0.91 | (0.41, 1.98) |
| PTEN/T2-ERG (Cat 2 v. 0) | 1 | 1.17 | 0.28 | 0.65 | (0.29, 1.42) |
| PTEN/T2-ERG (Cat 3 v. 0) | 1 | 0.14 | 0.71 | 0.86 | (0.39, 1.89) |
| BX GS | 2 | 7.19 | 0.03 |  |  |
| Bx GS (7 v. 6) | 1 | 6.86 | 0.01 | 0.40 | (0.20, 0.79) |
| Bx GS (8+ v. 6) | 1 | 1.35 | 0.24 | 0.69 | (0.36, 1.29) |

TABLE 27

| VARIABLE | DF | CHISQ | P-VALUE | HR | 95% CI |
|---|---|---|---|---|---|
| GPS | 1 | 66.67 | <0.01 | 1.07 | (1.05, 1.09) |
| PTEN Status | 1 | 0.86 | 0.35 | 0.78 | (0.46, 1.32) |
| BX GS | 2 | 6.43 | 0.04 |  |  |
| Bx GS (7 v. 6) | 1 | 6.12 | 0.01 | 0.42 | (0.21, 0.84) |
| Bx GS (8+ v. 6) | 1 | 1.15 | 0.28 | 0.71 | (0.37, 1.33) |

TABLE A

| Official Symbol: | Sequence ID: | SEQ ID NO: | Forward Primer Sequence: | SEQ ID NO: | Reverse Primer Sequence: | SEQ ID NO: | Probe Sequence: |
|---|---|---|---|---|---|---|---|
| ALDH1A2 | NM_170696.1 | 1 | CACGTCTGTCCCTCTCTGCT | 2 | GACCGTGGCTCAACTTTGTAT | 3 | TCTCTGTAGGGCCCAGCTCTCAGG |
| ANPEP | NM_001150.2 | 5 | CCACCTTGGACCAAAGTAAAGC | 6 | TCTCAGCGTCACCTGGTAGGA | 7 | CTCCCAACACGCTGAAACCG |
| AR | NM_000044.2 | 9 | CGACTTCACCGCACCTGAT | 10 | TGACACAAGTGGGACTGGGATA | 11 | ACCATGCCGCCAGGGTACACA |
| ARF1 | NM_001658.2 | 13 | CAGTAGAGAGATCCCCGCAACT | 14 | ACAAGCACATGGCTATGGAA | 15 | CTTGTCCTTGGGTCACCCTGCA |
| ASPN | NM_017680.4 | 17 | CATTGCCACTTCAACTCTAA | 18 | ATTGTTAGTGTCCAGGCTCT | 19 | TATCCCTTTGGAAGACCTTGCTTG |
| ATP5E | NM_006886.2 | 21 | CCGCTTTCGCTACAGCAT | 22 | TGGGAGTATCGGATGTAGCTG | 23 | TCCAGCGTCTTCCAGTAGGCCAC |
| AZGP1 | NM_001185.2 | 25 | GAGGCCAGCTAGGAAGCAA | 26 | CAGGAAGGGCAGCTACTGG | 27 | TCTGAGATCCACATTGCCTCCAA |
| BGN | NM_001711.3 | 29 | GAGCTCCCAAGGATGAC | 30 | CTTGTTGTTCACCAGGACGA | 31 | CAAGGGTCCCAGCACCTCTACGC |
| BIN1 | NM_004305.1 | 33 | CCTGCAAAAGGGAACAAGAG | 34 | CGTGGTTGGCGCACAGCAC | 35 | CTTCGCCTTCCAGATGGCTCC |
| BMP6 | NM_001718.4 | 37 | GTCAGAGACCTTGGTTCACCT | 38 | CTTAGTTGGCGTGTGTGACAG | 39 | TGAACCCCAGTATGTCCCCAAAC |
| C7 | NM_000587.2 | 41 | ATGTCTGAGTGTGAGGCGG | 42 | AGGCCTTATGCTGGTGACAG | 43 | ATGCTCTGCCCTCTGCATCTCAGA |
| CADM1 | NM_014333.2 | 45 | CCACCACCATCCTTACCATC | 46 | GATCCACTGCCCCTGATCG | 47 | TCTTCACCTGCTCGGGAATCTGTG |
| CDC276 | NM_001024736.1 | 49 | CCAAAGATGCGATACACAG | 50 | GGATGACTTGGGAATCATGTC | 51 | CCACTGTGCAGCCTTATTTCTCCAATG |
| CD44 | NM_000610.3 | 53 | GGCACCACTGCTTATGAAGG | 54 | GATGCTCATGGTGAATGAGG | 55 | ACTGGAACCAGAGAAGCACACCCTC |
| CDC20 | NM_001255.2 | 57 | AGTGACCTGCACTCGCTCT | 58 | GGCTTCCTTGGCTTTGCGCT | 59 | CCAATGACCCCCCTGCGCGCTGGC |
| CDKN2C | NM_001262.2 | 61 | TGAAGGGAACCTGCCCTTGCA | 62 | TGTGCTTCACCAGGAACTCCACC | 63 | TGGCTGCCAAAGAAGGCCACCTCCGGGT |
| CLTC | NM_004859.1 | 65 | ACCCTATGCAGACAGCCACAG | 66 | TGACTACAGGATCAGCGCTTC | 67 | TCTCACATGCTGTACCCAAAGCCA |
| COL1A1 | NM_000088.2 | 69 | GTGCCATCCAGCTGACC | 70 | CAGTGGTAGTGATGTTCTGGGA | 71 | TCCTGCGCCTGATGTCCACCG |
| COL1A2 | NM_000089.2 | 73 | CAGCCAAGAACTGGTATAGGAGCT | 74 | AAACTGGCTGCCAGCATTG | 75 | TCTCCTAGCCAGACGTGTTTCTGTCCTTG |
| COL3A1 | NM_000090.3 | 77 | GGAGGTTCTGTGGACCTGCTG | 78 | ACCAGGACTGCCACGTTC | 79 | CTCCTTGGTCCCAAGGTGTCAAAG |
| COL4A1 | NM_001845.4 | 81 | ACAAAGGCCTCCAAGGT | 82 | GAGTCCCAGGAAGAGACCTGCT | 83 | CTCCTTTGACACCAGGGATGCCAT |
| COL5A2 | NM_000393.3 | 85 | GGTCGAGGAACCCAAGGTG | 86 | GCCTGGAGGTCCAACTCTG | 87 | CCAGGAAATCTGTAGCACCAGGC |
| COL6A1 | NM_001848.2 | 89 | GGAGACCCTGGTGAAGCTG | 90 | TCTCCAGGGACACCAACG | 91 | CTTCTCTTCCCTGATCACCCTGCG |
| COL8A1 | NM_001850.3 | 93 | TGGTGTTCCAGGGCTTCT | 94 | CCCTGTAACCCTGATCCC | 95 | CCTAAGGGAGGAGCCAGGAATCCCA |

TABLE A-continued

| | | | | | |
|---|---|---|---|---|---|
| CSF1 | NM_000757.3 | 97 | TGCAGCGGCTGATTGACA | 98 | CAACTGTTCCTGGTCTACAAACTCA | 99 | TCAGATGGAGACCTCGTGCCAAATTACA |
| CSRP1 | NM_004078.1 | 101 | ACCCAAGAGACCCTGCCTCT | 102 | GCAGGGGTGAGTGATGT | 103 | CCACCCTTCTCCAGGACCCTTAG |
| CYP3A5 | NM_000777.2 | 105 | TCATTGCCCAGTATGGAGATG | 106 | GACAGGCTTGCCTTTCTCTG | 107 | TCCCGCCTCAAGTTTCTCACCAAT |
| DES | NM_001927.3 | 109 | ACTTCTCACTGGCCGACG | 110 | GCTCCACCTTCTCGTTGGT | 111 | TGAACCAGGAGTTTCTGACCACGC |
| DPP4 | NM_001935.3 | 113 | GTCCTGGGATCGGGAAGT | 114 | GTACTCCACCGGGATACAG | 115 | CGGCTATTCCACACTTGAACACGC |
| DUSP1 | NM_004417.2 | 117 | AGACATCAGCTCCTGGTTCA | 118 | GACAAACACCCTTCCTCCAG | 119 | CGAGGCCATTGACTTCATAGACTCCA |
| EGR1 | NM_001964.2 | 121 | GTCCCCGCTGCAGATCTCT | 122 | CTCCAGCTTAGGGTAGTTGTCCAT | 123 | CGGATCCTTTCCTCACTGCCCA |
| EGR3 | NM_004430.2 | 125 | CCATGTGATGAATGAGAGTG | 126 | TGCCTGAGAGAGGTGAGGT | 127 | ACCCAGTCTCACCTTCTCCCCACC |
| EGR | NM_004449.3 | 129 | CCAACACTAGGCTCCCCA | 130 | CCTCCGCCAGGTCTTTAGT | 131 | AGCCATATGCCTTCTCATCTGGGC |
| F2R | NM_001992.2 | 133 | AAGGAGCAAACCATCCAGG | 134 | GCAGGGTTTCATTGAGCAC | 135 | CCCGGGCTCAACATCACTACTGT |
| FAM107A | NM_007177.2 | 137 | TTCTGCCCAGGCCTTCCAC | 138 | AGGAGCTGGGGTGTACGGAGA | 139 | TCTCCGAGGCTCCCCAGGGCCCG |
| FAM13C | NM_198215.2 | 141 | ATCTTCAAAGCGAGAGACG | 142 | GCTGATACCACATGCTCTG | 143 | TCCTGACTTTCTCCGTGGCTCTC |
| FAP | NM_004460.2 | 145 | GTTGGCTCACGTGGGTTAC | 146 | GACAGGACCGAAACATTCTG | 147 | AGCCACTGCAAACATACTCGTTCATCA |
| FLNC | NM_001458.4 | 149 | CAGGACAATGGTGATGGCT | 150 | TGATGGTGTACTCCGGTCAG | 151 | ATGTGCTGCAGCTACCTGCCCAC |
| FN1 | NM_002026.2 | 153 | GGAAGTGACAGACGTGAAGGT | 154 | ACACAGCTAGCCGGTCACT | 155 | ACTTCAGGCGGGTGTCCAAGATGAT |
| FOS | NM_005252.2 | 157 | CGAGCCCCTTTGATGACTTCCT | 158 | GGAGCGGGCTGTGTCTCAGA | 159 | TCCCAGCATCATCCAGGCCCAG |
| GADD45B | NM_015675.1 | 161 | ACCCTCGACAAGACCACACT | 162 | TGGGAGTTCATGGGTACAGA | 163 | TGGGAGTTCATGGGTACAGA |
| GPM6B | NM_001001994.1 | 165 | ATGTGCTTGGAGTGGCCT | 166 | TGTAGAACATAAACACGGCA | 167 | CGCTGAGAACCAAACACACCCAG |
| GPS1 | NM_004127.4 | 169 | AGTACAAGCAGGCTGCCAAG | 170 | GCAGCTCAGGGAAGTCACA | 171 | CCTCCTGCCTGGCTTCCTTTGATCA |
| GSN | NM_000177.1 | 173 | CTTCTGCTAAGCGGTACATCGA | 174 | GGCTTCAAAGCCTTGCTTCAC | 175 | ACCCAGCCAATCGGATCGGC |
| GSTM1 | NM_000561.1 | 177 | AAGCTATGAGGAGAAAGAAGTACACGAT | 178 | GGCCCAGCTTGAATTTTCA | 179 | TCAGCCACTGGCTTCTGTCATATAATCAGGAG |
| GSTM2 | NM_000848.2 | 181 | CTGCAGGCACTCCCTGAAAT | 182 | CCAAGAAAACCATGGCTGCTT | 183 | CTGAAGCTCCTACTCACAGTTTCTGGG |
| HLF | NM_002126.4 | 185 | CACCCTGCAGGTGTCTGAG | 186 | GGTACCTAGGAGCAGAAGGTGA | 187 | TAAGTGATCTGCCCTCCAGTGGC |
| IGF1 | NM_000618.1 | 189 | TCCGGAGCTGTGATCTAAGGA | 190 | CGGACAGAGCGAGCTGACTT | 191 | TGTATTGCGCACCCCTCAAGCCTG |
| IGFBP2 | NM_000597.1 | 193 | GTGGACAGCACCATGAACA | 194 | CCTTCATACCCGACTTGAGG | 195 | CTTCCGGCCAGCACTGCCTC |
| IGFBP6 | NM_002178.1 | 197 | TGAACCCGAGAGACCAACAG | 198 | GTCTTGGACACCCCGCAGAT | 199 | ATCCAGGCACCTTACCACGCCCTC |
| IL6ST | NM_002184.2 | 201 | GGCCTAATGTTCCAGATCCT | 202 | AAAATTGCCTTGAGGAG | 203 | CATATTGCCCAGTGTCACCTCACA |

| | | | | | |
|---|---|---|---|---|---|
| INHBA | NM_002192.1 | 205 | GTGCCCGAGCCATATAGCA | 206 | CGGTAGTGTTGATGACTGTTGA |
| ITGA7 | NM_002206.1 | 209 | GATATGATTGGTCGCTGCTTTG | 210 | AGAACTTCCATTCCCACCAT |
| JUN | NM_002228.2 | 213 | GACTGCAAAGATGGTGAAACGA | 214 | TAGCCATAAGGTCCGCTCTC |
| KLK2 | NM_005551.3 | 217 | AGTCTCGGATTGTGGGAGG | 218 | TGTACACAGCCACCTGCC |
| KRT15 | NM_002275.2 | 221 | GCCTGGTTCTTCAGCAAGAC | 222 | CTTGCTGGTCTGGATCATTTC |
| KRT5 | NM_000424.2 | 225 | TCAGTGTGAAGGAGTTGGA | 226 | TGCCATATCCAGAGGAAACA |
| LAMB3 | NM_000228.1 | 229 | ACTGACCAAGCCTGAGACCT | 230 | GTCACACTTGCAGCATTTCA |
| LGALS3 | NM_002306.1 | 233 | AGCGGAAAATGGCAGACAAT | 234 | CTTGAGGGTTTGGGTTTCCA |
| MMP11 | NM_005940.2 | 237 | CCTGGAGGCTGCAACATACC | 238 | TACAATGGCTTTGGAGGATAGCA |
| MYBL2 | NM_002466.1 | 241 | GCCCAGATCGCCAAGATG | 242 | CTTTTGATGGTAGAGTTCCAGTGATTC |
| NFAT5 | NM_006599.2 | 245 | CTGAACCCCTCTCCTGGTC | 246 | AGGAAACGATGGCGAGGT |
| OLFML3 | NM_020190.2 | 249 | TCAGAACTGAGGCGACAC | 250 | CCAGATAGTCTACCTCCCGCT |
| PAGE4 | NM_007003.2 | 253 | GAATCTCAGCAAGAGGAACCA | 254 | GTTCTTCGATCGGAGGTGTT |
| PGK1 | NM_000291.1 | 257 | AGAGCCAGTTGCTGTAGAACTCAA | 258 | CTGGGCCTACACAGTCCTTCA |
| PPAP2B | NM_003713.3 | 261 | ACAAGCACCATCCCAGTGA | 262 | CACGAAGAAAACTATGCAGCAG |
| PPP1R12A | NM_002480.1 | 265 | CGGCAAGGGGTTGATATAGA | 266 | TGCCTGGCATCTCTAAGCA |
| PRKCA | NM_002737.1 | 269 | CAAGCAATGCGTCATCAATGT | 270 | GTAAATCCGCCCCCTCTTCT |
| SDC1 | NM_002997.1 | 273 | GAAATTGACGAGGGGTGTCT | 274 | AGGAGCTAACGGAGAACCTG |
| SFRP4 | NM_003014.2 | 277 | TACAGGATGAGGCTGGGC | 278 | GTTGTTAGGGCAAGGGGC |
| SHMT2 | NM_005412.4 | 281 | AGCGGGGTGCTAGAGCTTGTA | 282 | ATGGCACTTCGGTCTTCCA |
| SLC22A3 | NM_021977.2 | 285 | ATCGTCAGCGAGTTTGACCT | 286 | CAGGATGGCTTGGGTGAG |
| SMAD4 | NM_005359.3 | 289 | GGACATTACTGGCCTGTTCACA | 290 | ACCAATACTCAGAGCAGGATGA |
| SPARC | NM_003118.1 | 293 | TCTTCCCGTACACTGGCAGTTC | 294 | AGTCGGTGTGGGAGAGTA |
| SRC | NM_005417.3 | 297 | TGAGGAGTGGTATTTTGGCAAGA | 298 | CTCTCGGGTTCTCTGCATTGA |
| SRD5A2 | NM_000348.2 | 301 | GTAGGTCCTGGCGTTCTG | 302 | TCCCTGGAAGGGTAGGAGTAA |
| STAT5B | NM_012448.1 | 305 | CCAGTGGTGGTGATCGTTCA | 306 | GCAAAAGCATTGTCCCAGAGA |

| | | |
|---|---|---|
| | 207 | ACGTCCGGGTCCTCCACTGTCCTTCC |
| | 211 | CAGCCAGGACCTGGCCATCCG |
| | 215 | CTATGACGATGCCCTCAACGCCTC |
| | 219 | TTGGGAATGCTTCTCACACTCCCA |
| | 223 | TGAACAAAGAGGTGGCCTCCAACA |
| | 227 | CCAGTCAACATCTCTGTTGTCACAAGCA |
| | 231 | CCACTCGCCATACTGGGTGCAGT |
| | 235 | ACCCAGATAACGCATCATGGAGCGA |
| | 239 | ATCCTCCTGAAGCCCTTTTCGCAGC |
| | 243 | CAGCATTGTCGTCTCCCCTGGCA |
| | 247 | CGAGAATCAGTCCCGTGAGTTC |
| | 251 | CAGACGATCCACTCTCCCGAGAT |
| | 255 | CCAACTGACAATCAGGATATTGAACCTGG |
| | 259 | TCTCTGCTGGGCAAGGATGTTCTGTTC |
| | 263 | ACCAGGGGTCCTTGAGCAAATCCT |
| | 267 | CCGTTCTTCTTCTTTGAGCTGC |
| | 271 | CAGCCTCTGCGGAATGGATCACACT |
| | 275 | CTCTGAGCGCCTATGTAAGGCCA |
| | 279 | CCTGGGACAGCCTATGTAAGGCCA |
| | 283 | CCATCACTGCCAACAAGAGACACCTG |
| | 287 | CAGCATCCACGCATTGACACAGAC |
| | 291 | TGCATTCCAGCCTCCCATTTCCA |
| | 295 | TGGACCAGCACCCCATTGACGG |
| | 299 | AACCGCTCTGACTCCCGTCGGTG |
| | 303 | AGAACACCACTCAGAATCCCCAGGC |
| | 307 | CAGCCAGGACAACAATGCGACGG |

TABLE A-continued

| | | | | |
|---|---|---|---|---|
| TGFB1I1 | NM_001042454.1 | 309 | GCTACTTTGAGCGCTTCTCG | 310 | GGTCACCATCTGTGTCG | 311 | CAAGATGTGGCTTCTGCAACCAGC |
| THBS2 | NM_003247.2 | 313 | CAAGACTGGCTACATCAGAGTCTTAGTG | 314 | CAGCCTAGGTTTGGTCATAGATAGG | 315 | TGAGTCTGCCATGACCTGTTTTCTTCAT |
| TNFRSF10B | NM_003842.2 | 317 | CTCTGAGACAGTGCTTCGATGACT | 318 | CCATGAGGCCCAACTTCCT | 319 | CAGACTTGTGCCCTTTGACTCC |
| TPM2 | NM_213674.1 | 321 | AGAGAGATGCAGCTGAAGGAG | 322 | CCACCTCTTCATATTTGCGG | 323 | CCAAGCACATCGCTGAGGATTCAG |
| TPX2 | NM_012112.2 | 325 | TCAGCTGTGAGCTGCGATA | 326 | ACGGTTCCTAGGTTTGAGGTTAAGA | 327 | CAGGTCCCATTGCCGGGCG |
| TUBB2A | NM_001069.1 | 329 | CGAGGACGAGGCTTAAAAAC | 330 | ACCATGTCTGAGGACAACAG | 331 | TCTCAGATCAATGTGCATCCTTAGTGAA |
| UBE2T | NM_014176.1 | 333 | TGTTCTCAAATTGCCACCAA | 334 | AGAGGTCAACACAGTTGCGA | 335 | AGGTGCTTGGAGACCATCCCTCAA |
| VCL | NM_003373.2 | 337 | GATACCACAACTCCCATCAAGCT | 338 | TCCCTGTTAGGCGCATCAG | 339 | AGTGGCAGCCACGCGCC |
| ZFP36 | NM_003407.1 | 341 | CATTAACCCACTCCCCTGA | 342 | CCCCCACCATCATGAATACT | 343 | CAGGTCCCCAAGTGTGCAAGCTC |

| Official Symbol: | SEQ ID NO: | Amplicon Sequence: |
|---|---|---|
| ALDH1A2 | 4 | CACGTCTGTCCCTCTGCTTTCTCTGTAGGGCCCAGCTCTCAGGAATACAAAGTTGAGCCACGGTC |
| ANPEP | 8 | CCACCTTGGACCAAAGTAAAGCTGGAATCGTTACCGCCTCCCAACACGCTGAAACCCGATTCCTACCGGGTGACGCTGAGA |
| AR | 12 | CGACTTCACCGACCGCGATGTGTGTACCCTGGCGGCATGGTGAGCAGAGTGCCCTATCCGAGTCCCACTTGTCA |
| ARF1 | 16 | CAGTAGAGATCCCCGCCAACTCCGCTTGTCCTTGGGTCACCCTGCCATTCCATAGCCATGTGCTTGT |
| ASPN | 20 | CATTGCCACTTCAACTCTAAGGAATATTTTGAGATAATCCTTTGGAAGAACCTTGCTTGGAAGAGCCTGGACACTAACAAT |
| ATP5E | 24 | CCGCTTTCGCTACAGCATGGTGCCTACTGAGGACTGGCTCAGCTACTACATCCGATACTCCCA |
| AZGP1 | 28 | GAGGCCAGCTAGGAAGCAAGGGTTGGAGGCAATGTGGGATTCAGACCCAGTAGCTGCCCTTCCTG |
| BGN | 32 | GAGCTCCCAAGGATGACTTCAAGGGTCTTCGCCTCCAGATCAGAGCTCAACCACG |
| BIN1 | 36 | CCTGCAAAAGGGAACAGAGCCCTTGCGCTGCAGCCATCTCTGTGCTCCAGCATAAGGCCT |
| BMP6 | 40 | GTCAGACCTTGGTTCACCTTATGAACCCCGAGATGCAGAGCAGGCATGAAGAGGCTCGATCAGGGCAGTGGATC |
| C7 | 44 | ATGTCTGAGTGTGAGGCCGGGCGTCTGAGATGCAGAGCATCTCTGTCACCAGCATAAGGCCT |
| CADM1 | 48 | CCACCACCATCCTTACCATCATCACAGATTCACAGACCACTGTGCAGCCCTTATTTCTCAATGACATGATTCCAAGTCATCC |
| CD276 | 52 | CCAAAGGATGCGATACACAGACCACTGTGCAGCCCTTATTCTCAATGACATGATTCCAAGTCATCC |
| CD44 | 56 | GGCACCACTGCTTATGAAGGAAACTGGAACCCAGAAGAACACACCCCATCCCAATGCACCCCATGCCGCGCTGGAGTTCCTGGTGAAGACACA |
| CDC20 | 60 | AGTGACCTTGCACTCGCTGCTTCAGCTGATGCAGCTGATGAGGCCAACGGATGCGTGAGCATGGTAGCTA |
| CDKN2C | 64 | TGAAGGGAACCTGCCCTTGCACTTGGCTGCCAAAAGAAGAGCACCCACCCTCCGGGTGTGGTCCTGGTGAAGCACA |
| CLTC | 68 | ACCGTATGGACAGCAGCCACAGCCTGCTTTGGGTACAGCATGTGAGATGAAGCCTGATCCTGTAGTCA |

TABLE A-continued

| | | |
|---|---|---|
| COL1A1 | 72 | GTGGCCATCCAGCTGACCTTCCTGCGCCTGAGCCTCCAGAACATCACCTACCACTG |
| COL1A2 | 76 | CAGCCAAGAACTGGTATAGGAGCTCCAAGGACAAGAAACACTCTGGCTAGGAGAACTATCAATGCTGGCAGCCAGTTT |
| COL3A1 | 80 | GGAGGTTCTGGACCTGCTGGTCCTCCTCCTGGTCCCAAGGTGTCAAAGGTGAACGTGGCAGTCCTGGT |
| COL4A1 | 84 | ACAAAGGCCTCCCAGGATTGGATGCATCCCTGGTGTCAAAGGAGAAGCAGTCTTCCTGGGACTC |
| COL5A2 | 88 | GGTCGAGGAACCCAAGTCCGCTGGTGTCCTACAGGATTTCCTGGTTCTGCGGGCAGGAGTTGGACCTCCAGGC |
| COL6A1 | 92 | GGAGACCCTGGTGAAGCTGGCCCGCAGGGTGATCAGGGAGAAGAGGCCCCGTTGGTGTCCTGGAGA |
| COL8A1 | 96 | TGGTGTTCCAGGGCTTCTCGGACTTAGGGAGAGCCAGGAATCCCAGGGGATCAGGGTTTACAGGG |
| CSF1 | 100 | TGCAGCGGCTGATTGACAGTCAGATGAGAGACCTCGTGCCAAATTACATTGAGTTGTAGACCAGGAACAGTTG |
| CSRP1 | 104 | ACCCAAGACCCTGCCTCTTCCACTCCTCCACCCTTCTCCAGGACCCTTAGATCACACTCCACCCCTGC |
| CYP3A5 | 108 | TCATTGCCCAGTATGGACGATGTATTGGTGAGAAACTTGAGGCTGGAAGCAGAGAAAGCAAGCCTGTC |
| DES | 112 | ACTTCTCACTGGCCGACCGCGGTGAACCAGGAGTTCTGACCACGCGCACCAACGAGAAGGTGGAGC |
| DPP4 | 116 | GTCCTGGGATCGGGAAGTGGCGTGTTCAAGTGTGGAATAGCCGTGGCCGTCTATCCGGTGGAGTAC |
| DUSP1 | 120 | AGACATCAGCTCCTGGTTCAACGAGGCCATTGACTTCATATGACTCCTTCCTCACTCGCCCACCATGGACAACTACCCTAAGCTGGAG |
| EGR1 | 124 | GTCCCCGTCGAGATCTCTGACCCGTTCGGATCTCCGCCACCAGTCCTTCCATACCCAGTCTCACCTTCCCCCACCGTCTAAGACCTGGCAG |
| EGR3 | 128 | CCATGTGATGATGAATGAGTCTCCTTTTCCATACCCAGTCTGTCAGCTACCTGCCACCTTCATCTGGGCACTTACTACTAAAGACCTGGCGGAGG |
| ERG | 132 | CCAACACTAGGCTCCCCACCAGTGCCCGGCTCAACATCACTACCTGTCATGATGTCTCAATGAAACCTGC |
| F2R | 136 | AAGGAGCAAACCATCCAGGTGCCCGGCTCAACATCACTACCTGTCATGATGTCTCAATGAAACCCTGC |
| FAM107A | 140 | TTCTGCCCAGGCCTTCCCACCAGGAATCTCCGAGGCTGCCCAGGGCCCCGCTTCTCCGTACACCCAGCTCCT |
| FAM13C | 144 | ATCTTCAAAGCGGAGAGCGGGAGGAGCCACGAGGAGAAAGTCAGGAGACAGAGACATGTGTATCCAGC |
| FAP | 148 | GTTGGCTCACGTGGGTTACTGATGAACAGAGTATGTTGCAGTGGCTAAAAGAGTCAGAATGTTTCGGTCCTGTC |
| FLNC | 152 | CAGGAGCAAATGGTGATGGCTCATGTGCTGTCAGCTACCTGCCACGAGCCTGGCGAGTACACCATCA |
| FN1 | 156 | GGAAGTGACAGACGTGAAGATGCACCATCATGTGACACACCGCCAGTGGTCGAGAGTGCAGTGACCGGCTACCGTGT |
| FOS | 160 | CGAGCCCTTTGATGACTTCCTGTTCCCAGCATCATCCAGGCCGTGGCTGCTCTGAGACAGCCCGCTCC |
| GADD45B | 164 | ACCCTCGACAAGACCACCACTTTGGGACTTGGGAGCTGGGTGTGTTCTCAGCGGTGCCCGTGTTTATGTTCTACA |
| GPM6B | 168 | ATGTGCTTGGAGTGGCCTGGCTGGGTGTTTGGTTTCTCAGCGGTGCCCGTGTTTATGTTCTACA |
| GPS1 | 172 | AGTACAAGCAGGCTGCCAAGTGCCTCCTCGCTGCCTCTGCTTCTTTGATCACTGACTTCCCTGAGCTGC |

TABLE A-continued

| Gene | # | Sequence |
|---|---|---|
| GSN | 176 | CTTCTGCTAAGCCGGTACATCGAGACGGACCCGACCAATCGGGATCGGCGACGCCCATCACCCTGGTGAAGCAAGGCTTTGAGCC |
| GSTM1 | 180 | AAGCTATGAGGAGAAAGAAGTACGATGGGGACGCTCCTGATTATGACAGAAGCCAGTGGCTGAATGAAAAATTCAAGCTGGGCC |
| GSTM2 | 184 | CTGCAGGCACTCCCTGAAATGTGAGACTAAGTGACTTCTGCCCTCCAGGTGGCGATCACCTTCTGCTCCTAGTGACC |
| HLF | 188 | CACCCTGCAGGTGTCTGAGACTAAGTGACTTCTGCCCTCCAGGTGGCGATCACCTTCTGCTCCTAGTGACC |
| IGF1 | 192 | TCCGGAGCTGTGATCTAAGGAGGCTGGAGATGTATTGCGCAGACCCTCAAGCCTGCCAAGTCAGCTCGCTCTGTCCG |
| IGFBP2 | 196 | GTGGACAGCACCATGACATGTTGGGCGGGAGGCAGTGCTGCCGAAGCCCTCAAGTCGGGTATGAAGG |
| IGFBP6 | 200 | TGAACCCGAGACCAACAGAGACCTTCAGGCACCTTACCACGCCTCCCAGCCCATTCTGCGGGTGTCCAAGAC |
| IL6ST | 204 | GGCCTAATGTTCCAGATCCTTCAAAGAGTCATATTGCCAGTGTCACTCTCCACTCAACAGTCATCAACCACTACCG |
| INHBA | 208 | GTGCCCGAGCCATATAGACAGGCACGTCCGGGTCTCACTGTCCTTCCTCACTCCGGATGAGTGTGATGGTGGGGAATGGAAGTTCT |
| ITGA7 | 212 | GATATGATTGGTCGCTGCTTTGTGCTCAGACGACCTTCTATGACAATGGCCCTCAACGCTCGTTCTCCCGTCCAGAGCGGACCTTATGGCTA |
| JUN | 216 | GACTGCAAAGATGGAAACGACCTTCTATGACAATGGCCCTCAACGCTCGTTCTCCCGTCCAGAGCGGACCTTATGGCTA |
| KLK2 | 220 | AGTCTCGATTGTGGAGGCTGGGAGTGTGAGAAGCATTCCCAACCCTGGCAGGTGGCTGTGTACA |
| KRT15 | 224 | GCCTGGTTCTTCAGCAAGCTGAGGAGCTGAACAAAGAGGTGGCCTCCAACACAGAAATGATCCAGACCAGCAAG |
| KRT5 | 228 | TCAGTGGAGAAGGAGTTGACCAGTCTGACCAGTCAACATCTCTGTTGTCACAAGCAGTGTTTCCTCTGGATATGGCA |
| LAMB3 | 232 | ACTGACCAAGCTCGAGACCTACTGCACCCAGTATGGCGAGTGCGAGATGAAATGCTGCAAGTGTGAC |
| LGALS3 | 236 | AGCGGAAAATGCCAGACACAATTTTTCGCTCAATCTGTCCCAGGCCGGATCCTCCTGAAGCCCTTTTCGCAGCACTGCTATCCTCCAAAGCCATTGTA |
| MMP11 | 240 | CCTGGAGGCTGCAACATACCCTCAATCTGTCCCAGGCCGGATCCTCCTGAAGCCCTTTTCGCAGCACTGCTATCCTCCAAAGCCATTGTA |
| MYBL2 | 244 | GCCGAGATCGCCAAGATGTTGCCAGGAGGACAGACAATGCTGTGAAGAATCACTGAACTCTACCATCAAAAG |
| NFAT5 | 248 | CTGAACCCCTCCTCGTCACCCAGAATCAGTCCCGTGGAGTTCCCCCTCCACCTCGCCATCGTTTCCT |
| OLFML3 | 252 | TCAGAACTTGAGGCCGACACCCATCTCCCGGAGAGTGGATCGTCTGGAGCGGAGGTAGACTATCGG |
| PAGE4 | 256 | GAATCTCAGCAAGAGAACCACCAACTGACAATCAGGATATTGAACCTGGACAAGAAGGAACACCTCCGATCGAAGAAC |
| PGK1 | 260 | AGAGACCAGTTGCTGTAGAACTGTGAACTCAAATCTCTGCTGGGCAAGGATGTTCTTCTTGAAGGACTGTGTAGGCCCAG |
| PPAP2B | 264 | ACAAGCACACCATCCCAGTGATGTTCTGGCAGGATTGCTCAAGGAGCCCTGGTGGCCTGCTGCATAGTTTTCTTCGTG |
| PPP1R12A | 268 | CGGCAAGGGGTTGATATAGAAGCAGCTCGAAAGGAAGAAGAACGAGATCATGCTTAGAGATGCCAGGCA |
| PRKCA | 272 | CAAGCAATGCGTCATCAATGTCCCCAGCCTCTGCGGAATGGATCACACTGAGAGAGGCCGGATTAC |
| SDC1 | 276 | GAAATTGACGAGGGTGTCTTGGGCAGCTGGTCTCTGACGCTGCTCATCCAAGGCCAGTTCTCCGTTAGCTCCT |
| SFRP4 | 280 | TACAGGATGAGGCTGGGCATTGCCTGGACAGCCTATGTAAGCCCCTTGCCCTAACAAC |

TABLE A-continued

| | | |
|---|---|---|
| SHMT2 | 284 | AGCGGGTGCTAGAGCTTGTATCCATCACTGCCAACAAGAACACCTGTCCTGGAGACCGAAGTGCCAT |
| SLC22A3 | 288 | ATCGTCAGCGAGTTTGACCTTGTCTGTGTCAATGCGTGGATGCTGGACCTCACCCAAGCCATCCTG |
| SMAD4 | 292 | GGACATTACTGGCCTGTTCACAATGAGCTTGCATTCCAGCCTCCCATTTCCAATCATCCTGCTCCTGAGTATTGGT |
| SPARC | 296 | TCTTCCCTGTACACTGGCAGTTCGGCCAGCTGGACCAGCACCCCATTGACGGGTACCTCTCCCACACCGAGCT |
| SRC | 300 | TGAGGAGGTGGTATTTTGGCAAGATCACCAGACGGGAGTCAGAGCGGTTACTGCTCAATGCAGAGAACCCGAGAG |
| SRD5A2 | 304 | GTAGGTCTCCTGGCGTTCTGCCAGCTGGCCTGGGGATTCTGAGTGGTGTCTGCTTAGAGTTTACTCCTACCCTTCCAGGGA |
| STAT5B | 308 | CCAGTGGTGGTGATCGTTCATGCCAGCCAGGACAACAATGCAGCGGCCACTGTTCTCTGGGACAATGCTTTTGC |
| TGFB1I1 | 312 | GCTACTTTGAGCGCCTTCTCCGCCAAGATGTGGCTTCGAACCAGCCATCCGACACAAGATGGTGACC |
| THBS2 | 316 | CAAGACTGGCTACATCAGAGTCTTAGTGCATGAAGGAAAAACAGGTCATGGCAGACCTATCTATGACCAAACCTACGCTG |
| TNFRSF10B | 320 | CTCTGAGACAGTGCTTCGATGACTTTGCAGACTTGGTGTCCCTTTGACTCTCGGGAGCCGCTCATGAGGAAGTTGGGCCTCATGG |
| TPM2 | 324 | AGGAGATCGCAGTGAAGGAGGCCAAGCACATCGCTGAGGATTCAGAACCGCAAATATGAAGAGGTGG |
| TPX2 | 328 | TCAGCTGTGAGCTGCGGATACCCCGGCAATGGGACCTGCTCTTAACCTCAAACCTAGGACCGT |
| TUBB2A | 332 | CGAGGACGAGGCTTAAAAACTTCTCAGATCAATCGTCATCCTTAGTGAACTTCTGTTGTCCTCAAGCATGGT |
| UBE2T | 336 | TGTTCTCAAATTGCCACCAAAAGGTGCTTGGAGACCATCCCTCAACATCGCAACTGTGTTGACCTCT |
| VCL | 340 | GATACCACAACTCCCATCAAGTCTTGTTGGCAGTGGCAGTGGCAGCAGCACCGCGCCTCCTGATGCCCTAACAGGGA |
| ZFP36 | 344 | CATTAACCCACTCCCCTGACCTCACGCGCTGGGGCAGGTCCCCAAGTGTGCAAGCTCAGTATTCATGATGGTGGGGG |

What is claimed is:

1. A method of analyzing a biological sample containing cancer cells from a patient with prostate cancer, comprising:
   determining a level of RNA transcripts of each of a set of genes consisting of: BGN, COL1A1, SFRP4, FLNC, GSN, GSTM2, TPM2, AZGP1, KLK2, FAM13C, SRD5A2, and TPX2, and one or more reference genes, in the biological sample,
   normalizing the level of the RNA transcripts against the level of the one or more reference RNA transcripts from the sample to obtain normalized expression levels of the BGN, COL1A1, SFRP4, FLNC, GSN, GSTM2, TPM2, AZGP1, KLK2, FAM13C, SRD5A2, and TPX2 RNA transcripts,
   assigning the RNA transcripts to gene groups selected from a cellular organization gene group, an androgen gene group, a stromal response gene group, and a proliferation gene group;
   wherein the cellular organization group comprises FLNC, GSN, TPM2, and GSTM2, the androgen group comprises FAM13C, KLK2, AZGP1 and SRD5A2, the stromal response group comprises BGN, COL1A1, and SFRP4, and the proliferation group comprises TPX2, and
   calculating one or more quantitative scores selected from (a) a stromal response group score obtained from normalized expression levels of the stromal response group genes wherein the stromal group score equals 0.527X BGN+0.457 X COL1A1+0.156 X SFRP4, (b) a cellular organization group score obtained from normalized expression levels of the cellular organization group genes wherein the cellular organization group score equals 0.163 X FLNC+0.504 X GSN+0.421 X TPM2+0.394 X GSTM2, (c) an androgen group score obtained from normalized expression levels of the androgen group genes wherein the androgen group score equals 0.634 X FAM13C+1.079 X KLK2+0.642 X AZGP1+0.997 X SRD5A2 threshold score where the SRD5A2 threshold score equals SRD5A2 if SRD5A2 is 5.5 or higher and equals 5.5 if SRD5A2 is less than 5.5, and (d) a TPX2 threshold score wherein the TPX2 threshold score equals TPX2 if TPX2 is 5.0 or higher and equals 5.0 if TPX2 is less than 5.0, wherein the gene symbols represent the normalized gene expression levels of the RNA transcripts of the respective genes.

2. The method of claim 1, wherein the biological sample is a tissue sample.

3. The method of claim 2, wherein the tissue sample is fixed, paraffin-embedded, or fresh, or frozen.

4. The method of claim 1, wherein the level of one or more RNA transcripts is determined by quantitative RT-PCR.

5. The method of claim 1, further comprising creating a report providing the one or more quantitative score results.

6. The method of claim 1, wherein the one or more reference transcripts comprise RNA transcripts from one or more of ARF1, ATP5E, CLTC, GPS1, and PGK1.

7. A method of treating a prostate cancer patient, comprising:
   administering active surveillance to the patient; wherein the patient was previously determined to have a low or intermediate risk of adverse pathology, non-organ-confined disease, high-grade disease, or high-grade or non-organ confined disease according to an analysis comprising:
   determining a level of RNA transcripts of each of a set of genes consisting of: BGN, COL1A1, SFRP4, FLNC, GSN, GSTM2, TPM2, AZGP1, KLK2, FAM13C, SRD5A2, and TPX2, and one or more reference genes, in a biological sample from the patient, normalizing the level of the RNA transcripts against the level of the one or more reference RNA transcripts from the sample to obtain normalized expression levels of the BGN, COL1A1, SFRP4, FLNC, GSN, GSTM2, TPM2, AZGP1, KLK2, FAM13C, SRD5A2, and TPX2 RNA transcripts, comparing the normalized expression levels to gene expression data in reference prostate cancer samples, wherein increased normalized expression levels of BGN, COL1A1, SFRP4, and TPX2 correlate with an increased likelihood of adverse pathology, non-organ-confined disease, high-grade disease, or high-grade or non-organ confined disease, and wherein increased normalized expression levels of FLNC, GSN, GSTM2, TPM2, AZGP1, KLK2, FAM13C, and SRD5A2 correlate with a decreased likelihood of adverse pathology, non-organ-confined disease, high-grade disease, or high-grade or non-organ confined disease, assigning the RNA transcripts to gene groups selected from a cellular organization gene group, an androgen gene group, a stromal response gene group, and a proliferation gene group; wherein the cellular organization group comprises FLNC, GSN, TPM2, and GSTM2, the androgen group comprises FAM13C, KLK2, AZGP1 and SRD5A2, the stromal response group comprises BGN, COL1A1, and SFRP4, and the proliferation group comprises TPX2, calculating one or more quantitative scores for the patient, and predicting the likelihood of one or more of adverse pathology, non-organ-confined disease, high-grade disease, or high-grade or non-organ-confined disease for the patient based on the one or more quantitative scores;

wherein the one or more quantitative scores are selected from a stromal response group score obtained from normalized expression levels of the stromal response group genes wherein the stromal group score equals 0.527 X BGN+0.457 X COL1A1+0.156 X SFRP4, a cellular organization group score obtained from normalized expression levels of the cellular organization group genes wherein the cellular organization group score equals 0.163 X FLNC+0.504 X GSN+0.421 X TPM2+0.394 X GSTM2, an androgen group score obtained from normalized expression levels of the androgen group genes wherein the androgen group score equals 0.634 X FAM13C+1.079 X KLK2+0.642 X AZGP1+0.997 X SRD5A2 threshold score where the SRD5A2 threshold score equals SRD5A2 if SRD5A2 is 5.5 or higher and equals 5.5 if SRD5A2 is less than 5.5, and a TPX2 threshold score wherein the TPX2 threshold score equals TPX2 if TPX2 is 5.0 or higher and equals 5.0 if TPX2 is less than 5.0, wherein the gene symbols represent the normalized gene expression levels of the RNA transcripts of the respective genes; and wherein the stromal response group score and the proliferation group score positively correlate with an likelihood of adverse pathology, non-organ-confined disease, high-grade disease, and high-grade or non-organ confined disease, and wherein cellular organization group score and androgen group score negatively correlate with a likelihood of adverse pathology, non-organ-confined disease, high-grade disease, and high-grade or non-organ confined disease.

8. The method of claim 1, wherein the method comprises determining the androgen group score.

9. The method of claim 7, wherein the method comprises determining the androgen group score.

10. The method of claim 1, wherein the method comprises determining the stromal group score.

11. The method of claim 7, wherein the method comprises determining the stromal group score.

12. The method of claim 1, wherein the method comprises determining the proliferation group score.

13. The method of claim 7, wherein the method comprises determining the proliferation group score.

* * * * *